United States Patent [19]

Shinjo et al.

[11] Patent Number: 5,364,559
[45] Date of Patent: Nov. 15, 1994

[54] FERROELECTRIC CHIRAL SMECTIC LIQUID CRYSTAL COMPOSITION AND LIQUID CRYSTAL DEVICE USING SAME

[75] Inventors: Kenji Shinjo, Atsugi; Takao Takiguchi, Tokyo; Hiroyuki Kitayama, Sagamihara; Kazuharu Katagiri, Tama; Masataka Yamashita, Hiratsuka; Takeshi Togano, Yokohama; Masahiro Terada, Atsugi; Junko Sato, Hiratsuka; Masanobu Asaoka, Yokohama; Takashi Iwaki, Isehara; Yoshiko Kimura, Hiratsuka, all of Japan

[73] Assignee: Canon Kabushiki Kaisha, Tokyo, Japan

[21] Appl. No.: 94,927

[22] Filed: Jul. 22, 1993

Related U.S. Application Data

[63] Continuation of Ser. No. 370,981, Jun. 23, 1989, abandoned.

[30] Foreign Application Priority Data

| Jun. 24, 1988 | [JP] | Japan | 63-157675 |
| Jul. 13, 1988 | [JP] | Japan | 63-175786 |
| Jul. 27, 1988 | [JP] | Japan | 63-187478 |
| Jul. 28, 1988 | [JP] | Japan | 63-189705 |
| Jul. 29, 1988 | [JP] | Japan | 63-188111 |
| Jun. 9, 1989 | [JP] | Japan | 1-147983 |

[51] Int. Cl.⁵ .................. C09K 19/06; C09K 19/34; C09K 19/30; G02F 1/13
[52] U.S. Cl. ............... 252/299.60; 252/299.1; 252/299.63; 252/299.66; 252/299.01; 252/299.67; 359/104
[58] Field of Search .......... 252/299.61, 299.63, 252/299.66, 299.01; 359/104

[56] References Cited

U.S. PATENT DOCUMENTS

| 4,753,752 | 6/1988 | Raynes et al. | 252/299.65 |
| 4,874,544 | 10/1989 | Yong et al. | 252/299.61 |
| 4,911,863 | 3/1990 | Sage et al. | 252/299.65 |
| 4,917,821 | 4/1990 | Mori et al. | 252/299.63 |
| 4,952,699 | 8/1990 | Yong et al. | 548/136 |

FOREIGN PATENT DOCUMENTS

| 0178647 | 4/1986 | European Pat. Off. |
| 0267585 | 5/1988 | European Pat. Off. |
| 0294852 | 12/1988 | European Pat. Off. |
| 0315958 | 5/1989 | European Pat. Off. |

*Primary Examiner*—Robert L. Stoll
*Assistant Examiner*—C. Harris
*Attorney, Agent, or Firm*—Fitzpatrick, Cella, Harper & Scinto

[57] ABSTRACT

A ferroelectric chiral smectic liquid crystal composition, comprising at least one compound represented by the following formula (I):

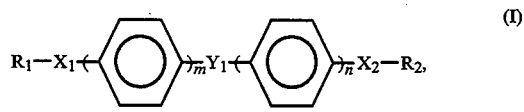

wherein $R_1$ and $R_2$ respectively denote a linear or branched alkyl group having 1-18 carbon atoms capable of having a substituent; $X_1$ and $X_2$ respectively denote a single bond, —O—,

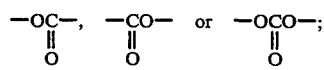

$Y_1$ denotes —CH$_2$O— or —OCH$_2$—; and m and n are respectively 1 or 2; and at least one compound represented by the following formula (II):

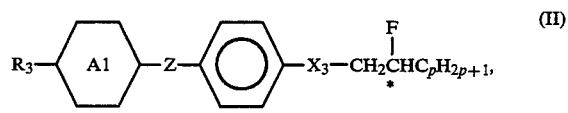

wherein $R_3$ denotes a linear or branched alkyl group having 1-18 carbon atoms capable of having a substituent; $X_3$ denotes a single bond, —O— or (Abstract continued on next page.)

Z denotes a single bond or $-\underset{\underset{O}{\|}}{C}O-$;
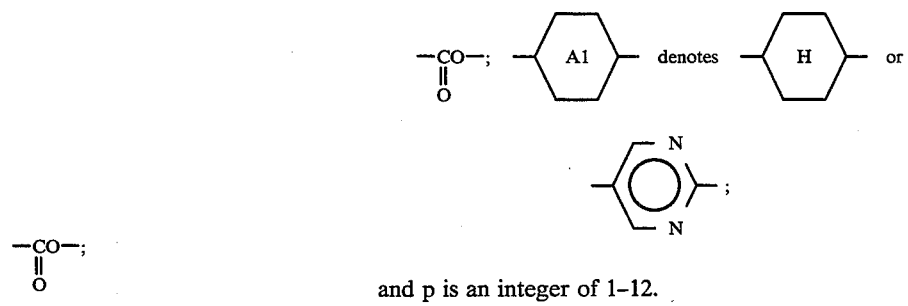
and p is an integer of 1–12.
13 Claims, 3 Drawing Sheets

FERROELECTRIC CHIRAL SMECTIC LIQUID CRYSTAL COMPOSITION AND LIQUID CRYSTAL DEVICE USING SAME

This application is a continuation of application Ser. No. 370,981 filed Jun. 23, 1989, now abandoned.

FIELD OF THE INVENTION AND RELATED ART

The present invention relates to a liquid crystal composition used in a liquid crystal display device, a liquid crystal-optical shutter, etc., more particularly to a novel liquid crystal composition with improved responsiveness to an electric field and a liquid crystal device using the liquid crystal composition.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the abovementioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. A high response speed can be obtained by (a) increasing the spontaneous polarization, (b) lowering the viscosity $\eta$, or (c) increasing the applied voltage. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that a remarkable increase in response speed may not be attained as a result.

Further, if it is assumed that the operation temperature of an actual display device is 5°-40° C., the response speed changes by a factor of about 20, so that it actually exceeds the range controllable by driving voltage and frequency.

As described hereinabove, commercialization of a ferroelectric liquid crystal device requires a ferroelectric chiral smectic liquid crystal composition having a low viscosity, a high-speed responsiveness and a small temperature-dependence of response speed.

In a representative FLC cell structure, a pair of substrates are disposed, each substrate of e.g. glass being provided with an electrode pattern of e.g. ITO, further thereon with a layer of e.g. $SiO_2$ (about 1000 Å) for preventing short circuit between the pair of substrates and further thereon with a film of e.g. polyimide (PI; such as SP-510, 710, . . . available from Toray K.K.) of about 500 Å in thickness, which is then treated for alignment control by rubbing with e.g. an acetate fiber-planted cloth. Such a pair of substrates are disposed opposite to each other so that their alignment control directions are symmetrical and the spacing between the substrates is held at 1-3 microns.

On the other hand, it is known that the ferroelectric liquid crystal molecules under such nonhelical conditions are disposed in succession so that their directors (longer molecular axes) are gradually twisted between the substrates and do not show a uniaxial orientation or alignment (i.e., in a splay alignment state). A problem in this case is a low transmittance through the liquid crystal layer.

Transmitted light intensity I through a liquid crystal is given by the following equation with respect to the incident light intensity $I_0$ under cross nicols when the uniaxial alignment of the molecules is assumed:

$$I = I_0 \sin^2(4\theta a) \sin^2(\pi \Delta n d / \lambda) \qquad (1),$$

wherein $\Delta n$ denotes the refractive index anisotropy of the FLC; d, the cell thickness; $\lambda$, the wavelength of the incident light; and $\theta a$, a half of the angle between two stable states (tilt angle).

When a conventional FLC cell is used, it has been experimentally known that $\theta a$ is 5-8 degrees under a twisted alignment condition. The control of physical properties affecting the term $\Delta n d \pi / \lambda$ cannot be easily performed, so that it is desired to increase $\theta a$ to increase I. However, this has not been successfully accomplished by only a static alignment technique.

With respect to such a problem, it has been proposed to utilize a torque relating to a dielectric anisotropy $\Delta \epsilon$ of an FLC (1983 SID report from AT & T; Japanese Laid-Open Patent Applns. 245142/1986, 246722/1986, 246723/1986, 246724/1986, 249024/1986 and 249025/1986). More specifically, a liquid crystal molecule having a negative $\Delta \epsilon$ tends to become parallel to the substrates under application of an electric field. By utilizing this property, if an effective value of AC electric field is applied even in a period other than switching, the above-mentioned twisted alignment is removed, so that $\theta a$ is increased to provide an increased transmittance (AC stabilization effect). A torque $\Gamma P_S$ acting on FLC molecules involved in switching of states and a torque $\Gamma \Delta \epsilon$ acting on FLC molecules relating to the AC stabilization effect are respectively proportional to physical properties as shown in the following formulas:

$$\Gamma P_S \propto P_S \cdot E \qquad (2)$$

$$\Gamma \Delta \epsilon \propto \tfrac{1}{2} \Delta \epsilon \cdot \epsilon_0 \cdot E^2 \qquad (3)$$

The above formula (3) apparently shows that the sign and absolute value of $\Delta \epsilon$ of the FLC play an important role.

FIG. 4 attached hereto shows the change of $\theta a$ versus $V_{rms}$ experimentally measured for 4 FLCs having different values of $\Delta \epsilon$. The measurement was conducted under application of AC rectangular pulses of 60 KHz so as to remove the influence of $P_S$. The curves (A)-(D) correspond to the results obtained by using FLCs showing the following $\Delta \epsilon$ values (A) $\Delta \epsilon \approx -5.5$, (B) $\Delta \epsilon \approx -3.0$, (C) $\Delta \epsilon \approx -0$, (D) $\Delta \epsilon \approx 1.0$.

As is clear from the graph in FIG. 8, a larger negative value of $\Delta \epsilon$ provides a large $\theta a$ at a lower voltage and thus contributes to provision of an increased I.

The transmittances obtained by using the liquid crystals (A) and (C) were 15% for (A) and 6% for (C) (under application of rectangular AC waveforms of 60 kHz and $\pm 8$ V), thus showing a clear difference.

As is known from the above examples, the display characteristics of an SSFLC (Surface-Stabilized FLC) can be remarkably changed by controlling the properties relating to $\Delta \epsilon$ and $P_S$.

In order to provide a ferroelectric liquid crystal composition having a negatively large $\Delta \epsilon$, it is most effective to include a compound having a negative $\Delta \epsilon$ with a large absolute value. For example, it is possible to obtain a compound having a negatively large $\Delta \epsilon$ by introducing a halogen or dyano group in a shorter axis direction of a molecule or by introducing a heterocyclic skeleton in a molecule.

The magnitude of $\Delta \epsilon$ of a compound having a negative $\Delta \epsilon$ substantially varies depending on the structure thereof. Some examples of such compounds are shown below:

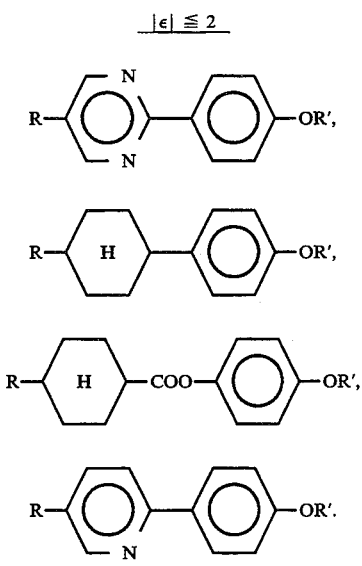

-continued

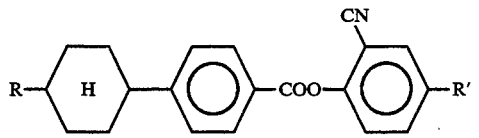

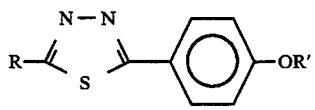

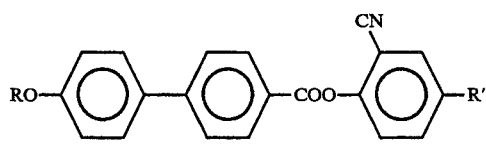

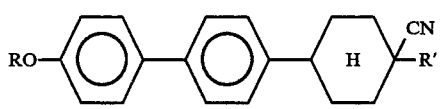

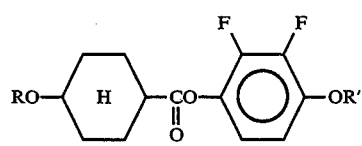

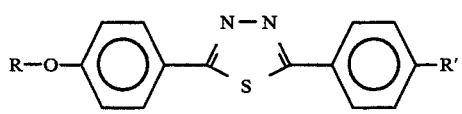

$5 < |\epsilon| \leq 10$

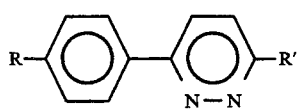

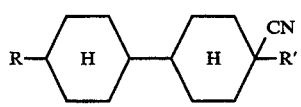

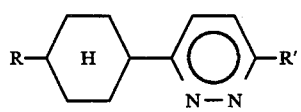

$|\epsilon| > 10$

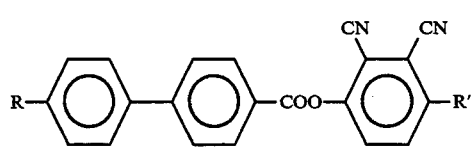

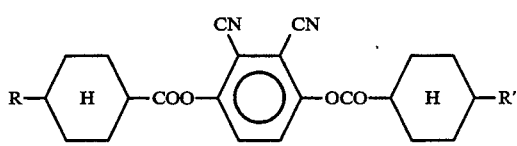

-continued

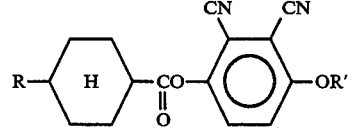

Herein, R and R' respectively denote an alkyl group. These may be classified roughly into three groups including compounds having a negatively small $\Delta\epsilon$ ($|\Delta\epsilon| \leq 2$), compounds having a negatively medium $\Delta\epsilon$ ($2 < |\Delta\epsilon| \leq 10$) and compounds having a negatively large $\Delta\epsilon$ ($|\Delta\epsilon| > 10$). Among these, compounds having a $|\Delta\epsilon|$ of $\leq 2$ have little effect of increasing $|\Delta\epsilon|$. Compounds having a $|\Delta\epsilon|$ of $> 10$ are very effective in increasing $|\Delta\epsilon|$ but those available heretofore are only dicyanohydroquinone derivatives.

However, a dicyanohydroquinone derivative, while it has a large $|\Delta\epsilon|$-increasing effect, has a high viscosity, so that it is liable to degrade a switching characteristic when its content is increased. On the other hand, among the compounds having a medium $|\Delta\epsilon|$ ($2 < |\Delta\epsilon| \leq 10$), some compounds have a moderately low viscosity while their $|\Delta\epsilon|$-increasing effect is somewhat lower than those having a large $|\Delta\epsilon|$.

From the above consideration, it is essential to select a compound having a negative anisotropy, preferably one having a $|\Delta\epsilon|$ of $> 2$, and mixing it with an appropriately selected other compound in a properly selected mixing ratio.

SUMMARY OF THE INVENTION

An object of the present invention is to provide a chiral smectic liquid crystal composition having a large response speed and a decrease temperature-dependence of the response speed adapted for providing a practical ferroelectric liquid crystal device.

Another object of the present invention is to provide a liquid crystal composition further containing a mesomorphic compound having a negative dielectric anisotropy to show an AC stabilization effect providing remarkably improved display characteristics.

A further object of the present invention is to provide a liquid crystal device using such a liquid crystal composition and showing improved driving and display characteristics.

According to the present invention, there is provided a ferroelectric chiral smectic liquid crystal composition, comprising at least one compound represented by the following formula (I):

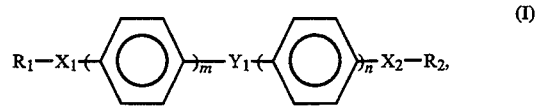

wherein $R_1$ and $R_2$ respectively denote a linear or branched alkyl group having 1-18 carbon atoms capable of having a substituent; $X_1$ and $X_2$ respectively denote a single bond, —O—,

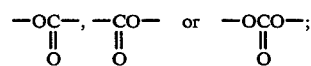

$Y_1$ denotes —CH$_2$O— or —OCH$_2$—; and m and n are respectively 1 or 2; and at least one optically active compound represented by the following formula (II):

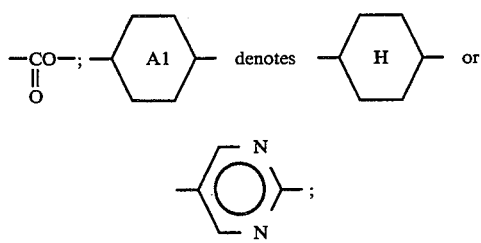

wherein $R_3$ denotes a linear or branched alkyl group having 1–18 carbon atoms capable of having a substituent; $X_3$ denotes a single bond, —O— or $$-\underset{\underset{O}{\|}}{C}O-;$$

Z denotes a single bond or

A1 denotes  or ;

and p is an integer of 1–12.

According to the present invention, there is further provided a ferroelectric liquid crystal composition as described above further comprising a mesomorphic compound having a negative dielectric anisotropy, which is preferably one having a $\Delta\epsilon < -2$, more preferably $\Delta\epsilon < -5$, most preferably $\Delta\epsilon < -10$.

The present invention further provides a liquid crystal device comprising a pair of substrates and such a ferroelectric liquid crystal composition as described above disposed between the electrode plates.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
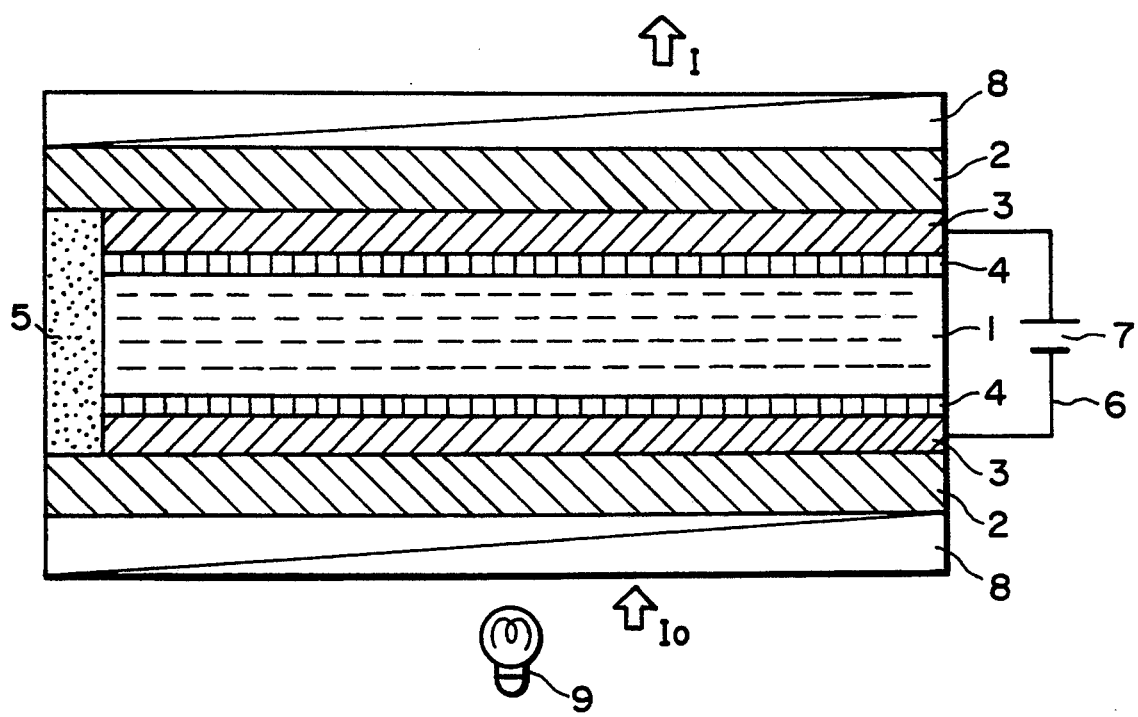
FIG. 1 is a schematic sectional view of a liquid crystal display device using a ferroelectric liquid crystal.

Preferred examples of the compounds represented by the above-mentioned general formula (I) may include those represented by the following formulas (I-a) to (I-f).

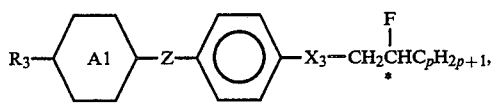  (I-a)

(I-b)

(I-c)

(I-d)

(I-e)

(I-f)

In the formulas (I-a) to (I-f), $R_1$, $R_2$, $X_1$ and $X_2$ are respectively the same as in the general formula (I). Preferred examples of $X_1$ and $X_2$ may include the following combinations (I-i) to (I-viii):

(I-i) $X_1$ is a single bond and $X_2$ is a single bond,
(I-ii) $X_1$ is a single bond and $X_2$ is —O—,
(I-iii) $X_1$ is a single bond and $X_2$ is $$-\underset{\underset{O}{\|}}{C}O-,$$

(I-iv) $X_1$ is a single bond and $X_2$ is $$-O\underset{\underset{O}{\|}}{C}-,$$

(I-v) $X_1$ is —O— and $X_2$ is a single bond,
(I-vi) $X_1$ is —O— and $X_2$ is —O—,
(I-vii) $X_1$ is —O— and $X_2$ is $$-\underset{\underset{O}{\|}}{C}O-,$$

(I-viii) $X_1$ is —O— and $X_2$ is $$-O\underset{\underset{O}{\|}}{C}-.$$

Further, preferred examples of $R_1$ and $R_2$ in the formulas (I-a) to (I-f) may include the following combinations (I-ix) to (I-xii):

(I-xi) $R_1$ is an n-alkyl group and $R_2$ is

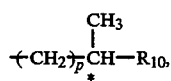

wherein p is 0–7 and $R_{10}$ is a linear or branched alkyl group.

(I-x) $R_1$ is

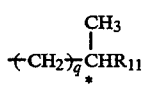

and $R_2$ is

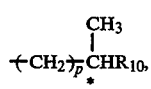

wherein p and q are respectively 0–7 and $R_{10}$ and $R_{11}$ are respectively a linear or branched alkyl group.

(I-xi) $R_1$ is an n-alkyl group and $R_2$ is

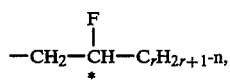

wherein r is 1–12.

(I-xii) $R_1$ is an n-alkyl group and $R_2$ is

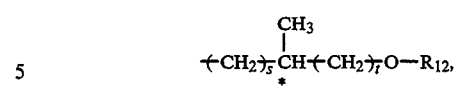

wherein s is 0–7, t is 0 or 1 and $R_{12}$ is a linear or branched alkyl group.

Preferred examples of the optically active compounds represented by the above-mentioned general formula (II) may include those represented by the following formulas (II-a) and (II-b).

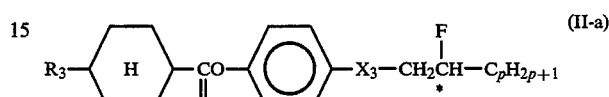

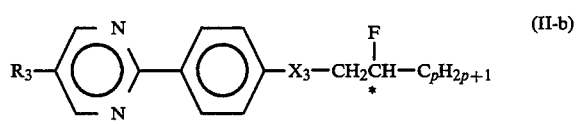

In the above-formulas (II-a) and (II-b), $R_3$, $X_3$ and p are the same as in the general formula (II).

Specific examples of the compounds represented by the above-mentioned general formula (I) may include those shown by the following structural formulas.

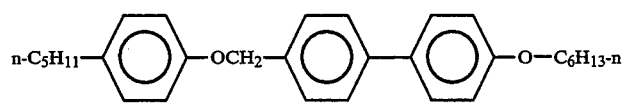

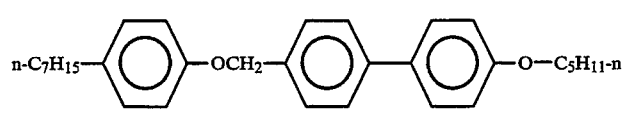

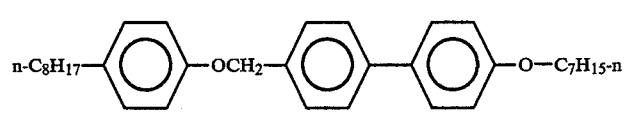

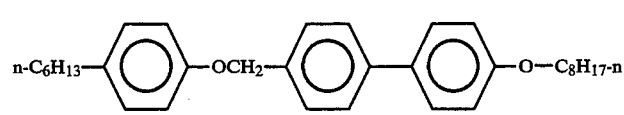

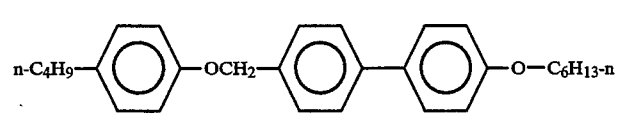

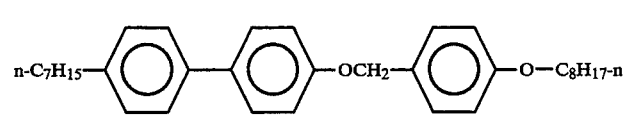

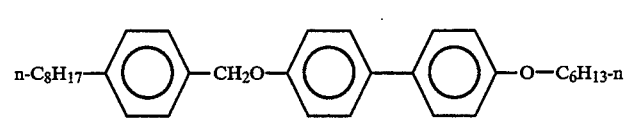

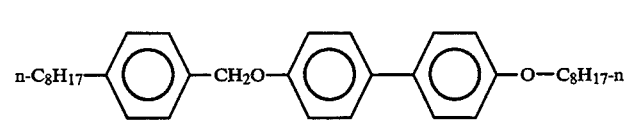

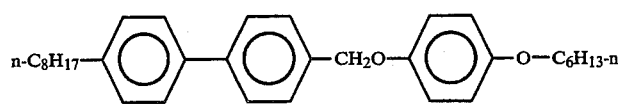
(1-9)
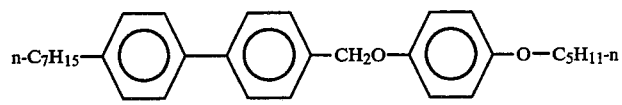
(1-10)
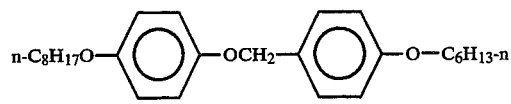
(1-11)
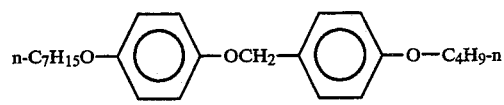
(1-12)
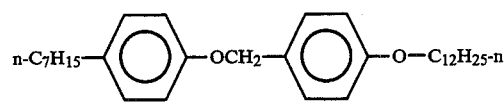
(1-13)
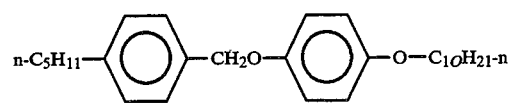
(1-14)
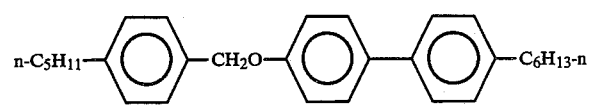
(1-15)
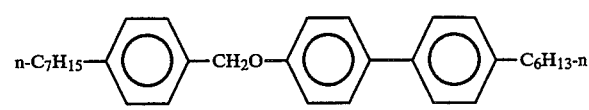
(1-16)
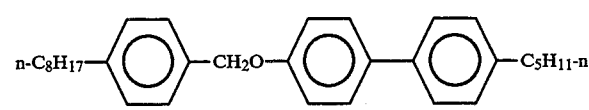
(1-17)
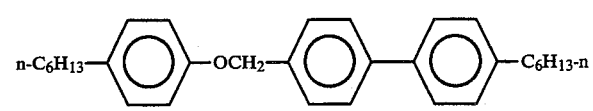
(1-18)
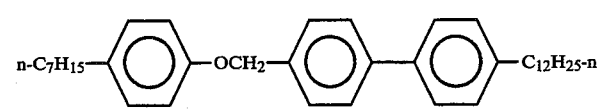
(1-19)
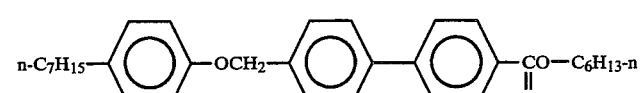
(1-20)
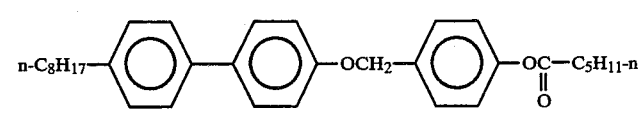
(1-21)

-continued
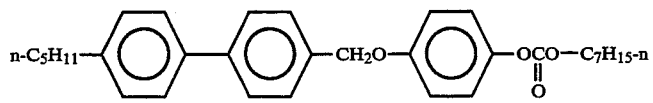 (1-22)
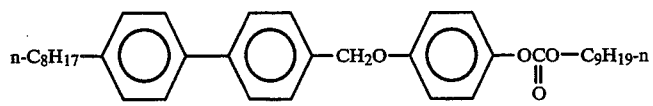 (1-23)
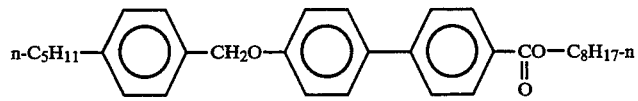 (1-24)
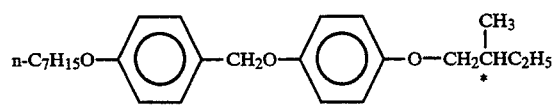 (1-25)
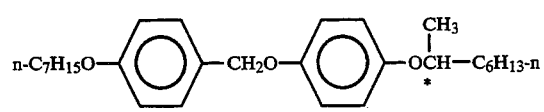 (1-26)
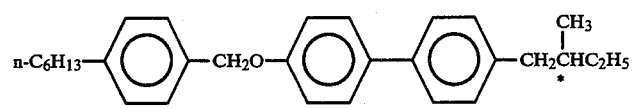 (1-27)
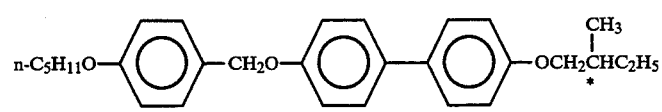 (1-28)
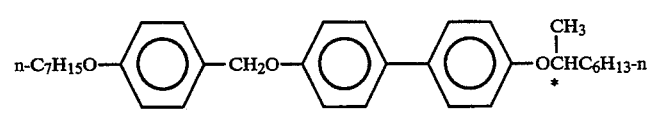 (1-29)
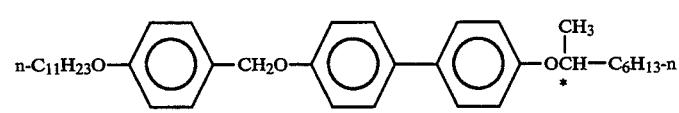 (1-30)
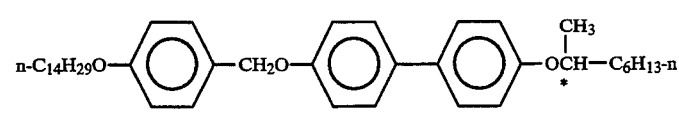 (1-31)
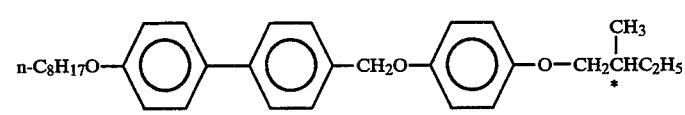 (1-32)
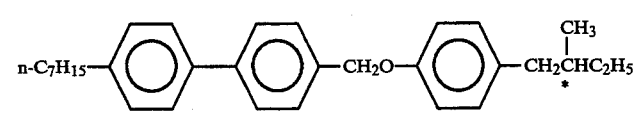 (1-33)
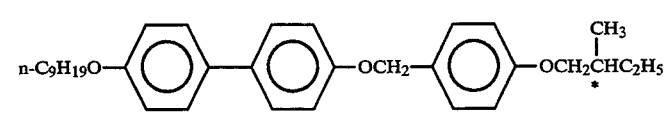 (1-34)
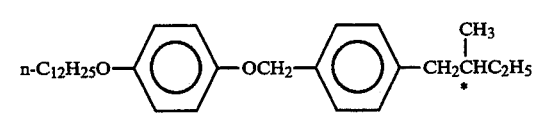 (1-35)

-continued
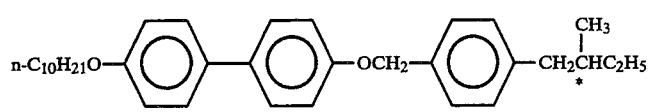 (1-36)
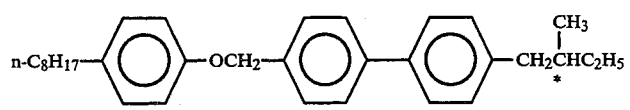 (1-37)
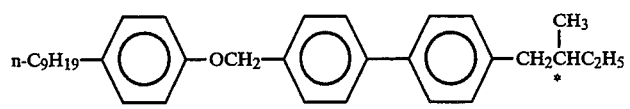 (1-38)
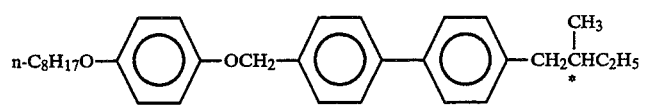 (1-39)
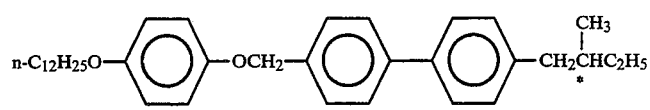 (1-40)
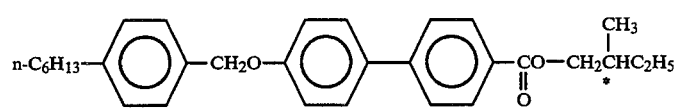 (1-41)
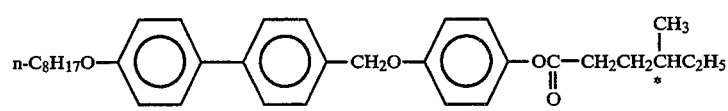 (1-42)
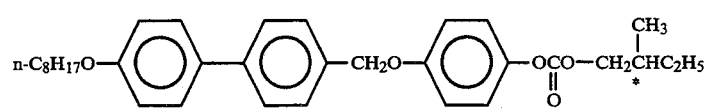 (1-43)
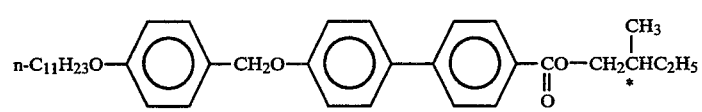 (1-44)
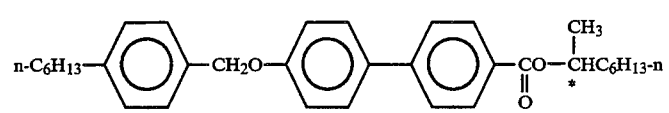 (1-45)
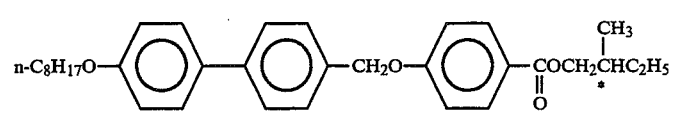 (1-46)
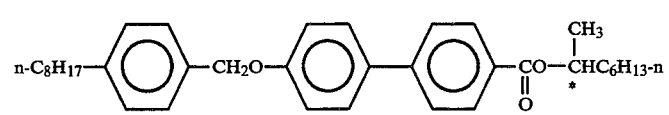 (1-47)
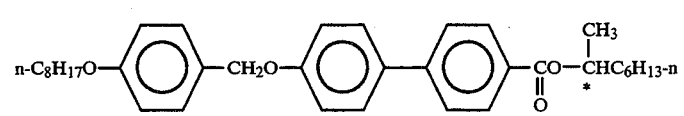 (1-48)

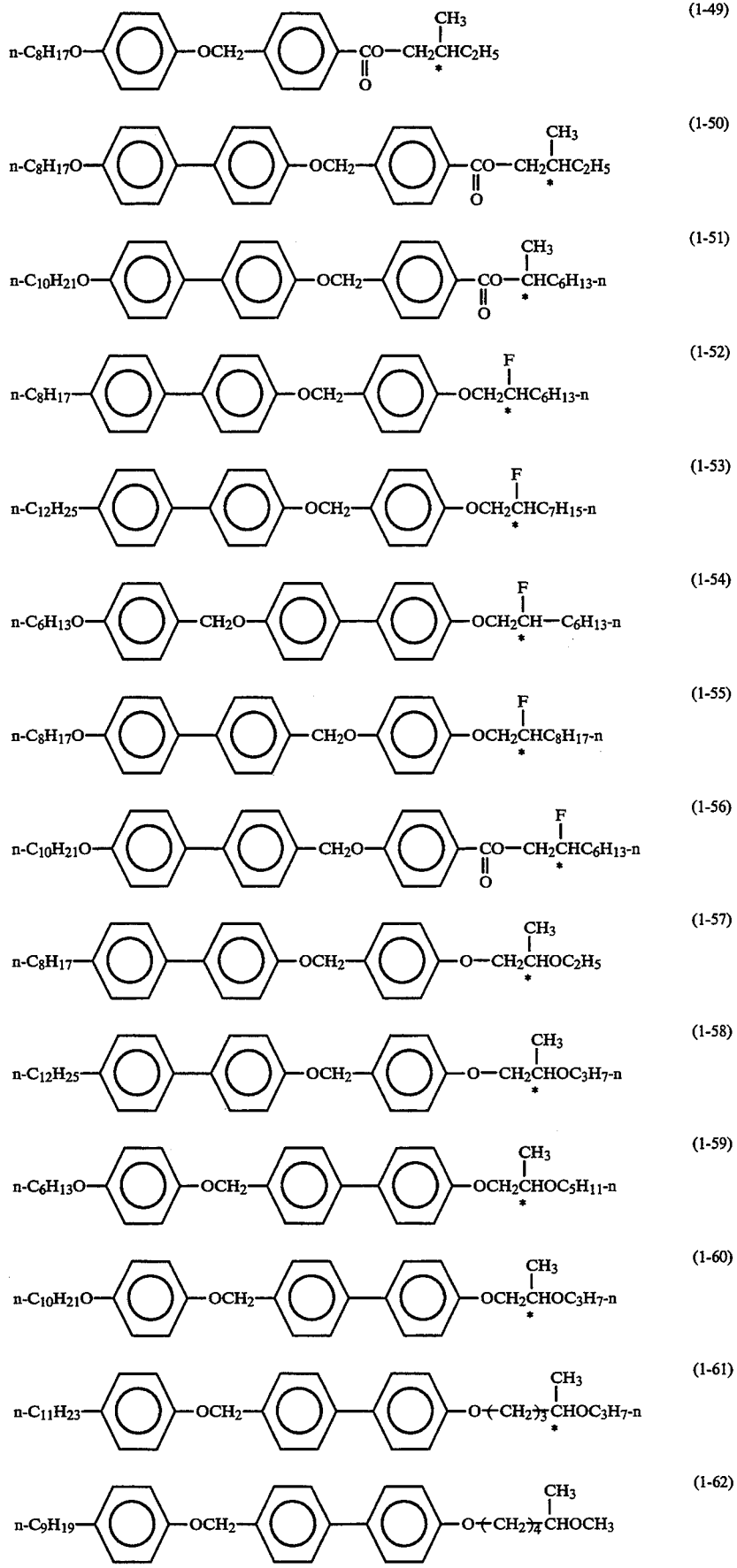

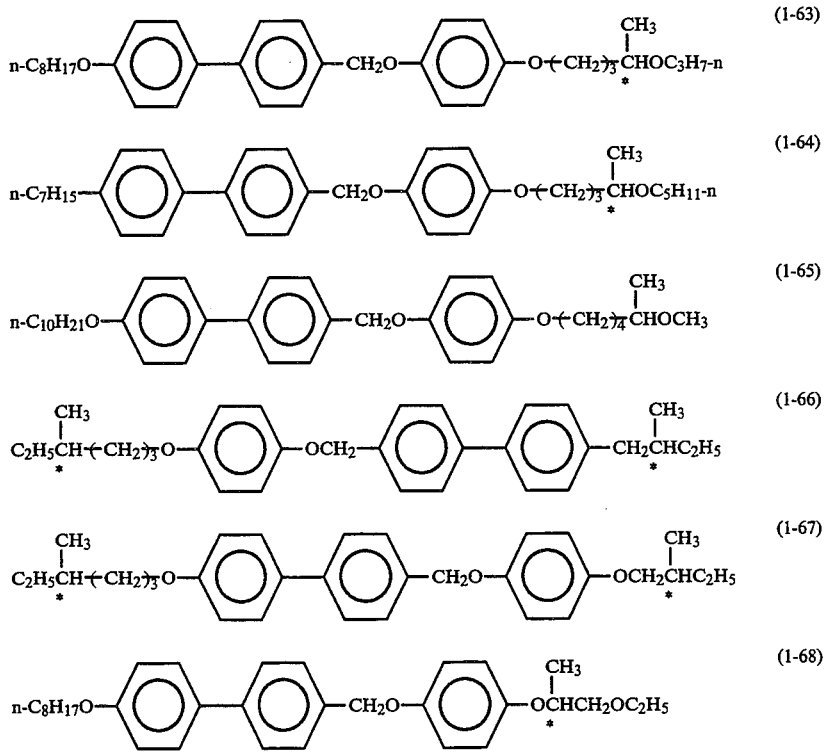

The compounds represented by the formula (I) may be synthesized through processes as disclosed by, e.g., Japanese Patent Laid-Open Applications (KOKAI) 149547/1985 and 63633/1986.

A representative example of synthesis of a compound represented by the formula (I) is described below.

SYNTHESIS EXAMPLE 1

(Synthesis of Compound Example No. 1-54)

1.0 g of (4.81 mmol) of the following alcohol derivative was placed in a 30 ml-round-bottomed flask.

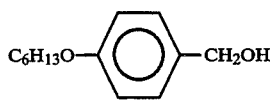

Under cooling, 3 ml of thionyl chloride was added, followed by temperature increase to room temperature under stirring. Further, the flask was equipped with a cooling pipe, and the mixture was heat-refluxed for 4 hours on an external bath of 70°–80° C. After the reaction, excessive thionyl chloride was distilled off to obtain an acid chloride, which was then dissolved in 15 ml of toluene.

Then, 0.33 g of sodium hydride (60% in paraffin) was placed in a 200 ml three-necked flask and washed several times with dry n-hexane. Then, 15 ml of a solution in tetrahydrofuran (THF) of 1.52 g (4.81 mmol) of the following phenol derivative;

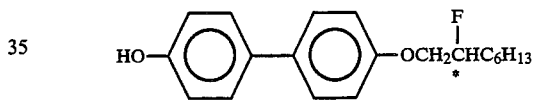

was added thereto dropwise at room temperature, and further 20 ml of dimethylsulfoxide (DMSO) was added, followed by 1 hour of stirring. Then, the aboveprepared solution of the acid chloride in toluene was slowly added dropwise thereto, and after the addition, stirring was further continued for 16 hours at room temperature. After the reaction, the product was poured into about 200 ml of iced water, followed by separation of the organic layer and two times of extraction of the aqueous layer with 50 ml of benzene. The benzene extract was mixed with the organic layer separated in advance were washed two times with 5%-hydrochloric acid aqueous solution, once with ion-exchange water and once with 5%-NaOH aqueous solution, followed further by washing of the organic layer with ion-exchange water until the aqueous layer showed a neutral pH value.

The organic layer was separated and dried with magnesium sulfate, followed by distilling-off of the solvent to obtain a crude product, which was then purified by silica gel column chromatography with the use of a developer mixture of n-hexane/dichloromethane (=3/10).

A crystal obtained after distilling-off of the solvent was recrystallized from n-hexane and dried under vacuum at room temperature to obtain 0.69 g of the finally purified objective product. The yield was 28.5%.

Elementary analysis data (wt. %)

-continued

|                 | C     | H    | N    |
|-----------------|-------|------|------|
| Calculating data | 78.33 | 8.57 | 0.00 |
| Measuring data   | 78.96 | 8.69 | 0.02 |

Phase transition temperature (°C.)

Cryst. $\xrightarrow{88.7}$ S$_5$ $\xrightarrow{101.2}$ S$_4$ $\xrightarrow{106.2}$ S$_3$ $\xrightarrow{141.4}$ $\xleftarrow{77.8}$ S$_2$ $\xrightarrow[170.6]{171.4}$ SmC* $\xleftarrow[178.1]{180.7}$ Iso.

SYNTHESIS EXAMPLE 2

(Synthesis of Compound Example No. 1-68)

1.25 g (4.01 mmol) of the following alcohol derivative was placed in a 30 ml-round-bottomed flask.

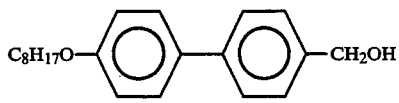

Under cooling, 3 ml of thionyl chloride was added, followed by temperature increase to room temperature under stirring. Further, the flask was equipped with a cooling pipe, and the mixture was heat-refluxed for 4 hours on an external bath of 70°-80° C. After the reaction, excessive thionyl chloride was distilled off to obtain an acid chloride, which was then dissolved in 15 ml of toluene.

Then, 0.31 g of sodium hydride (60% in paraffin) was placed in a 200 ml three-necked flask and washed several times with dry n-hexane. Then, 15 ml of a solution in tetrahydrofuran (THF) of 0.79 g (4.01 mmol) of the following phenol derivative;

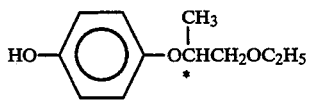

was added thereto dropwise at room temperature, and further 20 ml of dimethylsulfoxide (DMSO) was added, followed by 1 hour of stirring. Then, the aboveprepared solution of the acid chloride in toluene was slowly added dropwise thereto, and after the addition, stirring was further continued for 16 hours at room temperature. After the reaction, the product was poured into about 200 ml of iced water, followed by separation of the organic layer and two times of extraction of the aqueous layer with 50 ml of benzene. The benzene extract was mixed with the organic layer separated in advance were washed two times with 5%-hydrochloric acid aqueous solution, once with ion-exchange water and once with 5%-NaOH aqueous solution, followed further by washing of the organic layer with ion-exchange water until the aqueous layer showed a neutral pH value.

The organic layer was separated and dried with magnesium sulfate, followed by distilling-off of the solvent to obtain a crude product, which was then purified by silica gel column chromatography with the use of a developer mixture of n-hexane/dichloromethane (=3/10).

A crystal obtained after distilling-off of the solvent was recrystallized from n-hexane and dried under vacuum at room temperature to obtain 0.51 g of the finally purified objective product. The yield was 26.0%.

| Elementary analysis data (wt. %) | | | |
|---|---|---|---|
| | C | H | N |
| Calculating data | 78.33 | 8.63 | 0.00 |
| Measuring data | 78.62 | 8.86 | 0.02 |

Phase transition temperature (°C.)

Cryst. $\xleftarrow[39.9]{58.6}$ S$_3$ $\xleftarrow[42.4]{69.5}$ S$_2$ $\xleftarrow[95.1]{95.6}$ S$_1$ $\xleftarrow[117.1]{118.5}$ Iso.

S$_2$, S$_3$: un-identified

IR spectrum (cm$^{-1}$): 2975, 2925, 2850, 1610, 1510, 1470, 1380, 1295, 1280, 1240, 1220, 1130, 1020, 1000, 810.

Specific examples of the compounds represented by the above-mentioned general formula (II) may include those shown by the following structural formulas.

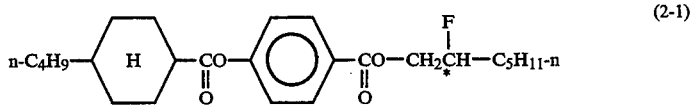

(2-1)

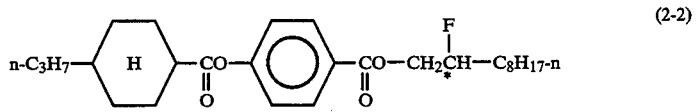

(2-2)

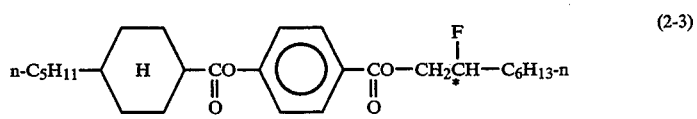

(2-3)

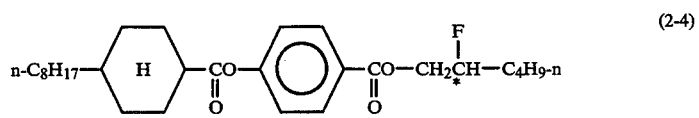

(2-4)

-continued
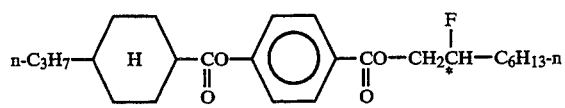
(2-5)
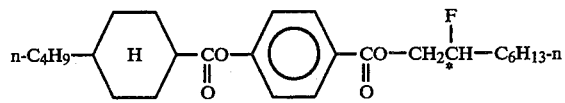
(2-6)
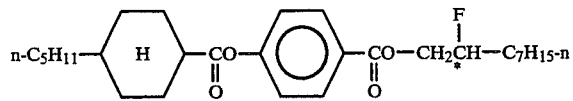
(2-7)
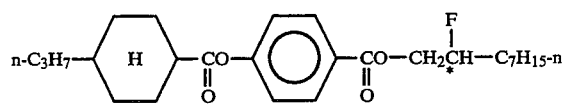
(2-8)
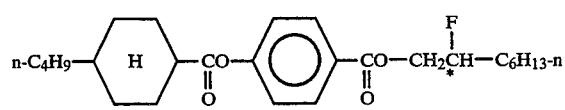
(2-9)
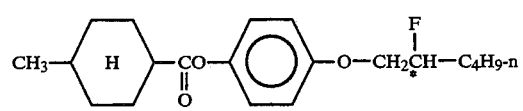
(2-10)
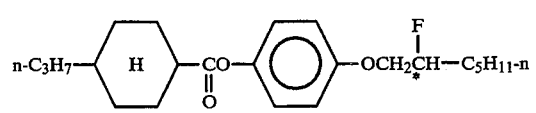
(2-11)
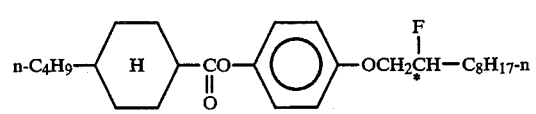
(2-12)
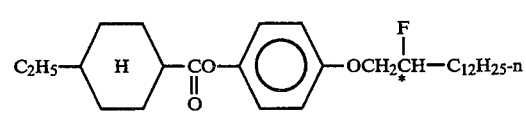
(2-13)
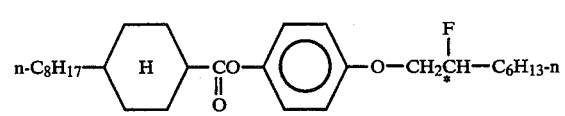
(2-14)
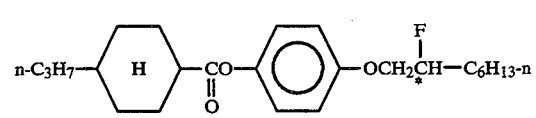
(2-15)
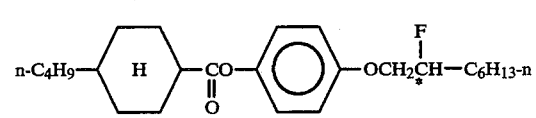
(2-16)
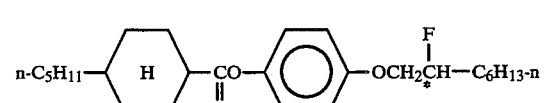
(2-17)
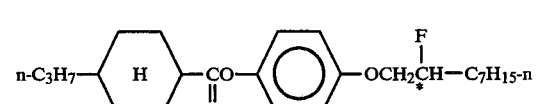
(2-18)

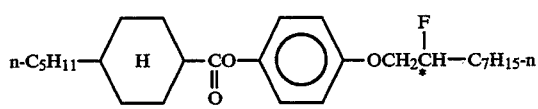 (2-19)
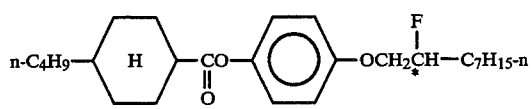 (2-20)
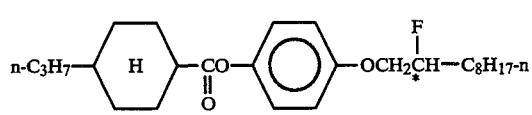 (2-21)
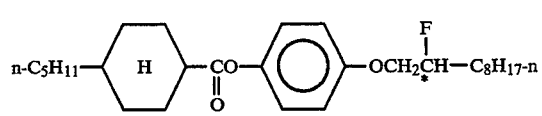 (2-22)
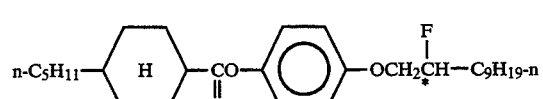 (2-23)
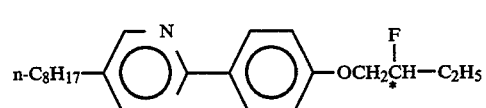 (2-24)
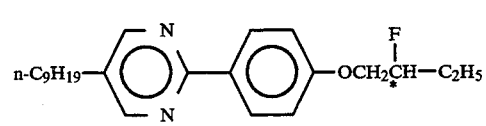 (2-25)
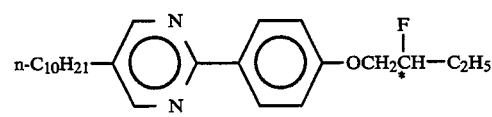 (2-26)
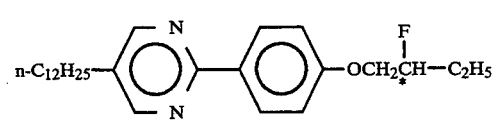 (2-27)
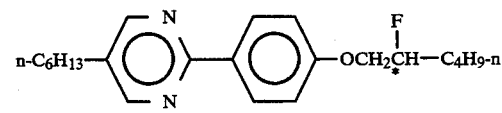 (2-28)
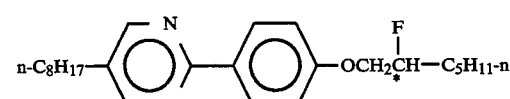 (2-29)
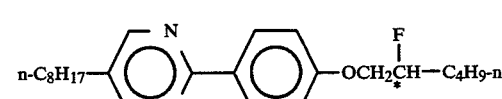 (2-30)
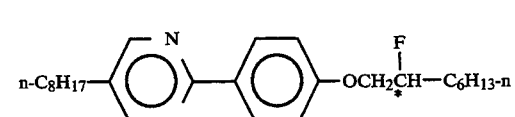 (2-31)

-continued (2-32) n-C₈H₁₇—[pyrimidine]—[phenyl]—OCH₂C*H(F)—C₇H₁₅-n (2-33) n-C₈H₁₇—[pyrimidine]—[phenyl]—OCH₂C*H(F)—C₈H₁₇-n (2-34) n-C₉H₁₉—[pyrimidine]—[phenyl]—OCH₂C*H(F)—C₅H₁₁-n (2-35) n-C₉H₁₉—[pyrimidine]—[phenyl]—OCH₂C*H(F)—C₆H₁₃-n (2-36) n-C₉H₁₉—[pyrimidine]—[phenyl]—OCH₂C*H(F)—C₇H₁₅-n (2-37) n-C₉H₁₉—[pyrimidine]—[phenyl]—OCH₂C*H(F)—C₈H₁₇-n (2-38) n-C₁₀H₂₁—[pyrimidine]—[phenyl]—OCH₂C*H(F)—C₄H₉-n (2-39) n-C₁₀H₂₁—[pyrimidine]—[phenyl]—OCH₂C*H(F)—C₅H₁₁-n (2-40) n-C₁₀H₂₁—[pyrimidine]—[phenyl]—OCH₂C*H(F)—C₆H₁₃-n (2-41) n-C₁₀H₂₁—[pyrimidine]—[phenyl]—OCH₂C*H(F)—C₇H₁₅-n (2-42) n-C₁₀H₂₁—[pyrimidine]—[phenyl]—OCH₂C*H(F)—C₈H₁₇-n (2-43) n-C₁₀H₂₁—[pyrimidine]—[phenyl]—OCH₂C*H(F)—C₉H₁₉-n (2-44) n-C₁₀H₂₁—[pyrimidine]—[phenyl]—OCH₂C*H(F)—C₁₀H₂₁-n

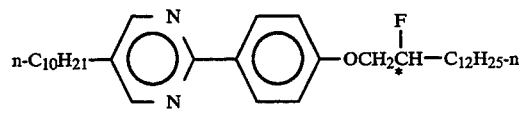 (2-45)
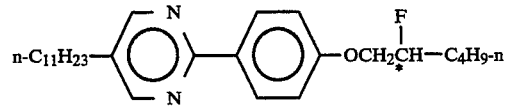 (2-46)
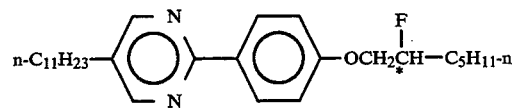 (2-47)
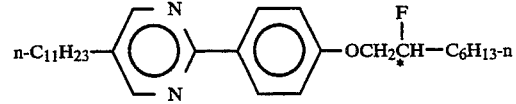 (2-48)
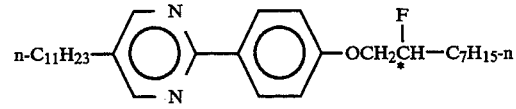 (2-49)
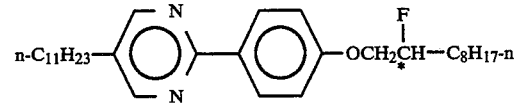 (2-50)
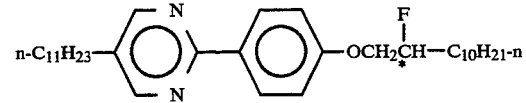 (2-51)
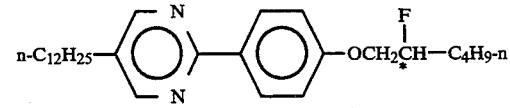 (2-52)
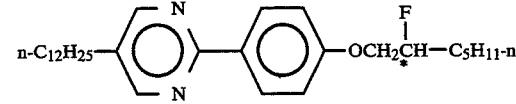 (2-53)
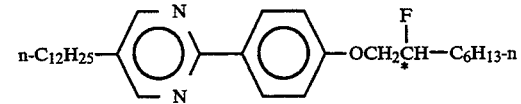 (2-54)
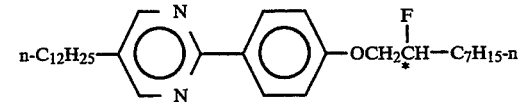 (2-55)
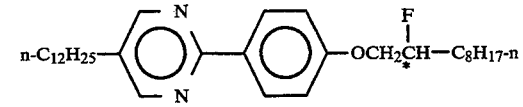 (2-56)
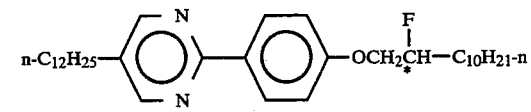 (2-57)

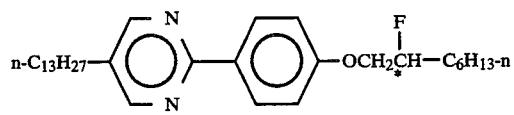 (2-58)
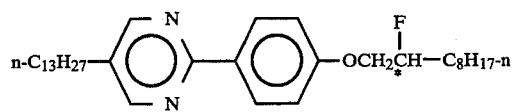 (2-59)
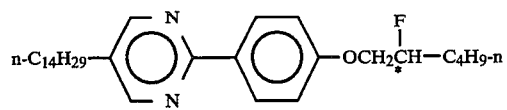 (2-60)
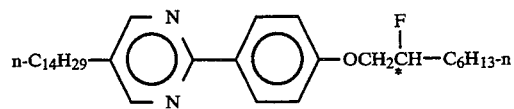 (2-61)
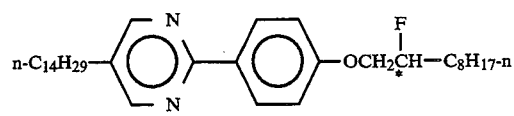 (2-62)
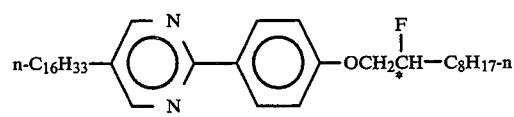 (2-63)
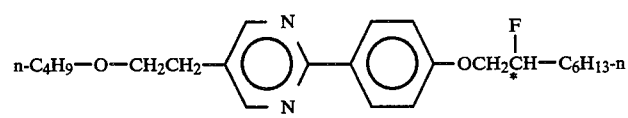 (2-64)
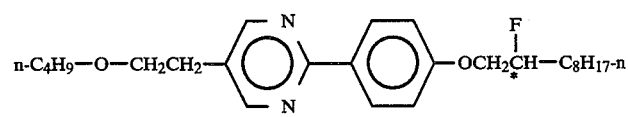 (2-65)
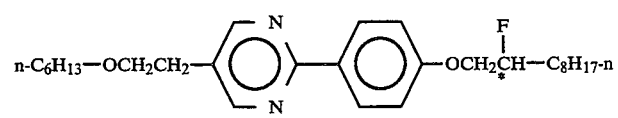 (2-66)
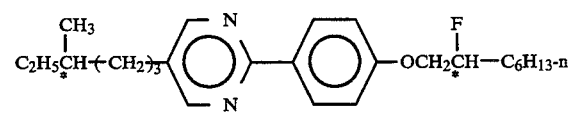 (2-67)
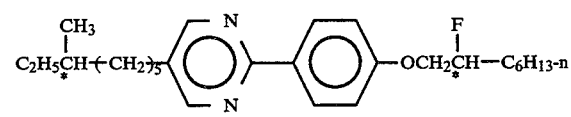 (2-68)
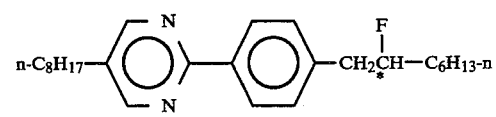 (2-69)
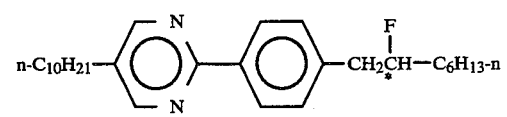 (2-70)

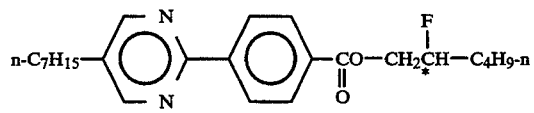 (2-71)
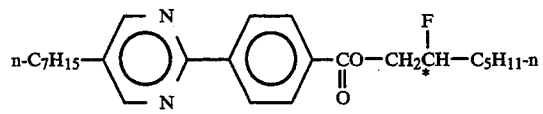 (2-72)
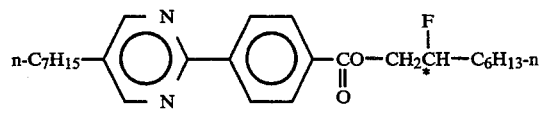 (2-73)
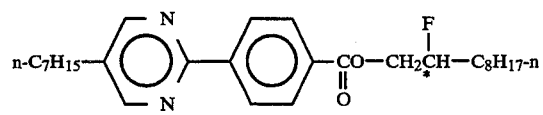 (2-74)
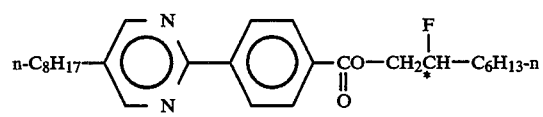 (2-75)
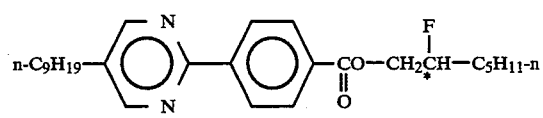 (2-76)
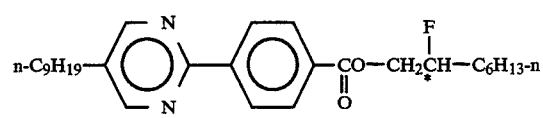 (2-77)
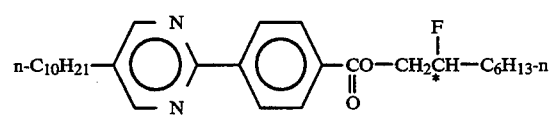 (2-78)
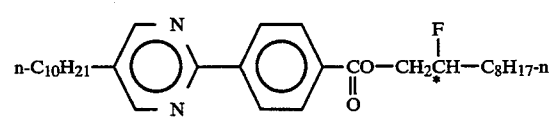 (2-79)
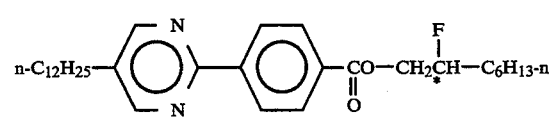 (2-80)
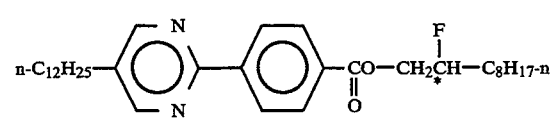 (2-81)
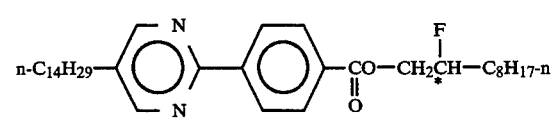 (2-82)
The compounds represented by the general formula (II) may be synthesized through the following reaction schemes 2-A, 2-B and 2-C.

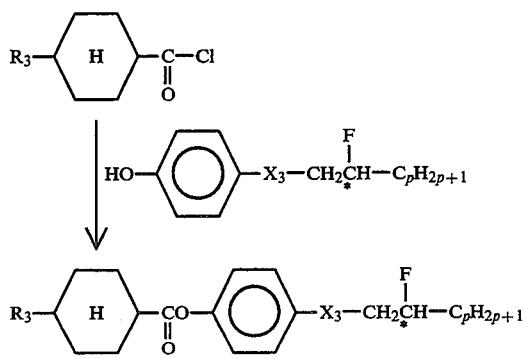

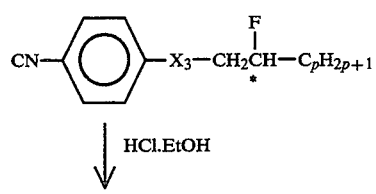

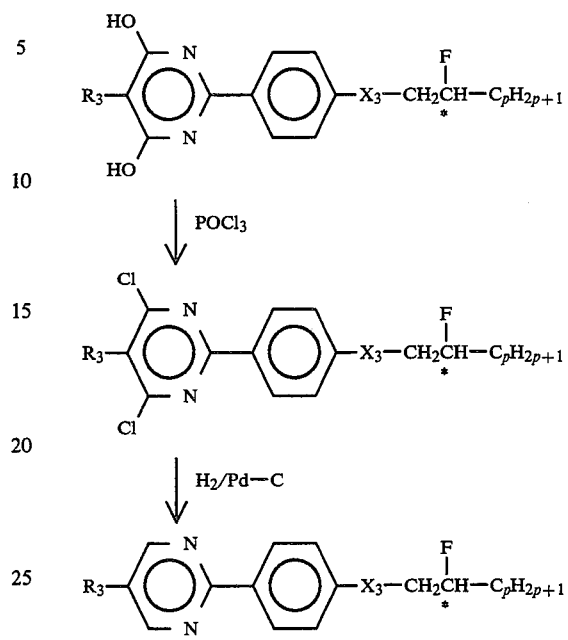

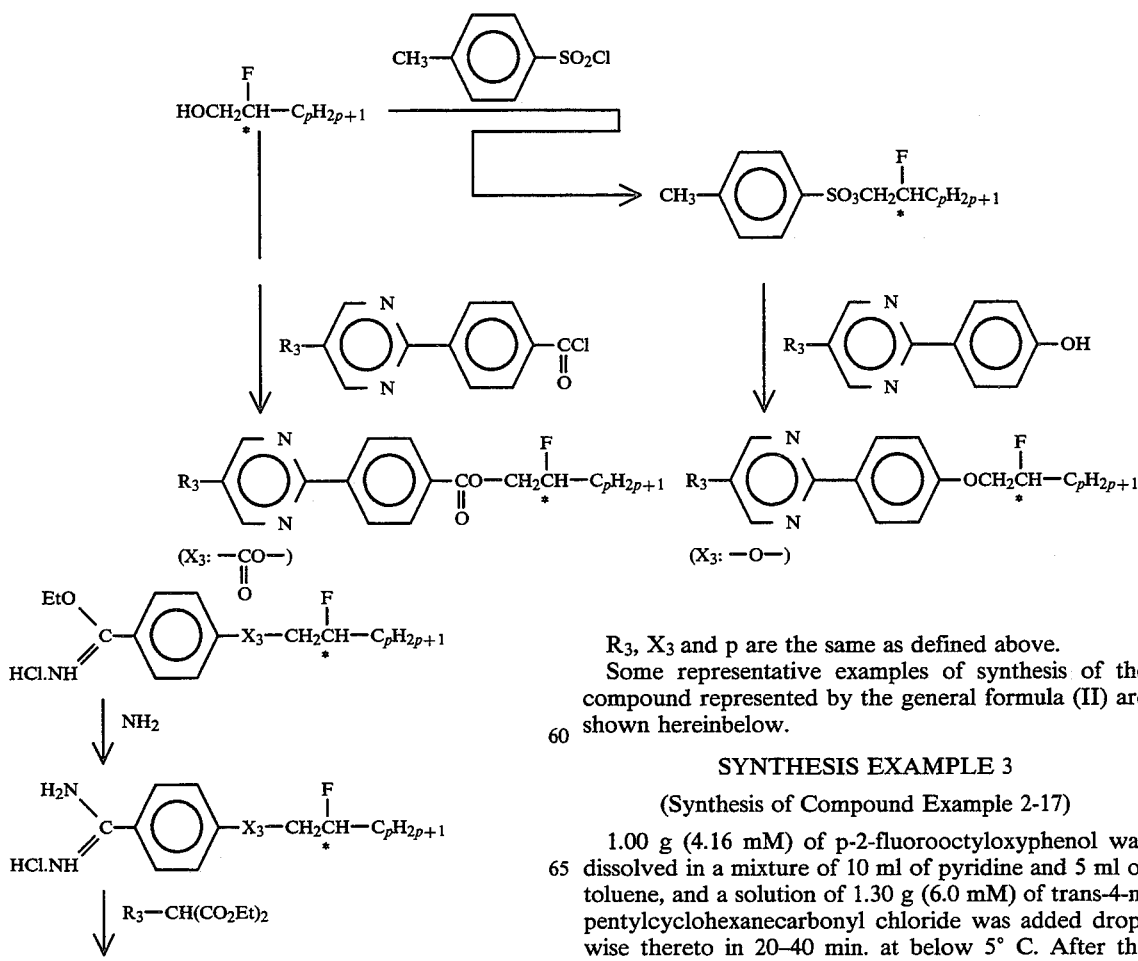

$R_3$, $X_3$ and p are the same as defined above.

Some representative examples of synthesis of the compound represented by the general formula (II) are shown hereinbelow.

SYNTHESIS EXAMPLE 3

(Synthesis of Compound Example 2-17)

1.00 g (4.16 mM) of p-2-fluorooctyloxyphenol was dissolved in a mixture of 10 ml of pyridine and 5 ml of toluene, and a solution of 1.30 g (6.0 mM) of trans-4-n-pentylcyclohexanecarbonyl chloride was added dropwise thereto in 20–40 min. at below 5° C. After the addition, the mixture was stirred overnight at room temperature to obtain a white precipitate.

After the reaction, the reaction product was extracted with benzene, and the resultant benzene layer was washed with distilled water, followed by drying with magnesium sulfate and distilling-off of the benzene, purification by silica gel column chromatography and recrystallization from ethanol/methanol to obtain 1.20 g (2.85 mM) of trans-4-n-pentylcyclohexanecarboxylic acid-p-2-fluorooctyloxyphenyl-ester. (Yield: 68.6%)

NMR data (ppm) 0.83–2.83 ppm (34H, m) 4.00–4.50 ppm (2H, q) 7.11 ppm (4H, s)

IR data (cm$^{-1}$) 3456, 2928, 2852, 1742, 1508, 1470, 1248, 1200, 1166, 1132, 854.

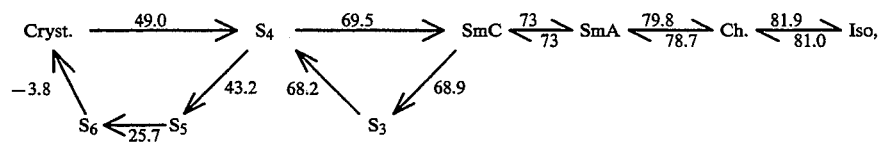

Herein, the respective symbols denote the following phases, Iso.: isotropic phase, Ch.: cholesteric phase, SmA: smectic A phase, SmC: smectic C phase, $S_3$–$S_6$: phases of higher other than SmC or SmC* (chiral smectic C phase), and Cryst.: crystal phase.

SYNTHESIS EXAMPLE 4

(Synthesis of Compound Example 2-29)

In a vessel sufficiently replaced with nitrogen, 0.40 g (3.0 mmol) of (−)-2-fluoroheptanol and 1.00 g (13 mmol) of dry pyridine were placed and dried for 30 min. under cooling on an ice bath. Into the solution, 0.69 g (3.6 mmol) of p-toluenesulfonyl chloride was added, and the mixture was stirred for 5 hours. After the reaction, 10 ml of 1N-HCl was added, and the resultant mixture was subjected to two times of extraction with 10 ml of methylene chloride. The extract liquid was washed once with 10 ml of distilled water and dried with an appropriate amount of anhydrous sodium sulfate, followed by distilling-off of the solvent to obtain 0.59 g (2.0 mmol) of (+)-2-fluoroheptyl p-toluenesulfonate.

The yield was 66%, and the product showed the following optical rotation and IR data.

Optical rotation: $[\alpha]_D^{26.4}$ +2.59 degrees (c=1, CHCl$_3$) $[\alpha]_{435}^{23.6}$ +9.58 degrees (c=1, CHCl$_3$)

IR (cm$^{-1}$): 2900, 2850, 1600, 1450, 1350, 1170, 1090, 980, 810, 660, 550

0.43 g (1.5 mmol) of the thus obtained (+)-2-fluoroheptyl p-toluenesulfonate and 0.28 g (1.0 mmol) of 5-octyl-2-(4-hydroxyphenyl)pyrimidine were mixed with 0.2 ml of 1-butanol, followed by sufficient stirring. To the solution was quickly added a previously obtained alkaline solution of 0.048 g (1.2 mmol) of sodium hydroxide in 1.0 ml of 1-butanol, followed by 5.5 hours of heat-refluxing. After the reaction, 10 ml of distilled water was added, and the mixture was extracted respectively once with 10 ml of benzene and 5 ml of benzene, followed by drying with an appropriate amount of anhydrous sodium sulfate, distilling-off of the solvent and purification by silica gel column chromatography (chloroform) to obtain 0.17 g (0.43 mmol) of objective (+)-5-octyl-2-[4-(2-fluoroheptyloxy)phenyl]pyrimidine.

The yield was 43%, and the product showed the following optical rotation and IR data.

Optical rotation: $[\alpha]_D^{25.6}$ +0.44 degree (c=1, CHCl$_3$) $[\alpha]_{435}^{22.4}$ +4.19 degrees (c=1, CHCl$_3$)

IR (cm$^{-1}$) 2900, 2850, 1600, 1580, 1420, 1250, 1260, 800, 720, 650, 550.

In a preferred embodiment, the ferroelectric chiral smectic liquid crystal composition according to the present invention further comprises at least one compound represented by any of the following formulas (III) to (V);

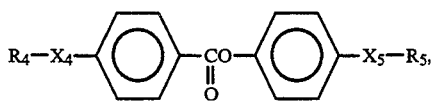

wherein $R_4$ and $R_5$ respectively denote a linear or branched alkyl group having 1–18 carbon atoms capable of having a substituent, at least one of $R_4$ and $R_5$ being optically active; $X_4$ denotes a single bond, —O—,

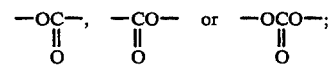

and $X_5$ denotes a single bond, —O—,

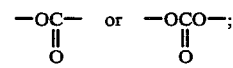

Formula (IV):

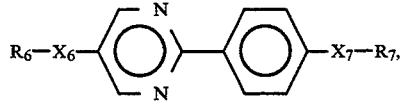

wherein $R_6$ and $R_7$ respectively denote a linear or branched alkyl group having 1–18 carbon atoms capable of having an alkoxy group of 1–12 carbon atoms; $X_6$ and $X_7$ respectively denote a single bond, —O—,

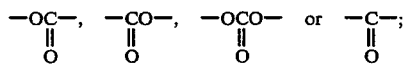

Formula (V):

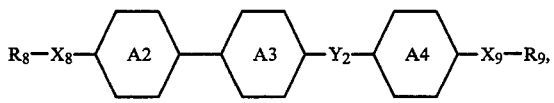

wherein $R_8$ and $R_9$ respectively denote a linear or branched alkyl group having 1–18 carbon atoms capable of having a substituent; and $X_8$ and $X_9$ respectively denote a single bond, —O—,

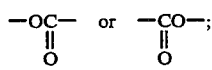

Y2 denotes

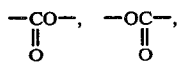

—CH2—, —OCH2— or a single bond;

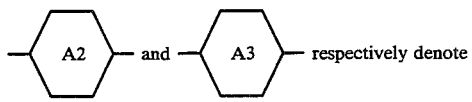 respectively denote

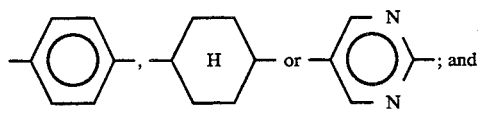; and

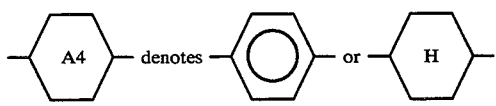

with proviso that at least one of

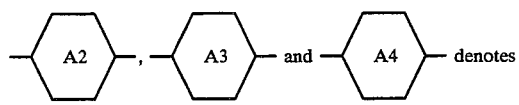 denotes

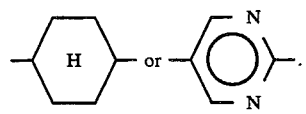.

In the formula (III), preferred examples of X4 may include —O— and

, and those of X5 may include —O— and

.

Further, preferred examples of R4 and R5 may include the following combinations (III-i) to (III-v):
(III-i) R4 is an n-alkyl group and R5 is

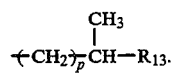

(III-ii) R4 is

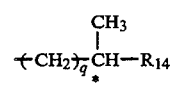

and R5 is an n-alkyl group.
(III-iii) R4 is

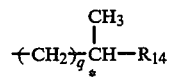

and R5 is

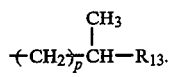

(III-iv) R4 is an n-alkyl group and R5 is

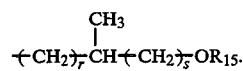

(III-v) R4 is

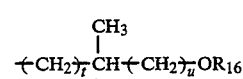

and R5 is an n-alkyl group.

In the above-formulas (III-i) to (III-v), $R_{13}$ to $R_{16}$ are respectively a linear or branched alkyl group, p, q, and r and t are respectively 0–7, and s and u are respectively 0 or 1.

Further, preferred examples of the compounds represented by the above-mentioned general formula (IV) may include those represented by the following formulas (IV-a) to (IV-p).

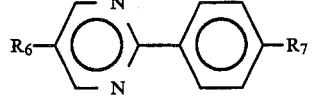 (IV-a)

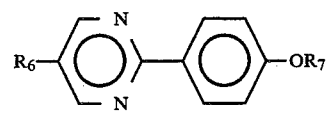 (IV-b)

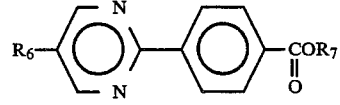 (IV-c)

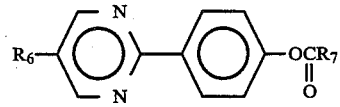 (IV-d)

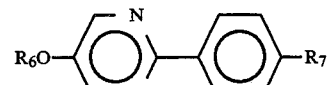 (IV-e)

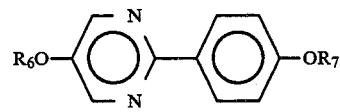 (IV-f)

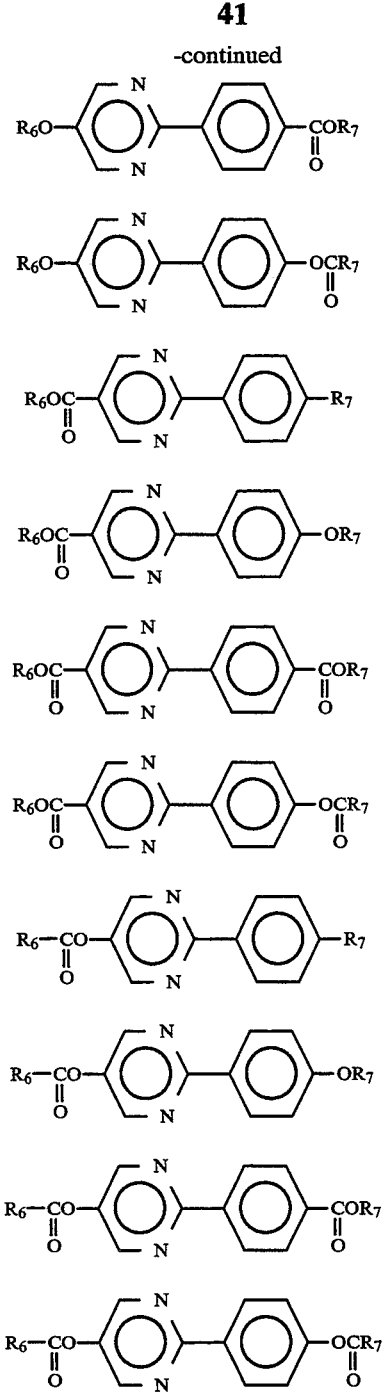

In the formula (IV-a) to (IV-p), $R_6$ and $R_7$ are respectively the same as in the general formula (IV).

Further, preferred examples of $R_6$ and $R_7$ in the formulas (IV-a) to (IV-p) may include the following combinations (IV-i) to (IV-vi):

(IV-i) $R_6$ is an n-alkyl group and $R_7$ is an n-alkyl group.

(IV-ii) $R_6$ is an n-alkyl group and $R_7$ is

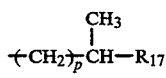

(optically active or inactive).

(IV-iii) $R_6$ is an alkyl group and $R_7$ is

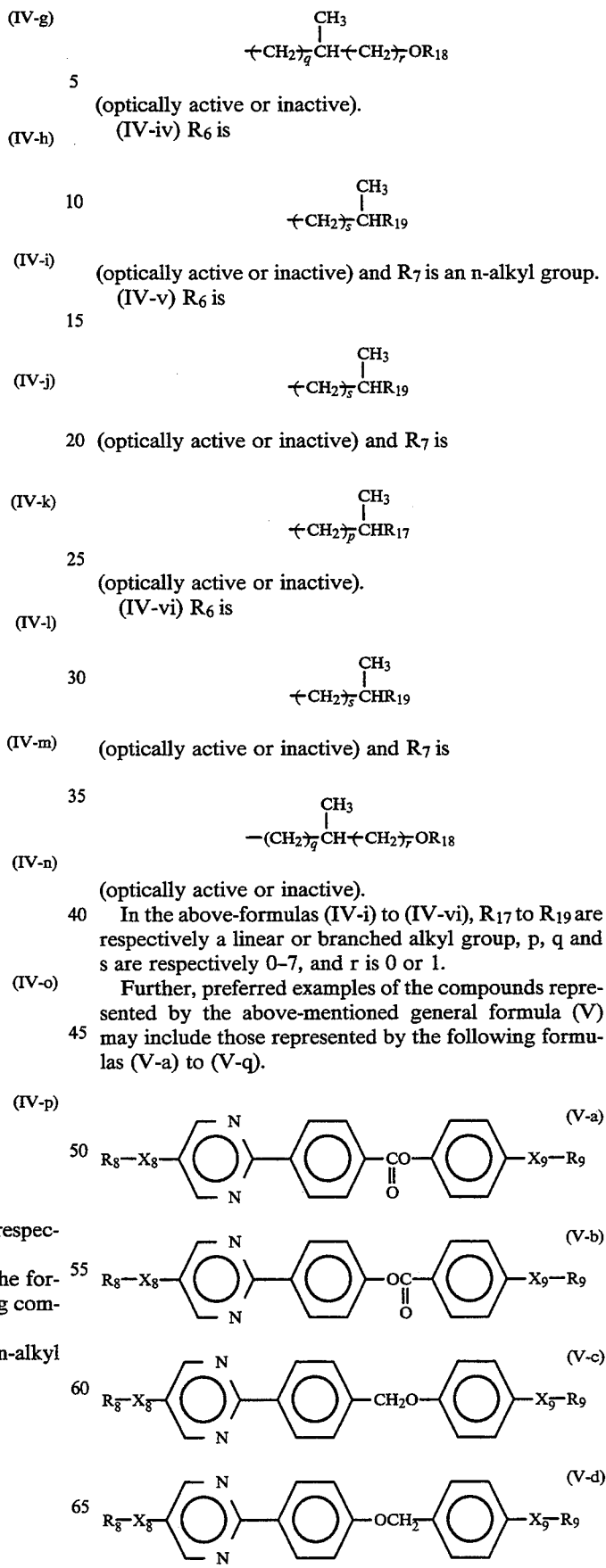

(optically active or inactive).

(IV-iv) $R_6$ is $$\mathrm{+CH_2\!\!\rightarrow_{\!\!s}\!\!\overset{\overset{\displaystyle CH_3}{|}}{CH}R_{19}}$$

(optically active or inactive) and $R_7$ is an n-alkyl group.

(IV-v) $R_6$ is $$\mathrm{+CH_2\!\!\rightarrow_{\!\!s}\!\!\overset{\overset{\displaystyle CH_3}{|}}{CH}R_{19}}$$

(optically active or inactive) and $R_7$ is $$\mathrm{+CH_2\!\!\rightarrow_{\!\!p}\!\!\overset{\overset{\displaystyle CH_3}{|}}{CH}R_{17}}$$

(optically active or inactive).

(IV-vi) $R_6$ is $$\mathrm{+CH_2\!\!\rightarrow_{\!\!s}\!\!\overset{\overset{\displaystyle CH_3}{|}}{CH}R_{19}}$$

(optically active or inactive) and $R_7$ is $$\mathrm{-(CH_2)_{\!q}\!\!\overset{\overset{\displaystyle CH_3}{|}}{CH}\!\!+\!CH_2\!\!\rightarrow_{\!\!r}\!OR_{18}}$$

(optically active or inactive).

In the above-formulas (IV-i) to (IV-vi), $R_{17}$ to $R_{19}$ are respectively a linear or branched alkyl group, p, q and s are respectively 0–7, and r is 0 or 1.

Further, preferred examples of the compounds represented by the above-mentioned general formula (V) may include those represented by the following formulas (V-a) to (V-q).

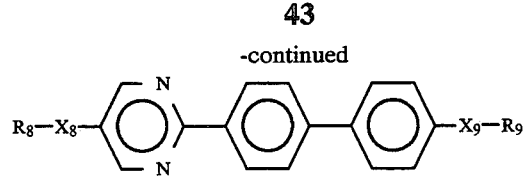 (V-e)

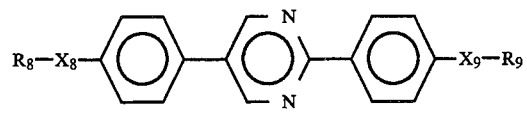 (V-f)

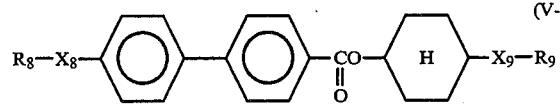 (V-g)

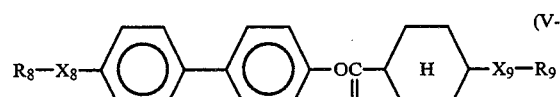 (V-h)

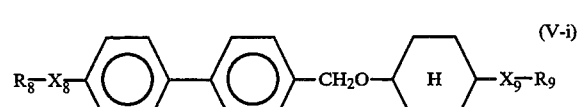 (V-i)

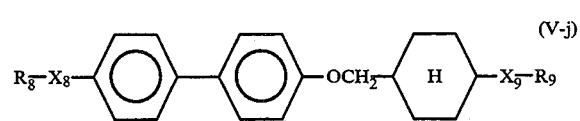 (V-j)

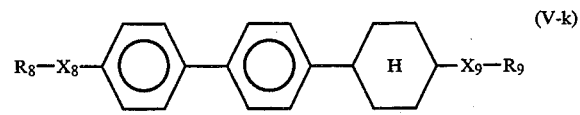 (V-k)

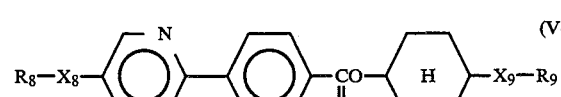 (V-l)

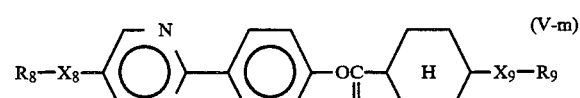 (V-m)

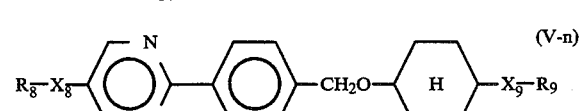 (V-n)

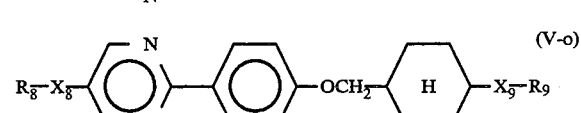 (V-o)

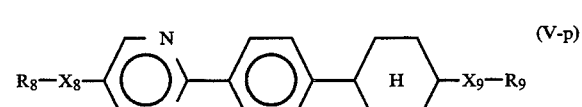 (V-p)

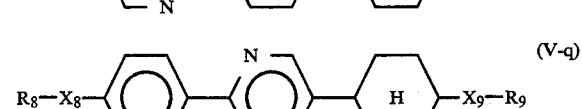 (V-q)

In the formulas (V-a) to (V-q), $R_8$, $R_9$, $X_8$ and $X_9$ are respectively the same as in the general formula (V).

Preferred examples of $X_8$ and $X_9$ may include the following combinations (V-i) to (V-viii):
 (V-i) $X_8$ is a single bond and $X_9$ is a single bond,
 (V-ii) $X_8$ is a single bond and $X_9$ is —O—,
 (V-iii) $X_8$ is —O— and $X_9$ is a single bond,
 (V-iv) $X_8$ is —O— and $X_9$ is —O—,
 (V-v) $X_8$ is

and $X_9$ is a single bond,
 (V-vi) $X_8$ is

and $X_9$ is —O—,
 (V-vii) $X_8$ is

and $X_9$ is a single bond,
 (V-viii) $X_8$ is

and $X_9$ is —O—.

Further, preferred examples of $R_8$ and $R_9$ in the formula (V-a) to (V-q) may include a linear alkyl group.

Specific examples of the compounds represented by the above-mentioned general formula (III) may include those shown by the following structural formulas.

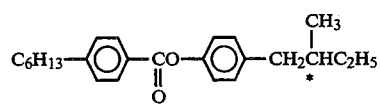 (3-1)

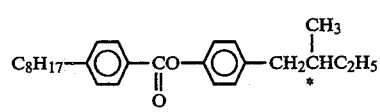 (3-2)

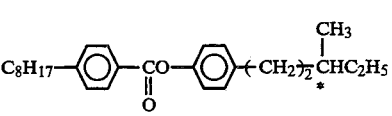 (3-3)

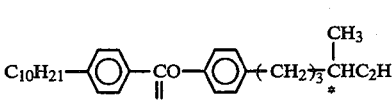 (3-4)

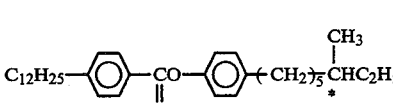 (3-5)

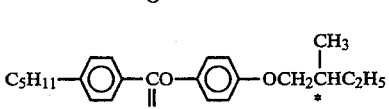 (3-6)

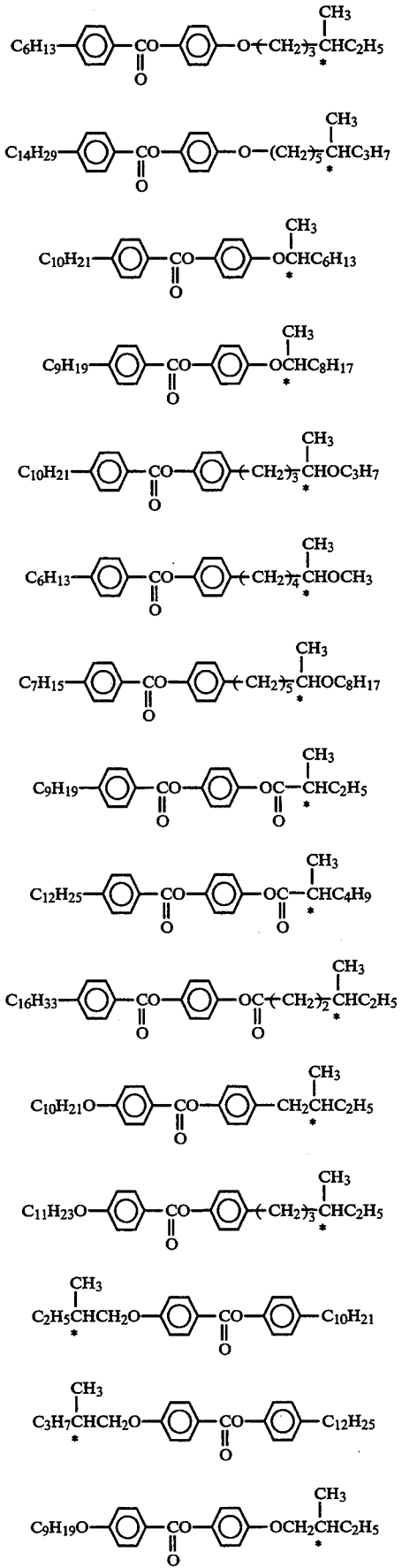
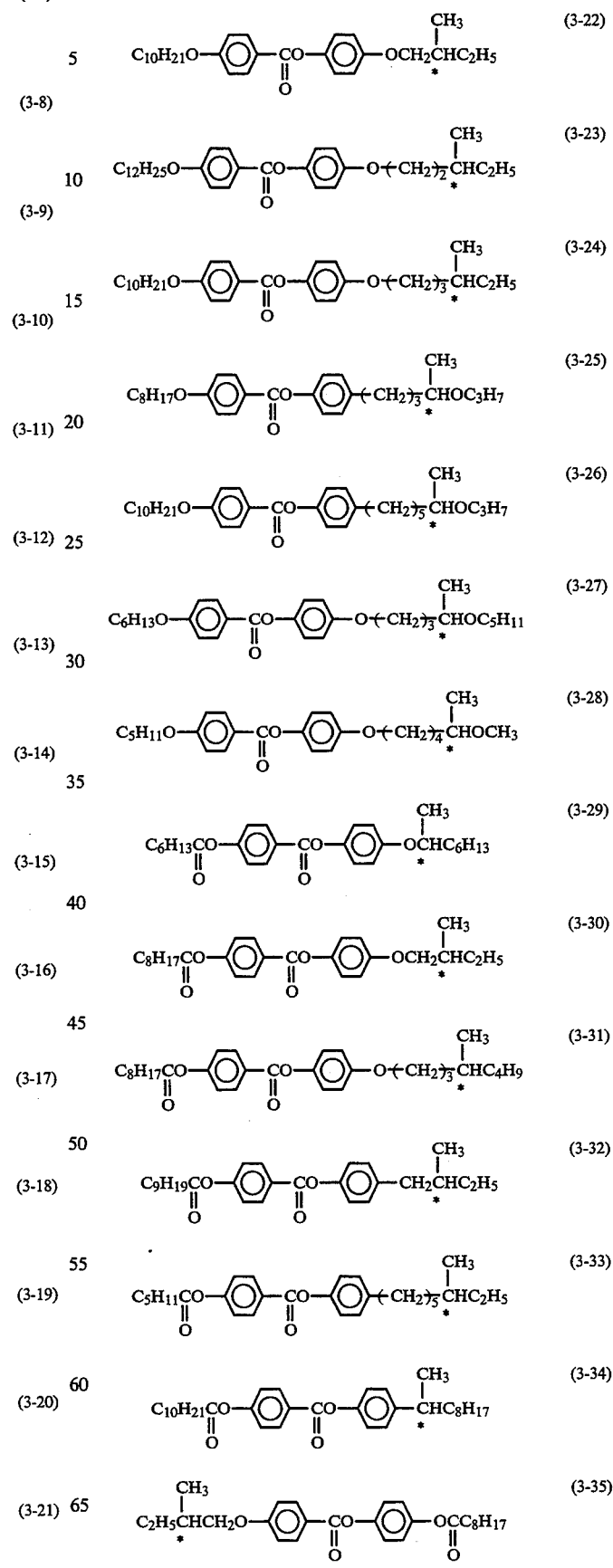

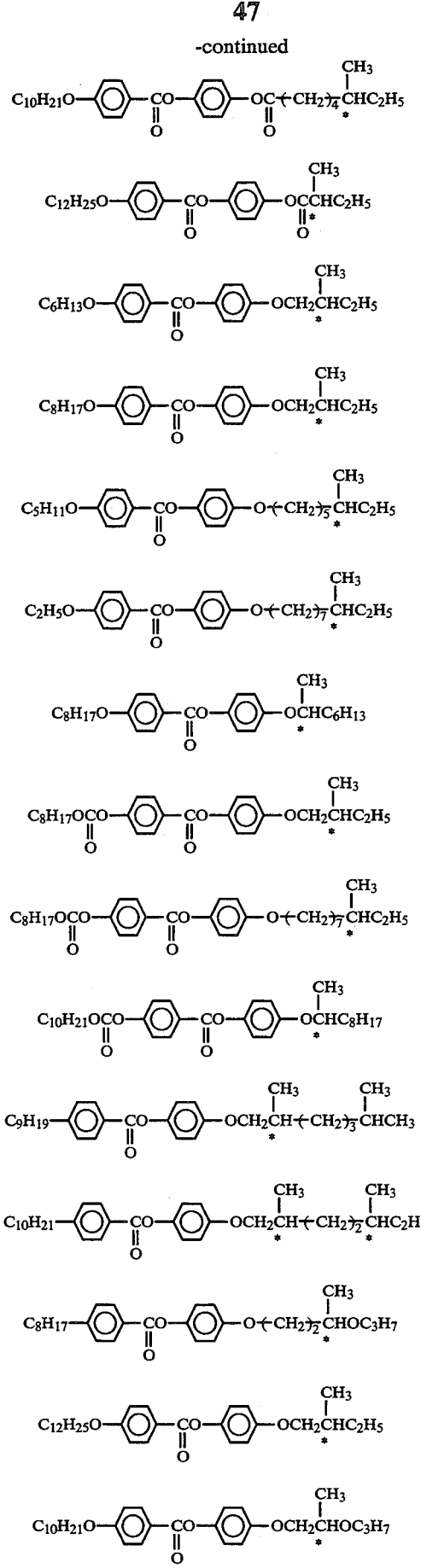
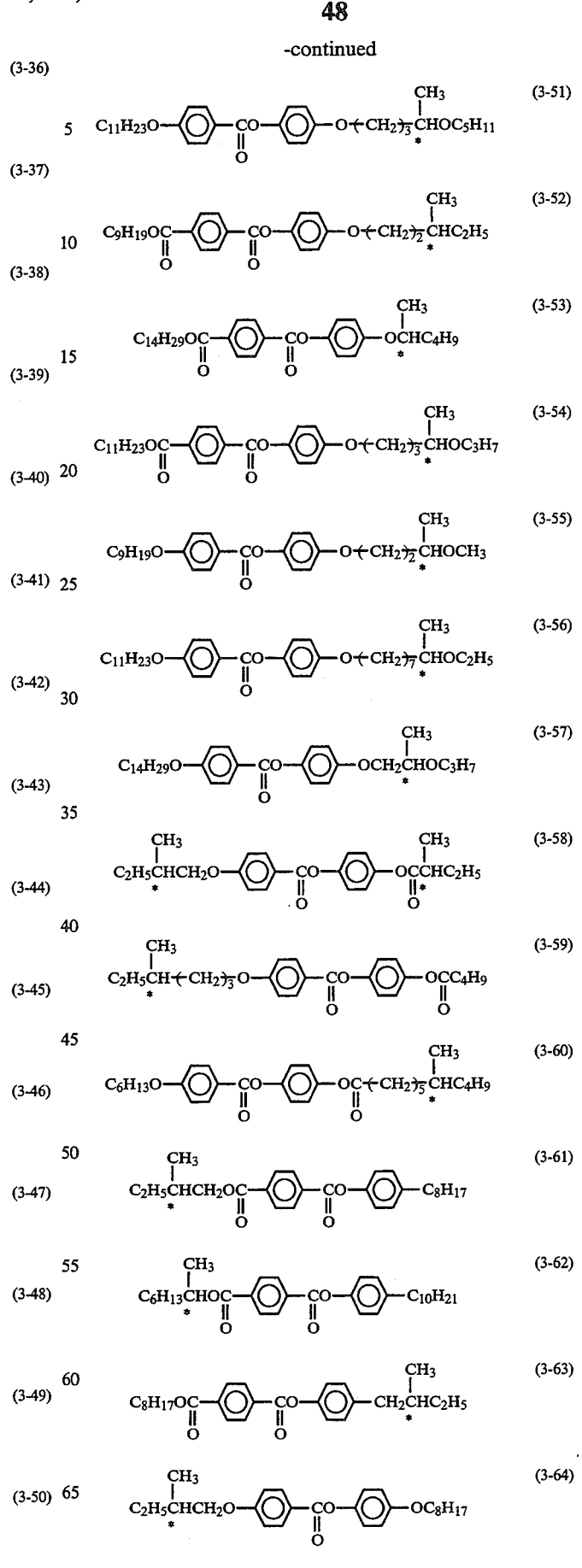

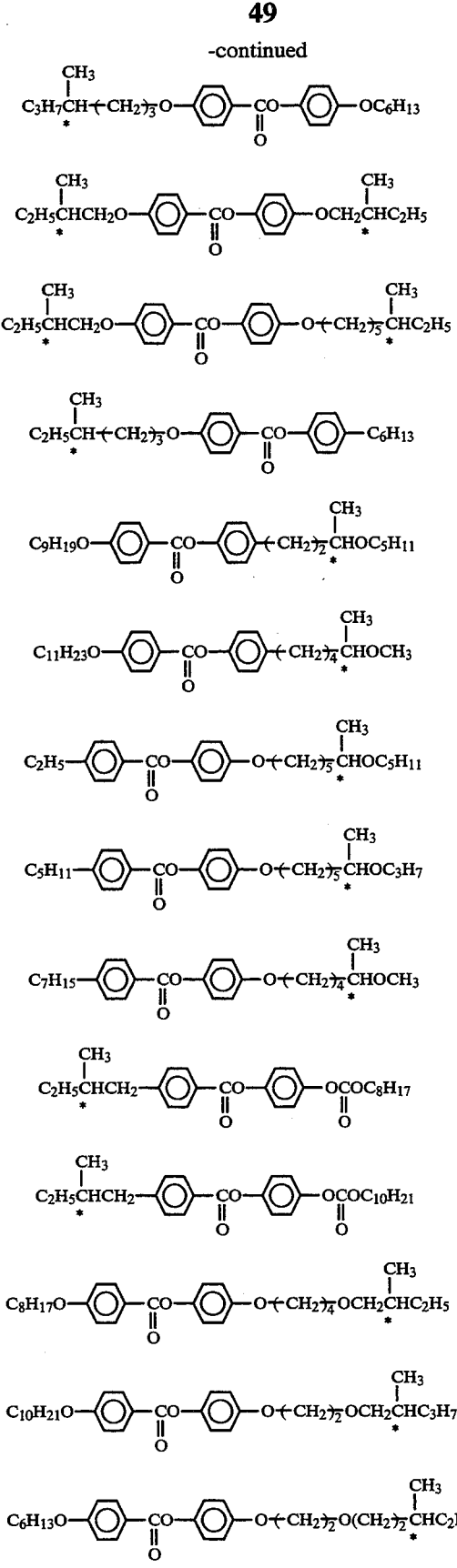
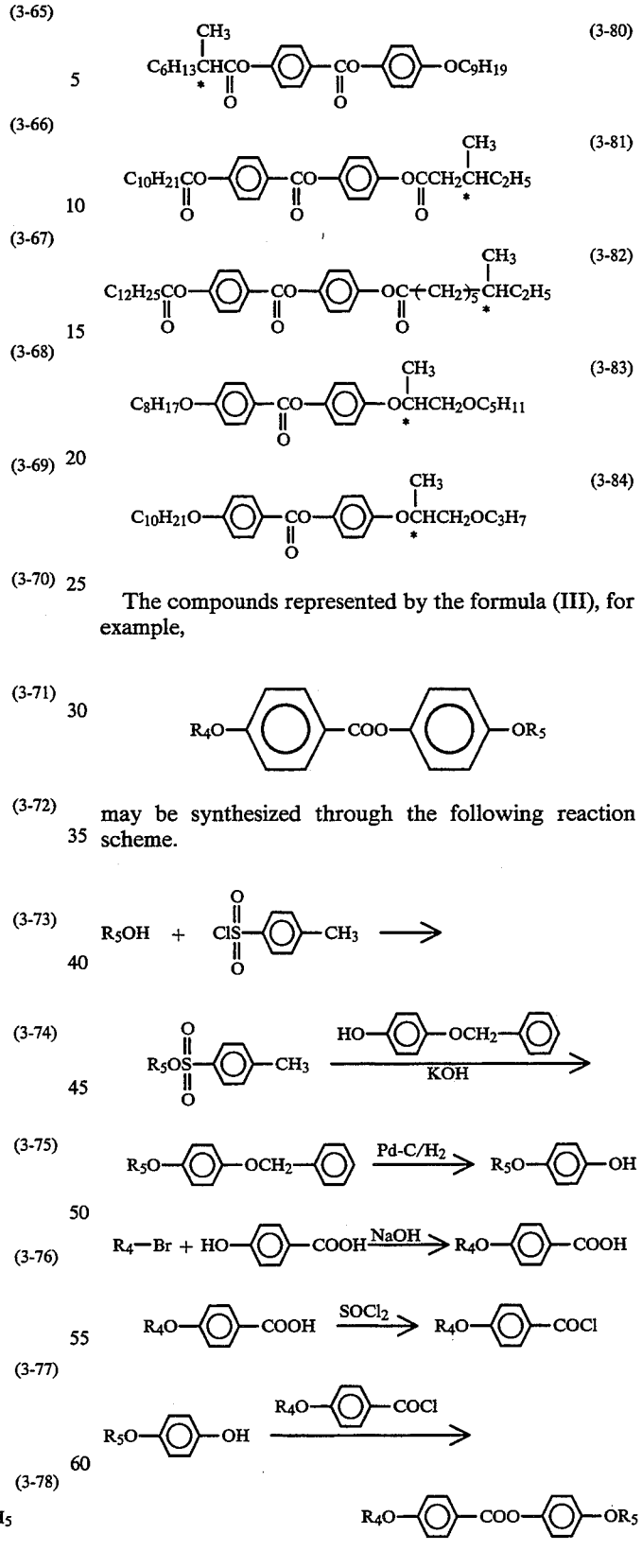
The compounds represented by the formula (III), for example,
$$R_4O-\phenyl-COO-\phenyl-OR_5$$
may be synthesized through the following reaction scheme.
$R_4$ and $R_5$ are the same as defined above.
Specific examples of the compounds represented by the above-mentioned general formula (IV) may include those shown by the following structural formulas.

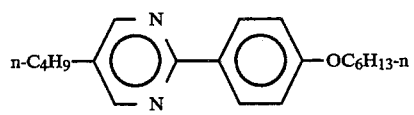 (4-1)
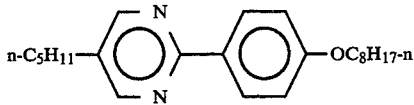 (4-2)
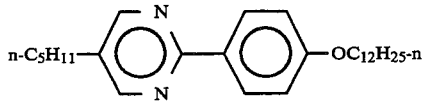 (4-3)
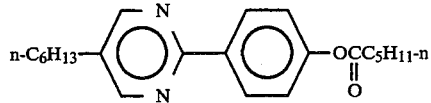 (4-4)
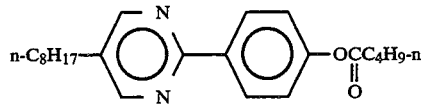 (4-5)
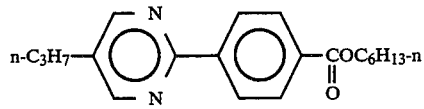 (4-6)
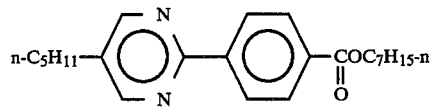 (4-7)
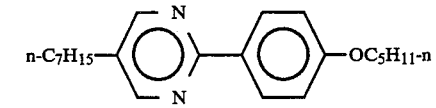 (4-8)
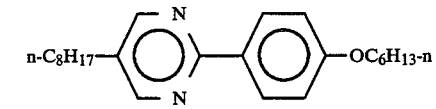 (4-9)
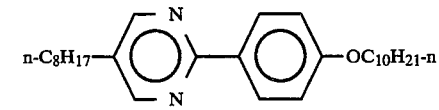 (4-10)
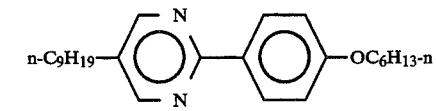 (4-11)
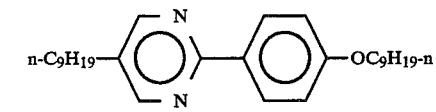 (4-12)
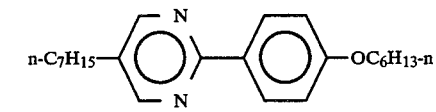 (4-13)
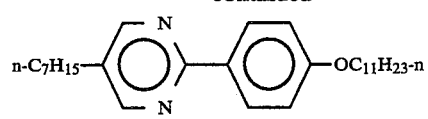 (4-14)
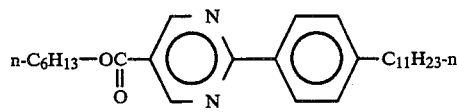 (4-15)
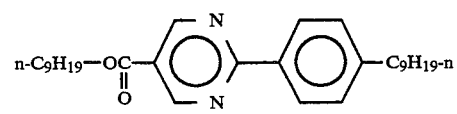 (4-16)
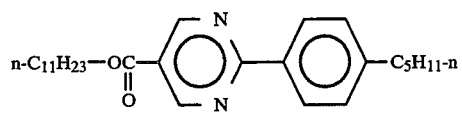 (4-17)
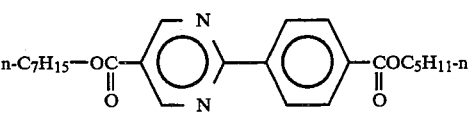 (4-18)
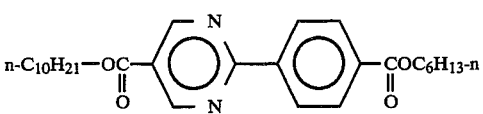 (4-19)
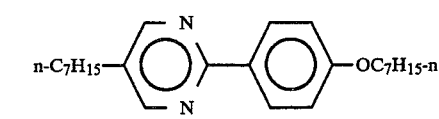 (4-20)
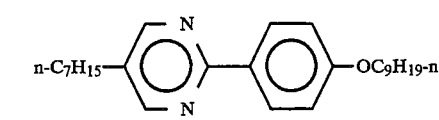 (4-21)
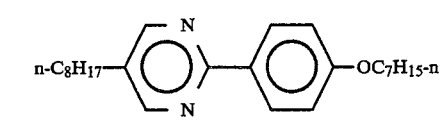 (4-22)
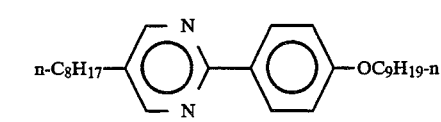 (4-23)
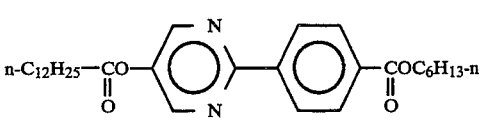 (4-24)
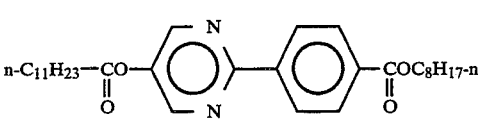 (4-25)
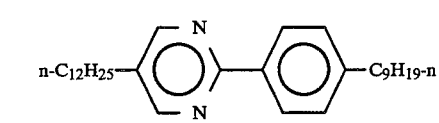 (4-26)

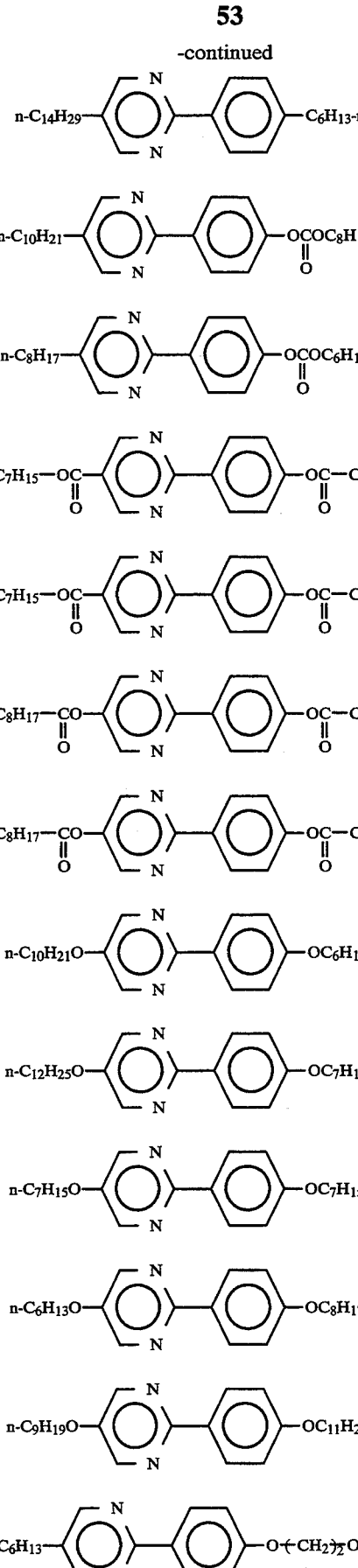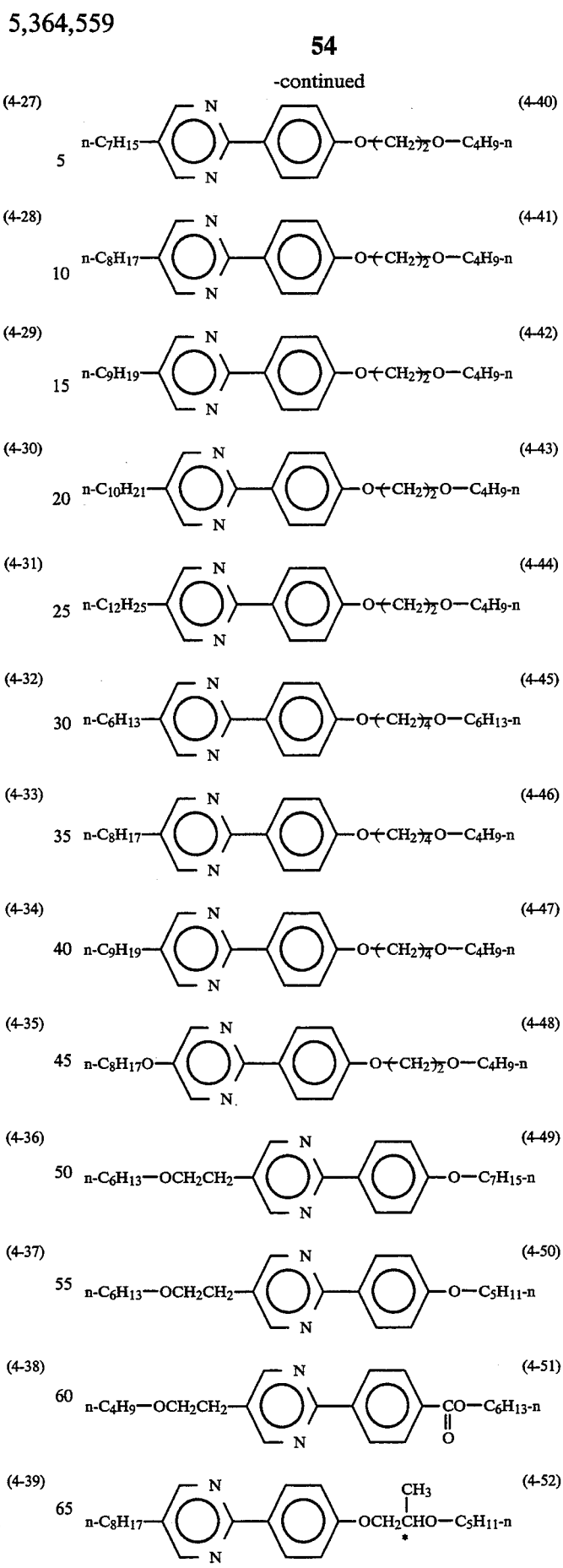

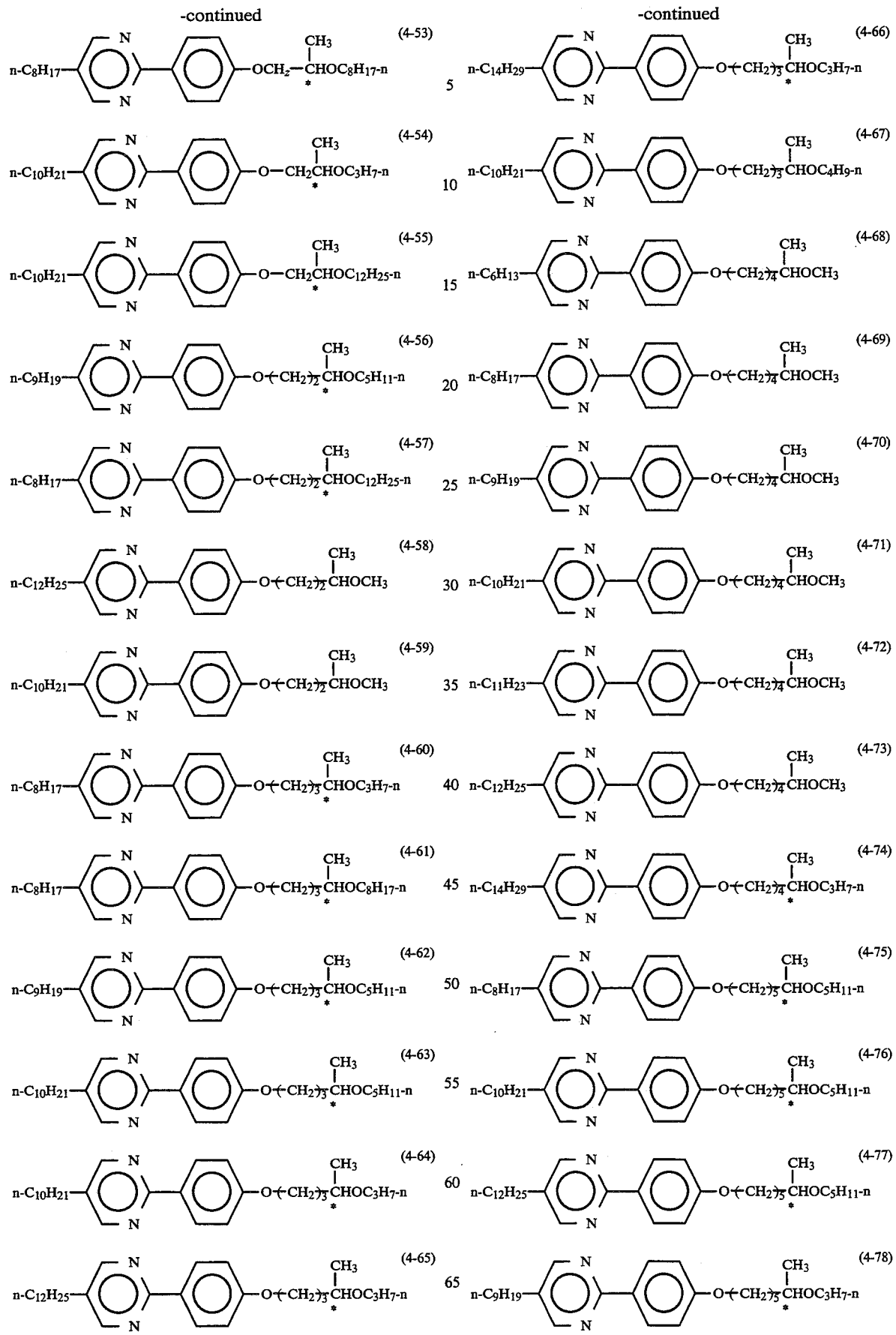

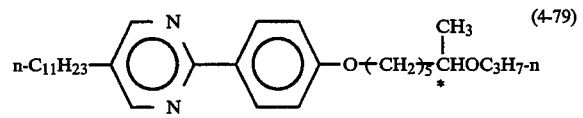 (4-79)
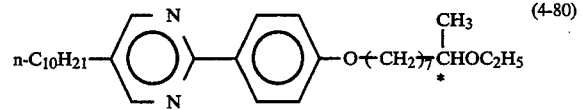 (4-80)
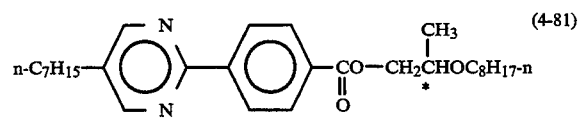 (4-81)
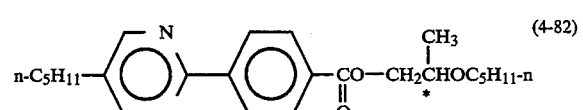 (4-82)
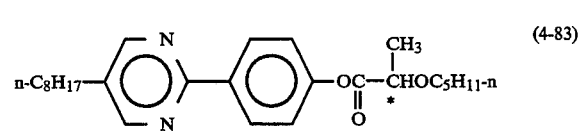 (4-83)
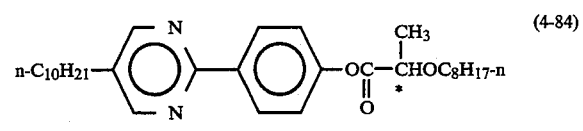 (4-84)
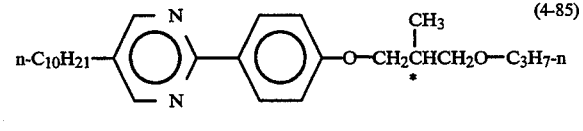 (4-85)
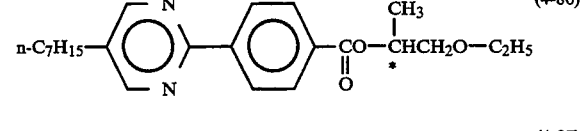 (4-86)
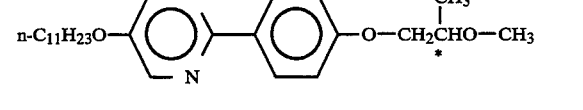 (4-87)
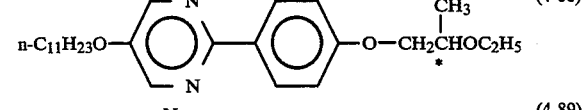 (4-88)
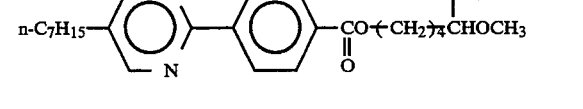 (4-89)
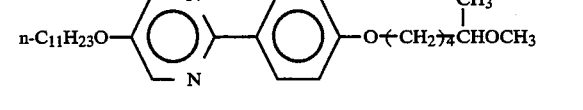 (4-90)
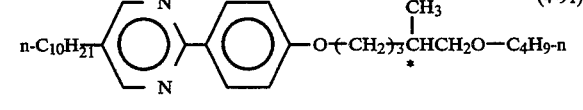 (4-91)
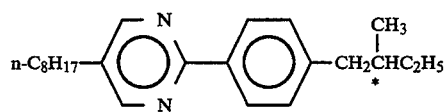 (4-92)
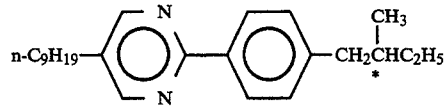 (4-93)
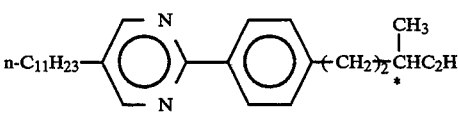 (4-94)
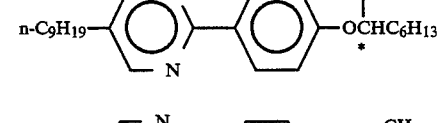 (4-95)
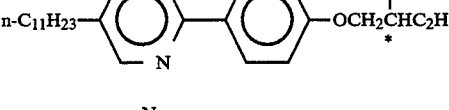 (4-96)
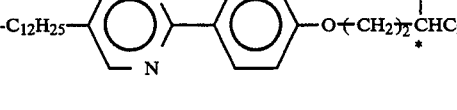 (4-97)
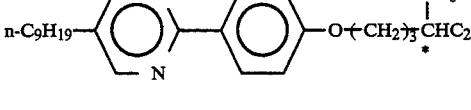 (4-98)
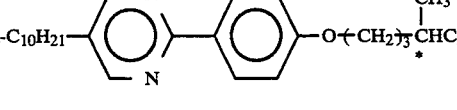 (4-99)
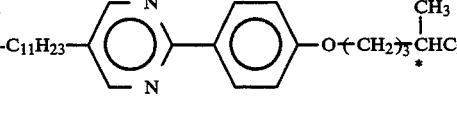 (4-100)
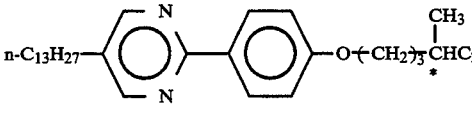 (4-101)
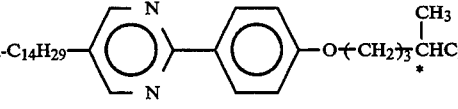 (4-102)
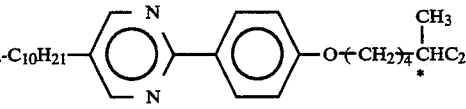 (4-103)
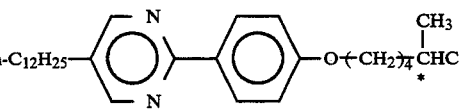 (4-104)

(4-105) n-C$_6$H$_{13}$–[pyridine]–[phenyl]–O(CH$_2$)$_3$CH(CH$_3$)C$_2$H$_5$*

(4-106) n-C$_7$H$_{15}$–[pyridine]–[phenyl]–O(CH$_2$)$_3$CH(CH$_3$)C$_2$H$_5$*

(4-107) n-C$_8$H$_{17}$–[pyridine]–[phenyl]–O(CH$_2$)$_3$CH(CH$_3$)C$_2$H$_5$*

(4-108) n-C$_9$H$_{19}$–[pyridine]–[phenyl]–O(CH$_2$)$_3$CH(CH$_3$)C$_2$H$_5$*

(4-109) n-C$_{10}$H$_{21}$–[pyridine]–[phenyl]–O(CH$_2$)$_3$CH(CH$_3$)C$_2$H$_5$*

(4-110) n-C$_{12}$H$_{25}$–[pyridine]–[phenyl]–O(CH$_2$)$_3$CH(CH$_3$)C$_2$H$_5$*

(4-111) n-C$_{14}$H$_{29}$–[pyridine]–[phenyl]–O(CH$_2$)$_3$CH(CH$_3$)C$_2$H$_5$*

(4-112) n-C$_8$H$_{17}$–[pyridine]–[phenyl]–O(CH$_2$)$_7$CH(CH$_3$)C$_2$H$_5$*

(4-113) n-C$_8$H$_{17}$–[pyridine]–[phenyl]–CO(CH$_2$)$_4$CH(CH$_3$)C$_2$H$_5$*

(4-114) n-C$_{11}$H$_{23}$–[pyridine]–[phenyl]–CO(CH$_2$)$_3$CH(CH$_3$)C$_2$H$_5$*

(4-115) n-C$_8$H$_{17}$–[pyridine]–[phenyl]–OC(O)(CH$_2$)$_2$CH(CH$_3$)C$_2$H$_5$*

(4-116) n-C$_{11}$H$_{23}$–[pyridine]–[phenyl]–OC(O)(CH$_2$)$_2$CH(CH$_3$)C$_2$H$_5$*

(4-117) n-C$_6$H$_{13}$–[pyridine]–[phenyl]–OC(O)(CH$_2$)$_4$CH(CH$_3$)C$_2$H$_5$*

(4-118) n-C$_{10}$H$_{21}$–[pyridine]–[phenyl]–OC(O)(CH$_2$)$_4$CH(CH$_3$)C$_2$H$_5$*

(4-119) n-C$_{14}$H$_{29}$–[pyridine]–[phenyl]–OC(O)(CH$_2$)$_4$CH(CH$_3$)C$_2$H$_5$*

(4-120) n-C$_7$H$_{15}$–[pyridine]–[phenyl]–CO(O)(CH$_2$)$_3$CH(CH$_3$)C$_2$H$_5$*

(4-121) n-C$_{11}$H$_{23}$–[pyridine]–[phenyl]–CO(O)(CH$_2$)$_3$CH(CH$_3$)C$_2$H$_5$*

(4-122) C$_2$H$_5$CH(CH$_3$)(CH$_2$)$_5$*–[pyridine]–[phenyl]–O–C$_8$H$_{17}$-n (4-123) C$_2$H$_5$CH(CH$_3$)(CH$_2$)$_5$*–[pyridine]–[phenyl]–O–C$_{11}$H$_{23}$-n (4-124) C$_2$H$_5$CH(CH$_3$)(CH$_2$)$_5$*–[pyridine]–[phenyl]–OC(O)–C$_8$H$_{17}$-n (4-125) n-C$_{10}$H$_{21}$–[pyridine]–[phenyl]–O(CH$_2$)$_2$OCH$_2$CH(CH$_3$)C$_2$H$_5$*

(4-126) n-C$_{12}$H$_{25}$–[pyridine]–[phenyl]–O(CH$_2$)$_2$O–CH$_2$CH(CH$_3$)C$_2$H$_5$*

(4-127) n-C$_{14}$H$_{29}$–[pyridine]–[phenyl]–O(CH$_2$)$_3$OCH$_2$CH(CH$_3$)C$_2$H$_5$*

(4-128) n-C$_{12}$H$_{25}$–[pyridine]–[phenyl]–O(CH$_2$)$_4$OCH$_2$CH(CH$_3$)C$_2$H$_5$*

(4-129) n-C$_9$H$_{19}$–[pyridine]–[phenyl]–CO(O)CH(CH$_3$)CH$_2$C$_2$H$_5$*

-continued
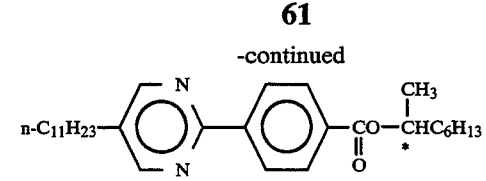 (4-130)
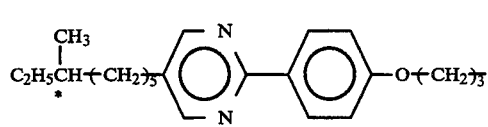 (4-131)
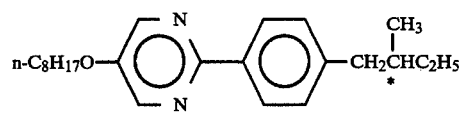 (4-132)
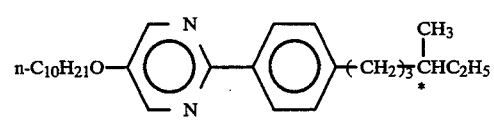 (4-133)
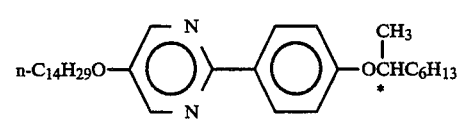 (4-134)
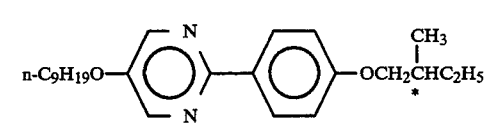 (4-135)
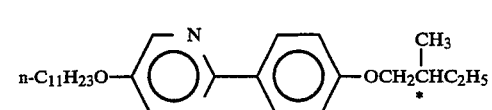 (4-136)
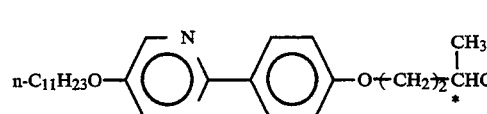 (4-137)
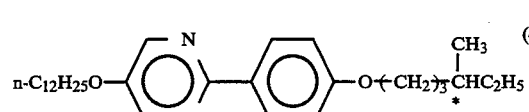 (4-138)
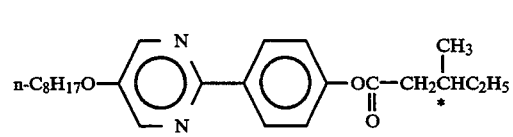 (4-139)
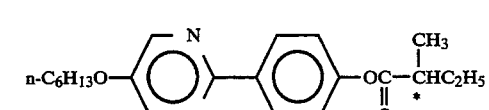 (4-140)
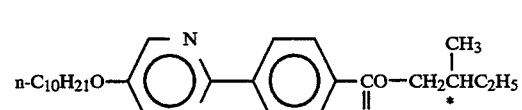 (4-141)
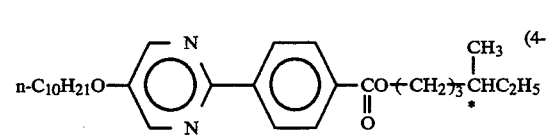 (4-142)
-continued
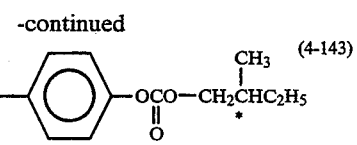 (4-143)
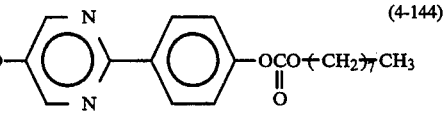 (4-144)
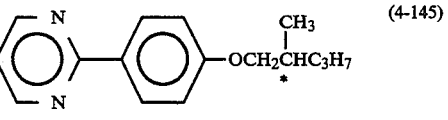 (4-145)
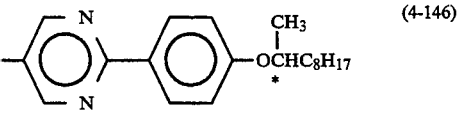 (4-146)
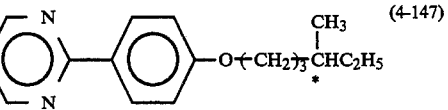 (4-147)
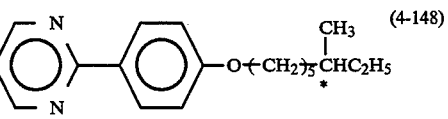 (4-148)
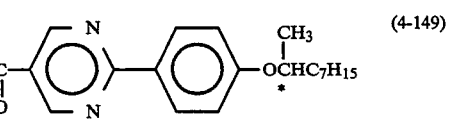 (4-149)
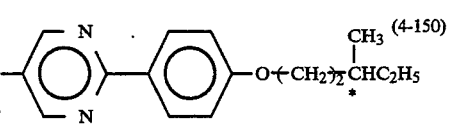 (4-150)
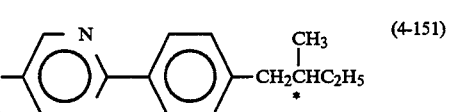 (4-151)
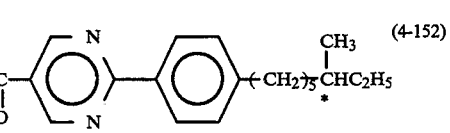 (4-152)
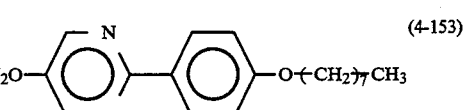 (4-153)
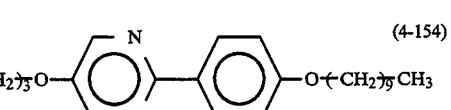 (4-154)
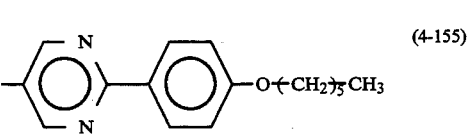 (4-155)

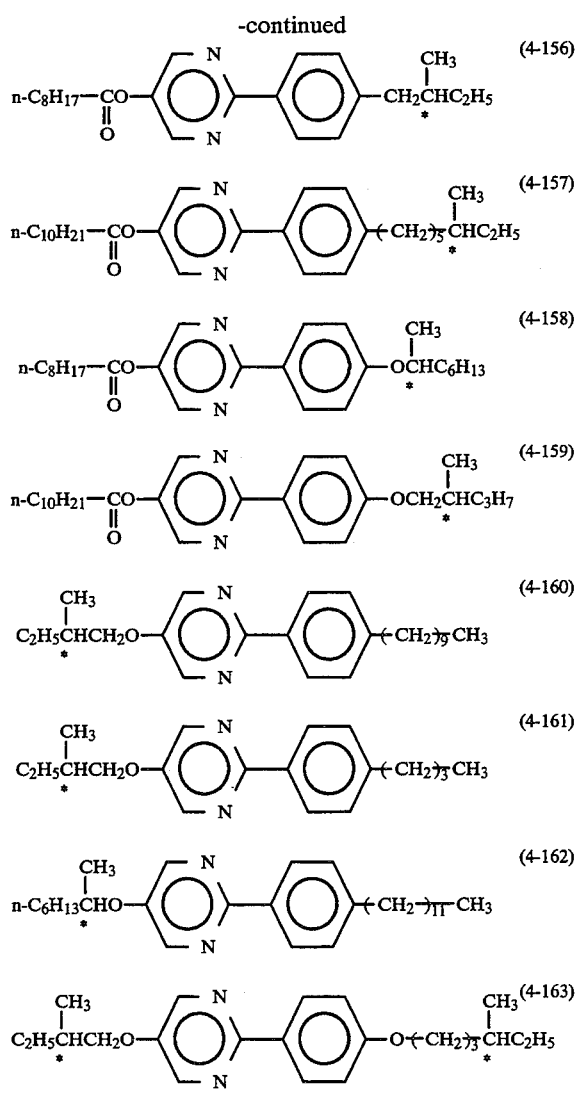
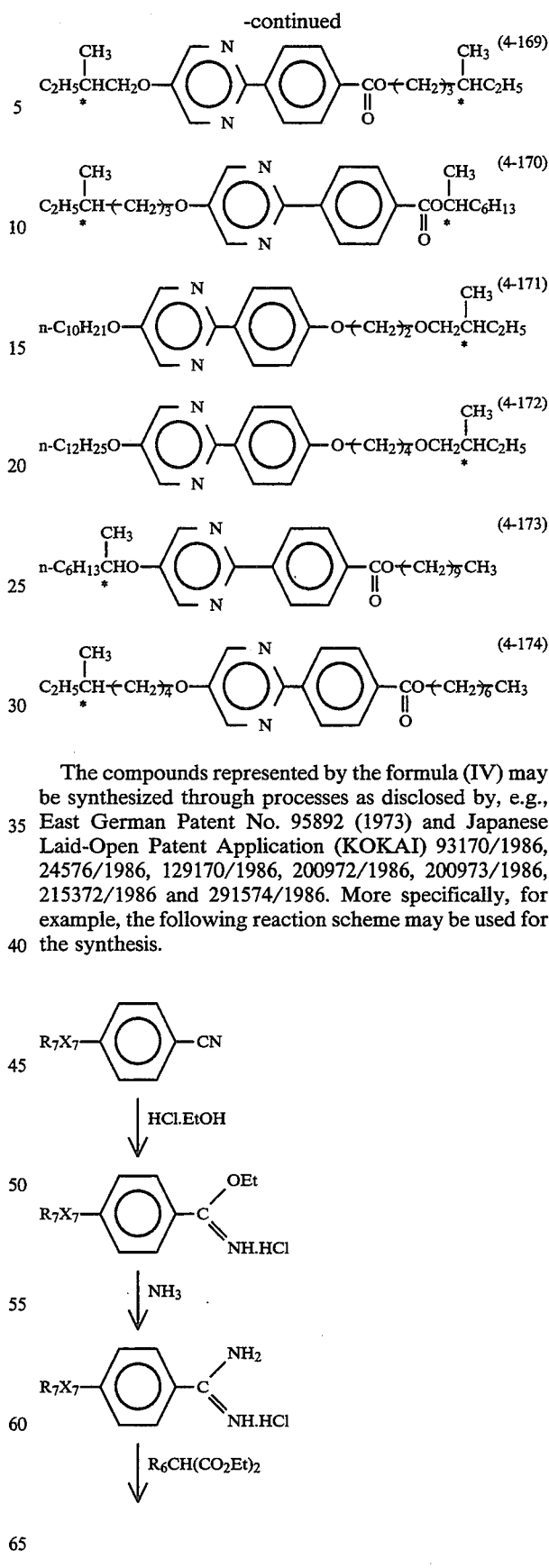
The compounds represented by the formula (IV) may be synthesized through processes as disclosed by, e.g., East German Patent No. 95892 (1973) and Japanese Laid-Open Patent Application (KOKAI) 93170/1986, 24576/1986, 129170/1986, 200972/1986, 200973/1986, 215372/1986 and 291574/1986. More specifically, for example, the following reaction scheme may be used for the synthesis.

-continued

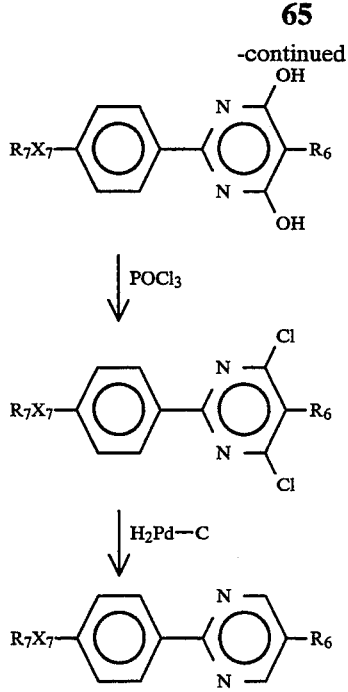

$R_6$, $R_7$ amd $X_7$ are the same as defined above.

Representative examples of synthesis of a compound represented by the formula (IV) are described below.

SYNTHESIS EXAMPLE 5

(Synthesis of Compound Example No. 4-71)

A solution of 1.83 g (9.6 mmol) of p-toluenesulfonic acid chloride in 5 ml of pyridine was added dropwise to a solution of 1.06 g (8.0 mmol) of 5-methoxyhexanol in 5 ml of pyridine below 5° C. on an iced water bath. After stirring for 6 hours at room temperature, the reaction mixture was injected into 100 ml of cold water and, after being acidified with 6N-hydrochloric acid, was extracted with isopropyl ether. The organic layer was washed with water and dried with anhydrous magnesium sulfate, followed by distilling-off of the solvent to obtain 5-methoxyhexyl-p-toluenesulfonate.

Separately, 2.0 g (6.41 mmol) of 5-decyl-2-(p-hydroxyphenyl)pyrimidine and 0.61 g of potassium hydroxide were added to 10 ml of dimethylformamide, and the mixture was stirred for 40 min. at 100° C. To the mixture was added the above-prepared 5-methoxyhexyl-p-toluenesulfonate followed by 4 hours of stirring under heating at 100° C. After the reaction, the reaction mixture was poured into 100 ml of cold water and extracted with benzene, followed by washing with water, drying with anhydrous magnesium sulfate and distilling-off of the solvent, to obtain a pale yellow oily product. The product was purified by column chromatography (silica gel—ethyl acetate/benzene=1/9) and recrystallized from hexane to obtain 1.35 g of 5-decyl-2-[4-(5'-methoxyhexyloxy)phenyl]pyrimidine.

Phase transition temperature (°C.)

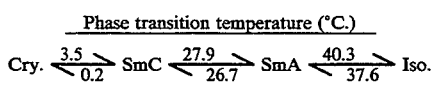

SYNTHESIS EXAMPLE 6

(Synthesis of Compound Example No. 4-76)

A solution of 2.26 g of p-toluene-sulfonic acid chloride in 5 ml of pyridine was added dropwise to a solution of 2.04 g of 6-pentyloxyheptanol in 8 ml of pyridine for 7 min. below 5° C. on an iced water bath. After stirring for 5 hours at room temperature, the reaction mixture was injected into 150 ml of cold water and, after being acidified to about pH 3 with 6N-hydrochloric acid, was extracted with ethyl acetate. The organic layer was washed with water and dried with anhydrous magnesium sulfate, followed by distilling-off of the solvent to obtain 2.98 g of 6-pentyloxyheptyl-p-toluenesulfonate.

Separately, 3.12 g of 5-n-decyl-2-(4-hydroxyphenyl)-pyrimidine and 0.53 g of potassium hydroxide were added to 14 ml of dimethylformamide, and the mixture was stirred for 3 hours at 100° C. To the mixture was added the above-prepared 2.98 g of 6-pentyloxyheptyl-p-toluenesulfonate followed by 5 hours of stirring under heating at 100° C. After the reaction, the reaction mixture was poured into 200 ml of cold water and acidified to about pH 3 with 6N-hydrochloric acid and extracted with benzene, followed by washing with water, drying with anhydrous magnesium sulfate and distilling-off of the solvent, to obtain 4.71 g of crude product. The product was purified by silica gel column chromatography (n-hexane/ethyl acetate=10/2) and recrystallized from hexane to obtain 1.56 g of 5-n-decyl-2-[4-(6-pentyloxyheptyloxy)phenyl]pyrimidine.

IR (cm$^{-1}$) 2924, 2852, 1610, 1586, 1472, 1436, 1254, 1168, 1096, 798

Phase transition temperature (°C.)

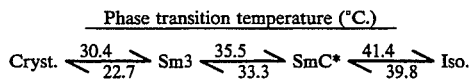

The compounds other than those in Example 5 and 6 represented by the above formula (IV) may also be synthesized through the following reaction schemes 4-A and 4-B.

Reaction scheme 4-A

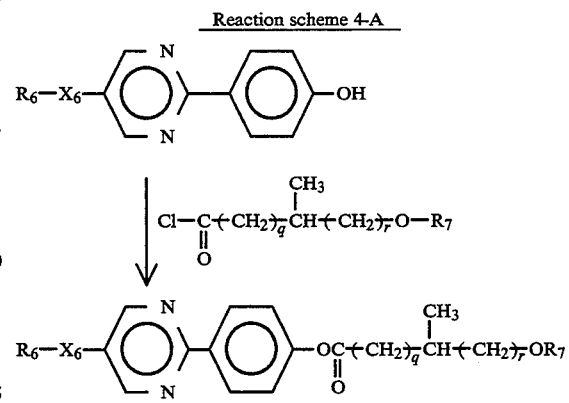

Reaction scheme 4-B

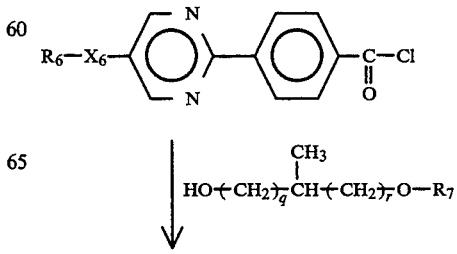

-continued
Reaction scheme 4-B

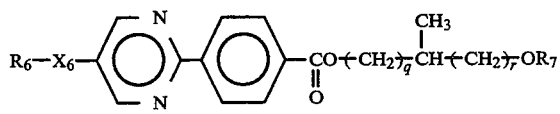

$R_6$, $R_7$, $X_6$, q and r are the same as defined above.

Specific examples of the compounds represented by the above-mentioned general formula (V) may include those shown by the following structural formulas.

(5-1) $C_6H_{13}$—[pyrimidine]—[phenyl]—[phenyl]—$OC_6H_{13}$ (5-2) $C_7H_{15}$—[pyrimidine]—[phenyl]—[phenyl]—$OC_9H_{19}$ (5-3) $C_{10}H_{21}$—[pyrimidine]—[phenyl]—[phenyl]—$OC_5H_{11}$ (5-4) $C_{12}H_{25}$—[pyrimidine]—[phenyl]—[phenyl]—$OC_7H_{15}$ (5-5) $C_3H_7$—[pyrimidine]—[phenyl]—[phenyl]—$OC_{11}H_{23}$ (5-6) $C_4H_9O$—[pyrimidine]—[phenyl]—[phenyl]—$OC_5H_{11}$ (5-7) $C_7H_{15}O$—[pyrimidine]—[phenyl]—[phenyl]—$OC_8H_{17}$ (5-8) $C_8H_{17}$—[pyrimidine]—[phenyl]—[phenyl]—$OCOC_6H_{13}$ (5-9) $C_{10}H_{21}$—[pyrimidine]—[phenyl]—[phenyl]—$OCOC_4H_9$ (5-10) $C_8H_{17}$—[pyrimidine]—[phenyl]—[phenyl]—$C_5H_{11}$ (5-11) $C_7H_{15}$—[pyrimidine]—[phenyl]—[phenyl]—$C_6H_{13}$ (5-12) $C_5H_{11}$—[pyrimidine]—[phenyl]—[phenyl]—$C_6H_{13}$

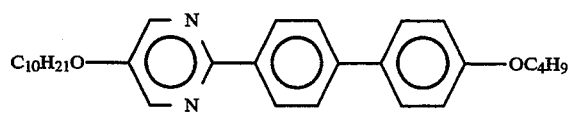 (5-13)
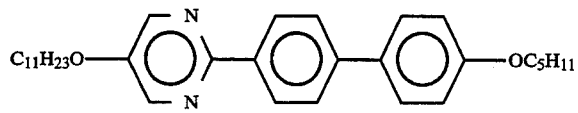 (5-14)
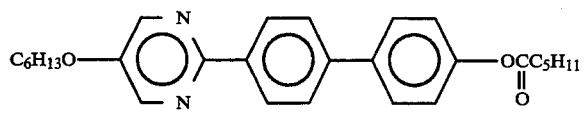 (5-15)
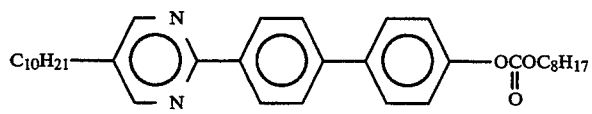 (5-16)
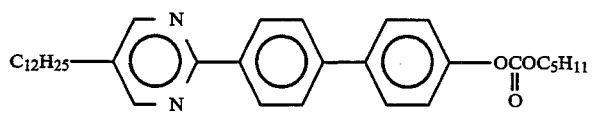 (5-17)
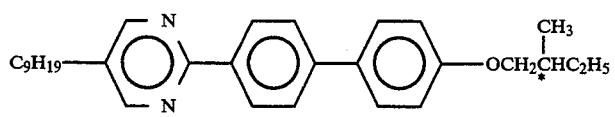 (5-18)
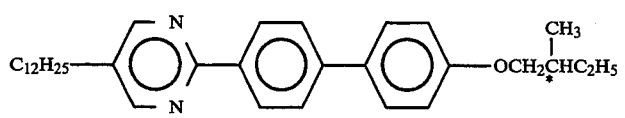 (5-19)
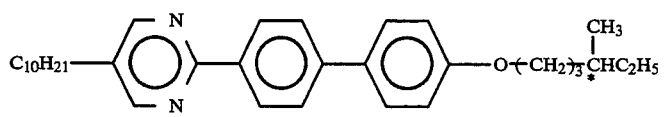 (5-20)
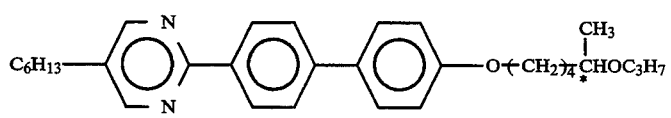 (5-21)
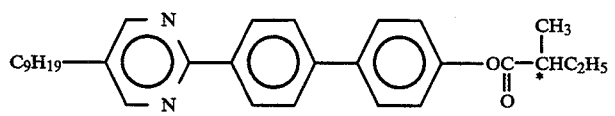 (5-22)
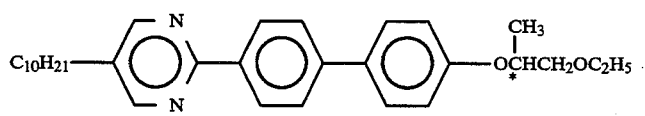 (5-23)
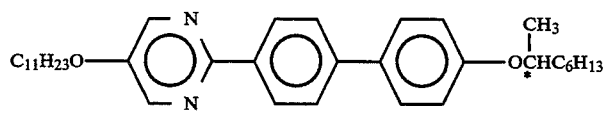 (5-24)
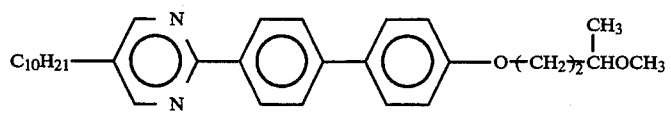 (5-25)

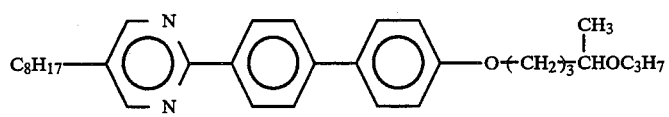 (5-26)
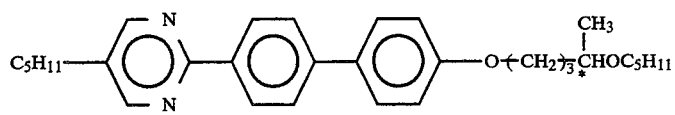 (5-27)
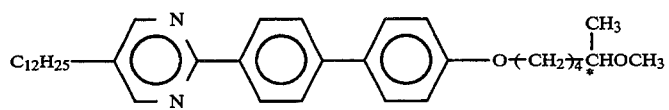 (5-28)
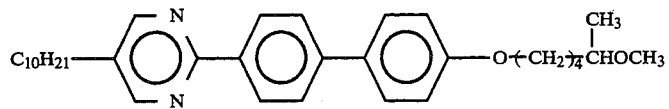 (5-29)
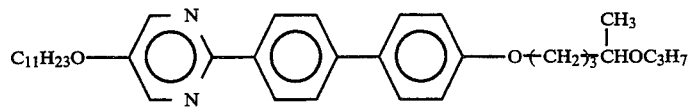 (5-30)
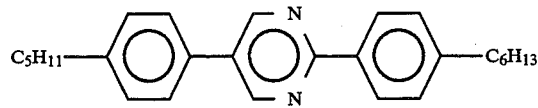 (5-31)
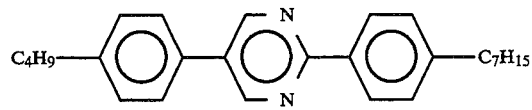 (5-32)
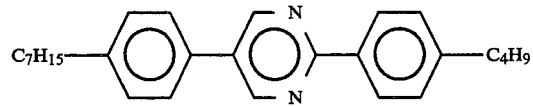 (5-33)
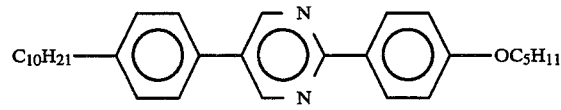 (5-34)
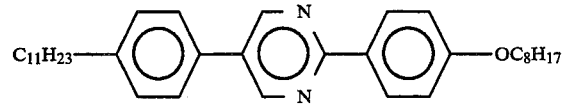 (5-35)
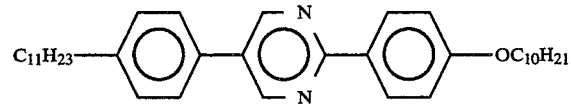 (5-36)
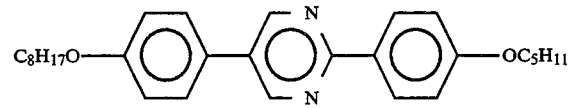 (5-37)
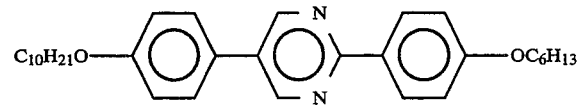 (5-38)

-continued
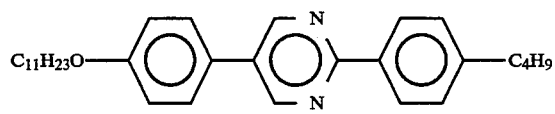 (5-39)
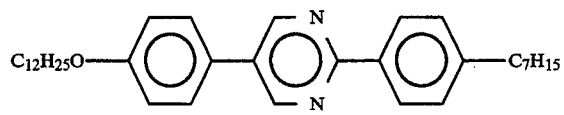 (5-40)
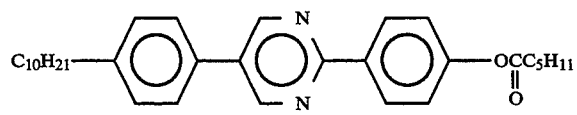 (5-41)
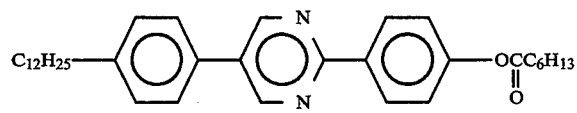 (5-42)
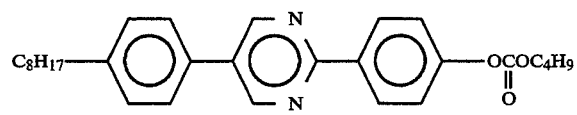 (5-43)
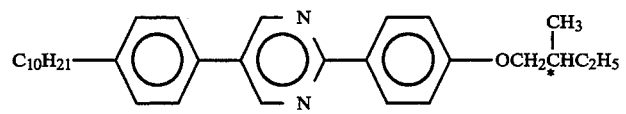 (5-44)
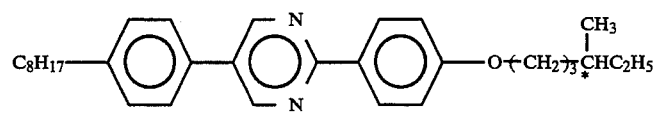 (5-45)
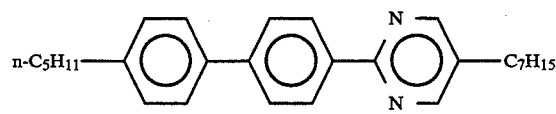 (5-46)
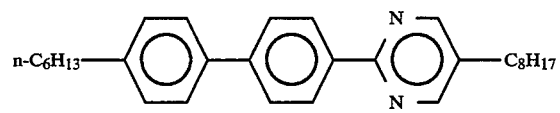 (5-47)
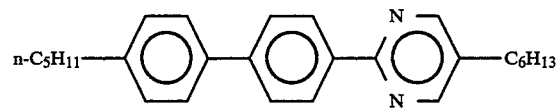 (5-48)
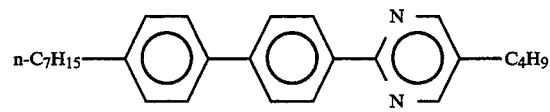 (5-49)
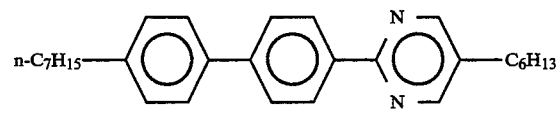 (5-50)
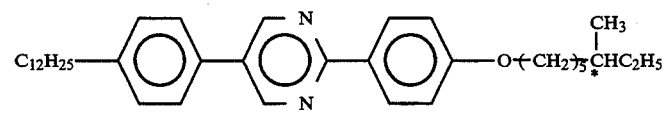 (5-51)

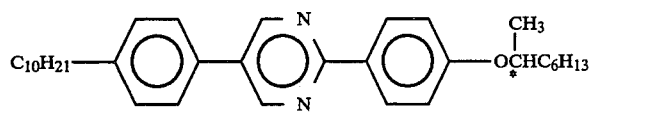 (5-52)
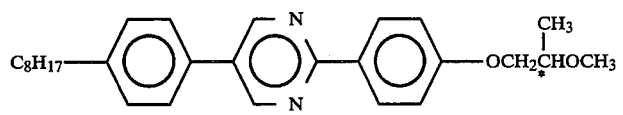 (5-53)
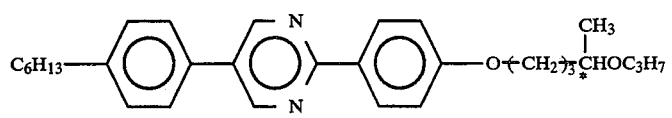 (5-54)
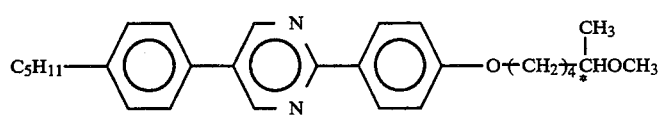 (5-55)
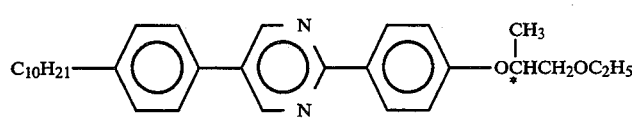 (5-56)
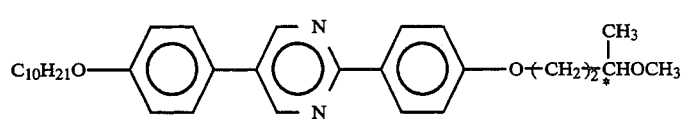 (5-57)
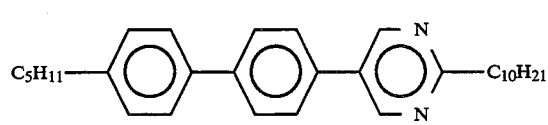 (5-58)
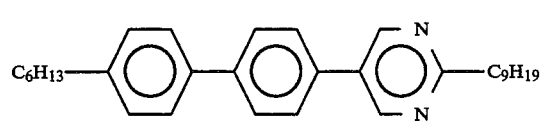 (5-59)
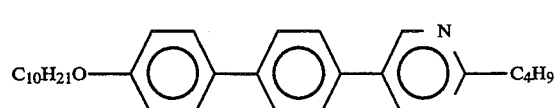 (5-60)
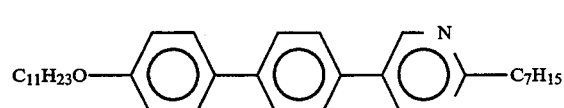 (5-61)
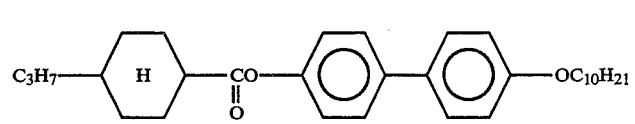 (5-62)
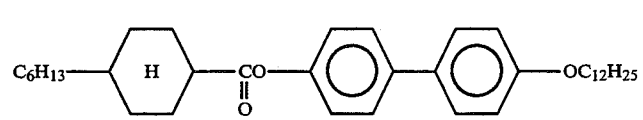 (5-63)
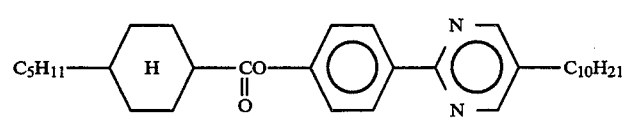 (5-64)

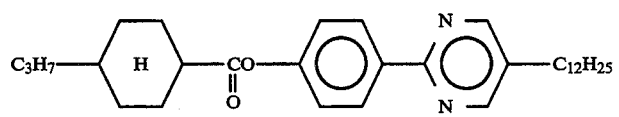 (5-65)
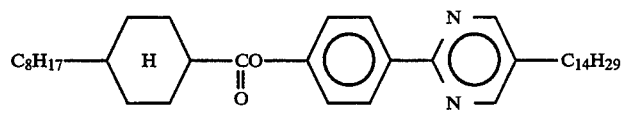 (5-66)
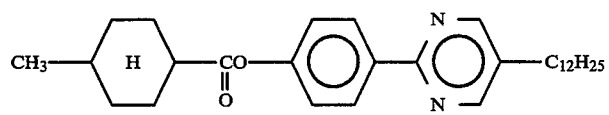 (5-67)
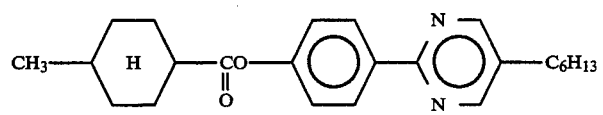 (5-68)
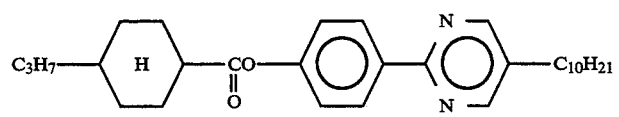 (5-69)
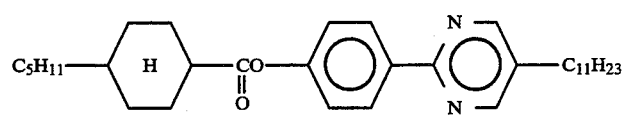 (5-70)
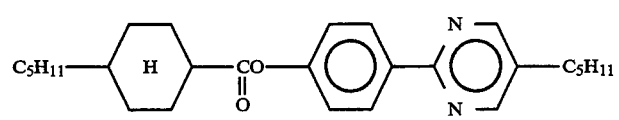 (5-71)
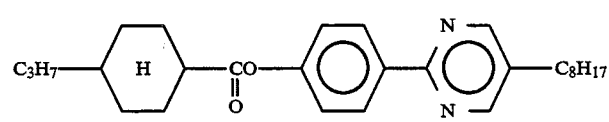 (5-72)
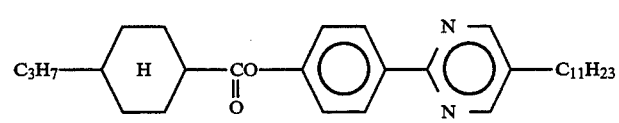 (5-73)
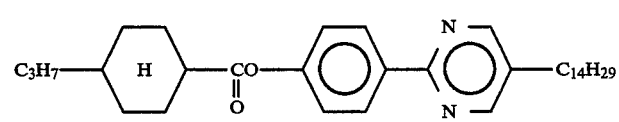 (5-74)
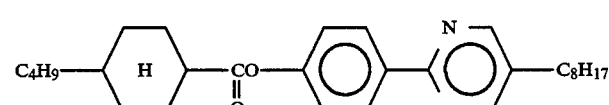 (5-75)
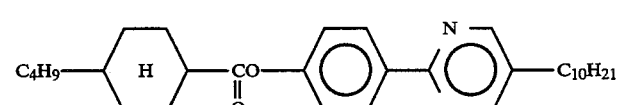 (5-76)
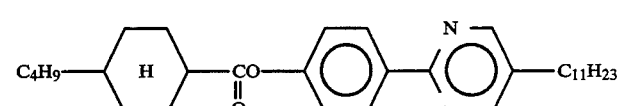 (5-77)

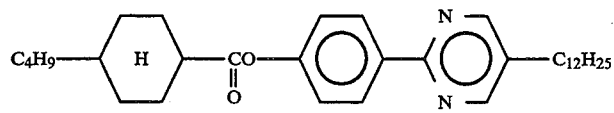
(5-78)
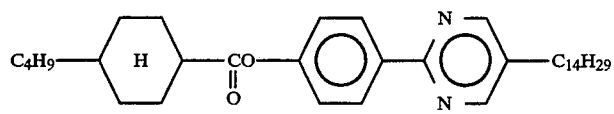
(5-79)
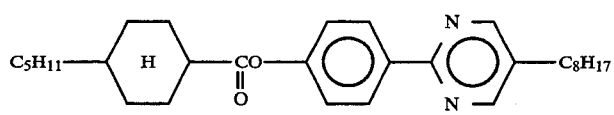
(5-80)
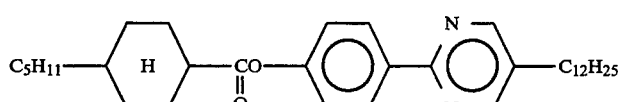
(5-81)
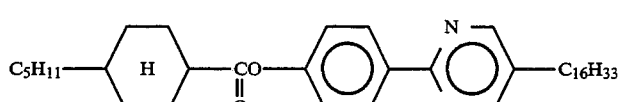
(5-82)
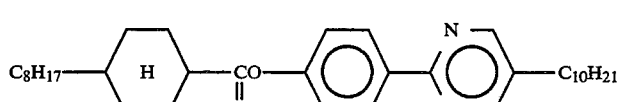
(5-83)
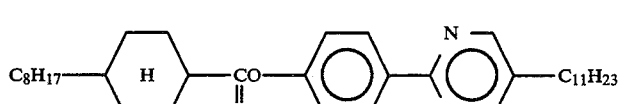
(5-84)
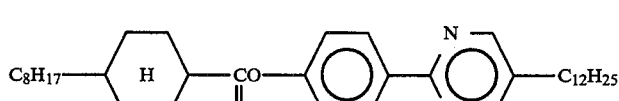
(5-85)
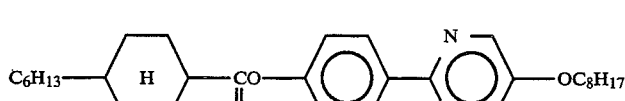
(5-86)
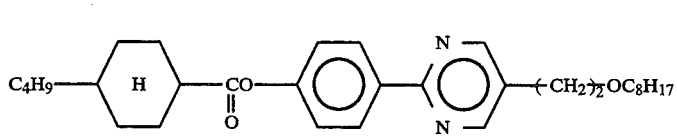
(5-87)
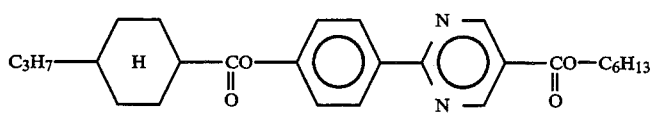
(5-88)
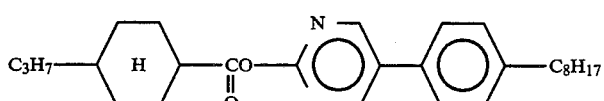
(5-89)
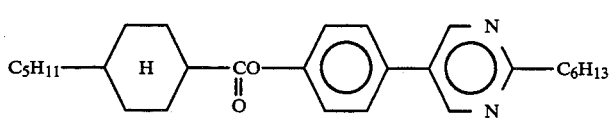
(5-90)

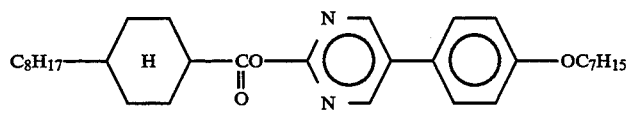 (5-91)
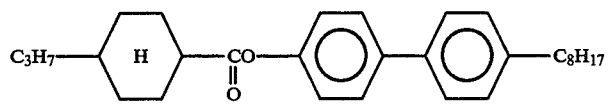 (5-92)
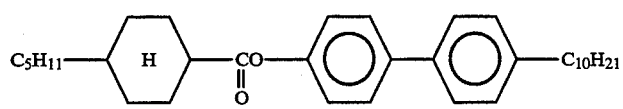 (5-93)
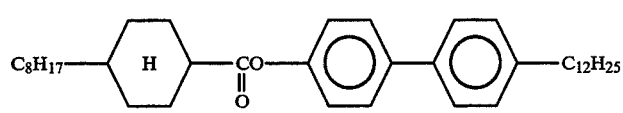 (5-94)
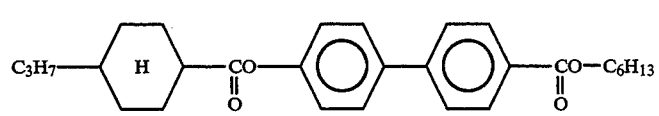 (5-95)
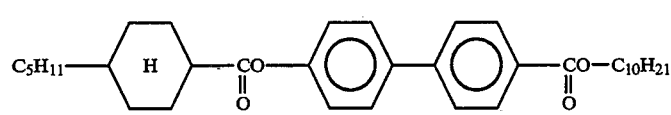 (5-96)
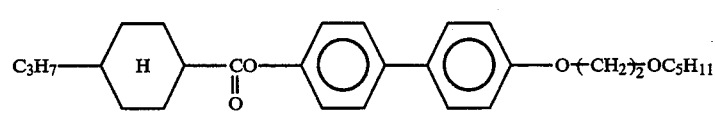 (5-97)
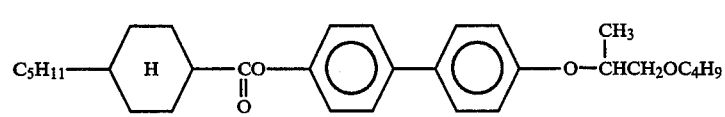 (5-98)
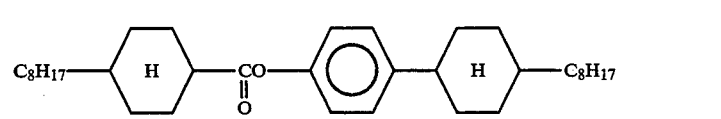 (5-99)
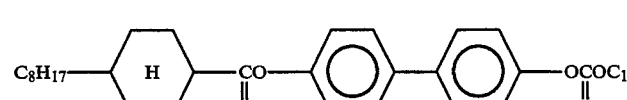 (5-100)
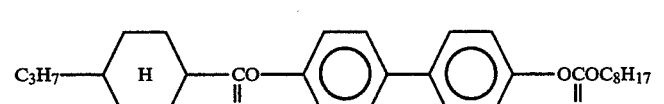 (5-101)
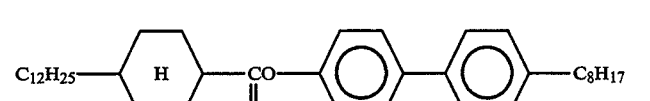 (5-102)
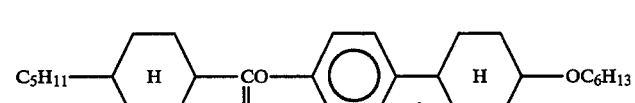 (5-103)

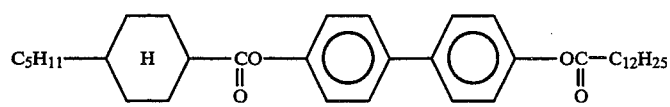 (5-104)
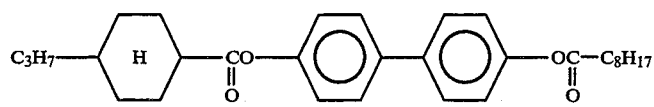 (5-105)
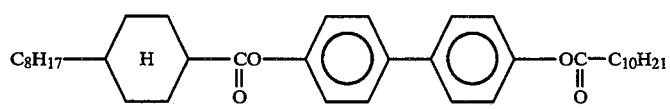 (5-106)
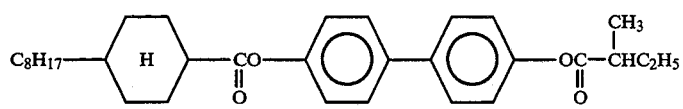 (5-107)
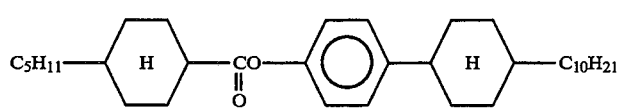 (5-108)
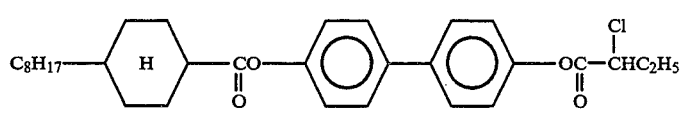 (5-109)
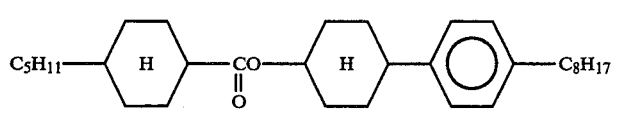 (5-110)
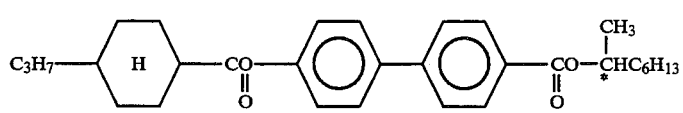 (5-111)
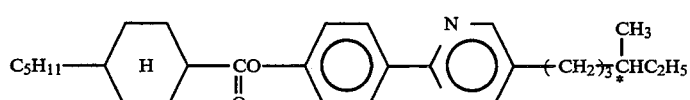 (5-112)
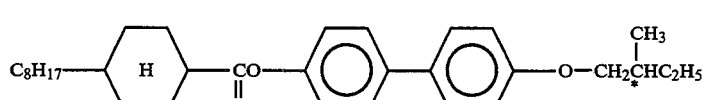 (5-113)
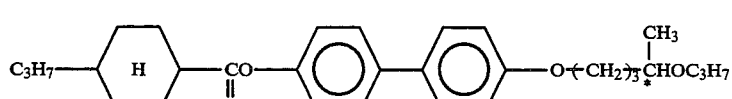 (5-114)
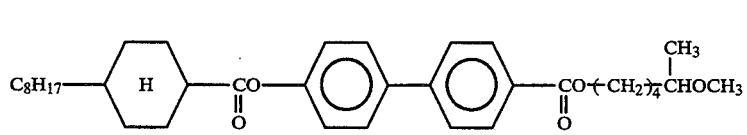 (5-115)
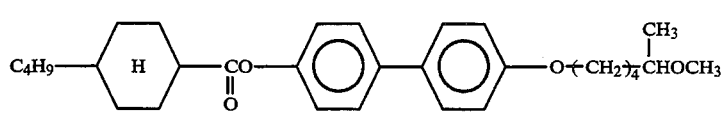 (5-116)

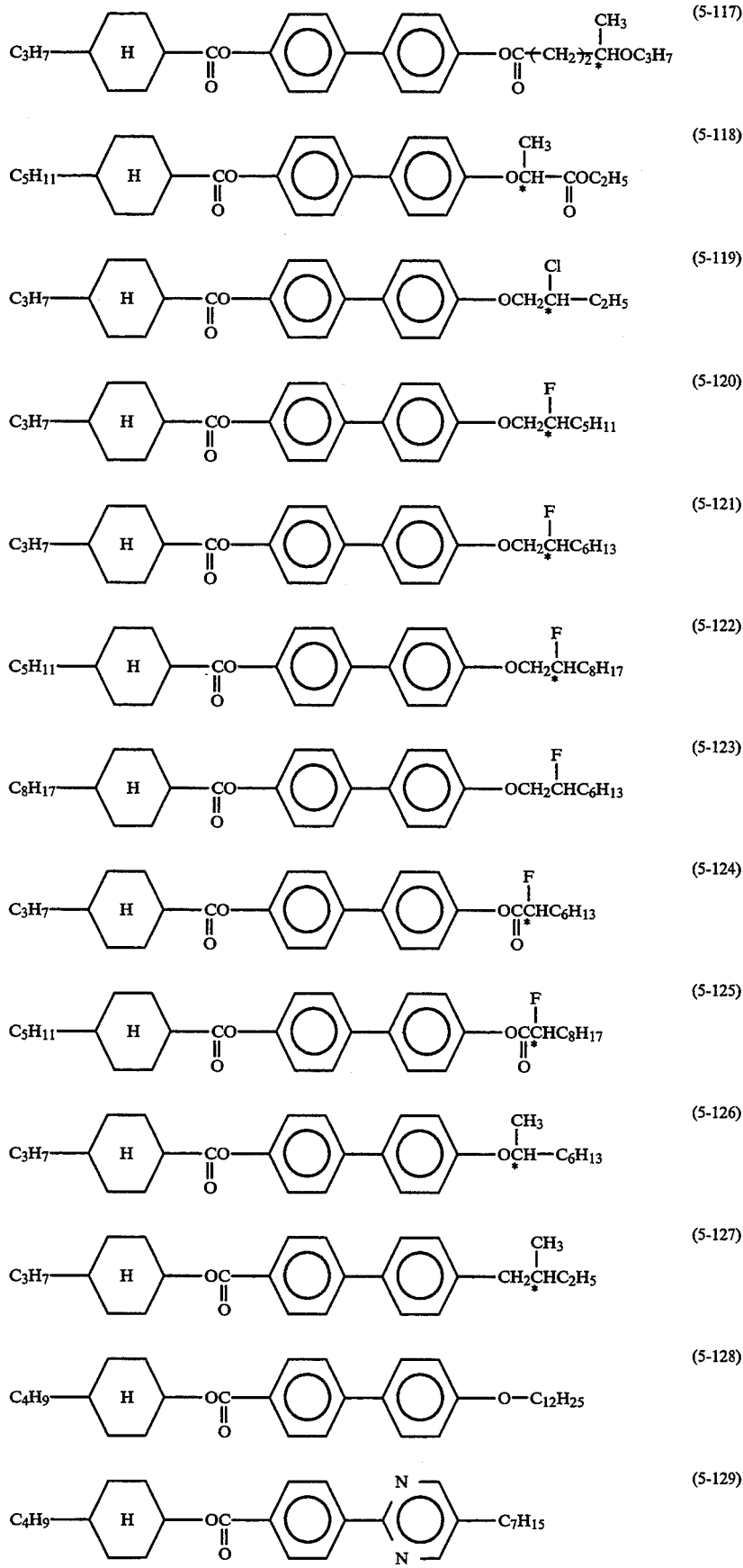

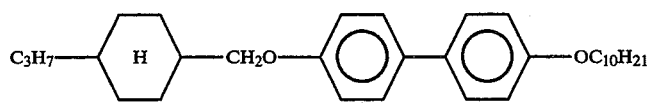 (5-130)
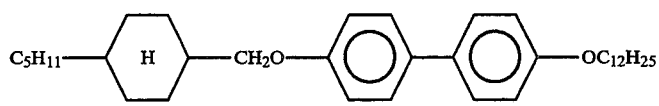 (5-131)
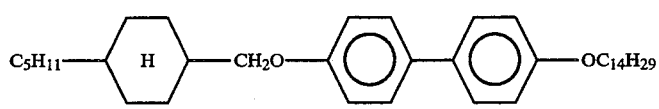 (5-132)
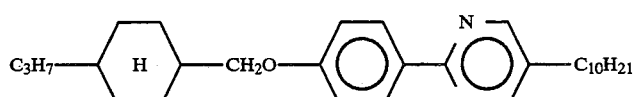 (5-133)
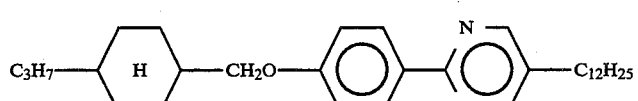 (5-134)
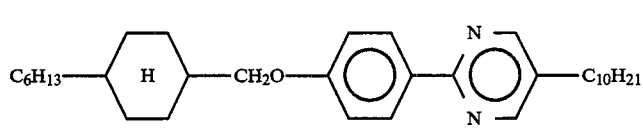 (5-135)
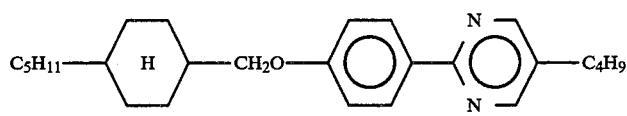 (5-136)
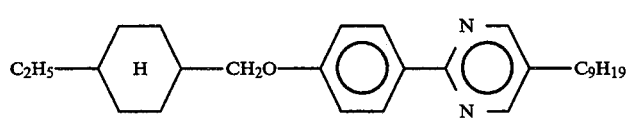 (5-137)
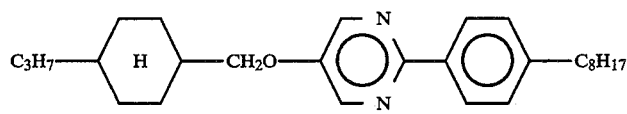 (5-138)
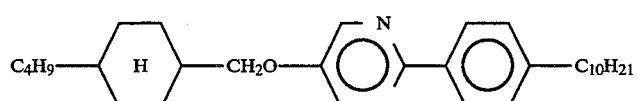 (5-139)
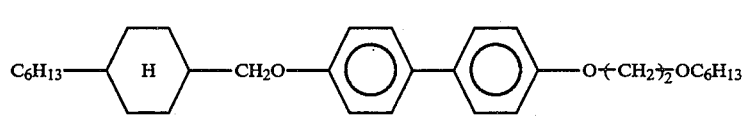 (5-140)
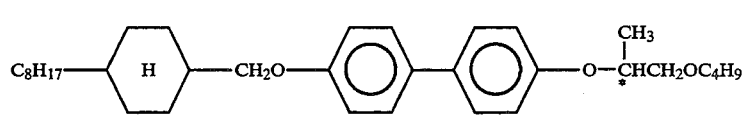 (5-141)
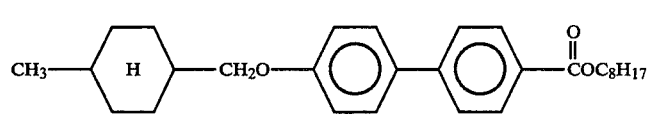 (5-142)

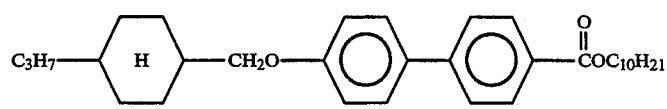 (5-143)
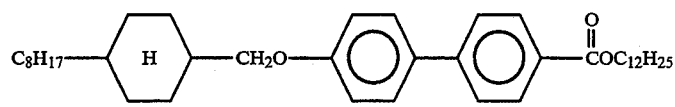 (5-144)
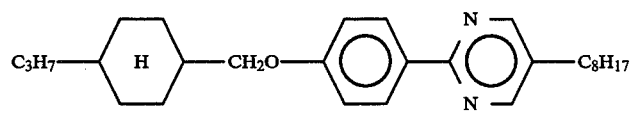 (5-145)
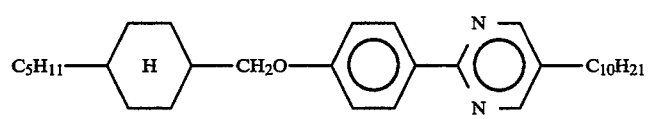 (5-146)
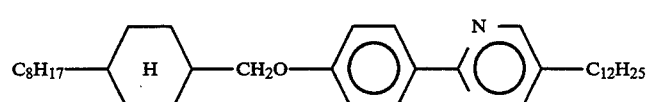 (5-147)
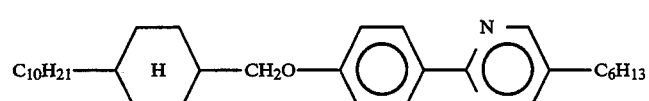 (5-148)
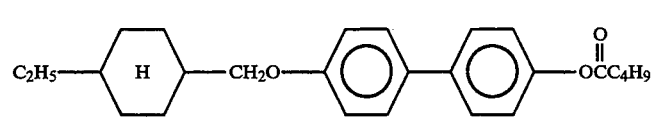 (5-149)
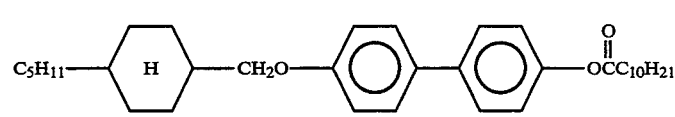 (5-150)
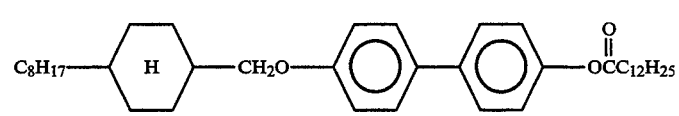 (5-151)
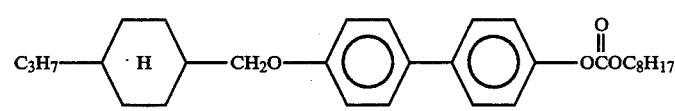 (5-152)
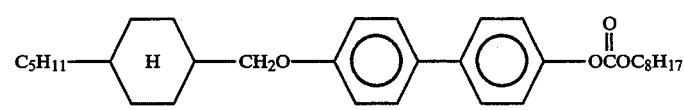 (5-153)
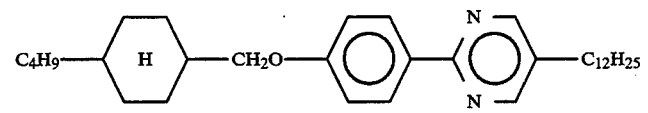 (5-154)
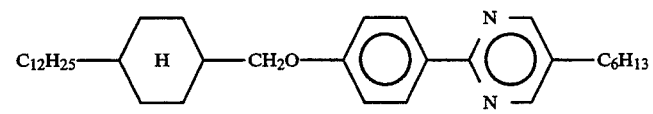 (5-155)

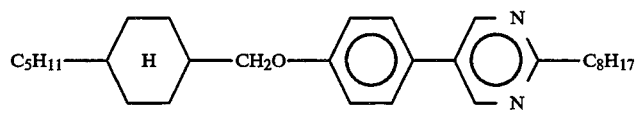 (5-156)
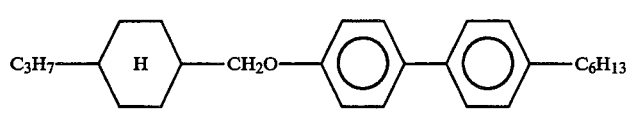 (5-157)
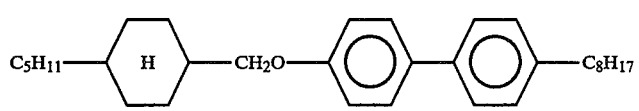 (5-158)
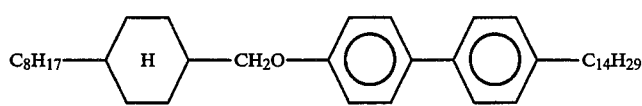 (5-159)
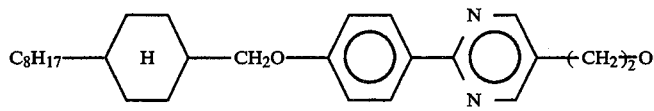 (5-160)
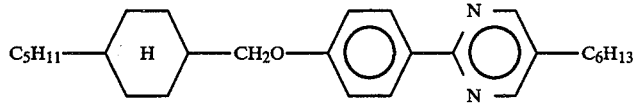 (5-161)
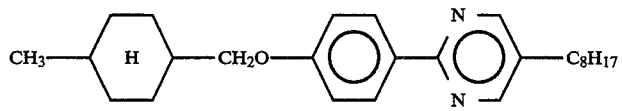 (5-162)
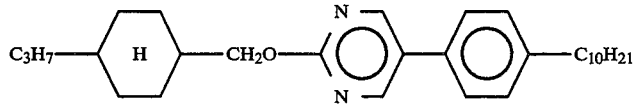 (5-163)
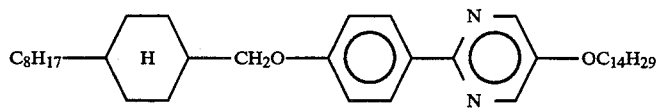 (5-164)
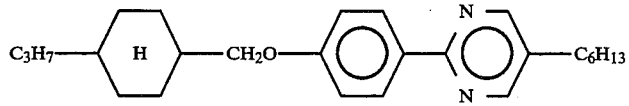 (5-165)
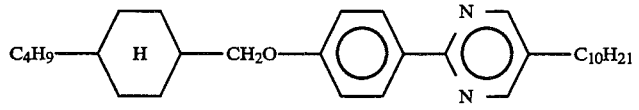 (5-166)
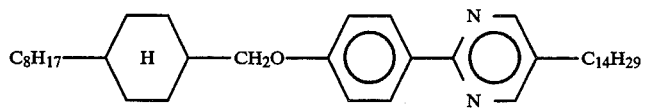 (5-167)
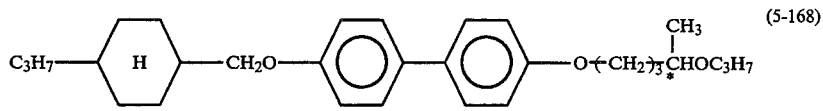 (5-168)

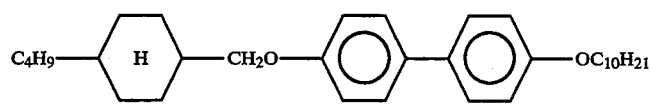
(5-169)
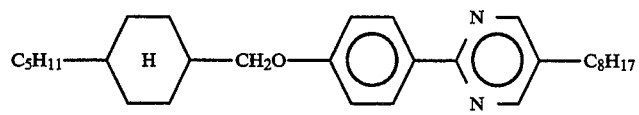
(5-170)
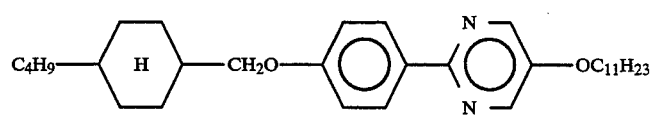
(5-171)
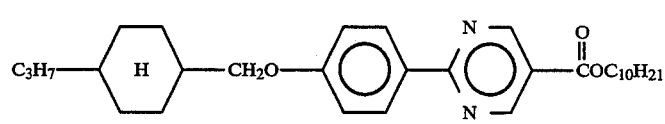
(5-172)
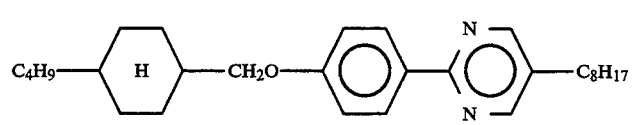
(5-173)
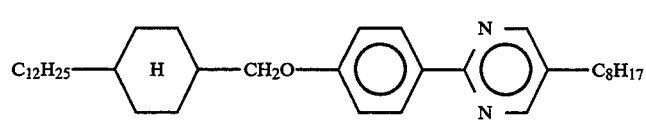
(5-174)
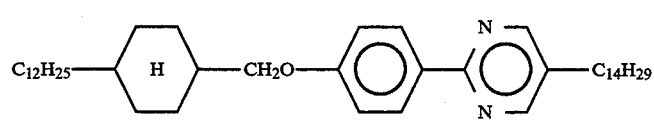
(5-175)
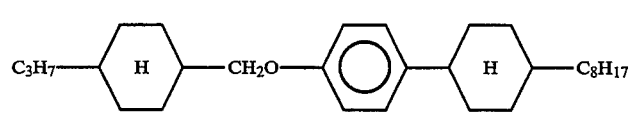
(5-176)
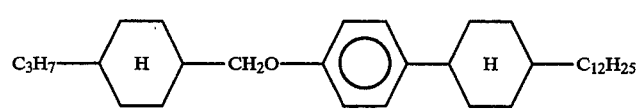
(5-177)
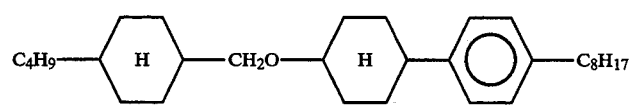
(5-178)
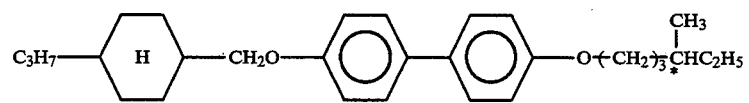
(5-179)
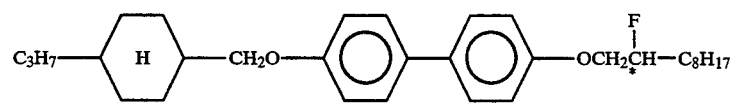
(5-180)
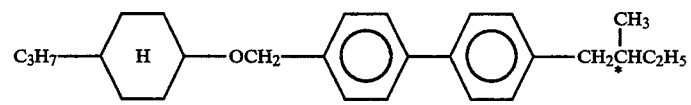
(5-181)

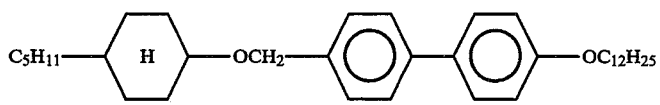
(5-182)

Representative examples of synthesis of compounds represented by the formula (V) are described below.

SYNTHESIS EXAMPLE 7

(Synthesis of Compound Example No. 5-65)

1.0 g (2.94 mmol) of 5-dodecyl-2-(4'-hydroxyphenyl)-pyrimidine was dissolved in respectively 4 ml of toluene and pyridine. A solution of 0.55 g of trans-4-n-propylcyclohexanecarbonyl chloride (manufactured by Kanto Kagaku K.K.) in 4 ml of toluene was gradually added dropwise thereto below 5° C. on an iced water bath. After the addition, the mixture was stirred for 12 hours at room temperature, and the reaction mixture was poured into 100 ml of iced water, followed by acidification with 6N-hydrochloric acid and extraction with benzene. The extracted solution was successively washed with water, 5%-sodium hydrogen carbonate aqueous solution and water, followed by drying with magnesium sulfate and distilling-off of the solvent, to obtain a cream-colored crude product. The crude product was purified by column chromatography and recrystallized from ethanol/ethyl acetate mixture solvent to obtain 0.94 g of objective compound. Yield: 64.8%.

Phase transition temperature (°C.)

$$Cryst. \underset{61.5}{\overset{64.9}{\rightleftarrows}} Sm3 \underset{75.4}{\overset{76.3}{\rightleftarrows}} SmC \underset{107.4}{\overset{108.1}{\rightleftarrows}} N \underset{152.0}{\overset{152.8}{\rightleftarrows}} Iso.$$

SYNTHESIS EXAMPLE 8

(Synthesis of Compound Example No. 5-133)

(1) A small amount of triethylamine was added to 10 g (53.6 mmol) of trans-4-n-propylcyclohexanecarbonyl chloride dissolved in 30 ml of ethanol, followed by 10 hours of stirring at room temperature. The reaction mixture was poured into 100 ml of iced water, acidified with 6N-hydrochloric acid and extracted with isopropyl ether. The organic layer was repeatedly washed with water until the aqueous layer became a neutral, followed by drying with magnesium sulfate, distilling-off of the solvent and purification by silica gel column chromatography to obtain 9.9 g of ethyl trans-4-n-propylcyclohexylcarboxylate.

(2) 0.73 g (19.1 mmol) of lithium aluminum hydride was added to 30 ml of dry ether, heat-refluxed for 1 hour and cooled to 10° C. on an iced water bath, and a solution of 5 g (25.5 mmol) of ethyl trans-4-n-propylcyclohexylcarboxylate in 30 ml of dry ether was gradually added dropwise thereto. After the addition, the mixture was stirred for 1 hour and further heat-refluxed for 1 hour, followed by treatment with ethyl acetate and with 6N-hydrochloric acid and pouring into 200 ml of iced water. The resultant mixture was extracted with isopropyl ether and the organic layer was successively washed with water, sodium hydroxide aqueous solution and water, followed by drying with magnesium sulfate, distilling-off of the solvent and purification by silica gel column chromatography to obtain 3.5 g of trans-4-n-propylcyclohexylmethanol.

(3) 3.4 g (22.4 mmol) of trans-4-n-propylcyclohexylmethanol was dissolved in 20 ml of pyridine. A solution of 5.3 g of p-toluenesulfonyl chloride in 20 ml of pyridine was added dropwise thereto below 5° C. on an iced water bath under cooling, followed by 10 hours of stirring at room temperature and pouring into 200 ml of iced water. The resultant mixture was acidified with 6N-hydrochloric acid and extracted with isopropyl ether. The organic layer was repeatedly washed with water until the aqueous layer became neutral, followed by drying with magnesium sulfate and distilling-off of the solvent, to obtain trans-4-n-propylcyclohexylmethyl-p-toluenesulfonate.

(4) 6.3 g (20.2 mmol) of 5-decyl-2-(4'-hydroxyphenyl)pyrimidine was dissolved in 40 ml of dimethylformamide, 1.5 g of potassium hydroxide (85%) was added thereto, followed by 1 hour of stirring at 100° C., 6.9 g of trans-4-n-propylcyclohexylmethyl-p-toluenesulfonate was added thereto, followed further by 4 hour of stirring at 100° C. After the reaction, the reaction mixture was poured into 200 ml of iced water and extracted with benzene. The organic layer was washed with water and dried with magnesium sulfate, followed by distilling-off of the solvent, purification by silica gel column chromatography and recrystallization from ethanol/ethyl acetate mixture solvent to obtain the above compound Example No. 5-133.

IR (cm$^{-1}$): 2920, 2840, 1608, 1584, 1428, 1258, 1164, 800

Phase transition temperature (°C.)

$$Cryst. \underset{62.9}{\overset{82.0}{\rightleftarrows}} Sm2 \underset{86.8}{\overset{91.3}{\rightleftarrows}} SmC \underset{97.8}{\overset{98.6}{\rightleftarrows}} N \underset{136.8}{\overset{137.6}{\rightleftarrows}} Iso.$$

Sm2: smectic phase other than SmA and SmC (un-identified)

Further, in the case where Z is a single bond, for example, compounds represented by the formula:

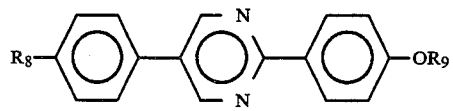

may be synthesized through the following reaction scheme.

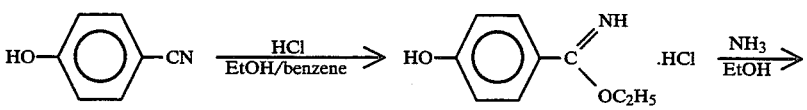

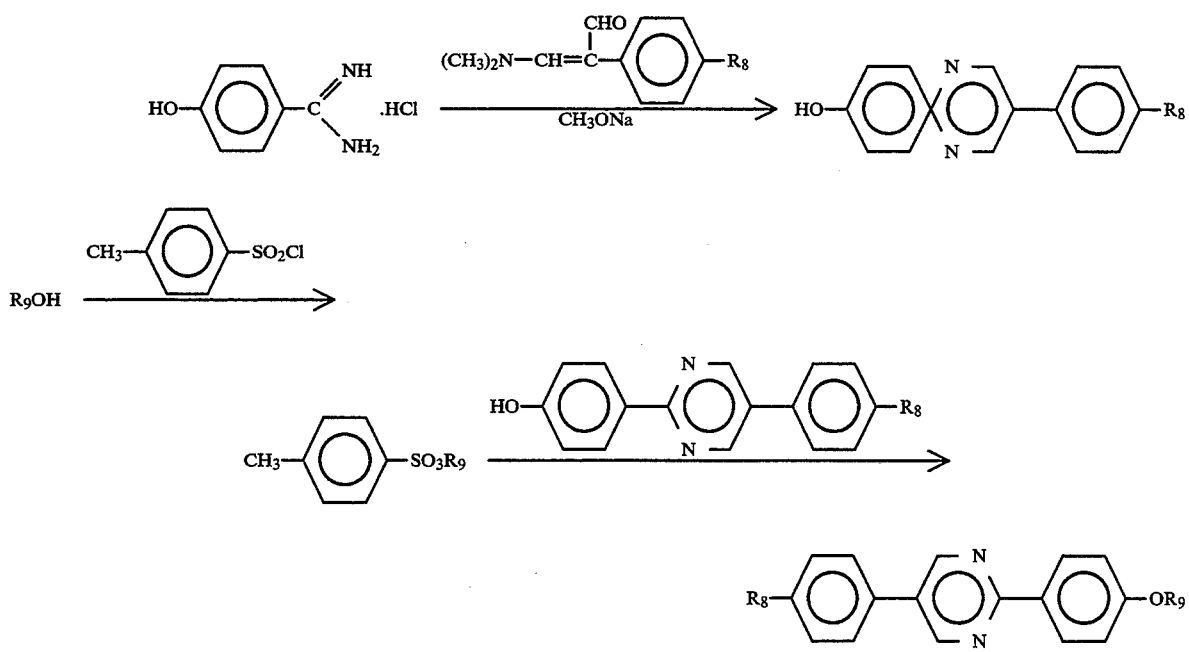

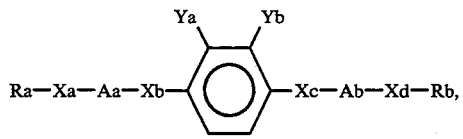

In a preferred embodiment, the ferroelectric chiral smectic liquid crystal composition according to the present invention further comprises a mesomorphic compound having a negative dielectric anisotropy, which is preferably selected from those represented by the following formulas (VI-1) to (Vi-5):

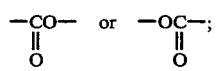

wherein Ra and Rb respectively denote a linear or branched alkyl group capable of having a substituent; Xa and Xd respectively denote a single bond, —O—, $$-\underset{\underset{O}{\|}}{C}O- \quad \text{or} \quad -O\underset{\underset{O}{\|}}{C}-;$$

Xb and Xc respectively denote a single bond, $$-\underset{\underset{O}{\|}}{C}O-, \quad -O\underset{\underset{O}{\|}}{C}-$$

or —CH$_2$CH$_2$—; Aa and Ab respectively denote a single bond,

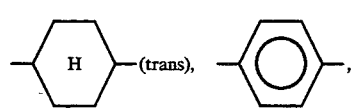

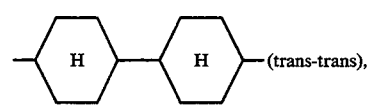

or

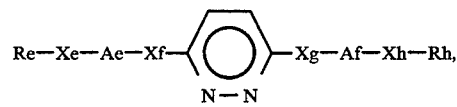

with proviso that when Aa and Ab are both single bonds, Xb and Xc are both single bonds, and Xa and Xd are both single bonds or —O—, or Xa is $$-\underset{\underset{O}{\|}}{C}O-$$

and Xd is $$-O\underset{\underset{O}{\|}}{C}-;$$

and Ya and Yb are respectively cyano group, halogen or hydrogen with proviso that Ya and Yb cannot be hydrogen simultaneously;

Formula (VI-2):

Re—Xe—Ae—Xf—[ring]—Xg—Af—Xh—Rh, wherein Re and Rf respectively denote a linear or branched alkyl group capable of having a substituent; Xe and Xh are respectively a single bond, —O—,

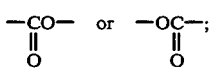

Xf and Xg are respectively —CO—,

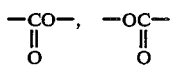

or a single bond; and Ae and Af are respectively

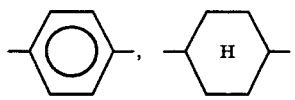

or a single bond with proviso that Ae and Af cannot be a single bond simultaneously;

Formula (VI-3):

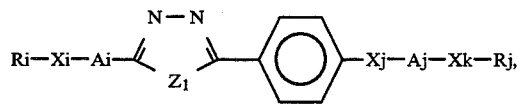

wherein Ai is a single bond or

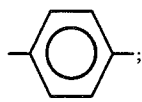

Aj is a single bond,

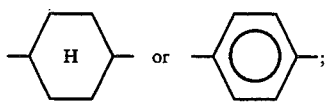

Ri and Rj are respectively a linear or branched alkyl group capable of having a substituent with proviso that Ri and Rj are linear alkyl groups when Aj is a single bond; $Z_1$ is —O— or —S—; Xi and Xk are respectively a single bond, —O—,

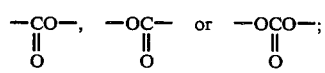

Xj is a single bond,

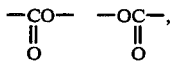

—CH$_2$O— or —OCH$_2$— with proviso that Xi is a single bond when Ai is a single bond, Xj is not a single bond when Aj is

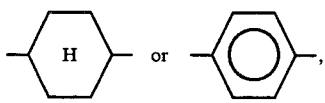

and Xk is a single bond when Aj is a single bond;

Formula (VI-4):

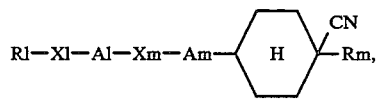

wherein Rl and Rm are respectively a linear or branched alkyl group capable of having a substituent; Al and Am are respectively a single bond,

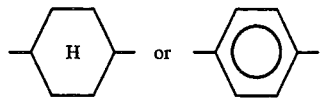

with proviso that Al and Am cannot be a single bond simultaneously; Xl is a single bond, —O—,

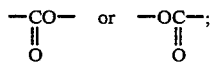

and Xm is a single bond,

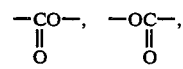

—CH$_2$CH$_2$— or —C≡C—,

Formula (VI-5):

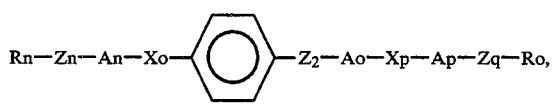

wherein Rn and Ro are respectively a linear or branched alkyl group capable of having a substituent; Xn and Xq are respectively a single bond, —O—,

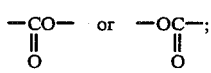

Xo and Xp are respectively a single bond,

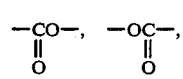

—CH$_2$O—, —OCH$_2$— or —CH$_2$CH$_2$—; An and Ap are respectively a single bond,

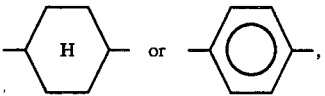

Ao is

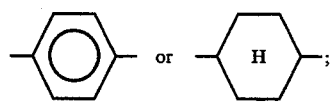 and $Z_2$ is
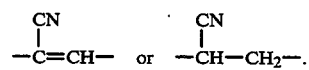.
In the above formulas (VI-1) to (VI-5), the alkyl groups Ra–Ro may respectively have 1–18 carbon atoms, preferably 4–16 carbon atoms, further preferably 6–12 carbon atoms.
Specific examples of mesomorphic compounds represented by the general formulas (VI-1) to (VI-5) may respectively include those denoted by the structural formulas shown below.
Formula (VI-1)
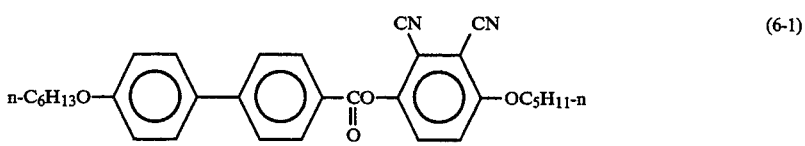 (6-1)
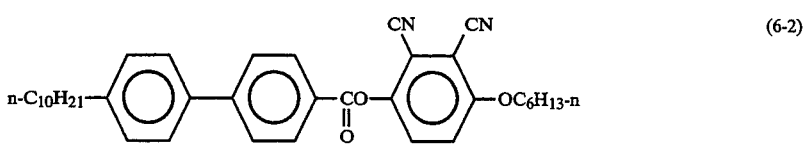 (6-2)
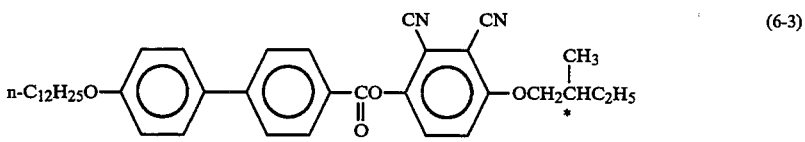 (6-3)
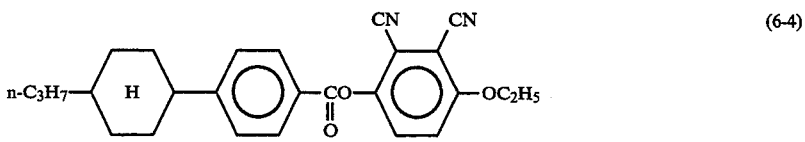 (6-4)
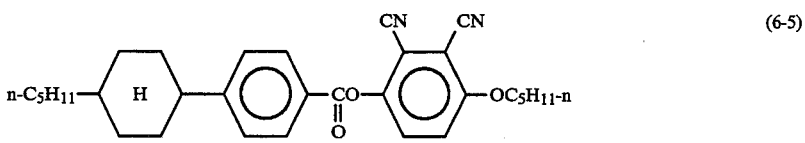 (6-5)
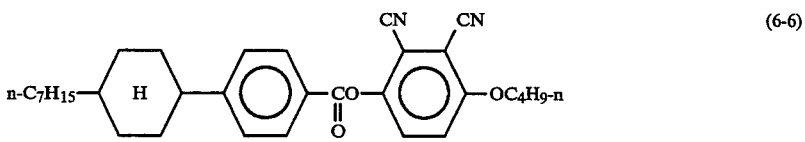 (6-6)
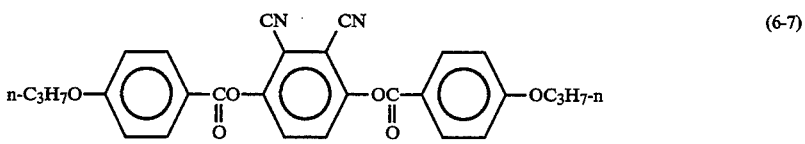 (6-7)
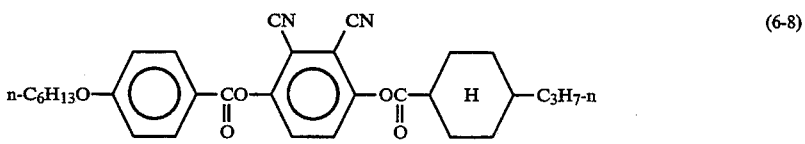 (6-8)
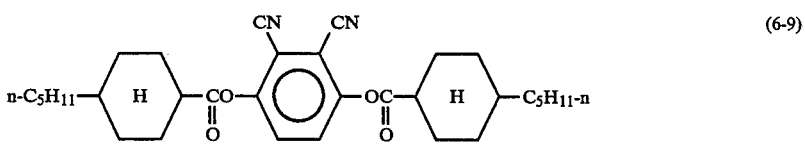 (6-9)

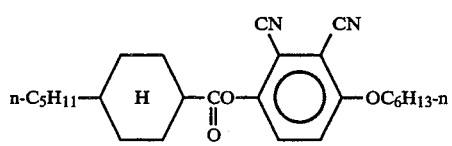 (6-10)
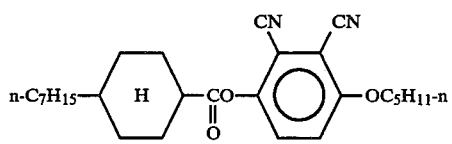 (6-11)
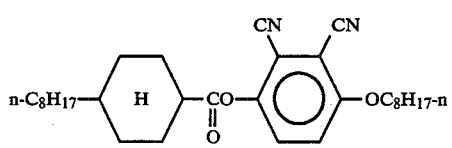 (6-12)
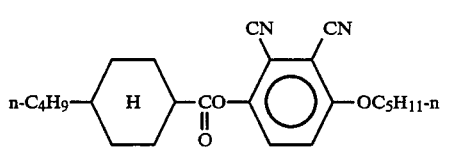 (6-13)
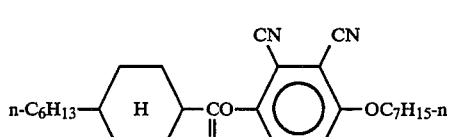 (6-14)
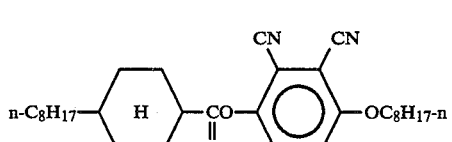 (6-15)
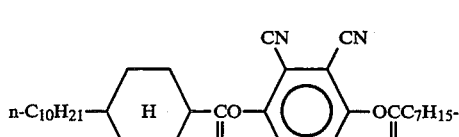 (6-16)
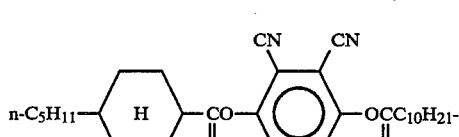 (6-17)
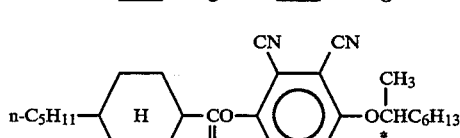 (6-18)
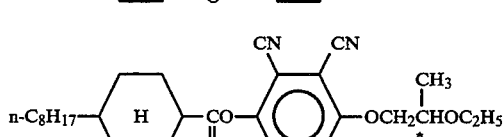 (6-19)
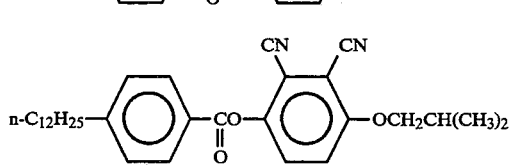 (6-20)

-continued
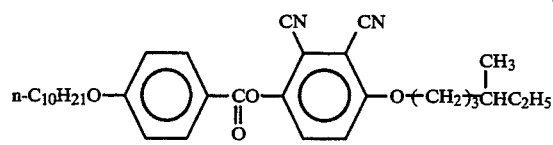 (6-21)
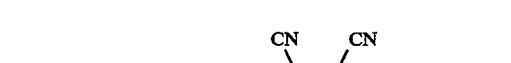 (6-22)
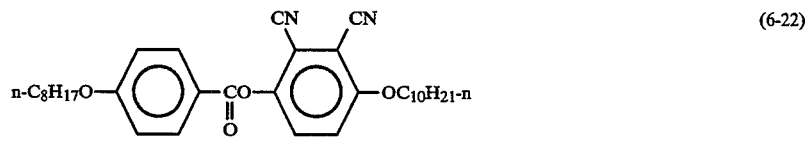 (6-23)
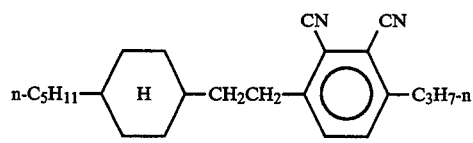 (6-24)
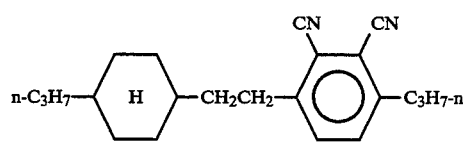 (6-25)
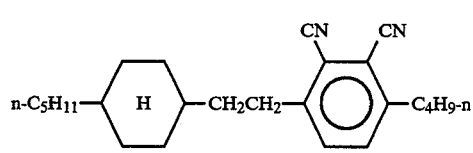 (6-26)
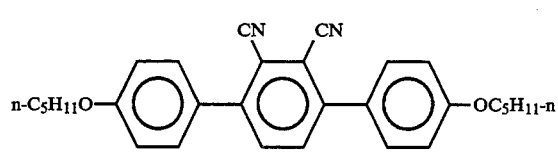 (6-27)
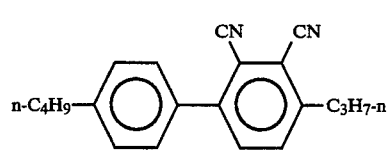 (6-28)
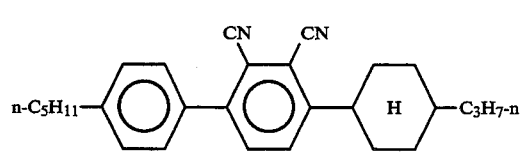 (6-29)
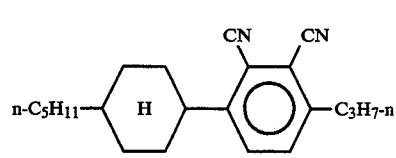 (6-30)
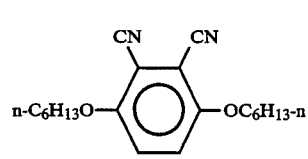 (6-31)

-continued
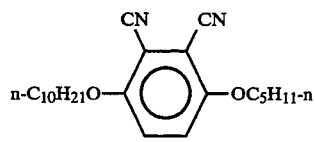 (6-32)
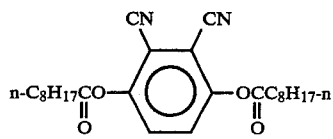 (6-33)
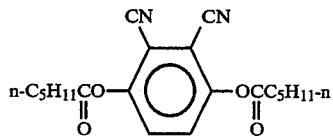 (6-34)
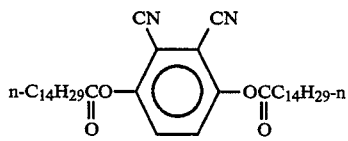 (6-35)
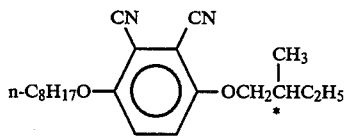 (6-36)
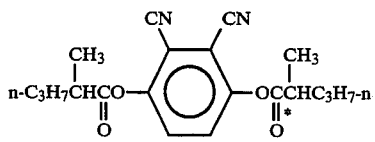 (6-37)
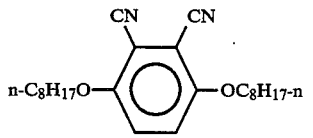 (6-38)
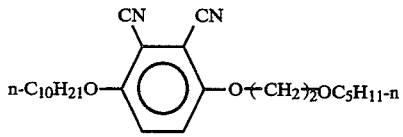 (6-39)
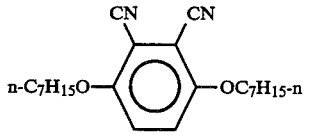 (6-40)
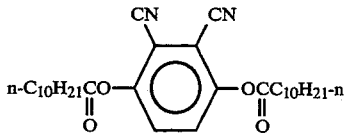 (6-41)
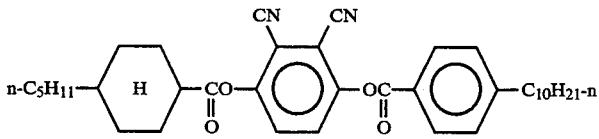 (6-42)

-continued
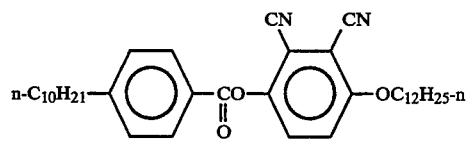 (6-43)
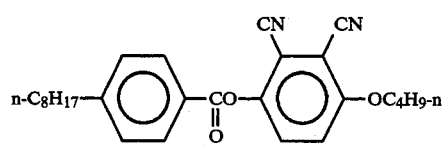 (6-44)
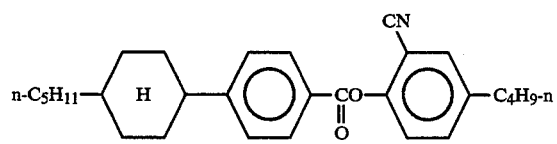 (6-45)
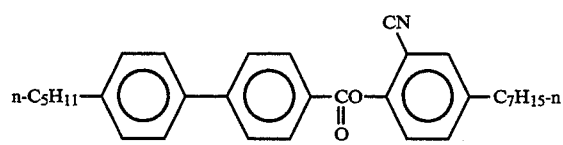 (6-46)
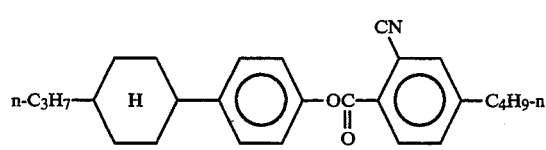 (6-47)
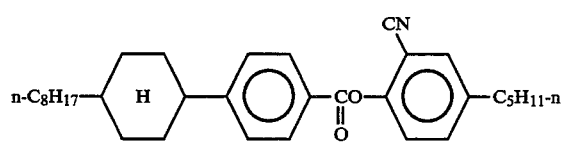 (6-48)
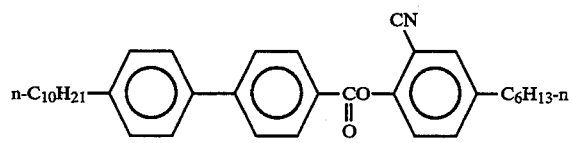 (6-49)
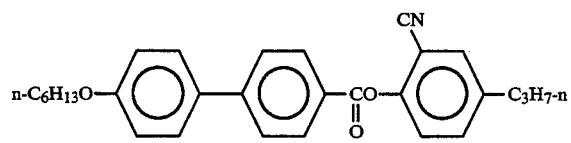 (6-50)
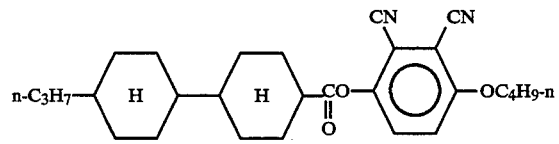 (6-51)
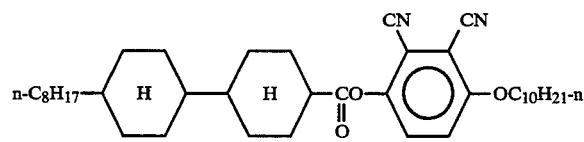 (6-52)
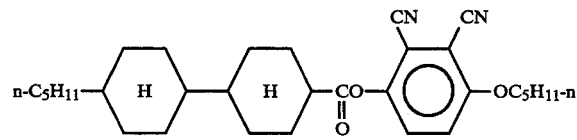 (6-53)

-continued
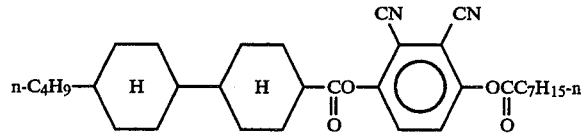 (6-54)
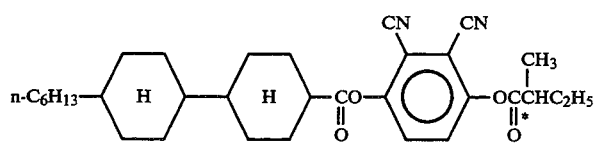 (6-55)
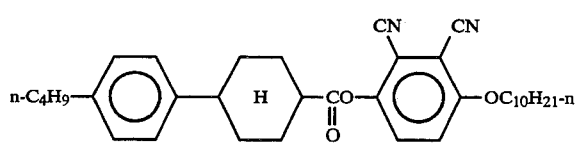 (6-56)
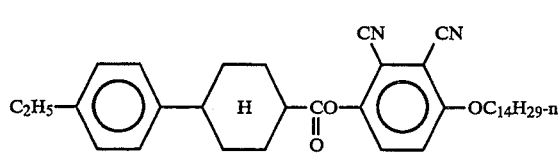 (6-57)
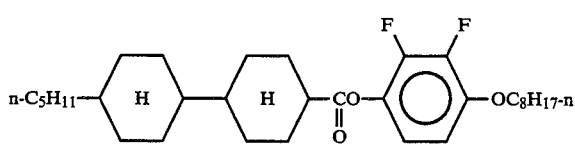 (6-58)
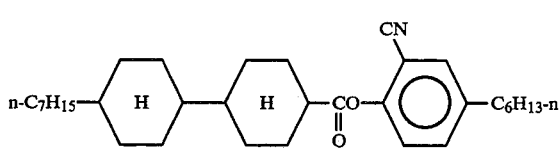 (6-59)
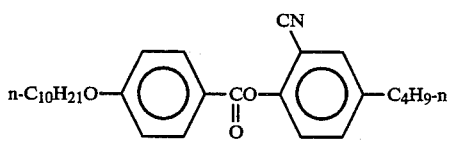 (6-60)
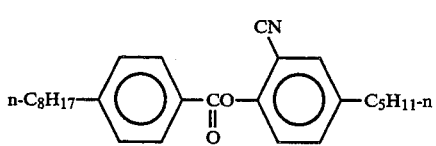 (6-61)
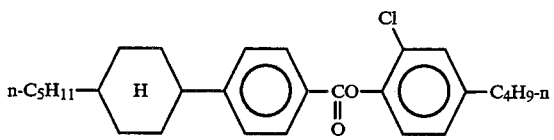 (6-62)
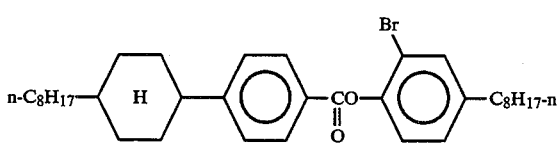 (6-63)
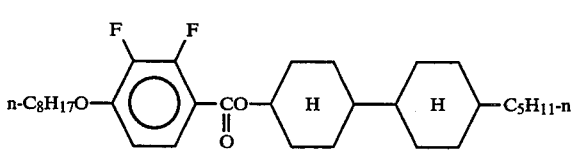 (6-64)

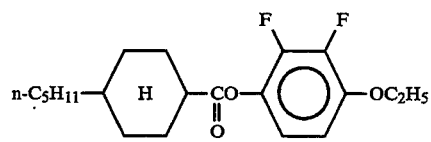 (6-65)
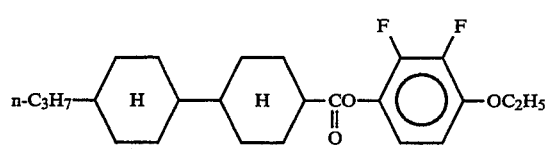 (6-66)
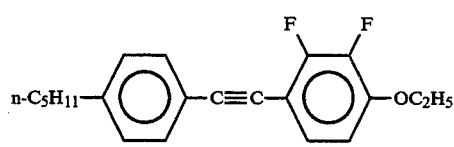 (6-67)
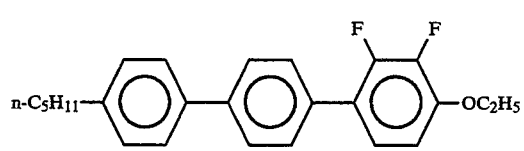 (6-68)
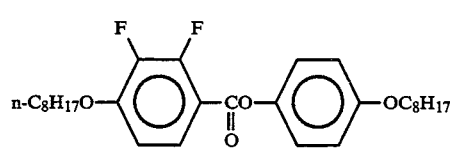 (6-69)
Formula (VI-2)
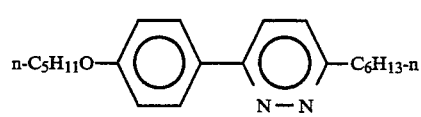 (6-70)
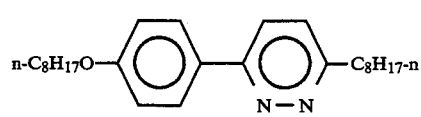 (6-71)
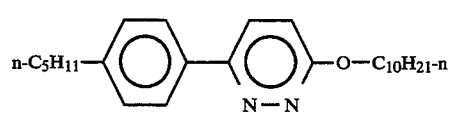 (6-72)
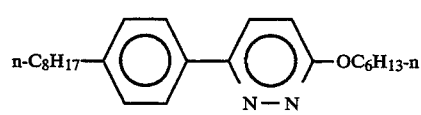 (6-73)
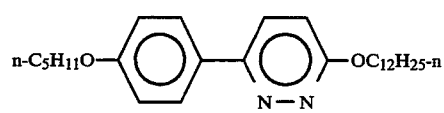 (6-74)
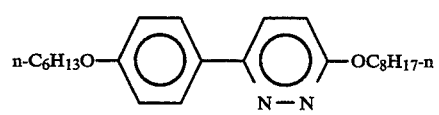 (6-75)
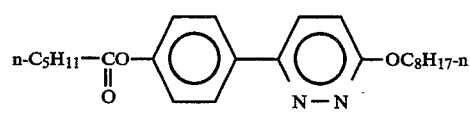 (6-76)

-continued
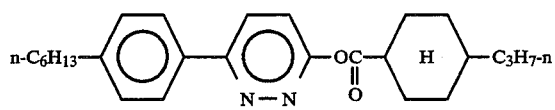 (6-77)
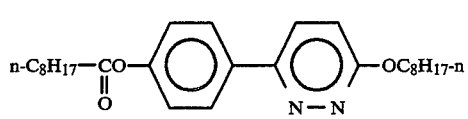 (6-78)
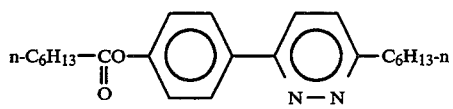 (6-79)
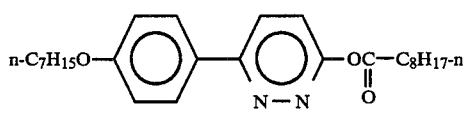 (6-80)
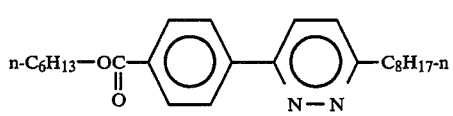 (6-81)
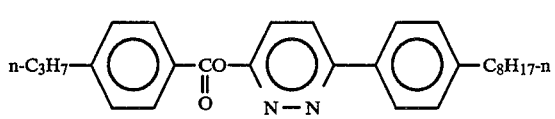 (6-82)
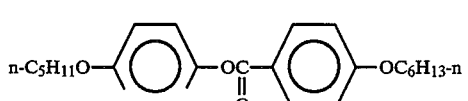 (6-83)
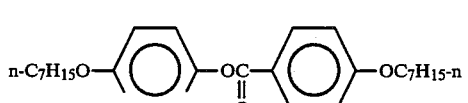 (6-84)
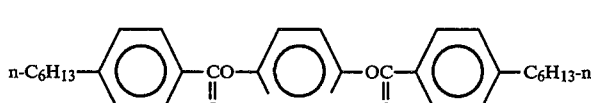 (6-85)
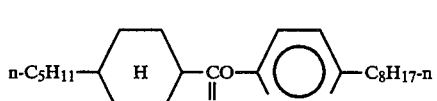 (6-86)
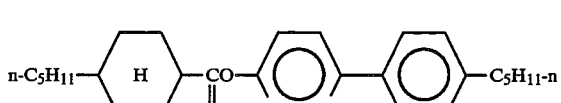 (6-87)
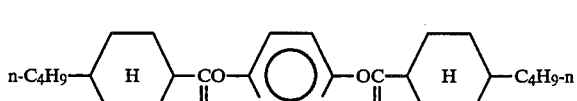 (6-88)
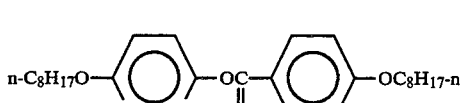 (6-89)
Formula (VI-3)

-continued
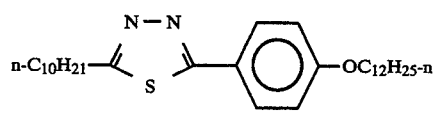 (6-90)
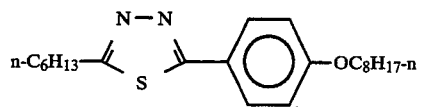 (6-91)
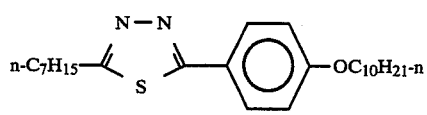 (6-92)
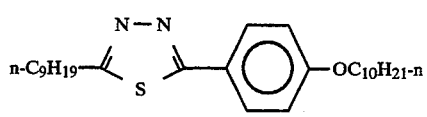 (6-93)
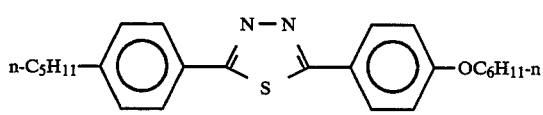 (6-94)
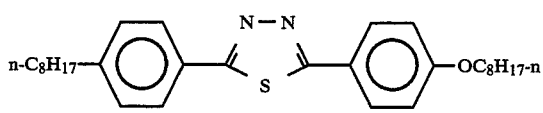 (6-95)
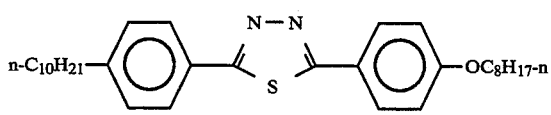 (6-96)
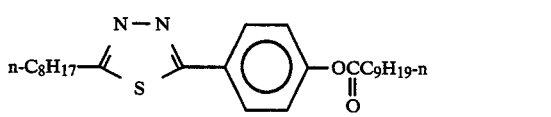 (6-97)
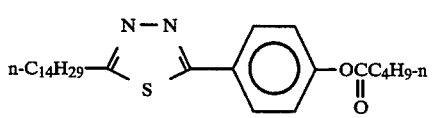 (6-98)
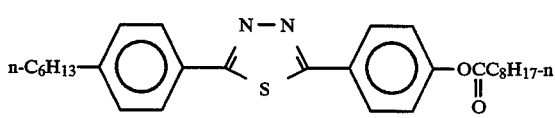 (6-99)
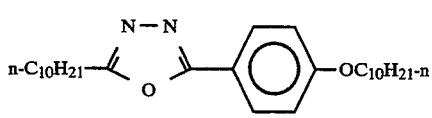 (6-100)
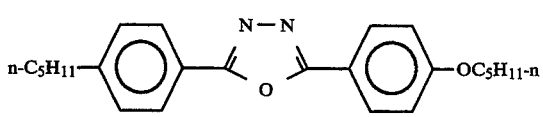 (6-101)
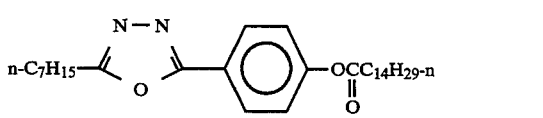 (6-102)

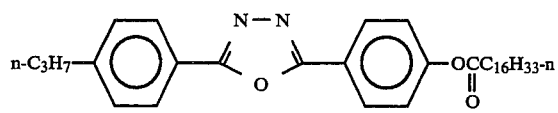 (6-103)
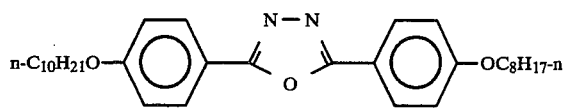 (6-104)
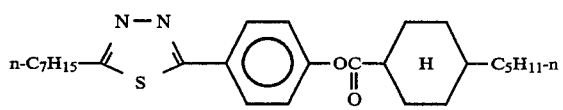 (6-105)
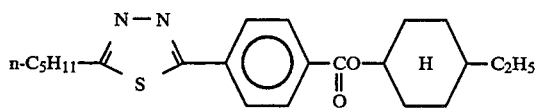 (6-106)
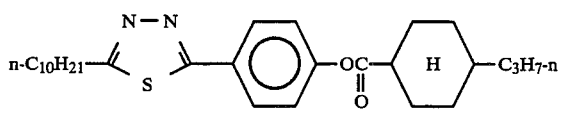 (6-107)
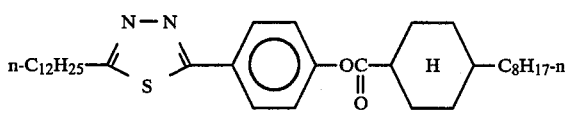 (6-108)
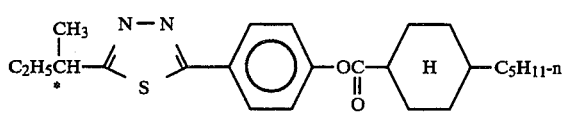 (6-109)
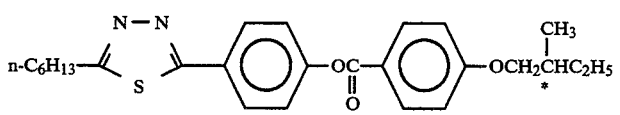 (6-110)
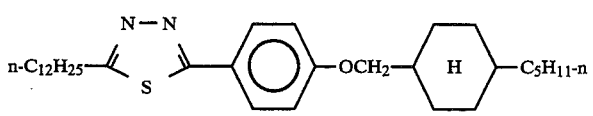 (6-111)
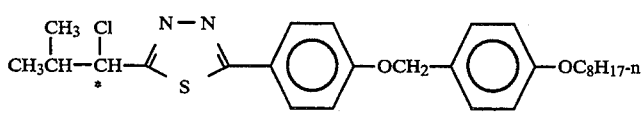 (6-112)
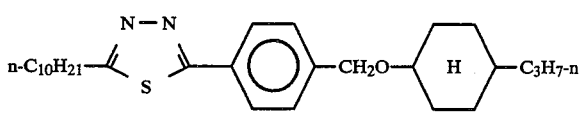 (6-113)
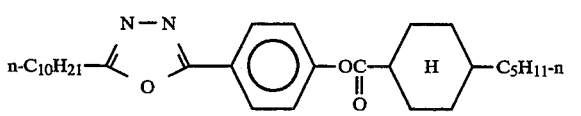 (6-114)
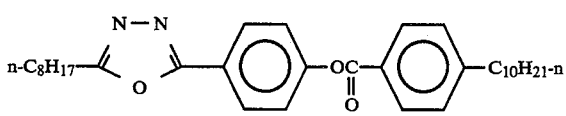 (6-115)

-continued (6-116) $C_2H_5CH(CH_2)_2$-[oxadiazole with CH$_3$, N=N, O]-⟨Ph⟩-O-C(=O)-⟨Ph⟩-OCH$_2$CH(CH$_3$)*OC$_2$H$_5$ (6-117) $C_2H_5CH(CH_3)$-[oxadiazole]-⟨Ph⟩-OCH$_2$-⟨Ph⟩-OC$_9$H$_{19}$-n (6-118) n-C$_6$H$_{13}$-[oxadiazole]-⟨Ph⟩-OCH$_2$-⟨H⟩-C$_2$H$_5$-n (6-119) n-C$_9$H$_{19}$-[oxadiazole]-⟨Ph⟩-CH$_2$O-⟨H⟩-C$_8$H$_{17}$-n (6-120) CH$_3$-[oxadiazole]-⟨Ph⟩-O-C(=O)-⟨Ph⟩-OC$_{12}$H$_{25}$-n Formula (VI-4)

(6-121) n-C$_4$H$_9$-⟨H⟩-⟨H⟩(CN)-C$_4$H$_9$-n (6-122) n-C$_8$H$_{17}$-⟨H⟩-⟨H⟩(CN)-C$_8$H$_{17}$-n (6-123) n-C$_7$H$_{15}$-⟨Ph⟩-⟨Ph⟩-⟨H⟩(CN)-C$_6$H$_{13}$-n (6-124) n-C$_8$H$_{17}$O-⟨Ph⟩-⟨Ph⟩-⟨H⟩(CN)-C$_8$H$_{17}$-n (6-125) n-C$_9$H$_{19}$O-⟨Ph⟩-⟨Ph⟩-⟨H⟩(CN)-C$_8$H$_{17}$-n (6-126) n-C$_8$H$_{17}$-⟨Ph⟩-⟨Ph⟩-⟨H⟩(CN)-C$_4$H$_9$-n (6-127) n-C$_{12}$H$_{25}$-⟨Ph⟩-⟨H⟩(CN)-C$_5$H$_{11}$-n (6-128) n-C$_7$H$_{15}$-⟨Ph⟩-⟨Ph⟩-⟨H⟩(CN)-C$_4$H$_9$-n

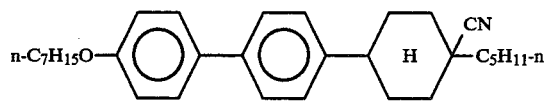 (6-129)
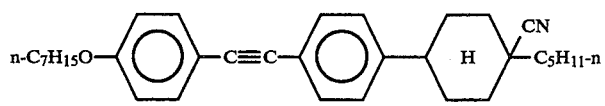 (6-130)
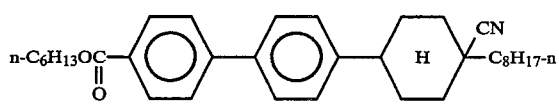 (6-131)
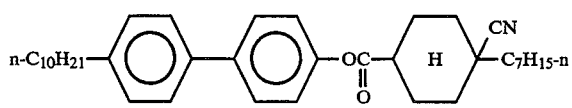 (6-132)
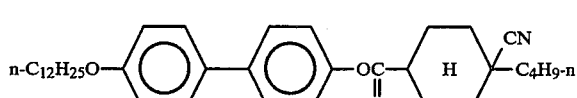 (6-133)
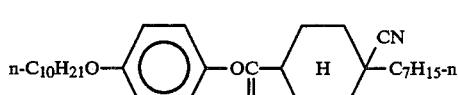 (6-134)
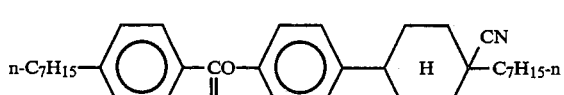 (6-135)
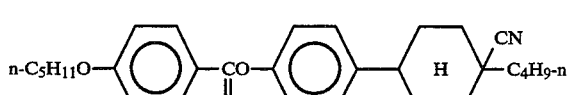 (6-136)
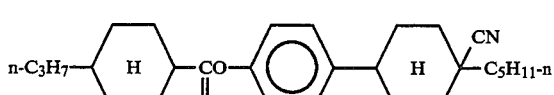 (6-137)
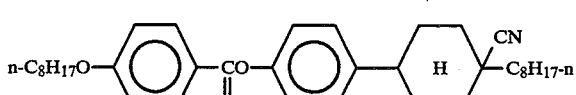 (6-138)
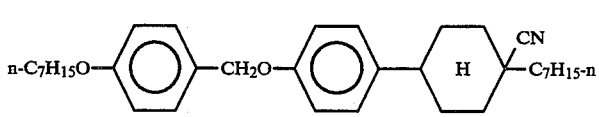 (6-139)
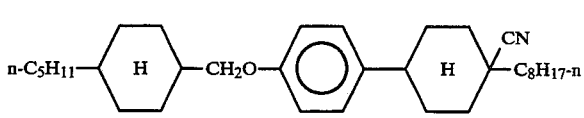 (6-140)
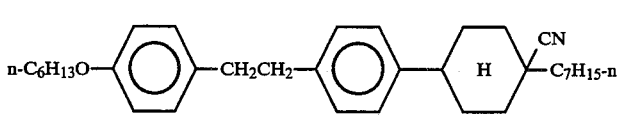 (6-141)
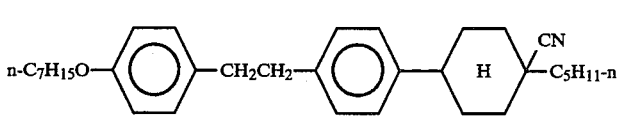 (6-142)

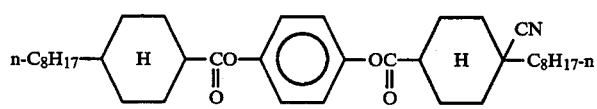 (6-143)
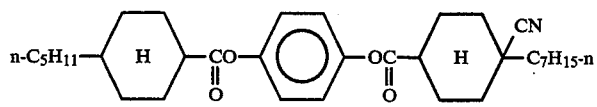 (6-144)
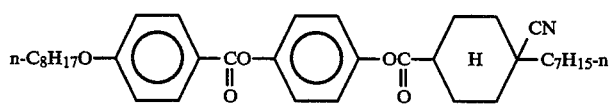 (6-145)
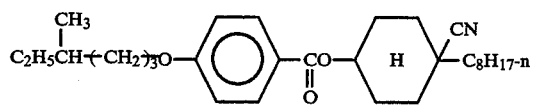 (6-146)
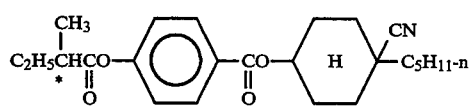 (6-147)
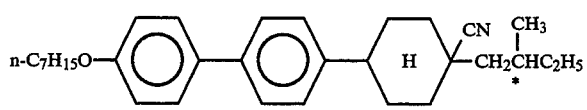 (6-148)
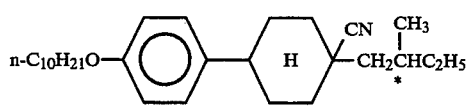 (6-149)
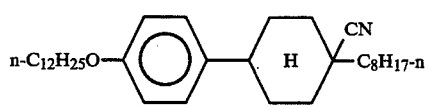 (6-150)
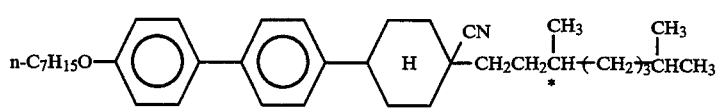 (6-151)
Formula (VI-5)
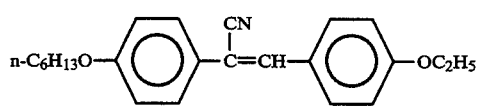 (6-152)
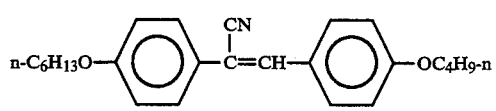 (6-153)
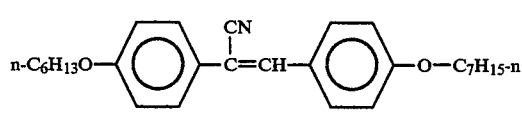 (6-154)
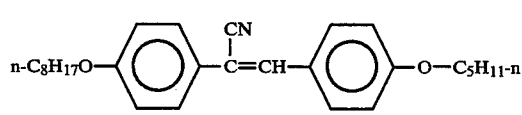 (6-155)

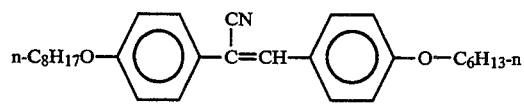 (6-156)
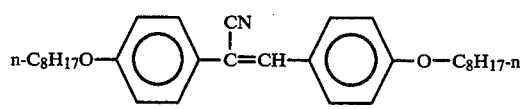 (6-157)
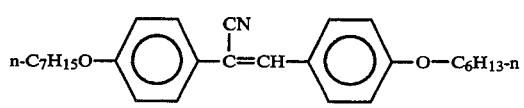 (6-158)
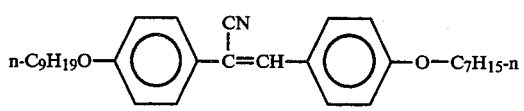 (6-159)
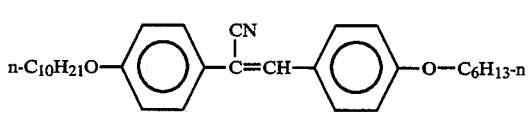 (6-160)
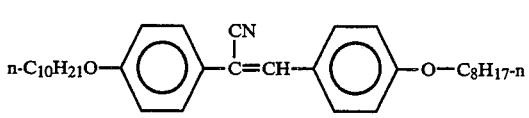 (6-161)
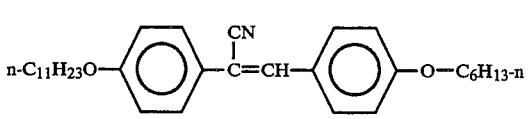 (6-162)
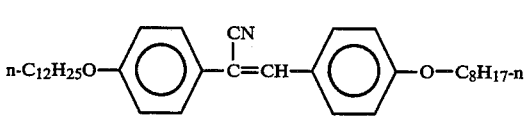 (6-163)
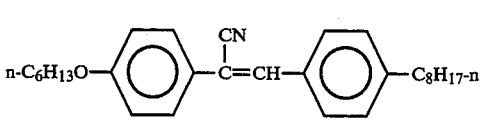 (6-164)
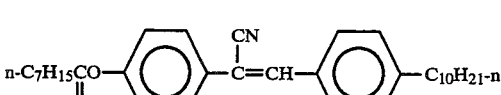 (6-165)
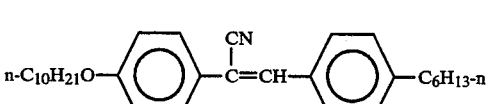 (6-166)
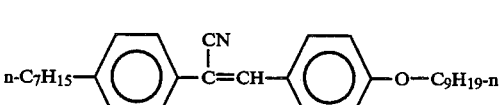 (6-167)
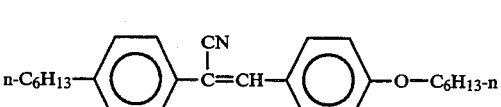 (6-168)
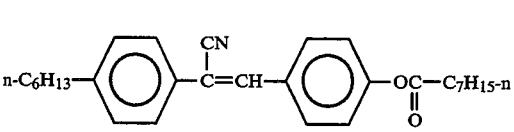 (6-169)

-continued
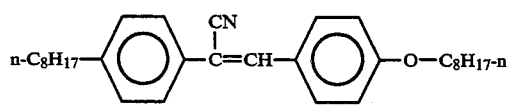 (6-170)
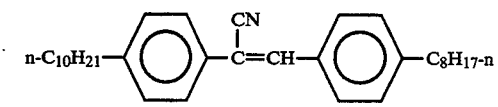 (6-171)
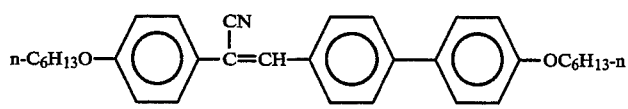 (6-172)
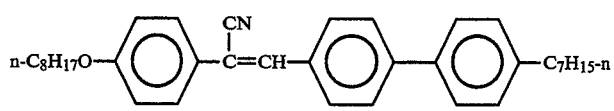 (6-173)
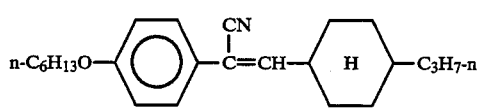 (6-174)
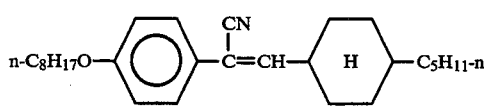 (6-175)
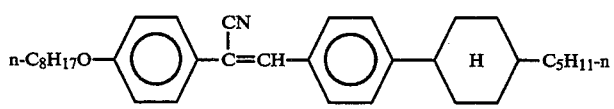 (6-176)
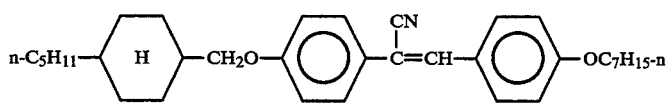 (6-177)
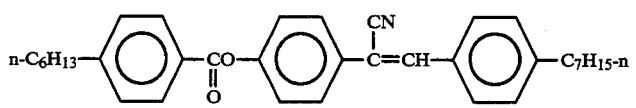 (6-178)
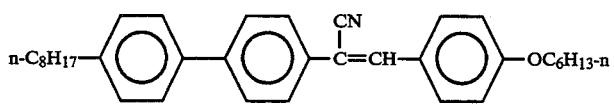 (6-179)
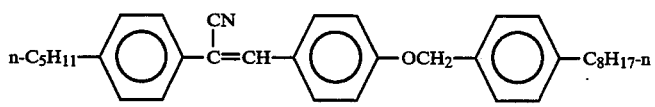 (6-180)
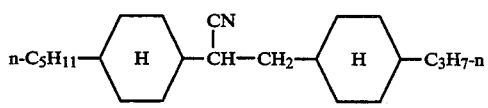 (6-181)
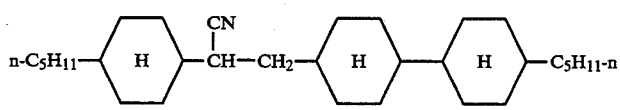 (6-182)

-continued

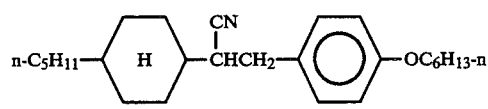 (6-183)

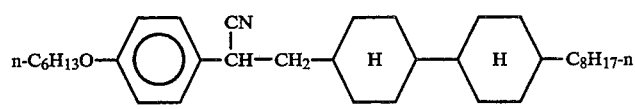 (6-184)

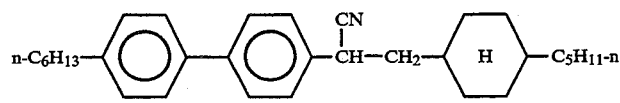 (6-185)

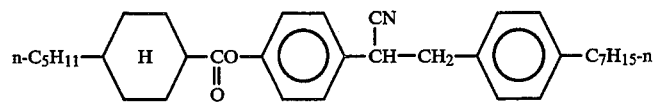 (6-186)

The mesomorphic compound having a negative dielectric anisotropy Ae may preferably have $\Delta\epsilon < -2$, preferably $\Delta\epsilon < -5$, further preferably $\Delta\epsilon < -10$.

The liquid crystal composition according to the present invention may be obtained by mixing at least one species of the compound represented by the formula (I), at least one species of the compound represented by the formula (II), optically at least one species of the compound represented by any one of the formulas (III)–(V) and/or at least one species of a mesomorphic compound having a negative dielectric anisotropy, and another mesomorphic compound in appropriate proportions. The liquid crystal composition according to the present invention may preferably be formulated as a ferroelectric liquid crystal composition, particularly a ferroelectric chiral smectic liquid crystal composition.

Specific examples of another mesomorphic compound as described above may include those denoted by the following structure formulas.

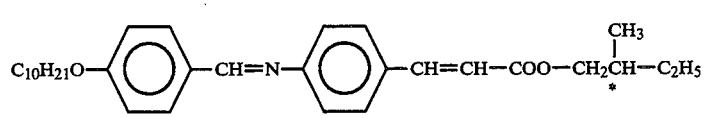 (1)

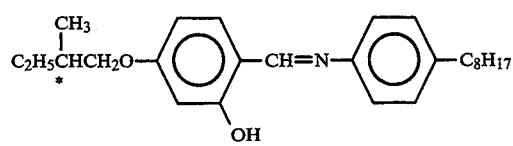 (2)

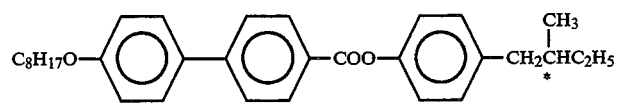 (3)

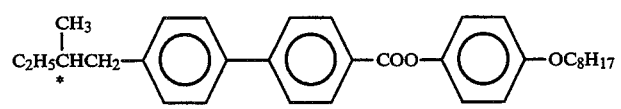 (4)

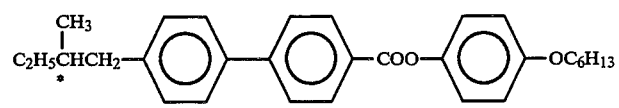 (5)

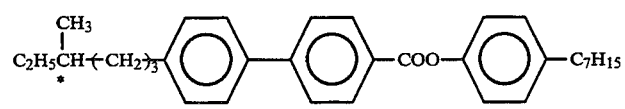 (6)

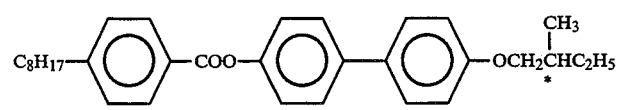 (7)

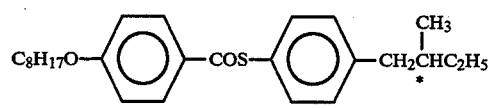 (8)
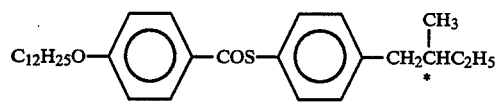 (9)
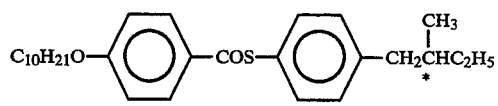 (10)
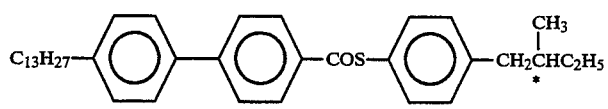 (11)
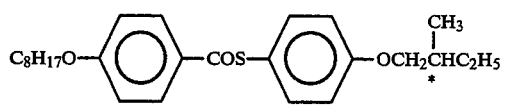 (12)
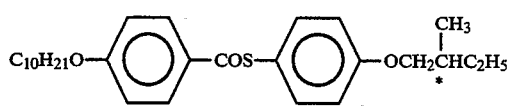 (13)
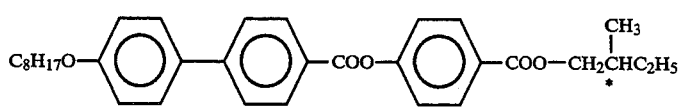 (14)
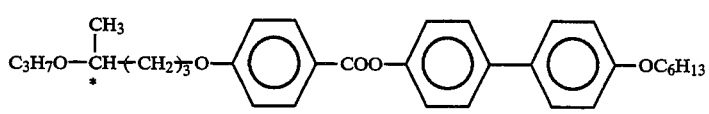 (15)
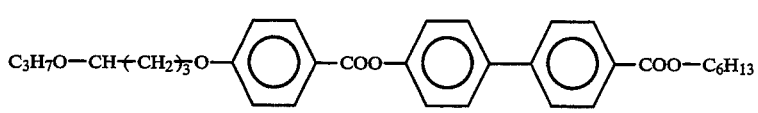 (16)
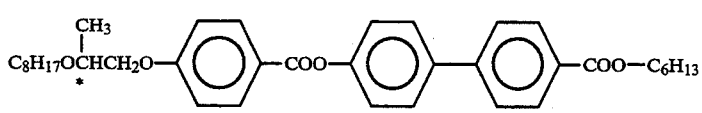 (17)
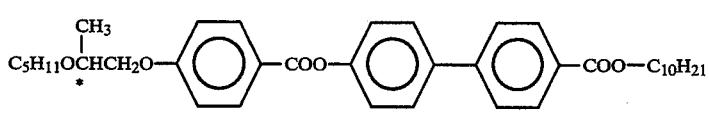 (18)
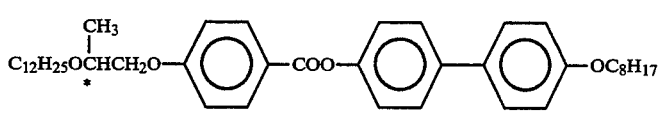 (19)
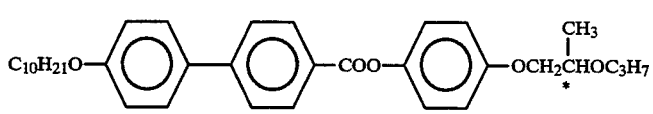 (20)
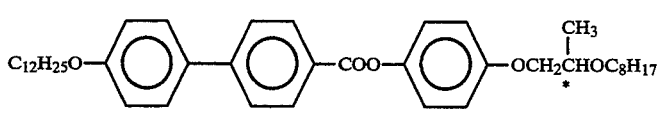 (21)

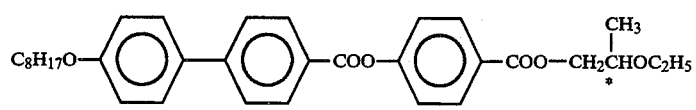 (22)
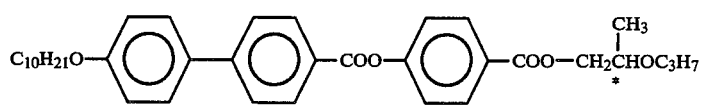 (23)
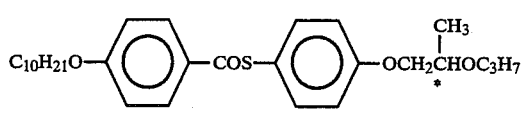 (24)
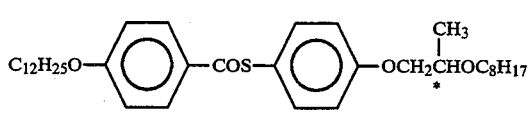 (25)
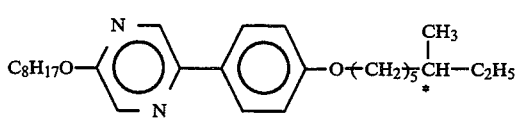 (26)
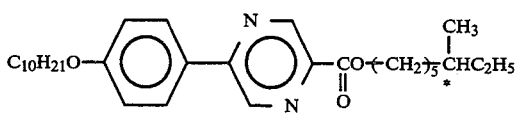 (27)
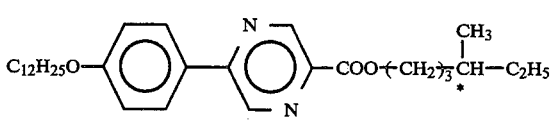 (28)
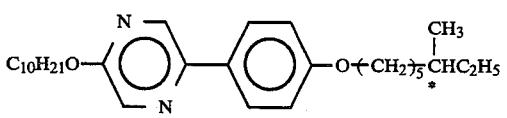 (29)
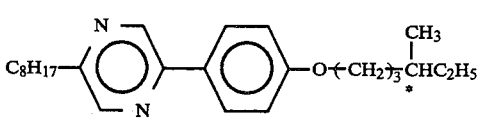 (30)
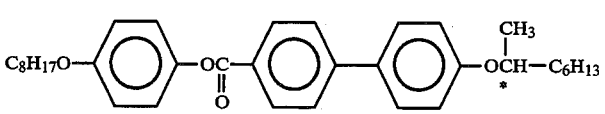 (31)
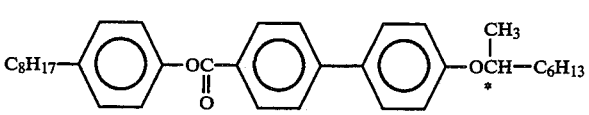 (32)
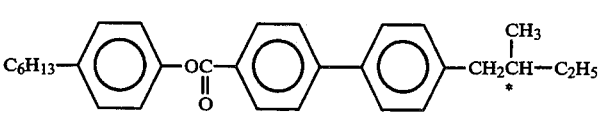 (33)
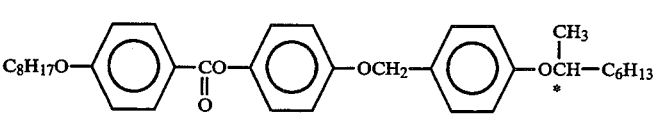 (34)

-continued
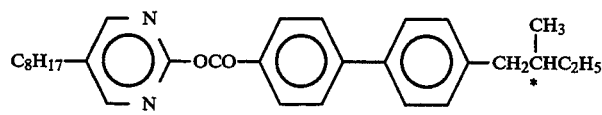 (35)
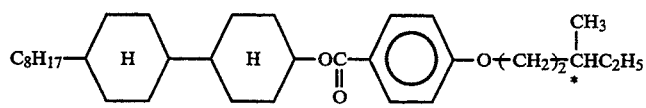 (36)
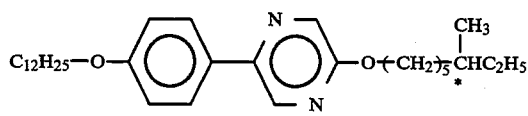 (37)
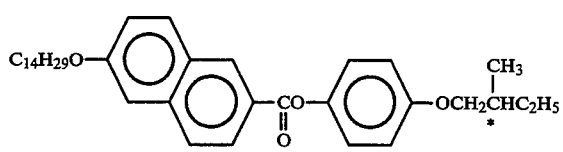 (38)
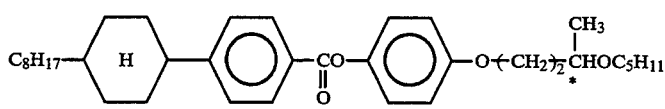 (39)
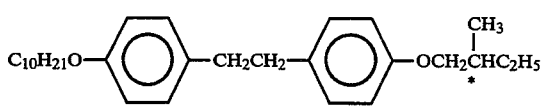 (40)
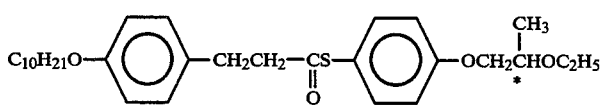 (41)
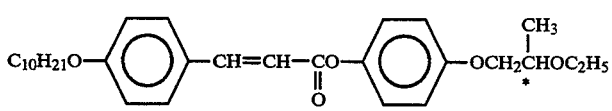 (42)
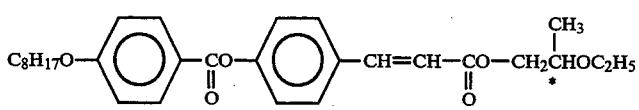 (43)
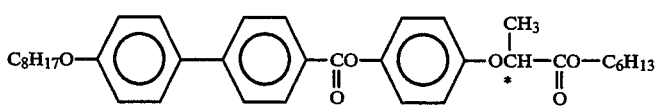 (44)
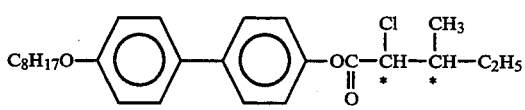 (45)
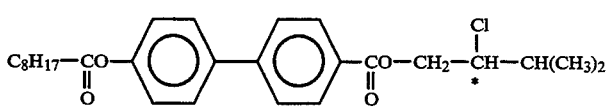 (46)
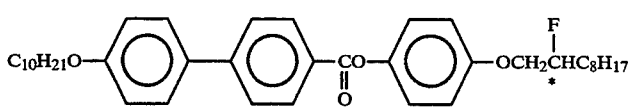 (47)

-continued
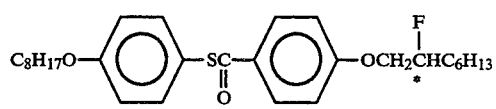 (48)
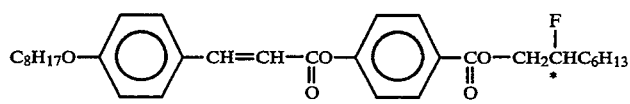 (49)
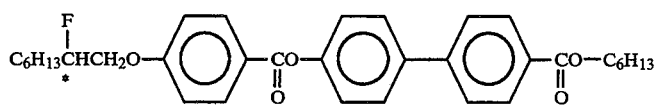 (50)
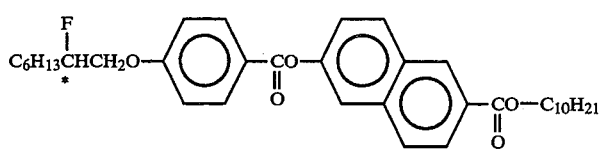 (51)
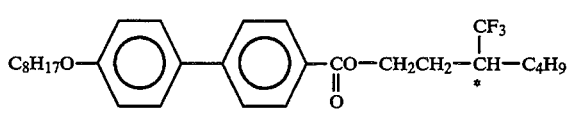 (52)
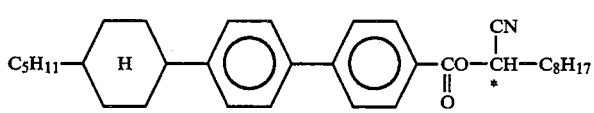 (53)
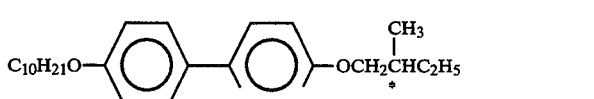 (54)
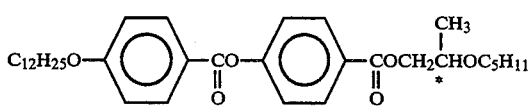 (55)
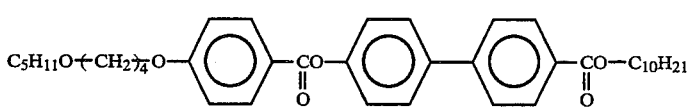 (56)
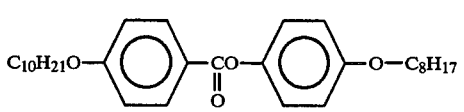 (57)
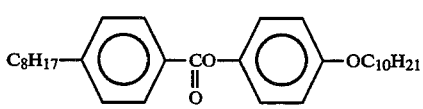 (58)
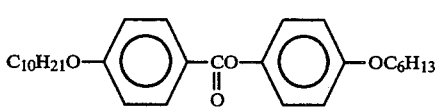 (59)
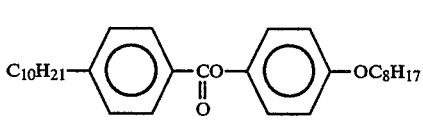 (60)

-continued
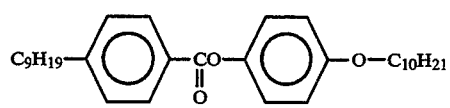 (61)
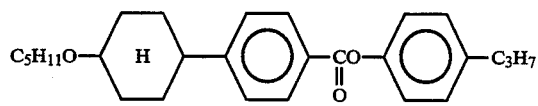 (62)
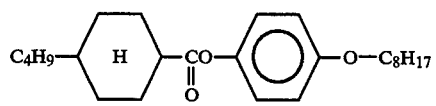 (63)
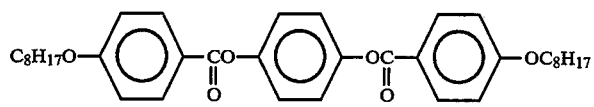 (64)
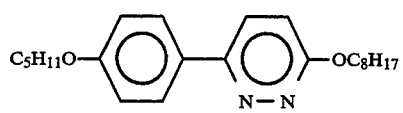 (65)
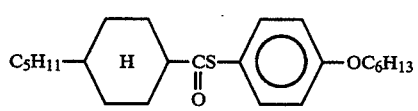 (66)
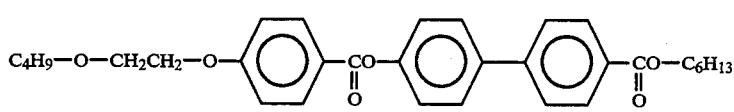 (67)
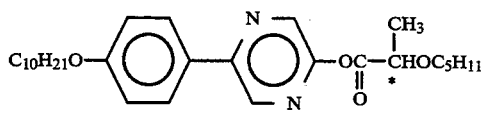 (68)
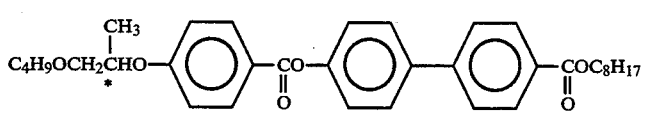 (69)
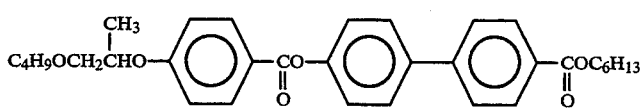 (70)
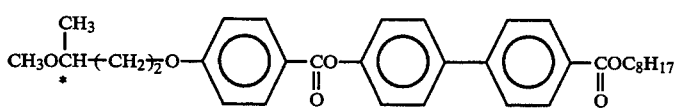 (71)
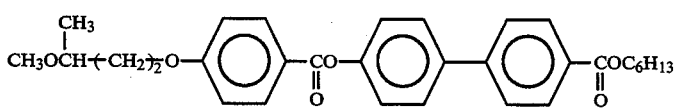 (72)
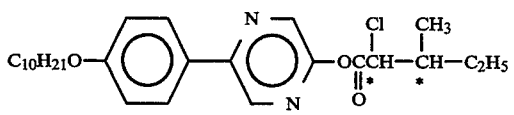 (73)

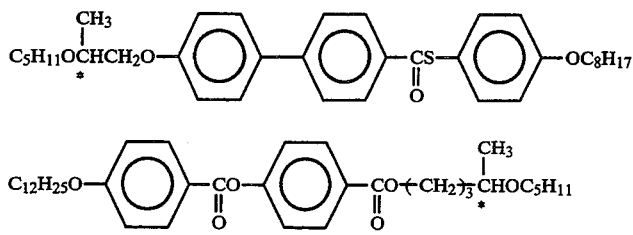

(74)

(75)

In formulating the liquid crystal composition according to the present invention, it is desirable to mix 1–300 wt. parts each, preferably 2–100 wt. parts each, of a compound represented by the formula (I) and a compound represented by the formula (II) (and optionally a compound represented by any of the formulas (III)-(V)) with 100 wt. parts of another mesomorphic compound as mentioned above which can be composed of two or more species.

Further, when two or more species of either one or both (or three or more) of the compounds represented by the formulas (I) and (II) (and (III)-(V)) are used, the two or more species of the compound of the formula (I) or (II) (or (III)-(V)) may be used in a total amount of 1–500 wt. parts, preferably 2–100 wt. parts, per 100 wt. parts of another mesomorphic compound as described above which can be composed of two or more species.

Further, the weight ratio of the compound of the formula (I)/the compound of the formula (II)(/the compound of the formula (III)-(V)) may desirably be 1–300-/1–300(/1–300), preferably 1–50/1–50(/1–50). When two or more species each of the compounds of the formulas (I) and (II) (and optionally (III)-(V)) are used, the weight ratio of the total amount of the compounds of the formula (I)/the total amounts of the compounds of the formula (II) (/the total amount of the compounds of any of the formula (III)-(V)) may desirably be 1–500-/1–500(/1–500), preferably 1–50/1–50(/1–50).

Further, the total amounts of the compounds of the formulas (I) and (II) (and optionally any of (III) to (V)) may desirably be 3–900 wt. parts, preferably 6–300 wt. parts, when one species each is selected from the formulas (I) and (II) (and any of (III) to (V)), or 3–1500 wt. parts, preferably 6–300 wt. parts, when two or more species are selected from at least one of the formulas (I), (II) and (III) to (V), respectively, with respect to 100 wt. parts of the above-mentioned another mesomorphic compound which may be composed or two or more species.

Further, a mesomorphic compound having a negative dielectric anisotropy as described above can be contained in a proportion of 1–98 wt. % of the liquid crystal composition of the present invention so as to provide a composition having a negative dielectric anisotropy. Particularly, when a mesomorphic compound having $< -2$ is used, it may be contained in a proportion of 1–70 wt. %, preferably 1–50 wt. %, of the liquid crystal composition of the present invention.

Further, the total of the compounds of the formulas (I) and (II) (and (III)-(V)) and the mesomorphic compound having a negative dielectric anisotropy can constitute 3–100 wt. % of the liquid crystal composition of the present invention.

The ferroelectric liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the ferroelectric liquid crystal device prepared as described above for explanation of the structure thereof.

Referring to FIG. 1, the ferroelectric liquid crystal device includes a ferroelectric liquid crystal layer I disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a selection of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer may have a thickness of ordinarily 30 Å–1 micron, preferably 30–3000 Å, further preferably 50–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer 1 in a thickness of generally 0.5 to 20 microns, preferably 1 to 5 microns.

The ferroelectric liquid crystal provided by the composition of the present invention may desirably assume a SmC* phase (chiral smectic C phase) in a wide temperature range including room temperature (particularly, broad in a lower temperature side) and also shows wide drive voltage margin and drive temperature margin when contained in a device.

Particularly, in order to show a good alignment characteristic to form a uniform monodomain, the ferroelectric liquid crystal may show a phase transition series comprising isotropic phase—Ch phase (cholesteric phase)—SmA phase (smectic A phase) SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
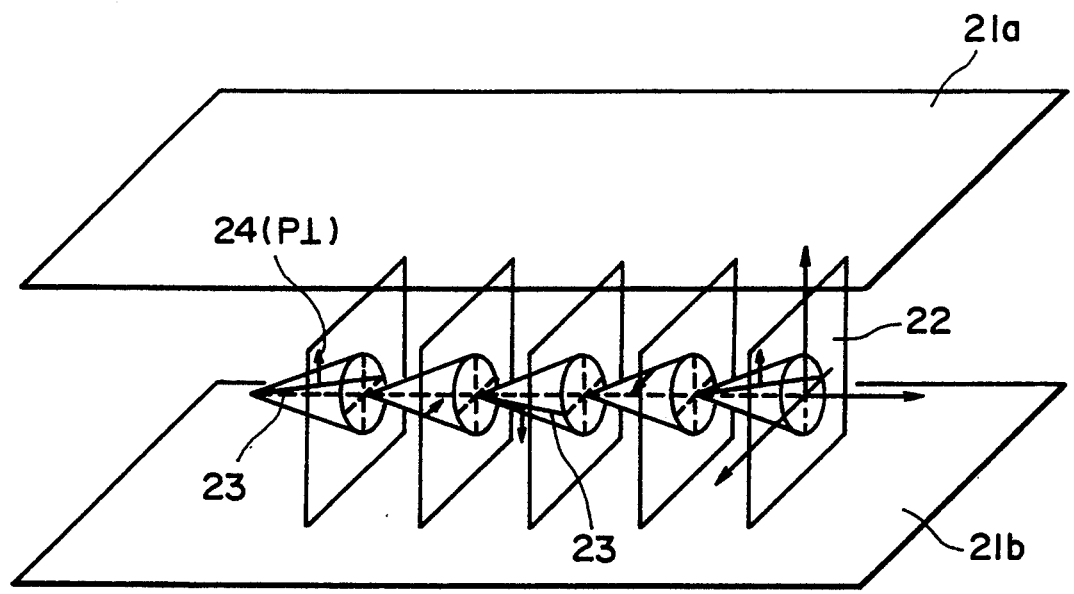
FIGS. 2 and 3 are schematic perspective views of a device cell embodiment for illustrating the operation principle of a ferroelectric liquid crystal device.

FIG. 2 is a schematic illustration of a ferroelectric liquid crystal cell (device) for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
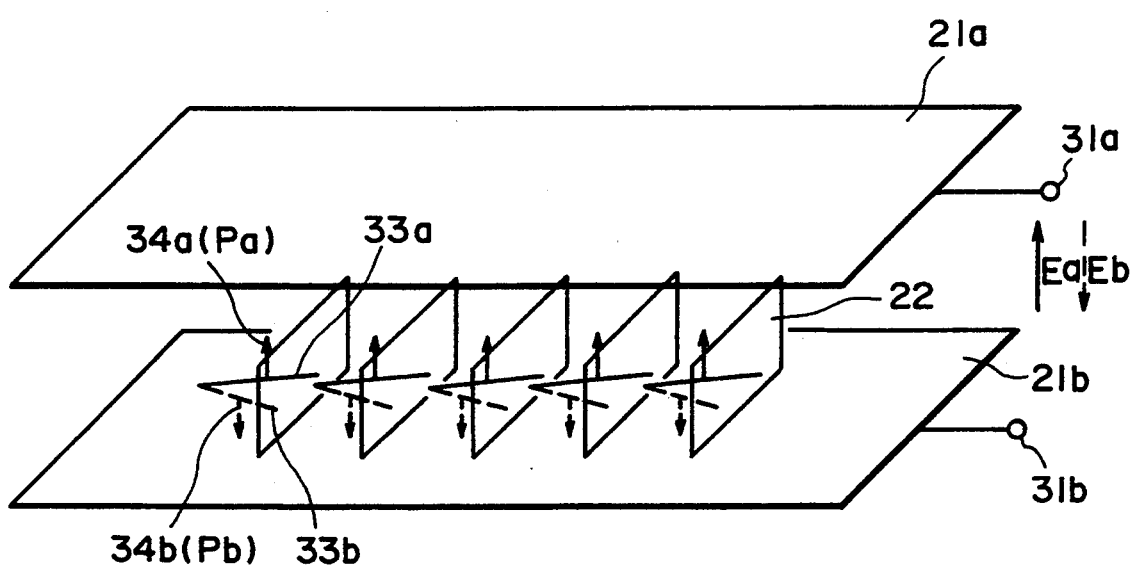
Figure 4:
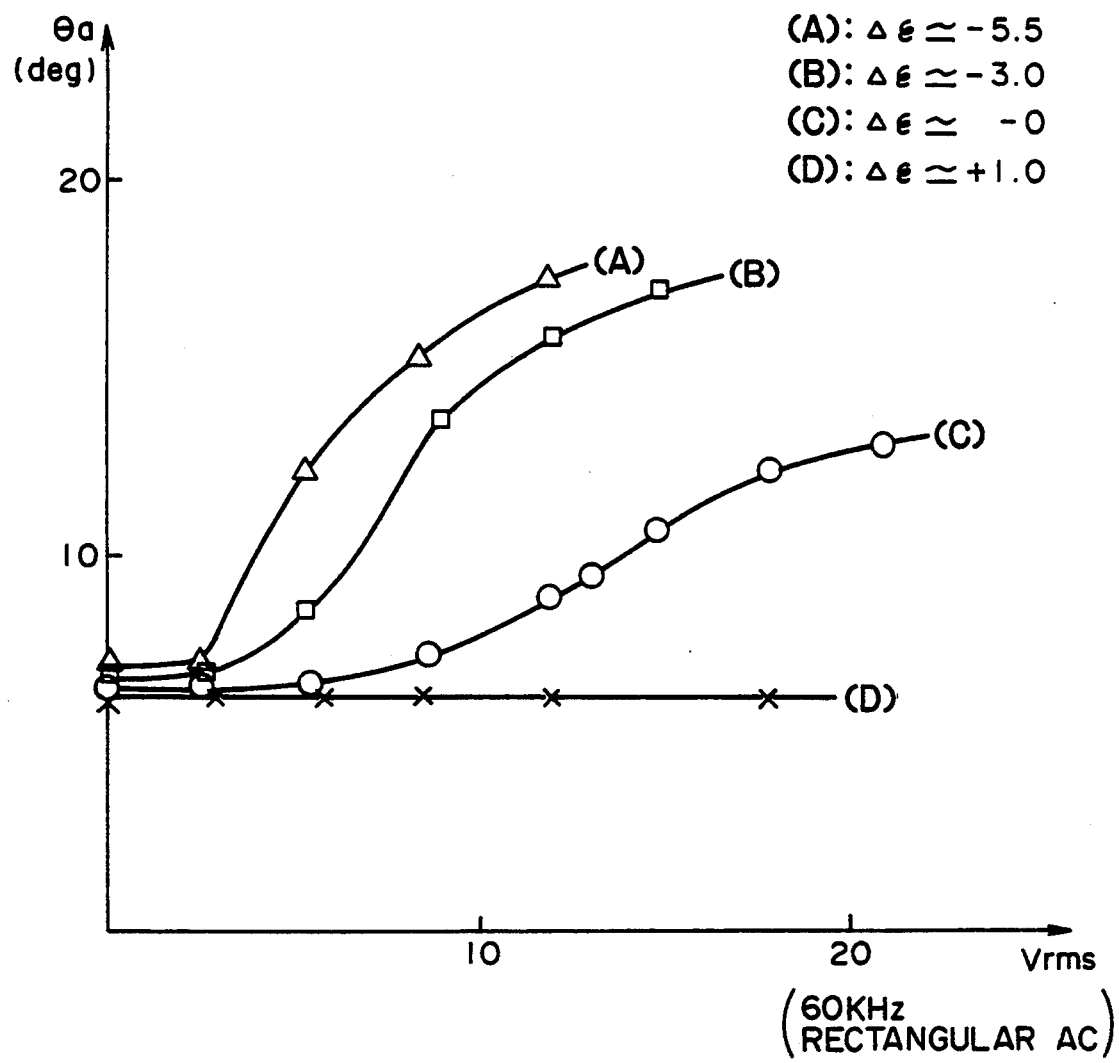
FIG. 4 is a graph showing changes in tilt angle $\theta$a versus effective voltage Vrms with respect to several ferroelectric liquid crystals having different values of dielectric anisotropy $\Delta\epsilon$.

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

When such a ferroelectric liquid crystal device comprising a ferroelectric liquid crystal composition as described above between a pair of electrode plates is constituted as a simple matrix display device, the device may be driven by a driving method as disclosed in Japanese Laid-Open Patent Applications (KOKAI) Nos. 193426/1984, 193427/1984, 156046/1985, 156047/1985, etc.

Hereinbelow, the present invention will be explained more specifically with reference to examples. It is however to be understood that the present invention is not restricted to these examples.

EXAMPLE 1

A liquid crystal composition 1-A was prepared by mixing the following compounds in respectively indicated proportions.

| Ex. Compound No. | Structural formula | Wt. parts |
|---|---|---|
| 8 | $C_8H_{17}O$—⟨⟩—COS—⟨⟩—$CH_2\overset{*}{C}HC_2H_5$ (with $CH_3$ branch) | 45 |

-continued

| Ex. Compound No. | Structural formula | Wt. parts |
| --- | --- | --- |
| 9 | 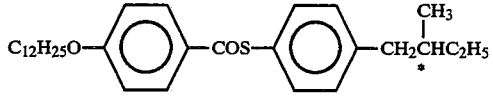 | 45 |
| 12 | 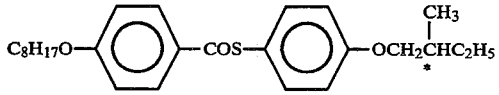 | 15 |
| 13 | 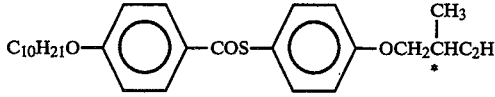 | 15 |
| 17 | 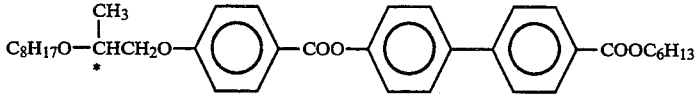 | 30 |
| 18 | 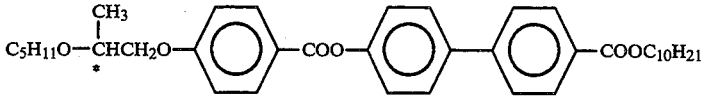 | 30 |
| 67 | 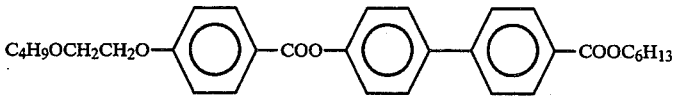 | 10 |

A liquid crystal composition 1-B was prepared by mixing the following example compounds 1-1 and 2-3 with the above prepared composition 1-A.

| Ex. Comp. No. | Structural formula | Wt. parts |
| --- | --- | --- |
| 1-1 | 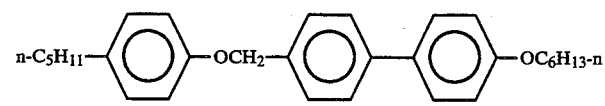 | 10 |
| 2-3 | 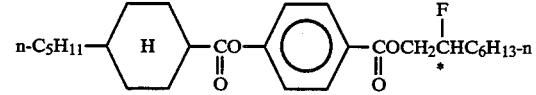 | 10 |
| Composition 1-A | | 80 |

The above-prepared liquid crystal composition 1-B was used to prepare a liquid crystal device in combination with a blank cell prepared in the following manner.

Two 1.1 mm-thick glass plates were provided and respectively coated with an ITO film to form an electrode for voltage application, which was further coated with an insulating layer of vapor-deposited $SiO_2$. The insulating layer was further coated with a 1.0 %-solution of polyimide resin precursor (SP-510, available from Toray K.K.) in dimethylacetoamide by a spinner coater rotating at 3000 rpm for 15 seconds. Thereafter, the coating film was subjected to heat curing at 300° C. for 60 min. to obtain about 120 Å-thick film. The coating film was rubbed with acetate fiber-planted cloth. The thus treated two glass plates were washed with isopropyl alcohol. After silica beads with an average particle size of 1.5 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 1.5 microns as measured by a Berek compensator.

Then, the above-prepared liquid crystal composition 1-B was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of an optical response time (time from voltage application until the transmittance change reaches 90% of the maximum) at specified temperatures under the application of a peak-to-peak voltage Vpp of 25 volts. The results are shown below.

|  | 10° C. | 25° C. | 40° C. |
|---|---|---|---|
| Response time | 960 μsec | 265 μsec | 85 μsec |

Further, a contrast of 12 was attained at 25° C. during the driving, and a clear switching function was observed.

dence of response speed (ratio of response time (10° C./40° C.)).

EXAMPLE 2

A liquid crystal composition 2-B was prepared by mixing the following example compounds in the indicated proportions with the liquid crystal composition 1-A prepared in Example 1.

| Ex. Comp. No. | Structural formula | wt. parts |
|---|---|---|
| 1-5 | n-$C_4H_9$—⬡—$OCH_2$—⬡—⬡—O—$C_6H_{13}$-n | 5 |
| 1-24 | n-$C_5H_{11}$—⬡—$CH_2O$—⬡—⬡—CO—$C_8H_{17}$-n (C=O) | 5 |
| 1-37 | n-$C_8H_{17}$—⬡—$OCH_2$—⬡—⬡—$CH_2CHC_2H_5$ ($CH_3$) * | 5 |
| 2-26 | n-$C_{10}H_{21}$—⟨N=N⟩—⬡—$OCH_2CHC_2H_5$ (F) * | 6 |
| 2-54 | n-$C_{12}H_{25}$—⟨N=N⟩—⬡—$OCH_2CHC_6H_{13}$ (F) * | 6 |
| Composition 1-A | | 73 |

COMPARATIVE EXAMPLE 1

A liquid crystal composition 1-C was prepared by omitting Example compound No. 1-1 from the liquid crystal composition 1-B, i.e., by adding only Example compound No. 2-3 to the liquid crystal composition 1-A, and a liquid crystal composition 1-D was prepared by omitting Example compound No. 2-3 from the composition 1-B, i.e., by adding only Example compound No. 1-1 to the composition 1-A.

Ferroelectric liquid crystal devices 1-A, 1-C and 1-D were prepared by using the compositions 1-A, 1-C and 1-D, respectively, instead of the composition 1-B, and subjected to measurement of optical response time, otherwise in the same manner as in Example 1. The results are shown below.

|  | Response time | | |
|---|---|---|---|
|  | 10° C. | 25° C. | 40° C. |
| 1-A | 1600 μsec | 430 μsec | 120 μsec |
| 1-C | 1150 μsec | 290 μsec | 90 μsec |
| 1-D | 1380 μsec | 380 μsec | 110 μsec |

As apparent from the above Example 1 and Comparative Example 1, the ferroelectric liquid crystal device containing the liquid crystal composition 1-B according to the present invention provided improved response speed and operation characteristic at a lower temperature and also provided a descreased temperature dependence of response speed (ratio of response time (10° C./40° C.)).

A ferroelectric liquid crystal device was prepared in the same manner as in Example 1 except that the above liquid crystal composition 2-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 940 μsec | 260 μsec | 85 μsec |

Further, a contrast of 13 was attained at 25° C. during the driving, and a clear switching function was observed. The bistability after termination of the voltage application was also good.

COMPARATIVE EXAMPLE 2

A liquid crystal composition 2-C was prepared by omitting Example compounds Nos. 1-5, 1-24 and 1-37 from the liquid crystal composition 2-B, i.e., by adding only Example compounds Nos. 2-26 and 2-54 to the liquid crystal composition 1-A, and a liquid crystal composition 2-D was prepared by omitting Example compounds Nos. 2-26 and 2-54 from the composition 1-B, i.e., by adding only Example compounds Nos. 1-5, 1-24 and 1-37 to the composition 1-A.

Ferroelectric liquid crystal devices 2-C and 2-D were prepared by using the compositions 2-C and 2-D, respectively, instead of the composition 1-B, and subjected to measurement of optical response time, otherwise in the same manner as in Example 1. The results are shown below.

|  | Response time | | |
|---|---|---|---|
|  | 10° C. | 25° C. | 40° C. |
| 2-C | 1500 μsec | 275 μsec | 95 μsec |
| 2-D | 1300 μsec | 330 μsec | 110 μsec |

As apparent from the above Example 2 and Comparative Example 2, the ferroelectric liquid crystal device containing the liquid crystal composition 2-B according to the present invention provided improved response speed and operation characteristic at a lower temperature and also provided a descreased temperature dependence of response speed.

EXAMPLE 3

A liquid crystal composition 3-A was prepared by mixing the following compounds in respectively indicated proportions.

| Ex. Compound No. | Structural formula | wt. parts |
|---|---|---|
| 8 | $C_8H_{17}O$—⌬—COS—⌬—$CH_2\overset{CH_3}{\underset{*}{C}H}C_2H_5$ | 40 |
| 9 | $C_{12}H_{25}O$—⌬—COS—⌬—$CH_2\overset{CH_3}{\underset{*}{C}H}C_2H_5$ | 40 |
| 12 | $C_8H_{17}O$—⌬—COS—⌬—$OCH_2\overset{CH_3}{\underset{*}{C}H}C_2H_5$ | 15 |
| 13 | $C_{10}H_{21}O$—⌬—COS—⌬—$OCH_2\overset{CH_3}{\underset{*}{C}H}C_2H_5$ | 15 |
| 17 | $C_8H_{17}O\overset{CH_3}{\underset{*}{C}H}CH_2O$—⌬—COO—⌬—⌬—$COOC_6H_{13}$ | 25 |
| 18 | $C_5H_{11}O\overset{CH_3}{\underset{*}{C}H}CH_2O$—⌬—COO—⌬—⌬—$COOC_{10}H_{21}$ | 25 |
| 67 | $C_4H_9OCH_2CH_2O$—⌬—COO—⌬—⌬—$COOC_6H_{13}$ | 10 |
| 57 | $C_{10}H_{21}O$—⌬—COO—⌬—$OC_8H_{17}$ | 5 |
| 60 | $C_{10}H_{21}$—⌬—COO—⌬—$OC_8H_{17}$ | 5 |

A liquid crystal composition 3-B was prepared by mixing the following example compounds 1-1 and 2-3 with the above prepared composition 3-A.

| Ex. Comp. No. | Structural formula | wt. parts |
|---|---|---|
| 1-1 | $n\text{-}C_5H_{11}$—⌬—$OCH_2$—⌬—⌬—$OC_6H_{13}\text{-}n$ | 10 |

-continued

| Ex. Comp. No. | Structural formula | wt. parts |
|---|---|---|
| 2-3 | n-C$_5$H$_{11}$—[H]—CO—O—[⌬]—COCH$_2$CH(F)—C$_6$H$_{13}$-n ‖O ‖O * | 10 |
| | Composition 3-A | 80 |

A ferroelectric liquid crystal device was prepared in the same manner as in Example 1 except that the above liquid crystal composition 3-B was used instead of the composition 1-B. The device was subjected to measurement of driving voltage margin and observation of switching states. In the device, a monodomain with a good and uniform alignment characteristic was observed. The results of the measurement are shown below.

| | 10° C. | 25° C. | 40° C. |
|---|---|---|---|
| Response time | 1280 μsec | 330 μsec | 115 μsec |

Further, a contrast of 14 was attained at 25° C. during the driving, and a clear switching function was observed. The bistability after termination of the voltage application was also good.

COMPARATIVE EXAMPLE 3

A liquid crystal composition 3-C was prepared by omitting Example compound No. 1-1 from the liquid crystal composition 3-B, i.e., by adding only Example compound No. 2-3 to the liquid crystal composition 3-A, and a liquid crystal composition 3-D was prepared by omitting Example compound No. 2-3 from the composition 3-B, i.e., by adding only Example compound No. 1-1 to the composition 3-A.

Ferroelectric liquid crystal devices 3-A, 3-C and 3-D were prepared by using the compositions 3-A, 3-C and 3-D, respectively, instead of the composition 1-B, and subjected to measurement of optical response time, otherwise in the same manner as in Example 1. The results are shown below.

| | Response time | | |
|---|---|---|---|
| | 10° C. | 25° C. | 40° C. |
| 3-A | 2000 μsec | 530 μsec | 158 μsec |
| 3-C | 1150 μsec | 380 μsec | 125 μsec |
| 3-D | 1750 μsec | 470 μsec | 145 μsec |

As apparent from the above Example 3 and Comparative Example 3, the ferroelectric liquid crystal device containing the liquid crystal composition 3-B according to the present invention provided improved response speed and operation characteristic at a lower temperature and also provided a descreased temperature dependence of response speed.

EXAMPLE 4

A liquid crystal composition 4-B was prepared by mixing the following example compounds in the indicated proportions with the liquid crystal composition 1-A prepared in Example 1.

| Ex. Comp. No. | Structural formula | wt. parts |
|---|---|---|
| 1-5 | n-C$_4$H$_9$—[⌬]—OCH$_2$—[⌬]—[⌬]—O—C$_6$H$_{13}$-n | 5 |
| 1-24 | n-C$_5$H$_{11}$—[⌬]—CH$_2$O—[⌬]—[⌬]—CO—C$_8$H$_{17}$-n ‖O | 5 |
| 1-37 | n-C$_8$H$_{17}$—[⌬]—OCH$_2$—[⌬]—[⌬]—CH$_2$CHC$_2$H$_5$ (CH$_3$) * | 5 |
| 2-26 | n-C$_{10}$H$_{21}$—[N⌬N]—[⌬]—OCH$_2$CHC$_2$H$_5$ (F) * | 6 |
| 2-54 | n-C$_{12}$H$_{25}$—[N⌬N]—[⌬]—OCH$_2$CHC$_6$H$_{13}$ (F) * | 6 |
| | Composition 3-A | 73 |

A ferroelectric liquid crystal device was prepared in the same manner as in Example 1 except that the above liquid crystal composition 4-B was used, and the device was subjected to measurement of driving voltage margin and observation of switching states. In the device, a monodomain with a good and uniform alignment characteristic was observed. The results of the measurement are shown below.

|  | 10° C. | 25° C. | 40° C. |
|---|---|---|---|
| Response time | 1210 μsec | 300 μsec | 110 μsec |

Further, a contrast of 13 was attained at 25° C. during the driving, and a clear switching function was observed. The bistability after termination of the voltage application was also good.

COMPARATIVE EXAMPLE 4

A liquid crystal composition 4-C was prepared by omitting Example compounds Nos. 1-5, 1-24 and 1-37 from the liquid crystal composition 4-B, i.e., by adding only Example compounds Nos. 2-26 and 2-54 to the liquid crystal composition 3-A, and a liquid crystal composition 4-D was prepared by omitting Example compounds Nos. 2-26 and 2-54 from the composition 4-B, i.e., by adding only Example compounds Nos. 1-5, 1-24 and 1-37 to the composition 3-A.

Ferroelectric liquid crystal devices 4-C and 4-D were prepared by using the compositions 4-C and 4-D, respectively, instead of the composition 1-B, and subjected to measurement of optical response time, otherwise in the same manner as in Example 1. The results are shown below.

|  | Response time | | |
|---|---|---|---|
|  | 10° C. | 25° C. | 40° C. |
| 4-C | 1440 μsec | 360 μsec | 120 μsec |
| 4-D | 1600 μsec | 420 μsec | 135 μsec |

As apparent from the above Example 4 and Comparative Example 4, the ferroelectric liquid crystal device containing the liquid crystal composition 4-B according to the present invention provided improved response speed and operation characteristic at a lower temperature and also provided a descreased temperature dependence of response speed.

EXAMPLE 5

A liquid crystal composition 5-A was prepared by mixing the following compounds in respectively indicated proportions.

| Ex. Compound No. | Structural formula | Wt. parts |
|---|---|---|
| 24 | $C_{10}H_{21}O$—⟨⟩—COS—⟨⟩—$OCH_2\overset{*}{C}H(CH_3)OC_3H_7$ | 10 |
| 25 | $C_{12}H_{25}O$—⟨⟩—COS—⟨⟩—$OCH_2\overset{*}{C}H(CH_3)OC_8H_{17}$ | 20 |
| 67 | $C_4H_9OCH_2CH_2O$—⟨⟩—COO—⟨⟩—⟨⟩—$COOC_6H_{13}$ | 15 |
| 4 | $C_2H_5\overset{*}{C}H(CH_3)CH_2$—⟨⟩—⟨⟩—COO—⟨⟩—$OC_8H_{17}$ | 10 |
| 5 | $C_2H_5\overset{*}{C}H(CH_3)CH_2$—⟨⟩—⟨⟩—COO—⟨⟩—$OC_6H_{13}$ | 20 |
| 57 | $C_{10}H_{21}O$—⟨⟩—COO—⟨⟩—$OC_8H_{17}$ | 15 |
| 58 | $C_8H_{17}$—⟨⟩—COO—⟨⟩—$OC_{10}H_{21}$ | 15 |
| 47 | $C_{10}H_{21}O$—⟨⟩—⟨⟩—COO—⟨⟩—$OCH_2\overset{*}{C}H(F)C_8H_{17}$ | 5 |

| Ex. Compound No. | Structural formula | Wt. parts |
|---|---|---|
| 51 | 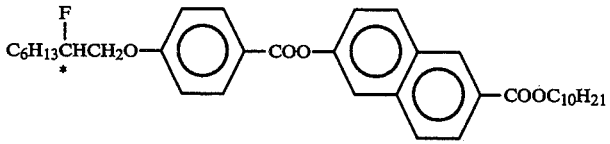 | 5 |

A liquid crystal composition 5-B was prepared by mixing the following example compounds 1-1 and 2-3 with the above prepared composition 5-A.

| Ex. Comp. No. | Structural formula | Wt. parts |
|---|---|---|
| 1-1 | 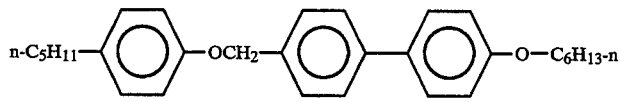 | 10 |
| 2-3 | 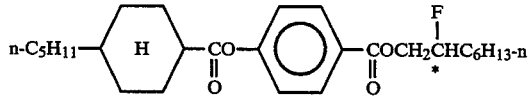 | 10 |
| Composition 5-A | | 80 |

A ferroelectric liquid crystal device 5-B was prepared in the same manner as in Example 1 except that the liquid crystal composition 5-B was used instead of the composition 1-B. The device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 365 μsec | 90 μsec | 35 μsec |

Further, a contrast of 14 was attained at 25° C. during the driving, and a clear switching function was observed. The bistability after termination of the voltage application was also good.

COMPARATIVE EXAMPLE 5

A liquid crystal composition 5-C was prepared by omitting Example compound No. 1-1 from the liquid crystal composition 5-B, i.e., by adding only Example compound No. 2-3 to the liquid crystal composition 5-A, and a liquid crystal composition 5-D was prepared by omitting Example compound No. 2-3 from the composition 5-B, i.e., by adding only Example compound No. 1-1 to the composition 5-A.

Ferroelectric liquid crystal devices 5-A, 5-C and 5-D were prepared by using the compositions 5-A, 5-C and 5-D, respectively, instead of the composition 1-B, and subjected to measurement of optical response time, otherwise in the same manner as in Example 1. The results are shown below.

| | Response time | | |
|---|---|---|---|
| | 10° C. | 25° C. | 40° C. |
| 5-A | 620 μsec | 170 μsec | 52 μsec |
| 5-C | 440 μsec | 115 μsec | 40 μsec |
| 5-D | 510 μsec | 140 μsec | 45 μsec |

As apparent from the above Example 5 and Comparative Example 5, the ferroelectric liquid crystal device containing the liquid crystal composition 5-B according to the present invention provided improved response speed and operation characteristic at a lower temperature and also provided a descreased temperature dependence of response speed.

EXAMPLE 6

A liquid crystal composition 6-B was prepared by mixing the following example compounds in the indicated proportions with the liquid crystal composition 5-A prepared in Example 5.

| Ex. Comp. No. | Structural formula | wt. parts |
|---|---|---|
| 1-5 | 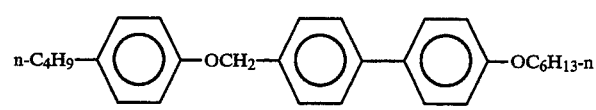 | 5 |
| 1-24 | 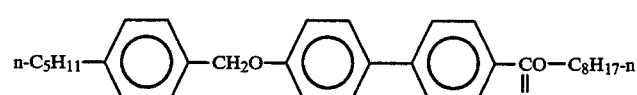 | 5 |

-continued

| Ex. Comp. No. | Structural formula | wt. parts |
| --- | --- | --- |
| 1-37 | n-C$_8$H$_{17}$—⟨◯⟩—OCH$_2$—⟨◯⟩—⟨◯⟩—CH$_2$\*CH(CH$_3$)C$_2$H$_5$ | 5 |
| 2-26 | n-C$_{10}$H$_{21}$—⟨N◯N⟩—⟨◯⟩—OCH$_2$\*CH(F)C$_2$H$_5$ | 6 |
| 2-54 | n-C$_{12}$H$_{25}$—⟨N◯N⟩—⟨◯⟩—OCH$_2$\*CH(F)C$_6$H$_{13}$ | 6 |
| Composition 5-A | | 73 |

A ferroelectric liquid crystal device was prepared in the same manner as in Example 1 except that the above liquid crystal composition 6-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time | 370 μsec | 95 μsec | 35 μsec |

Further, a contrast of 13 was attained at 25° C. during the driving, and a clear switching function was observed. The bistability after termination of the voltage application was also good.

COMPARATIVE EXAMPLE 6

A liquid crystal composition 6-C was prepared by omitting Example compounds Nos. 1-5, 1-24 and 1-37 from the liquid crystal composition 6-B, i.e., by adding only Example compounds Nos. 2-26 and 2-54 to the liquid crystal composition 5-A, and a liquid crystal composition 6-D was prepared by omitting Example compounds Nos. 2-26 and 2-54 from the composition 6-B, i.e., by adding only Example compounds Nos. 1-5, 1-24 and 1-37 to the composition 5-A.

Ferroelectric liquid crystal devices 6-C and 6-D were prepared by using the compositions 6-C and 6-D, respectively, instead of the composition 1-B, and subjected to measurement of optical response time, otherwise in the same manner as in Example 1. The results are shown below.

|  | Response time | | |
| --- | --- | --- | --- |
|  | 10° C. | 25° C. | 40° C. |
| 6-C | 490 μsec | 130 μsec | 45 μsec |
| 6-D | 530 μsec | 140 μsec | 45 μsec |

As apparent from the above Example 6 and Comparative Example 6, the ferroelectric liquid crystal device containing the liquid crystal composition 6-B according to the present invention provided improved response speed and operation characteristic at a lower temperature and also provided a decreased temperature dependence of response speed.

EXAMPLE 7

A blank cell was prepared in the same manner as in Example 1 except for omitting the SiO$_2$ layer to form an alignment control layer composed of the polyimide resin layer alone on each electrode plate. Four ferroelectric liquid crystal devices were prepared by filling such a blank cell with liquid crystal compositions 1-B, 1-C, 1-D and 1-A, respectively, prepared in Example 1 and Comparative Example 1. These liquid crystal devices were subjected to measurement of optical response time in the same manner as in Example 1. The results are shown below.

|  | Response time (μsec) | | |
| --- | --- | --- | --- |
|  | 10° C. | 25° C. | 40° C. |
| 1-B | 900 | 240 | 80 |
| 1-C | 1080 | 275 | 90 |
| 1-D | 1300 | 370 | 105 |
| 1-A | 1520 | 420 | 120 |

As is apparent from the above Example 7, also in the case of a different device structure, the device containing the ferroelectric liquid crystal composition 1-B according to the present invention provided improved operation characteristic at a lower temperature and also a decreased temperature dependence of response speed.

EXAMPLE 8-15

Liquid crystal compositions 8-B to 15-B were prepared by replacing the example compounds and the liquid crystal compositions used in Examples 1, 3 and 5 with example compounds and liquid crystal compositions shown in the following Table 1. Ferroelectric liquid crystal devices were prepared by respectively using these compositions instead of the composition 1-B, and subjected to measurement of optical response time and observation of switching states. In the devices, a monodomain with a good and uniform alignment characteristic was observed. The results of the measurement are shown in the following Table 1.

TABLE 1

| Ex. No. (Comp. No.) | Example compound No. or liquid crystal composition No. (weight parts) | | | | | | | Response time (μsec) | | |
|---|---|---|---|---|---|---|---|---|---|---|
| | | | | | | | | 10° C. | 25° C. | 40° C. |
| 8 (8-B) | 1-9 (3) | 1-27 (3) | 1-41 (6) | 2-10 (6) | 2-17 (6) | | 1A (76) | 940 | 250 | 85 |
| 9 (9-B) | 1-12 (4) | 1-52 (4) | 1-68 (4) | 2-28 (4) | 2-41 (4) | | 1A (80) | 945 | 255 | 85 |
| 10 (10-B) | 1-17 (3) | 1-57 (3) | 1-65 (6) | 2-1 (4) | 2-13 (4) | 2-23 (3) | 3A (77) | 1150 | 285 | 110 |
| 11 (11-B) | 1-29 (4) | 1-48 (2) | 1-61 (2) | 2-24 (6) | 2-40 (4) | 2-73 (2) | 3A (80) | 1200 | 300 | 110 |
| 12 (12-B) | 1-20 (4) | 1-33 (2) | 1-39 (3) | 2-6 (3) | 2-14 (6) | 2-22 (3) | 5A (79) | 360 | 95 | 35 |
| 13 (13-B) | 1-14 (4) | 1-48 (2) | 1-59 (4) | 2-31 (5) | 2-67 (5) | 2-82 (5) | 5A (75) | 320 | 85 | 30 |
| 14 (14-B) | 1-3 (4) | 1-45 (3) | 1-66 (3) | 2-8 (4) | 2-15 (4) | 2-20 (4) | 5A (78) | 360 | 95 | 35 |
| 15 (15-B) | 1-16 (3) | 1-35 (3) | 1-46 (9) | 2-35 (3) | 2-48 (4) | 2-63 (4) | 5A (74) | 330 | 85 | 30 |

As is apparent from the results shown in the above Table 1, the ferroelectric liquid crystal devices containing the liquid crystal composition 8-B to 15-B provided improved response speed and a decreased temperature dependence of the response speed.

EXAMPLE 16

A liquid crystal composition 16-A was prepared by mixing the following compounds in respectively indicated proportions.

| Ex. Compound No. | Structural formula | Wt. parts |
|---|---|---|
| 57 | 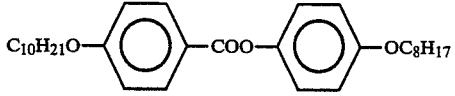 $C_{10}H_{21}O$—⌬—COO—⌬—$OC_8H_{17}$ | 6 |
| 58 | 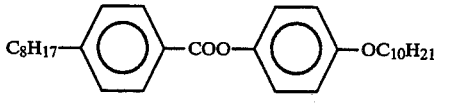 $C_8H_{17}$—⌬—COO—⌬—$OC_{10}H_{21}$ | 8 |
| 59 | 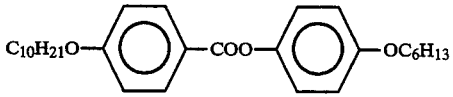 $C_{10}H_{21}O$—⌬—COO—⌬—$OC_6H_{13}$ | 9 |
| 60 | 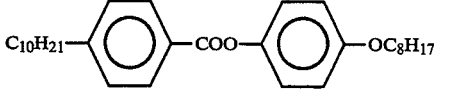 $C_{10}H_{21}$—⌬—COO—⌬—$OC_8H_{17}$ | 12 |
| 8 | 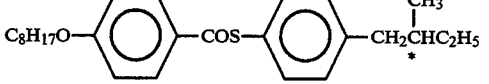 $C_8H_{17}O$—⌬—COS—⌬—$CH_2\overset{*}{C}H(CH_3)C_2H_5$ | 3 |
| 9 | 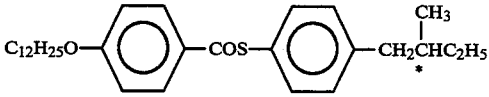 $C_{12}H_{25}O$—⌬—COS—⌬—$CH_2\overset{*}{C}H(CH_3)C_2H_5$ | 3 |
| 12 | 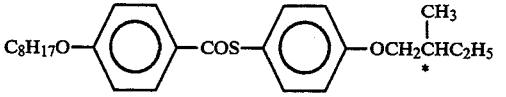 $C_8H_{17}O$—⌬—COS—⌬—$OCH_2\overset{*}{C}H(CH_3)C_2H_5$ | 3 |
| 13 | 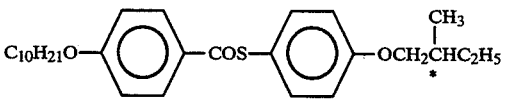 $C_{10}H_{21}O$—⌬—COS—⌬—$OCH_2\overset{*}{C}H(CH_3)C_2H_5$ | 3 |

-continued

| Ex. Compound No. | Structural formula | Wt. parts |
|---|---|---|
| 16 | 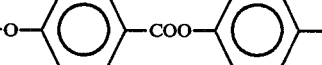 | 15 |
| 69 | 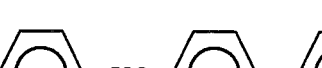 | 15 |
| 71 | 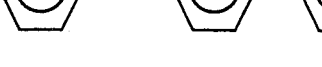 | 8 |
| 55 | 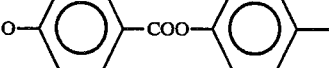 | 9 |
| 75 |  | 6 |

A liquid crystal composition 16-B was prepared by mixing the following example compounds 2-49, 2-10, 3-21 and 1-27 with the above prepared composition 16-A.

|  | 10° C. | 25° C. | 40° C. |
|---|---|---|---|
| Response time | 705 μsec | 246 μsec | 95 μsec |

| Ex. Comp. No. | Structural formula | Wt. parts |
|---|---|---|
| 2-49 | n-$C_{11}H_{23}$—[N=N phenyl]—[phenyl]—$OCH_2CHC_7H_{15}$-n (F, *) | 4 |
| 2-10 | $CH_3$—[H cyclohexyl]—CO—O—[phenyl]—$OCH_2CHC_4H_9$-n (F, *) | 4 |
| 3-21 | n-$C_9H_{19}O$—[phenyl]—CO—O—[phenyl]—$OCH_2CHC_2H_5$ ($CH_3$, *) | 3 |
| 1-27 | n-$C_6H_{13}$—[phenyl]—$CH_2O$—[phenyl]—[phenyl]—$CH_2CHC_2H_5$ ($CH_3$, *) | 6 |
| Composition 16-A |  | 83 |

A ferroelectric liquid crystal device was prepared in the same manner as in Example 1 except that the above liquid crystal composition 16-B was used instead of the composition 1-B. The device was subjected to measurement of driving voltage margin and observation of switching states. In the device, a monodomain with a good and uniform alignment characteristic was observed. The results of the measurement are shown below.

Further, a contrast of 12 was attained at 25° C. during the driving, and a clear switching function was observed.

COMPARATIVE EXAMPLE 16

A liquid crystal composition 16-C was prepared by omitting Example compounds Nos. 2-10 and 2-49 from the liquid crystal composition 16-B prepared in Example 16, i.e., by adding only Example compounds Nos. 3-10 and 1-27 to the liquid crystal composition 16-A, and a liquid crystal composition 16-D was prepared by omitting Example compound No. 3-21 from the composition 16-B, i.e., by adding only Example compounds Nos. 2-10, 2-49 and 1-27 to the composition 16-A, and a liquid crystal composition 16-E was prepared by omitting Example compound No. 1-27 from the composition 16-B, i.e., by adding only Example compounds Nos. 2-10, 2-49 and 3-21 to the composition 16-A. Ferroelectric liquid crystal devices 16-C, 16-D, 16-E and 16-A were prepared by using the compositions 16-C, 16-D, 16-E and 16-A, respectively, instead of the composition 16-B, and subjected to measurement of optical response time, otherwise in the same manner as in Example 16. The results are shown below.

|  | Response time | | |
|---|---|---|---|
|  | 10° C. | 25° C. | 40° C. |
| 16-A | 1155 μsec | 362 μsec | 133 μsec |
| 16-C | 1020 μsec | 353 μsec | 123 μsec |
| 16-D | 751 μsec | 259 μsec | 97 μsec |
| 16-E | 798 μsec | 271 μsec | 102 μsec |

As apparent from the above Example 16 and Comparative Example 16, the ferroelectric liquid crystal device containing the liquid crystal composition 16-B according to the present invention provided improved response speed and operation characteristic at a lower temperature and also provided a descreased temperature dependence of response speed (ratio of response time (10° C./40° C.)).

EXAMPLE 17

A liquid crystal composition 17-B was prepared by mixing the following example compounds in the indicated proportions with the liquid crystal composition 16-A prepared in Example 16.

A ferroelectric liquid crystal device was prepared in the same manner as in Example 16 except that the above liquid crystal composition 17-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 763 μsec | 267 μsec | 100 μsec |

Further, a contrast of 13 was attained at 25° C. during the driving, and a clear switching function was observed. The bistability after termination of the voltage application was also good.

COMPARATIVE EXAMPLE 17

A liquid crystal composition 17-C was prepared by omitting Example compounds Nos. 2-43 and 2-57 from the liquid crystal composition 17-B prepared in Example 17, i.e., by adding only Example compounds Nos. 3-26, 1-13 and 1-37 to the liquid crystal composition 16-A.

Ferroelectric liquid crystal devices 17-C and 16-A were prepared by using the compositions 17-C and 16-A, respectively, instead of the composition 16-B, and subjected to measurement of optical response time, otherwise in the same manner as in Example 16. The results are shown below.

|  | Response time | | |
|---|---|---|---|
|  | 10° C. | 25° C. | 40° C. |
| 16-A | 1155 μsec | 362 μsec | 133 μsec |
| 17-C | 999 μsec | 344 μsec | 127 μsec |

| Ex. Comp. No. | Structural formula | wt. parts |
|---|---|---|
| 2-43 | n-C$_{10}$H$_{21}$—[pyrimidine]—[phenyl]—OCH$_2$CHC$_9$H$_{19}$-n (F substituent, * chiral) | 3 |
| 2-57 | n-C$_{12}$H$_{25}$—[pyrimidine]—[phenyl]—OCH$_2$CHC$_{10}$H$_{21}$-n (F substituent, * chiral) | 3 |
| 3-26 | n-C$_{10}$H$_{21}$O—[phenyl]—CO—O—[phenyl]—(CH$_2$)$_5$CHOC$_3$H$_7$-n (CH$_3$ substituent, * chiral) | 3 |
| 1-13 | n-C$_7$H$_{15}$—[phenyl]—OCH$_2$—[phenyl]—OC$_{12}$H$_{25}$-n | 4 |
| 1-37 | n-C$_8$H$_{17}$—[phenyl]—OCH$_2$—[phenyl]—[phenyl]—CH$_2$CHC$_2$H$_5$ (CH$_3$ substituent, * chiral) | 5 |
| Composition 16-A | | 82 |

As apparent from the above Example 17 and Comparative Example 17, the ferroelectric liquid crystal device containing the liquid crystal composition 17-B according to the present invention provided improved response speed and operation characteristic at a lower temperature and also provided a descreased temperature dependence of response speed.

EXAMPLE 18

A liquid crystal composition 18-B was prepared by mixing the following example compounds in the indicated proportions with the liquid crystal composition 16-A prepared in Example 16.

the liquid crystal composition 18-B prepared in Example 18, i.e., by adding only Example compounds Nos. 3-3, 3-38 and 1-47 to the liquid crystal composition 16-A.

Ferroelectric liquid crystal devices 18-C and 16-A were prepared by using the compositions 18-C and 16-A, respectively, instead of the composition 16-B, and subjected to measurement of optical response time, otherwise in the same manner as in Example 16. The results are shown below.

| Ex. Comp. No. | Structural formula | wt. parts |
|---|---|---|
| 2-16 | n-$C_4H_9$—〈H〉—CO—O—〈○〉—O$CH_2$$\overset{*}{C}$H$C_6H_{13}$-n (with F substituent) | 4 |
| 2-20 | n-$C_4H_9$—〈H〉—CO—O—〈○〉—O$CH_2$$\overset{*}{C}$H$C_5H_{11}$-n (with F substituent) | 3 |
| 3-3 | n-$C_8H_{17}$—〈○〉—CO—O—〈○〉—(CH$_2$)$_2$$\overset{*}{C}$H$C_2H_5$ (with CH$_3$ substituent) | 5 |
| 3-38 | n-$C_6H_{13}$O—〈○〉—CO—O—〈○〉—OCH$_2$$\overset{*}{C}$HC$_2$H$_5$ (with CH$_3$ substituent) | 5 |
| 1-47 | n-$C_8H_{17}$—〈○〉—CH$_2$O—〈○〉—〈○〉—CO—O—$\overset{*}{C}$HC$_6H_{13}$-n (with CH$_3$ substituent) | 4 |
| Composition 16-A | | 79 |

A ferroelectric liquid crystal device was prepared in the same manner as in Example 16 except that the above liquid crystal composition 18-B was used, and the device was subjected to measurement of driving voltage margin and observation of switching states. In the device, a monodomain with a good and uniform alignment characteristic was observed. The results of the measurement are shown below.

| | 10° C. | 25° C. | 40° C. |
|---|---|---|---|
| Response time | 645 μsec | 226 μsec | 85 μsec |

Further, a contrast of 14 was attained at 25° C. during the driving, and a clear switching function was observed. The bistability after termination of the voltage application was also good.

COMPARATIVE EXAMPLE 18

A liquid crystal composition 18-C was prepared by omitting Example compounds Nos. 2-16 and 2-20 from

| | Response time | | |
|---|---|---|---|
| | 10° C. | 25° C. | 40° C. |
| 16-A | 1155 μsec | 362 μsec | 133 μsec |
| 18-C | 859 μsec | 291 μsec | 108 μsec |

As apparent from the above Example 18 and Comparative Example 18, the ferroelectric liquid crystal device containing the liquid crystal composition 18-B according to the present invention provided improved response speed and operation characteristic at a lower temperature and also provided a descreased temperature dependence of response speed.

EXAMPLE 19

A liquid crystal composition 19-A was prepared by mixing the following compounds in respectively indicated proportions.

| Ex. Compound No. | Structural formula | Wt. parts |
|---|---|---|
| 7 | $C_8H_{17}$—〈○〉—COO—〈○〉—〈○〉—OCH$_2$$\overset{*}{C}$HC$_2$H$_5$ (with CH$_3$ substituent) | 15 |

| Ex. Compound No. | Structural formula | Wt. parts |
|---|---|---|
| 15 | 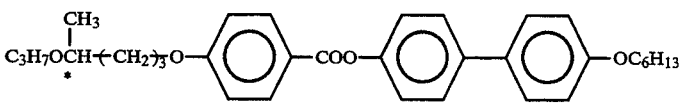 | 5 |
| 16 | 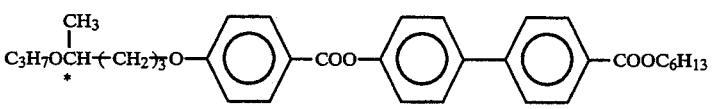 | 10 |
| 57 | 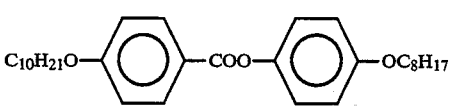 | 6 |
| 58 | 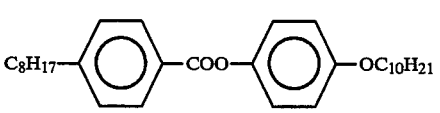 | 8 |
| 59 | 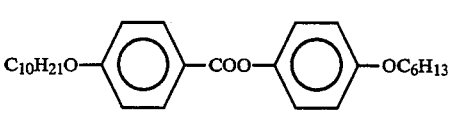 | 6 |
| 60 | 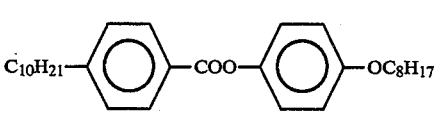 | 12 |
| 12 | 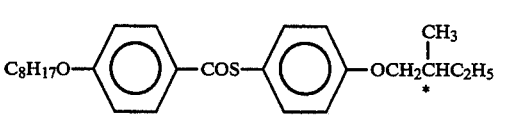 | 6 |
| 13 | 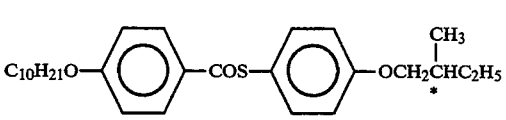 | 9 |
| 55 | 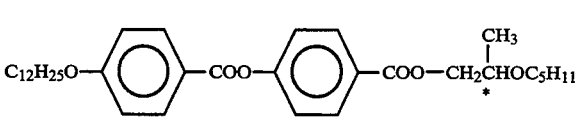 | 10 |
| 75 | 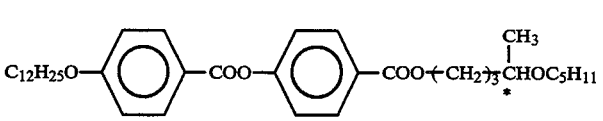 | 5 |
| 47 | 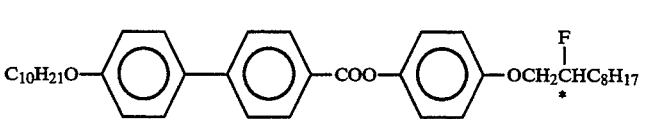 | 3 |
| 51 | 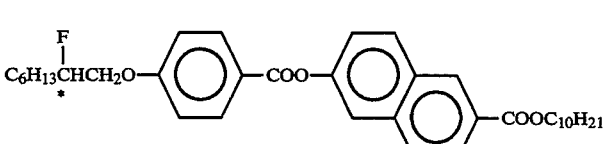 | 5 |
A liquid crystal composition 19-B was prepared by mixing the following example compounds 2-49, 2-10, 3-21 and 1-27 with the above prepared composition 19-A.

| Ex. Comp. No. | Structural formula | wt. parts |
|---|---|---|
| 2-49 | 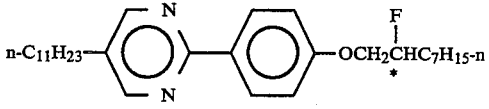 | 6 |
| 2-10 | 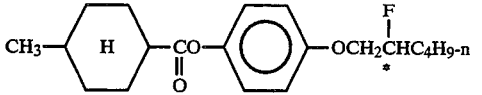 | 3 |
| 3-21 | 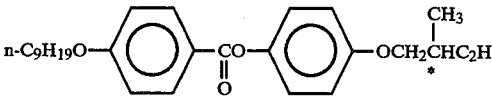 | 4 |
| 1-27 | 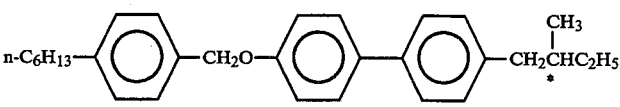 | 5 |
| | Composition 19-A | 82 |

A ferroelectric liquid crystal device 19-B was prepared in the same manner as in Example 16 except that the liquid crystal composition 19-B was used instead of the composition 16-B. The device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 777 μsec | 268 μsec | 100 μsec |

Further, a contrast of 13 was attained at 25° C. during the driving, and a clear switching function was observed.

COMPARATIVE EXAMPLE 19

A liquid crystal composition 19-C was prepared by omitting Example compounds Nos. 2-10 and 2-49 from the liquid crystal composition 19-B prepared in Example 19, i.e., by adding only Example compounds Nos. 3-21 and 1-27 to the liquid crystal composition 19-A, and a liquid crystal composition 19-D was prepared by omitting Example compound No. 3-21 from the composition 19-B, i.e., by adding only Example compounds Nos. 2-10, 2-49 and 1-27 to the composition 19-A, and a liquid crystal composition 19-E was prepared by omitting Example compound No. 1-27 from the composition 19-B, i.e., by adding only Example compounds Nos. 2-10, 2-49 and 3-21 to the composition 19-A.

Ferroelectric liquid crystal devices 19-C, 19-D, 19-E and 19-A were prepared by using the compositions 19-C, 19-D, 19-E and 19-A, respectively, instead of the composition 16-B, and subjected to measurement of optical response time, otherwise in the same manner as in Example 16. The results are shown below.

| | Response time (μsec) | | |
|---|---|---|---|
| | 10° C. | 25° C. | 40° C. |
| 19-A | 1360 | 430 | 147 |
| 19-C | 1137 | 382 | 138 |
| 19-D | 827 | 278 | 104 |
| 19-E | 876 | 292 | 109 |

As apparent from the above Example 19 and Comparative Example 19, the ferroelectric liquid crystal device containing the liquid crystal composition 19-B according to the present invention provided improved response speed and operation characteristic at a lower temperature and also provided a descreased temperature dependence of response speed.

EXAMPLE 20

A liquid crystal composition 20-B was prepared by mixing the following example compounds in the indicated proportions with the liquid crystal composition 19-A prepared in Example 19.

| Ex. Comp. No. | Structural formula | wt. parts |
|---|---|---|
| 2-23 | 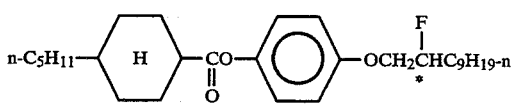 | 5 |
| 2-24 | 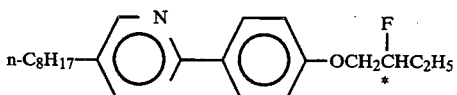 | 4 |

| Ex. Comp. No. | Structural formula | wt. parts |
|---|---|---|
| 3-42 | n-C$_8$H$_{17}$O—⟨phenyl⟩—CO(=O)—⟨phenyl⟩—OCH(CH$_3$)C$_6$H$_{13}$* | 3 |
| 1-62 | n-C$_9$H$_{19}$—⟨phenyl⟩—OCH$_2$—⟨phenyl⟩—⟨phenyl⟩—O(CH$_2$)$_4$CH(CH$_3$)OCH$_3$ | 6 |
| Composition 19-A | | 82 |

A ferroelectric liquid crystal device was prepared in the same manner as in Example 16 except that the above liquid crystal composition 20-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 716 μsec | 233 μsec | 92 μsec |

Further, a contrast of 12 was attained at 25° C. during the driving, and a clear switching function was observed. The bistability after termination of the voltage application was also good.

COMPARATIVE EXAMPLE 20

A liquid crystal composition 20-C was prepared by omitting Example compounds Nos. 3-42 and 1-62 from the liquid crystal composition 20-B prepared in Example 20, i.e., by adding only Example compounds Nos. 2-23 and 2-24 to the liquid crystal composition 19-A.

Ferroelectric liquid crystal devices 20-C and 19-A were prepared by using the compositions 20-C and 19-A, respectively, instead of the composition 16-B, and subjected to measurement of optical response time, otherwise in the same manner as in Example 16. The results are shown below.

|  | Response time (μsec) | | |
|---|---|---|---|
|  | 10° C. | 25° C. | 40° C. |
| 19-A | 1360 | 430 | 147 |
| 20-C | 938 | 331 | 121 |

As apparent from the above Example 20 and Comparative Example 20, the ferroelectric liquid crystal device containing the liquid crystal composition 20-B according to the present invention provided improved response speed and operation characteristic at a lower temperature and also provided a descreased temperature dependence of response speed.

EXAMPLE 21

A liquid crystal composition 21-B was prepared by mixing the following example compounds in the indicated proportions with the liquid crystal composition 19-A prepared in Example 19.

| Ex. Comp. No. | Structural formula | wt. parts |
|---|---|---|
| 2-5 | n-C$_3$H$_7$—⟨H⟩—CO(=O)—⟨phenyl⟩—COCH$_2$CH(F)C$_6$H$_{13}$-n* | 3 |
| 2-7 | n-C$_5$H$_{11}$—⟨H⟩—CO(=O)—⟨phenyl⟩—COCH$_2$CH(F)C$_7$H$_{15}$-n* | 4 |
| 3-76 | n-C$_8$H$_{17}$O—⟨phenyl⟩—CO(=O)—⟨phenyl⟩—O(CH$_2$)$_4$OCH$_2$CH(CH$_3$)C$_2$H$_5$* | 3 |
| 1-18 | n-C$_6$H$_{13}$—⟨phenyl⟩—OCH$_2$—⟨phenyl⟩—⟨phenyl⟩—C$_6$H$_{13}$-n | 6 |
| 1-38 | n-C$_9$H$_{19}$—⟨phenyl⟩—OCH$_2$—⟨phenyl⟩—⟨phenyl⟩—CH$_2$CH(CH$_3$)C$_2$H$_5$* | 3 |

-continued

| Ex. Comp. No. | Structural formula | wt. parts |
|---|---|---|
| | Composition 19-A | 81 |

A ferroelectric liquid crystal device was prepared in the same manner as in Example 16 except that the above liquid crystal composition 21-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 901 μsec | 318 μsec | 121 μsec |

Further, a contrast of 13 was attained at 25° C. during the driving, and a clear switching function was observed. The bistability after termination of the voltage application was also good.

COMPARATIVE EXAMPLE 21

A liquid crystal composition 21-C was prepared by omitting Example compounds Nos. 2-5, 2-7, 1-18 and 1-38 from the liquid crystal composition 21-B, i.e., by adding only Example compound No. 3-76 to the liquid crystal composition 19-A.

Ferroelectric liquid crystal devices 21-C and 19-A were prepared by using the compositions 21-C and 19-A, respectively, instead of the composition 16-B, and subjected to measurement of optical response time, otherwise in the same manner as in Example 16. The results are shown below.

| | Response time | | |
|---|---|---|---|
| | 10° C. | 25° C. | 40° C. |
| 19-A | 1360 μsec | 430 μsec | 147 μsec |
| 21-C | 1285 μsec | 413 μsec | 142 μsec |

As apparent from the above Example 21 and Comparative Example 21, the ferroelectric liquid crystal device containing the liquid crystal composition 21-B according to the present invention provided improved response speed and operation characteristic at a lower temperature and also provided a descreased temperature dependence of response speed.

EXAMPLE 22

A liquid crystal composition 22-A was prepared by mixing the following compounds in respectively indicated proportions.

| Ex. Compound No. | Structural formula | Wt. parts |
|---|---|---|
| 26 | $C_8H_{17}$—pyridine—phenyl—$O(CH_2)_3CHC_2H_5$ with $CH_3$ branch (*) | 4 |
| 27 | $C_{10}H_{21}O$—phenyl—pyridine—$COO(CH_2)_3CHC_2H_5$ with $CH_3$ branch (*) | 2 |
| 28 | $C_{12}H_{25}O$—phenyl—pyridine—$COO(CH_2)_3CHC_2H_5$ with $CH_3$ branch (*) | 3 |
| 29 | $C_{10}H_{21}$—pyridine—phenyl—$O(CH_2)_3CHC_2H_5$ with $CH_3$ branch (*) | 3 |
| 30 | $C_8H_{17}$—pyridine—phenyl—$O(CH_2)_3CHC_2H_5$ with $CH_3$ branch (*) | 3 |
| 37 | $C_{12}H_{25}O$—phenyl—pyridine—$O(CH_2)_3CHC_2H_5$ with $CH_3$ branch (*) | 5 |
| 57 | $C_{10}H_{21}O$—phenyl—COO—phenyl—$OC_8H_{17}$ | 9 |

-continued

| Ex. Compound No. | Structural formula | Wt. parts |
| --- | --- | --- |
| 58 | $C_8H_{17}$—〇—COO—〇—$OC_{10}H_{21}$ | 10 |
| 59 | $C_{10}H_{21}O$—〇—COO—〇—$OC_6H_{13}$ | 6 |
| 60 | $C_{10}H_{21}$—〇—COO—〇—$OC_8H_{17}$ | 15 |
| 7 | $C_8H_{17}$—〇—COO—〇—〇—$OCH_2\overset{*}{C}HC_2H_5$ (CH$_3$) | 5 |
| 15 | $C_3H_7O\overset{*}{C}H(CH_3)(CH_2)_3O$—〇—COO—〇—〇—$OC_6H_{13}$ | 5 |
| 69 | $C_4H_9OCH_2\overset{*}{C}HO(CH_3)$—〇—COO—〇—〇—$COOC_8H_{17}$ | 14 |
| 71 | $CH_3O\overset{*}{C}H(CH_3)(CH_2)_2O$—〇—COO—〇—〇—$COOC_8H_{17}$ | 16 |

A liquid crystal composition 22-B was prepared by mixing the following example compounds 2-49, 2-10, 3-21 and 1-27 with the above prepared composition 22-A.

the composition 16-B. The device was subjected to measurement of optical response time and observation of switching states. In the device, a monodomain with a good and uniform alignment characteristic was ob-

| Ex. Comp. No. | Structural formula | Wt. parts |
| --- | --- | --- |
| 2-49 | n-$C_{11}H_{23}$—〇(N,N)—〇—$OCH_2\overset{*}{C}HC_7H_{15}$-n (F) | 4 |
| 2-10 | $CH_3$—〇(H)—$\underset{O}{\overset{\parallel}{C}}$O—〇—$OCH_2\overset{*}{C}HC_4H_9$-n (F) | 6 |
| 3-21 | n-$C_9H_{19}O$—〇—$\underset{O}{\overset{\parallel}{C}}$O—〇—$OCH_2\overset{*}{C}HC_2H_5$ (CH$_3$) | 5 |
| 1-27 | n-$C_6H_{13}$—〇—$CH_2O$—〇—〇—$CH_2\overset{*}{C}HC_2H_5$ (CH$_3$) | 5 |
| | Composition 22-A | 80 |

A ferroelectric liquid crystal device 22-B was prepared in the same manner as in Example 16 except that the liquid crystal composition 22-B was used instead of served. The results of the measurement are shown below.

|  | 10° C. | 25° C. | 40° C. |
| --- | --- | --- | --- |
| Response time | 560 μsec | 207 μsec | 82 μsec |

Further, a contrast of 14 was attained at 25 ° C. during the driving, and a clear switching function was observed.

COMPARATIVE EXAMPLE 22

A liquid crystal composition 22-C was prepared by omitting Example compounds Nos. 2-10 and 2-49 from the liquid crystal composition 22-B prepared in Example 22, i.e., by adding only Example compounds Nos. 3-21 and 1-27 to the liquid crystal composition 22-A.

Ferroelectric liquid crystal devices 22-C and 22-A were prepared by using the compositions 22-C and 22-A, respectively, instead of the composition 16-B, and subjected to measurement of optical response time, otherwise in the same manner as in Example 16. The results are shown below.

|  | Response time (μsec) | | |
| --- | --- | --- | --- |
|  | 10° C. | 25° C. | 40° C. |
| 22-A | 872 | 285 | 115 |
| 22-C | 804 | 274 | 111 |

As apparent from the above Example 22 and Comparative Example 22, the ferroelectric liquid crystal device containing the liquid crystal composition 22-B according to the present invention provided improved response speed and operation characteristic at a lower temperature and also provided a descreased temperature dependence of response speed.

EXAMPLE 23

A liquid crystal composition 23-B was prepared by mixing the following example compounds in the indicated proportions with the liquid crystal composition 22-A prepared in Example 22.

A ferroelectric liquid crystal device was prepared in the same manner as in Example 16 except that the above liquid crystal composition 23-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time | 473 μsec | 180 μsec | 74 μsec |

Further, a contrast of 14 was attained at 25 ° C. during the driving, and a clear switching function was observed. The bistability after termination of the voltage application was also good.

COMPARATIVE EXAMPLE 23

A liquid crystal composition 23-C was prepared by omitting Example compound No. 3-42 from the liquid crystal composition 23-B prepared in Example 23, i.e., by adding only Example compounds Nos. 2-23, 2-24 and 1-62 to the liquid crystal composition 22-A.

Ferroelectric liquid crystal devices 23-C and 22-A were prepared by using the compositions 23-C and 22-A, respectively, instead of the composition 16-B, and subjected to measurement of optical response time, otherwise in the same manner as in Example 16. The results are shown below.

|  | Response time (μsec) | | |
| --- | --- | --- | --- |
|  | 10° C. | 25° C. | 40° C. |
| 22-A | 872 | 285 | 115 |
| 23-C | 621 | 229 | 91 |

As apparent from the above Example 23 and Comparative Example 23, the ferroelectric liquid crystal device containing the liquid crystal composition 23-B according to the present invention provided improved response speed and operation characteristic at a lower

| Ex. Comp No. | Structural formula | wt. parts |
| --- | --- | --- |
| 2-23 | n-C$_5$H$_{11}$—⟨H⟩—CO—⟨◯⟩—OCH$_2$CHC$_9$H$_{19}$-n, F, * | 3 |
| 2-24 | n-C$_8$H$_{17}$—⟨N◯N⟩—⟨◯⟩—OCH$_2$CHC$_2$H$_5$, F, * | 3 |
| 3-42 | n-C$_8$H$_{17}$O—⟨◯⟩—CO—⟨◯⟩—OCHC$_6$H$_{13}$, CH$_3$, * | 6 |
| 1-62 | n-C$_9$H$_{19}$—⟨◯⟩—OCH$_2$—⟨◯⟩—⟨◯⟩—O(CH$_2$)$_4$CHOCH$_3$, CH$_3$ | 5 |
| Composition 22-A | | 83 | temperature and also provided a descreased temperature dependence of response speed.

EXAMPLE 24

A liquid crystal composition 24-B was prepared by mixing the following example compounds in the indicated proportions with the liquid crystal composition 22-A prepared in Example 22.

Ferroelectric liquid crystal devices 24-C and 22-A were prepared by using the compositions 24-C and 22-A, respectively, instead of the composition 16-B, and subjected to measurement of optical response time, otherwise in the same manner as in Example 16. The results are shown below.

| Ex. Comp. No. | Structural formula | wt. parts |
|---|---|---|
| 2-75 | n-$C_8H_{17}$—[pyridine]—[phenyl]—COCH$_2$CHC$_6$H$_{13}$-n (F, *, O) | 5 |
| 2-80 | n-$C_{12}H_{25}$—[pyridine]—[phenyl]—COCH$_2$CHC$_6$H$_{13}$-n (F, *, O) | 3 |
| 3-24 | n-$C_{10}H_{21}$O—[phenyl]—CO—[phenyl]—O$(CH_2)_3$CHC$_2$H$_5$ (CH$_3$, *) | 4 |
| 3-70 | n-$C_{11}H_{23}$O—[phenyl]—CO—[phenyl]—$(CH_2)_4$CHOCH$_3$ (CH$_3$, *) | 3 |
| 1-33 | n-$C_7H_{15}$—[phenyl]—[phenyl]—CH$_2$O—[phenyl]—CH$_2$CHC$_2$H$_5$ (CH$_3$, *) | 5 |
| Composition 22-A | | 80 |

A ferroelectric liquid crystal device was prepared in the same manner as in Example 16 except that the above liquid crystal composition 24-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 583 μsec | 285 μsec | 115 μsec |

Further, a contrast of 13 was attained at 25° C. during the driving, and a clear switching function was observed. The bistability after termination of the voltage application was also good.

COMPARATIVE EXAMPLE 24

A liquid crystal composition 24-C was prepared by omitting Example compounds Nos. 2-75, 2-80, 3-24 and 3-70 from the liquid crystal composition 24-B prepared in Example 24, i.e., by adding only Example compound No. 1-33 to the liquid crystal composition 22-A.

| | Response time | | |
|---|---|---|---|
| | 10° C. | 25° C. | 40° C. |
| 22-A | 872 μsec | 285 μsec | 115 μsec |
| 24-C | 799 μsec | 282 μsec | 110 μsec |

As apparent from the above Example 24 and Comparative Example 24, the ferroelectric liquid crystal device containing the liquid crystal composition 24-B according to the present invention provided improved response speed and operation characteristic at a lower temperature and also provided a descreased temperature dependence of response speed.

EXAMPLE 25–32

Liquid crystal compositions 25-B to 32-B were prepared by replacing the example compounds and the liquid crystal compositions used in Examples 16, 19 and 22 with example compounds and liquid crystal compositions shown in the following Table 2. Ferroelectric liquid crystal devices were prepared by respectively using these compositions instead of the composition 16-B, and subjected to measurement of optical response time and observation of switching states. In the devices, a monodomain with a good and uniform alignment characteristic was observed. The results of the measurement are shown in the following Table 2.

TABLE 2

| Ex. No. (Comp. No.) | Example compound No. or liquid crystal composition No. (weight parts) | | | | | | Response time (μsec) | | |
|---|---|---|---|---|---|---|---|---|---|
| | | | | | | | 10° C. | 25° C. | 40° C. |
| 25 (25-B) | 2-15 (3) | 2-40 (2) | 2-48 (3) | 3-78 (4) | 3-43 (5) | 16-A (83) | 677 | 238 | 91 |
| 26 (26-B) | 2-65 (6) | 3-22 (4) | 3-48 (3) | 1-14 (5) | | 16-A (82) | 791 | 275 | 103 |
| 27 (27-B) | 2-6 (2) | 2-17 (7) | 3-11 (3) | 1-22 (5) | 1-27 (5) | 16-A (79) | 831 | 283 | 109 |
| 28 (28-B) | 2-13 (4) | 2-21 (3) | 2-34 (3) | 3-40 (5) | 1-39 (5) | 19-A (80) | 691 | 237 | 88 |
| 29 (29-B) | 2-1 (5) | 3-72 (4) | 1-17 (6) | 1-38 (4) | | 19-A (81) | 877 | 298 | 110 |
| 30 (30-B) | 2-74 (5) | 2-82 (3) | 3-1 (4) | 3-39 (4) | 1-3 (6) | 19-A (78) | 800 | 275 | 103 |
| 31 (31-B) | 2-11 (3) | 2-62 (5) | 3-23 (4) | 1-27 (6) | | 22-A (82) | 477 | 179 | 74 |
| 32 (32-B) | 2-51 (4) | 3-45 (3) | 3-79 (4) | 1-10 (6) | 1-63 (3) | 22-A (80) | 581 | 211 | 83 |

As is apparent from the results shown in the above Table 2, the ferroelectric liquid crystal devices containing the liquid crystal compositions 25-B to 32-B provided improved response speed and a decrease temperature dependence of the response speed.

EXAMPLE 33

A blank cell was prepared in the same manner as in Example 1 except for omitting the SiO₂ layer to form an alignment control layer composed of the polyimide resin layer alone on each electrode plate. Five ferroelectric liquid crystal devices were prepared by filling such a blank cell with liquid crystal compositions 16-B, 16-A, 16-C, 16-D and 16-E, respectively, prepared in Example 16 and Comparative Example 16. These liquid crystal devices were subjected to measurement of optical response time in the same manner as in Example 16. The results are shown below.

| | Response time (μsec) | | |
|---|---|---|---|
| | 10° C. | 25° C. | 40° C. |
| 16-B | 685 | 231 | 90 |
| 16-A | 1135 | 350 | 128 |
| 16-C | 1010 | 342 | 117 |
| 16-D | 744 | 238 | 94 |
| 16-E | 779 | 265 | 100 |

As is apparent from the above Example 33, also in the case of a different device structure, the device containing the ferroelectric liquid crystal composition 1-B according to the present invention provided improved operation characteristic at a lower temperature and also a decreased temperature dependence of response speed.

EXAMPLE 34

A liquid crystal composition 34-A was prepared by mixing the following compounds in respectively indicated proportions.

| Ex. Compound No. | Structural formula | Wt. parts |
|---|---|---|
| 57 | 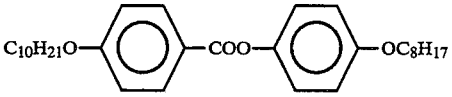 | 6 |
| 58 | 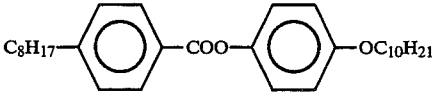 | 8 |
| 59 | 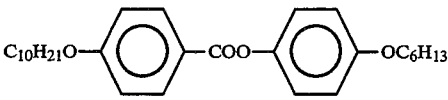 | 9 |
| 60 | 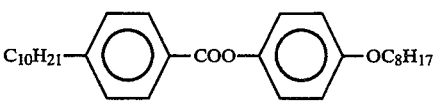 | 12 |
| 8 | 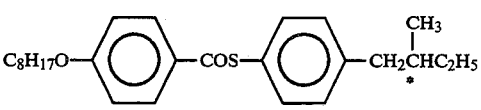 | 3 |

-continued

| Ex. Compound No. | Structural formula | Wt. parts |
|---|---|---|
| 9 | $C_{12}H_{25}O$—〔phenyl〕—COS—〔phenyl〕—$CH_2\overset{*}{C}H(CH_3)C_2H_5$ | 3 |
| 12 | $C_8H_{17}O$—〔phenyl〕—COS—〔phenyl〕—$OCH_2\overset{*}{C}H(CH_3)C_2H_5$ | 3 |
| 13 | $C_{10}H_{21}O$—〔phenyl〕—COS—〔phenyl〕—$OCH_2\overset{*}{C}H(CH_3)C_2H_5$ | 3 |
| 16 | $C_3H_7O\overset{*}{C}H(CH_3)(CH_2)_3O$—〔phenyl〕—COO—〔phenyl〕—〔phenyl〕—$COOC_6H_{13}$ | 15 |
| 69 | $C_4H_9OCH_2\overset{*}{C}H(CH_3)O$—〔phenyl〕—COO—〔phenyl〕—〔phenyl〕—$COOC_8H_{17}$ | 15 |
| 71 | $CH_3O\overset{*}{C}H(CH_3)(CH_2)_2O$—〔phenyl〕—COO—〔phenyl〕—〔phenyl〕—$COOC_8H_{17}$ | 8 |
| 55 | $C_{12}H_{25}O$—〔phenyl〕—COO—〔phenyl〕—COO—$CH_2\overset{*}{C}H(CH_3)OC_5H_{11}$ | 9 |
| 75 | $C_{12}H_{25}O$—〔phenyl〕—COO—〔phenyl〕—COO—$(CH_2)_3\overset{*}{C}H(CH_3)OC_5H_{11}$ | 6 |

A liquid crystal composition 34-B prepared by mixing the following example compounds 4-98, 4-136, 2-78, 1-37 and 1-40 with the above prepared composition 34-A.

| Ex. Comp. No. | Structural formula | Wt. parts |
|---|---|---|
| 4-98 | $n$-$C_9H_{19}$—〔pyrimidine〕—〔phenyl〕—$O(CH_2)_3\overset{*}{C}H(CH_3)C_2H_5$ | 6 |
| 4-136 | $n$-$C_{11}H_{23}O$—〔pyrimidine〕—〔phenyl〕—$OCH_2\overset{*}{C}H(CH_3)C_2H_5$ | 6 |
| 2-78 | $n$-$C_{10}H_{21}$—〔pyrimidine〕—〔phenyl〕—$CO\text{-}O\text{-}CH_2\overset{*}{C}H(F)C_6H_{13}\text{-}n$ | 7 |
| 1-37 | $n$-$C_8H_{17}$—〔phenyl〕—$OCH_2$—〔phenyl〕—〔phenyl〕—$CH_2\overset{*}{C}H(CH_3)C_2H_5$ | 3 |

-continued

| Ex. Comp. No. | Structural formula | Wt. parts |
| --- | --- | --- |
| 1-40 | n-C$_{12}$H$_{25}$O—〈◯〉—OCH$_2$—〈◯〉—〈◯〉—CH$_2$C*H(CH$_3$)C$_2$H$_5$ | 3 |
| Composition 34-A | | 75 |

A ferroelectric liquid crystal device was prepared in the same manner as in Example 1 except that the above liquid crystal composition 34-B was used instead of the composition 1-B. The device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time | 827 μsec | 300 μsec | 120 μsec |

Further, a contrast of 12 was attained at 25° C. during the driving, and a clear switching function was observed.

COMPARATIVE EXAMPLE 34

A liquid crystal composition 34-C was prepared by omitting Example compounds Nos. 4-145 and 4-98 from the liquid crystal composition 34-B prepared in Example 34, i.e., by adding only Example compounds Nos. 2-78, 1-37 and 1-40 to the liquid crystal composition 34-A, and a liquid crystal composition 34-D was prepared by omitting Example compound No. 2-78 from the composition 34-B, i.e., by adding only Example compounds Nos. 4-145, 4-98, 1-37 and 1-40 to the composition 34-A, and a liquid crystal composition 34-E was prepared by omitting Example compounds Nos. 1-37 and 1-40 from the composition 34-B, i.e., by adding only Example compounds Nos. 4-145, 4-98 and 2-78 to the composition 34-A.

Ferroelectric liquid crystal devices 34-C, 34-D, 34-E and 34-A were prepared by using the compositions 34-C, 34-D, 34-E and 34-A, respectively, instead of the composition 34-B, and subjected to measurement of optical response time, otherwise in the same manner as in Example 34. The results are shown below.

|  | Response time | | |
| --- | --- | --- | --- |
|  | 10° C. | 25° C. | 40° C. |
| 34-A | 1155 μsec | 362 μsec | 133 μsec |
| 34-C | 893 μsec | 313 μsec | 125 μsec |
| 34-D | 961 μsec | 339 μsec | 130 μsec |
| 34-E | 863 μsec | 307 μsec | 122 μsec |

As apparent from the above Example 34 and Comparative Example 34, the ferroelectric liquid crystal device containing the liquid crystal composition 34-B according to the present invention provided improved response speed and operation characteristic at a lower temperature and also provided a descreased temperature dependence of response speed (ratio of response time (10° C./40 ° C.)).

EXAMPLE 35

A liquid crystal composition 35-B was prepared by mixing the following example compounds in the indicated proportions with the liquid crystal composition 34-A prepared in Example 34.

| Ex. Comp. No. | Structural formula | wt. parts |
| --- | --- | --- |
| 4-67 | n-C$_{10}$H$_{21}$—〈N◯N〉—〈◯〉—O(CH$_2$)$_3$C*H(CH$_3$)OC$_4$H$_9$-n (racemate) | 6 |
| 4-103 | n-C$_{10}$H$_{21}$—〈N◯N〉—〈◯〉—O(OCH$_2$)$_4$C*H(CH$_3$)C$_2$H$_5$ | 5 |
| 4-140 | n-C$_6$H$_{13}$O—〈N◯N〉—〈◯〉—OC(O)—C*H(CH$_3$)C$_2$H$_5$ | 3 |
| 2-14 | n-C$_8$H$_{17}$—〈H◯〉—CO(O)—〈◯〉—O—CH$_2$C*H(F)C$_6$H$_{13}$-n | 6 |

-continued

| Ex. Comp. No. | Structural formula | wt. parts |
|---|---|---|
| 1-4 | n-$C_6H_{13}$—⟨○⟩—$OCH_2$—⟨○⟩—⟨○⟩—$OC_8H_{17}$-n | 5 |
| | Composition 34-A | 75 |

A ferroelectric liquid crystal device was prepared in the same manner as in Example 34 except that the above liquid crystal composition 35-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 770 μsec | 277 μsec | 110 μsec |

Further, a contrast of 12.5 was attained at 25 ° C. during the driving, and a clear switching function was observed. The bistability after termination of the voltage application was also good.

COMPARATIVE EXAMPLE 35

A liquid crystal composition 35-C was prepared by omitting Example compound No. 2-14 from the liquid crystal composition 35-B prepared in Example 35, i.e., by adding only Example compounds Nos. 4-67, 4-140, 4-103 and 1-4 to the liquid crystal composition 34-A.

Ferroelectric liquid crystal devices 35-C and 34-A were prepared by using the compositions 35-C and 34-A, respectively, instead of the composition 34-B, and subjected to measurement of optical response time, otherwise in the same manner as in Example 34. The results are shown below.

| | Response time | | |
|---|---|---|---|
| | 10° C. | 25° C. | 40° C. |
| 34-A | 1155 μsec | 362 μsec | 133 μsec |
| 35-C | 892 μsec | 323 μsec | 123 μsec |

As apparent from the above Example 35 and Comparative Example 35, the ferroelectric liquid crystal device containing the liquid crystal composition 35-B according to the present invention provided improved response speed and operation characteristic at a lower temperature and also provided a descreased temperature dependence of response speed.

EXAMPLE 36

A liquid crystal composition 36-B was prepared by mixing the following example compounds in the indicated proportions with the liquid crystal composition 34-A prepared in Example 34.

| Ex. Comp. No. | Structural formula | wt. parts |
|---|---|---|
| 4-35 | n-$C_{12}H_{25}O$—⟨N○N⟩—⟨○⟩—$OC_7H_{15}$-n | 6 |
| 4-148 | n-$C_{12}H_{25}O$—⟨N○N⟩—⟨○⟩—$O(CH_2)_{\overline{3}}\overset{*}{C}H(CH_3)C_2H_5$ | 4 |
| 2-6 | n-$C_4H_9$—⟨H⟩—CO(O)—⟨○⟩—CO(O)—$CH_2\overset{*}{C}H(F)$—$C_6H_{13}$-n | 3 |
| 2-39 | n-$C_{10}H_{21}$—⟨N○N⟩—⟨○⟩—$OCH_2\overset{*}{C}H(F)$—$C_5H_{11}$-n | 6 |
| 1-27 | n-$C_6H_{13}$—⟨○⟩—$CH_2O$—⟨○⟩—⟨○⟩—$CH_2\overset{*}{C}H(CH_3)C_2H_5$ | 4 |
| | Composition 34-A | 77 |

A ferroelectric liquid crystal device was prepared in the same manner as in Example 34 except that the above liquid crystal composition 36-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 700 μsec | 254 μsec | 101 μsec |

Further, a contrast of 13 was attained at 25° C. during the driving, and a clear switching function was observed. The bistability after termination of the voltage application was also good.

COMPARATIVE EXAMPLE 36

A liquid crystal composition 36-C was prepared by omitting Example compounds Nos. 2-39 and 2-6 from the liquid crystal composition 36-B prepared in Example 36, i.e., by adding only Example compounds Nos. 4-35, 4-148 and 1-27 to the liquid crystal composition 34-A.

Ferroelectric liquid crystal devices 36-C and 34-A were prepared by using the compositions 36-C and 34-A, respectively, instead of the composition 34-B, and subjected to measurement of optical response time, otherwise in the same manner as in Example 34. The results are shown below.

|  | Response time | | |
|---|---|---|---|
|  | 10° C. | 25° C. | 40° C. |
| 34-A | 1155 μsec | 362 μsec | 133 μsec |
| 36-C | 926 μsec | 318 μsec | 120 μsec |

As apparent from the above Example 36 and Comparative Example 36, the ferroelectric liquid crystal device containing the liquid crystal composition 36-B according to the present invention provided improved response speed and operation characteristic at a lower temperature and also provided a descreased temperature dependence of response speed.

EXAMPLE 37

A liquid crystal composition 37-A was prepared by mixing the following compounds in respectively indicated proportions.

| Ex. Compound No. | Structural formula | Wt. parts |
|---|---|---|
| 7 | 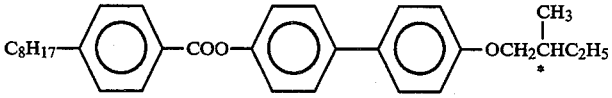 | 15 |
| 15 | 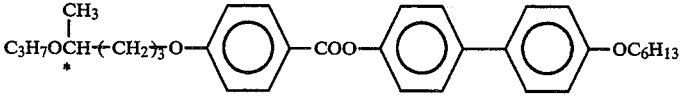 | 5 |
| 16 | 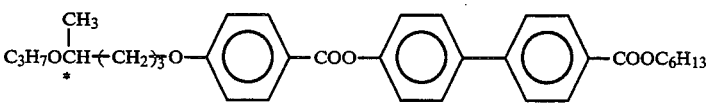 | 10 |
| 57 | 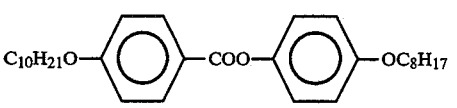 | 5 |
| 58 | 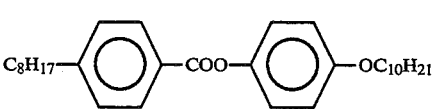 | 8 |
| 59 | 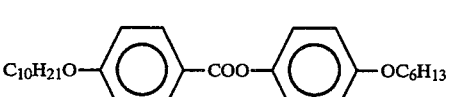 | 5 |
| 60 | 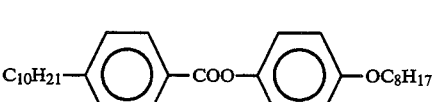 | 12 |
| 12 | 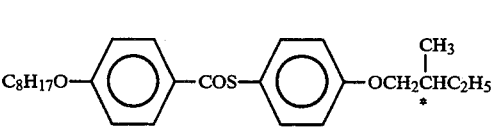 | 9 |

-continued

| Ex. Compound No. | Structural formula | Wt. parts |
|---|---|---|
| 13 | $C_{10}H_{21}O$—⌬—COS—⌬—$OCH_2\overset{*}{\underset{|}{C}}(CH_3)C_2H_5$ | 6 |
| 69 | $C_4H_9OCH_2\overset{*}{\underset{|}{C}}(CH_3)HO$—⌬—COO—⌬—⌬—$COOC_8H_{17}$ | 5 |
| 55 | $C_{12}H_{25}O$—⌬—COO—⌬—$COOCH_2\overset{*}{\underset{|}{C}}(CH_3)HOC_5H_{11}$ | 15 |
| 75 | $C_{12}H_{25}O$—⌬—COO—⌬—$COO(CH_2)_3\overset{*}{\underset{|}{C}}(CH_3)HOC_5H_{11}$ | 5 |

A liquid crystal composition 37-B was prepared by mixing the following example compounds 4-98, 4-136, 2-78, 1-37 and 1-40 with the above prepared composition 37-A.

|  | 10° C. | 25° C. | 40° C. |
|---|---|---|---|
| Response time | 831 μsec | 297 μsec | 117 μsec |

| Ex. Comp. No. | Structural formula | wt. parts |
|---|---|---|
| 4-98 | $n\text{-}C_9H_{19}$—[pyridine]—⌬—$O(CH_2)_3\overset{*}{\underset{|}{C}}(CH_3)HC_2H_5$ | 4 |
| 4-136 | $n\text{-}C_{11}H_{23}O$—[pyridine]—⌬—$OCH_2\overset{*}{\underset{|}{C}}(CH_3)H\text{—}C_2H_5$ | 7 |
| 2-78 | $n\text{-}C_{10}H_{21}$—[pyridine]—⌬—$\underset{O}{\underset{||}{C}}O\text{—}CH_2\overset{*}{\underset{|}{C}}(F)HC_6H_{13}\text{-}n$ | 6 |
| 1-37 | $n\text{-}C_8H_{17}$—⌬—$OCH_2$—⌬—⌬—$CH_2\overset{*}{\underset{|}{C}}(CH_3)HC_2H_5$ | 3 |
| 1-40 | $n\text{-}C_{12}H_{25}O$—⌬—$OCH_2$—⌬—⌬—$CH_2\overset{*}{\underset{|}{C}}(CH_3)HC_2H_5$ | 4 |
| | Composition 37-A | 76 |

A ferroelectric liquid crystal device 37-B was prepared in the same manner as in Example 34 except that the liquid crystal composition 37-B was used instead of the composition 34-B. The device was subjected to measurement of optical response time and observation of switching states. In the device, a monodomain with a good and uniform alignment characteristic was observed. The results of the measurement are shown below.

Further, a contrast of 13 was attained at 25° C. during the driving, and a clear switching function was observed.

COMPARATIVE EXAMPLE 37

A liquid crystal composition 37-C was prepared by omitting Example compounds Nos. 4-145 and 4-98 from the liquid crystal composition 37-B prepared in Example 37, i.e., by adding only Example compounds Nos. 2-78, 1-37 and 1-40 to the liquid crystal composition 37-A, and a liquid crystal composition 37-D was prepared by omitting Example compound No. 2-78 from the composition 37-B, i.e., by adding only Example compounds Nos. 4-145, 4-98, 1-37 and 1-30 to the composition 37-A, and a liquid crystal composition 37-E was prepared by omitting Example compounds Nos. 1-37 and 1-40 from the composition 37-B, i.e., by adding only Example compounds Nos. 4-145, 4-98 and 2-78 to the composition 37-A.

Ferroelectric liquid crystal devices 37-A, 37-C, 37-D and 37-E were prepared by using the compositions 37-A, 37-C, 37-D and 37-E, respectively, instead of the composition 1-B, and subjected to measurement of optical response time, otherwise in the same manner as in Example 1. The results are shown below.

|      | Response time (μsec) | | |
|------|-------|-------|-------|
|      | 10° C. | 25° C. | 40° C. |
| 37-A | 1410  | 435   | 155   |
| 37-C | 936   | 333   | 132   |
| 37-D | 1170  | 407   | 151   |
| 37-E | 905   | 325   | 123   |

As apparent from the above Example 37 and Comparative Example 37, the ferroelectric liquid crystal device containing the liquid crystal composition 37-B according to the present invention provided improved response speed and operation characteristic at a lower temperature and also provided a descreased temperature dependence of response speed.

EXAMPLE 38

A liquid crystal composition 38-B was prepared by mixing the following example compounds in the indicated proportions with the liquid crystal composition 37-A prepared in Example 37.

A ferroelectric liquid crystal device was prepared in the same manner as in Example 34 except that the above liquid crystal composition 38-B was used, and the device was subjected to measurement of optical response time and observation of switching states. In the device, a monodomain with a good and uniform alignment characteristic was observed. The results of the measurement are shown below.

|               | 10° C.   | 25° C.   | 40° C.   |
|---------------|----------|----------|----------|
| Response time | 745 μsec | 266 μsec | 104 μsec |

Further, a contrast of 12.5 was attained at 25° C. during the driving, and a clear switching function was observed. The bistability after termination of the voltage application was also good.

COMPARATIVE EXAMPLE 38

A liquid crystal composition 38-C was prepared by omitting Example compounds Nos. 4-71, 4-117 and 1-31 from the liquid crystal composition 38-B prepared in Example 38, i.e., by adding only Example compound No. 2-22 to the liquid crystal composition 37-A.

Ferroelectric liquid crystal devices 38-C and 37-A were prepared by using the compositions 38-C and 37-A, respectively, instead of the composition 34-B, and subjected to measurement of optical response time, otherwise in the same manner as in Example 34. The results are shown below.

|      | Response time (μsec) | | |
|------|-------|-------|-------|
|      | 10° C. | 25° C. | 40° C. |
| 37-A | 1410  | 435   | 155   |
| 38-C | 989   | 341   | 126   |

As apparent from the above Example 38 and Comparative Example 38, the ferroelectric liquid crystal device containing the liquid crystal composition 38-B according to the present invention provided improved response speed and operation characteristic at a lower temperature and also provided a descreased temperature dependence of response speed.

| Ex. Comp. No. | Structural formula | wt. parts |
|---|---|---|
| 4-71 | n-$C_{10}H_{21}$—[pyrimidine]—[phenyl]—O—$(CH_2)_4$—$\overset{*}{C}H(CH_3)OCH_3$ | 5 |
| 4-117 | n-$C_6H_{13}$—[pyrimidine]—[phenyl]—$OC(=O)$—$(CH_2)_4$—$\overset{*}{C}H(CH_3)CH_2C_2H_5$ | 5 |
| 2-22 | n-$C_5H_{11}$—[H cyclohexyl]—$CO(=O)$—[phenyl]—O—$CH_2\overset{*}{C}H(F)$—$C_8H_{17}$-n | 6 |
| 1-31 | n-$C_{14}H_{29}O$—[phenyl]—$CH_2O$—[phenyl]—[phenyl]—$O\overset{*}{C}H(CH_3)$—$C_6H_{13}$-n | 6 |
| Composition 37-A | — | 78 |

EXAMPLE 39

A liquid crystal composition 39-B was prepared by mixing the following example compounds in the indicated proportions with the liquid crystal composition 37-A prepared in Example 37.

| Ex. Comp. No. | Structural formula | wt. parts |
|---|---|---|
| 4-3 | n-$C_5H_{11}$—[pyridine]—[phenyl]—$OC_{12}H_{25}$-n | 5 |
| 4-54 | n-$C_{10}H_{21}$—[pyridine]—[phenyl]—O—$CH_2$CH*($CH_3$)—O—$C_3H_7$-n | 4 |
| 2-15 | n-$C_3H_7$—[cyclohexyl-H]—CO-O—[phenyl]—$OCH_2$CH*(F)$C_6H_{13}$-n | 4 |
| 2-27 | n-$C_{12}H_{25}$—[pyridine]—[phenyl]—$OCH_2$—CH*(F)$C_2H_5$ | 4 |
| 1-38 | n-$C_9H_{19}$—[phenyl]—$OCH_2$—[phenyl]—[phenyl]—$CH_2$CH*($CH_3$)$C_2H_5$ | 6 |
| | Composition 37-A | |

A ferroelectric liquid crystal device was prepared in the same manner as in Example 34 except that the above liquid crystal composition 39-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 707 μsec | 253 μsec | 99 μsec |

Further, a contrast of 13 was attained at 25° C. during the driving, and a clear switching function was observed. The bistability after termination of the voltage application was also good.

COMPARATIVE EXAMPLE 39

A liquid crystal composition 39-C was prepared by omitting Example compounds Nos. 2-27, 2-15 and 1-38 from the liquid crystal composition 39-B prepared in Example 39, i.e., by adding only Example compounds Nos. 4-3 and 4-54 to the liquid crystal composition 37-A. Ferroelectric liquid crystal devices 39-C and 37-A were prepared by using the compositions 39-C and 37-A, respectively, instead of the composition 34-B, and subjected to measurement of optical response time, otherwise in the same manner as in Example 34. The results are shown below.

| | Response time | | |
|---|---|---|---|
| | 10° C. | 25° C. | 40° C. |
| 37-A | 1410 μsec | 435 μsec | 155 μsec |
| 39-C | 1168 μsec | 385 μsec | 137 μsec |

As apparent from the above Example 39 and Comparative Example 39, the ferroelectric liquid crystal device containing the liquid crystal composition 39-B according to the present invention provided improved response speed and operation characteristic at a lower temperature and also provided a descreased temperature dependence of response speed.

EXAMPLE 40

A liquid crystal composition 40-A was prepared by mixing the following compounds in respectively indicated proportions.

| Ex. Compound No. | Structural formula | Wt. parts |
|---|---|---|
| 26 | $C_8H_{17}$—[pyridine]—[phenyl]—O—($CH_2$)$_5$CH*($CH_3$)$C_2H_5$ | 4 |

-continued

| Ex. Compound No. | Structural formula | Wt. parts |
|---|---|---|
| 27 | C$_{10}$H$_{21}$O—⟨Ph⟩—[pyrimidine]—COO$\text{+}$CH$_2\overline{)_3}$CH(CH$_3$)C$_2$H$_5$ * | 4 |
| 28 | C$_{12}$H$_{25}$O—⟨Ph⟩—[pyrimidine]—COO$\text{+}$CH$_2\overline{)_3}$CH(CH$_3$)C$_2$H$_5$ * | 6 |
| 29 | C$_{10}$H$_{21}$O—[pyrimidine]—⟨Ph⟩—O$\text{+}$CH$_2\overline{)_3}$CH(CH$_3$)C$_2$H$_5$ * | 6 |
| 30 | C$_8$H$_{17}$—[pyrimidine]—⟨Ph⟩—O$\text{+}$CH$_2\overline{)_3}$CH(CH$_3$)C$_2$H$_5$ * | 4 |
| 37 | C$_{12}$H$_{25}$O—⟨Ph⟩—[pyrimidine]—O$\text{+}$CH$_2\overline{)_3}$CH(CH$_3$)C$_2$H$_5$ * | 6 |
| 57 | C$_{10}$H$_{21}$O—⟨Ph⟩—COO—⟨Ph⟩—OC$_8$H$_{17}$ | 2 |
| 58 | C$_8$H$_{17}$—⟨Ph⟩—COO—⟨Ph⟩—OC$_{10}$H$_{21}$ | 5 |
| 59 | C$_{10}$H$_{21}$O—⟨Ph⟩—COO—⟨Ph⟩—OC$_6$H$_{13}$ | 4 |
| 60 | C$_{10}$H$_{21}$—⟨Ph⟩—COO—⟨Ph⟩—OC$_8$H$_{17}$ | 9 |
| 7 | C$_8$H$_{17}$—⟨Ph⟩—COO—⟨Ph⟩—⟨Ph⟩—OCH$_2$CH(CH$_3$)C$_2$H$_5$ * | 10 |
| 15 | C$_3$H$_7$OCH(CH$_3$)$\text{+}$CH$_2\overline{)_3}$O—⟨Ph⟩—COO—⟨Ph⟩—⟨Ph⟩—OC$_6$H$_{13}$ * | 5 |
| 69 | C$_4$H$_9$OCH$_2$CH(CH$_3$)O—⟨Ph⟩—COO—⟨Ph⟩—⟨Ph⟩—COOC$_8$H$_{17}$ * | 12 |
| 71 | CH$_3$OCH(CH$_3$)$\text{+}$CH$_2\overline{)_2}$O—⟨Ph⟩—COO—⟨Ph⟩—⟨Ph⟩—COOC$_8$H$_{17}$ * | 8 |

-continued

| Ex. Compound No. | Structural formula | Wt. parts |
|---|---|---|
| 32 | $C_8H_{17}$—⟨Ph⟩—OCO—⟨Ph⟩—⟨Ph⟩—O$\overset{CH_3}{\underset{*}{C}}$HC$_6$H$_{13}$ | 5 |
| 75 | $C_{12}H_{25}O$—⟨Ph⟩—COO—⟨Ph⟩—COO-(-CH$_2$-)$_3$$\overset{CH_3}{\underset{*}{C}}$HOC$_5$H$_{11}$ | 10 |

A liquid crystal composition 40-B was prepared by mixing the following example compounds 4-98, 4-136, 2-78, 1-37 and 1-40 with the above prepared composition 40-A.

| Ex. Comp. No. | Structural formula | Wt. parts |
|---|---|---|
| 4-98 | n-$C_9H_{19}$—⟨pyrimidine⟩—⟨Ph⟩—O-(-CH$_2$-)$_3$$\overset{CH_3}{\underset{*}{C}}$HC$_2$H$_5$ | 5 |
| 4-136 | n-$C_{11}H_{23}O$—⟨pyrimidine⟩—⟨Ph⟩—OCH$_2$$\overset{CH_3}{\underset{*}{C}}$HC$_2$H$_5$ | 3 |
| 2-78 | n-$C_{10}H_{21}$—⟨pyrimidine⟩—⟨Ph⟩—$\underset{O}{\overset{\|}{C}}$O—CH$_2$$\overset{F}{\underset{*}{C}}$H—C$_6$H$_{13}$-n | 8 |
| 1-37 | n-$C_8H_{17}$—⟨Ph⟩—OCH$_2$—⟨Ph⟩—⟨Ph⟩—CH$_2$$\overset{CH_3}{\underset{*}{C}}$HC$_2$H$_5$ | 2 |
| 1-40 | n-$C_{12}H_{25}O$—⟨Ph⟩—OCH$_2$—⟨Ph⟩—⟨Ph⟩—CH$_2$$\overset{CH_3}{\underset{*}{C}}$HC$_2$H$_5$ | 5 |
| Composition 40-A | | 77 |

A ferroelectric liquid crystal device 40-B was prepared in the same manner as in Example 34 except that the liquid crystal composition 40-B was used instead of the composition 34-B. The device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 530 μsec | 194 μsec | 81 μsec |

Further, a contrast of 13 was attained at 25° C. during the driving, and a clear switching function was observed.

COMPARATIVE EXAMPLE 40

A liquid crystal composition 40-C was prepared by omitting Example compound No. 2-78 from the liquid crystal composition 40-B prepared in Example 40, i.e., by adding only Example compounds Nos. 4-98, 4-145, 1-37 and 1-40 to the liquid crystal composition 40-A.

Ferroelectric liquid crystal devices 40-C and 40-A were prepared by using the compositions 40-C and 40-A, respectively, instead of the composition 34-B, and subjected to measurement of optical response time, otherwise in the same manner as in Example 34. The results are shown below.

|  | Response time (μsec) | | |
|---|---|---|---|
|  | 10° C. | 25° C. | 40° C. |
| 40-A | 762 | 246 | 98 |
| 40-C | 672 | 235 | 93 |

As apparent from the above Example 40 and Comparative Example 40, the ferroelectric liquid crystal device containing the liquid crystal composition 40-B according to the present invention provided improved response speed and operation characteristic at a lower temperature and also provided a descreased temperature dependence of response speed.

EXAMPLE 41

A liquid crystal composition 41-B was prepared by mixing the following example compounds in the indicated proportions with the liquid crystal composition 40-A prepared in Example 40.

| Ex. Comp. No. | Structural formula | wt. parts |
|---|---|---|
| 4-71 | n-$C_{10}H_{21}$—[pyrimidine]—[phenyl]—O-(-$CH_2$-)$_4$-CH($CH_3$)OCH$_3$ | 8 |
| 4-117 | n-$C_6H_{13}$—[pyrimidine]—[phenyl]—OC(=O)-(-$CH_2$-)$_4$-CH($CH_3$)CH$C_2H_5$* | 4 |
| 2-22 | n-$C_5H_{11}$—[H cyclohexyl]—CO(=O)—[phenyl]—OCH$_2$CH(F)—$C_8H_{17}$-n * | 8 |
| 1-31 | n-$C_{14}H_{29}$O—[phenyl]—CH$_2$O—[phenyl]—[phenyl]—OCH($CH_3$)—$C_6H_{13}$-n * | 5 |
| Composition 40-A | | 75 |

A ferroelectric liquid crystal device was prepared in the same manner as in Example 34 except that the above liquid crystal composition 41-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 435 μsec | 167 μsec | 70 μsec |

Further, a contrast of 12.5 was attained at 25° C. during the driving, and a clear switching function was observed. The bistability after termination of the voltage application was also good.

COMPARATIVE EXAMPLE 41

A liquid crystal composition 41-C was prepared by omitting Example compounds Nos. 4-71 and 4-117 from the liquid crystal composition 41-B prepared in Example 41, i.e., by adding only Example compounds Nos. 2-22 and 1-31 to the liquid crystal composition 40-A.

Ferroelectric liquid crystal devices 41-C and 40-A were prepared by using the compositions 41-C and 40-A, respectively, instead of the composition 34-B, and subjected to measurement of optical response time, otherwise in the same manner as in Example 34. The results are shown below.

| | Response time (μsec) | | |
|---|---|---|---|
| | 10° C. | 25° C. | 40° C. |
| 40-A | 762 | 246 | 98 |
| 41-C | 526 | 190 | 74 |

As apparent from the above Example 41 and Comparative Example 41, the ferroelectric liquid crystal device containing the liquid crystal composition 41-B according to the present invention provided improved response speed and operation characteristic at a lower temperature and also provided a descreased temperature dependence of response speed.

EXAMPLE 42

A liquid crystal composition 42-B was prepared by mixing the following example compounds in the indicated proportions with the liquid crystal composition 40-A prepared in Example 40.

| Ex. Comp. No. | Structural formula | wt. parts |
|---|---|---|
| 4-11 | n-$C_9H_{19}$—[pyrimidine]—[phenyl]—O$C_6H_{13}$-n | 5 |

| Ex. Comp. No. | Structural formula | wt. parts |
|---|---|---|
| 4-40 | n-C$_7$H$_{15}$—[pyrimidine]—[phenyl]—O(CH$_2$)$_2$OC$_4$H$_9$-n | 3 |
| 4-172 | n-C$_{12}$H$_{25}$O—[pyrimidine]—[phenyl]—O(CH$_2$)$_4$OCH$_2$CH(CH$_3$)C$_2$H$_5$ * | 3 |
| 2-66 | n-C$_6$H$_{13}$—O—CH$_2$CH$_2$—[pyrimidine]—[phenyl]—OCH$_2$CH(F)—C$_8$H$_{17}$-n * | 5 |
| 1-57 | n-C$_8$H$_{17}$—[phenyl]—[phenyl]—OCH$_2$—[phenyl]—OCH$_2$CH(CH$_3$)OC$_2$H$_5$ * | 4 |
| Composition 40-A | | 80 |

A ferroelectric liquid crystal device was prepared in the same manner as in Example 34 except that the above liquid crystal composition 42-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 489 μsec | 185 μsec | 78 μsec |

Further, a contrast of 13 was attained at 25° C. during the driving, and a clear switching function was observed. The histability after termination of the voltage application was also good.

COMPARATIVE EXAMPLE 42

A liquid crystal composition 42-C was prepared by omitting Example compounds Nos. 4-11, 4-40, 4-172 and 2-66 from the liquid crystal composition 42-B prepared in Example 42, i.e., by adding only Example compound No. 1-57 to the liquid crystal composition 40-A. Ferroelectric liquid crystal devices 42-C and 40-A were prepared by using the compositions 42-C and 40-A, respectively, instead of the composition 34-B, and subjected to measurement of optical response time, otherwise in the same manner as in Example 34. The results are shown below.

| | Response time | | |
|---|---|---|---|
| | 10° C. | 25° C. | 40° C. |
| 40-A | 762 μsec | 246 μsec | 98 μsec |
| 42-C | 723 μsec | 237 μsec | 95 μsec |

As apparent from the above Example 42 and Comparative Example 42, the ferroelectric liquid crystal device containing the liquid crystal composition 42-B according to the present invention provided improved response speed and operation characteristic at a lower temperature and also provided a descreased temperature dependence of response speed.

EXAMPLES 43–50

Liquid crystal compositions 43-B to 50-B were prepared by replacing the example compounds and the liquid crystal compositions used in Examples 34, 37 and 40 with example compounds and liquid crystal compositions shown in the following Table 3. Ferroelectric liquid crystal devices were prepared by respectively using these compositions instead of the composition 34-B, and subjected to measurement of optical response time and observation of switching states. In the devices, a monodomain with a good and uniform alignment characteristic was observed. The results of the measurement are shown in the following Table 3.

TABLE 3

| Ex. No. (Comp. No.) | Example compound No. or liquid crystal composition No. (weight parts) | | | | | | | Response time (μsec) | | |
|---|---|---|---|---|---|---|---|---|---|---|
| | | | | | | | | 10° C. | 25° C. | 40° C. |
| 43 | 4-5 | 4-21 | 4-53 | 4-133 | 2-18 | 1-21 | 34-A | 745 | 273 | 110 |
| (43-B) | (3) | (6) | (3) | (4) | (7) | (5) | (72) | | | |
| 44 | 4-58 | 4-92 | 4-105 | 2-76 | 1-5 | 1-35 | 34-A | 700 | 260 | 106 |
| (44-B) | (4) | (4) | (4) | (8) | (6) | (4) | (70) | | | |
| 45 | 4-107 | 4-147 | 2-3 | 2-40 | 1-42 | | 34-A | 857 | 309 | 123 |
| (45-B) | (5) | (5) | (4) | (6) | (6) | | (74) | | | |
| 46 | 4-37 | 4-81 | 2-29 | 2-75 | 1-37 | 1-60 | 37-A | 830 | 295 | 116 |
| (46-B) | (8) | (5) | (4) | (4) | (5) | (3) | (71) | | | |
| 47 | 4-9 | 4-147 | 4-157 | 2-8 | 1-53 | | 37-A | 882 | 317 | 127 |
| (47-B) | (7) | (5) | (4) | (6) | (4) | | (70) | | | |

TABLE 3-continued

| Ex. No. (Comp. No.) | Example compound No. or liquid crystal composition No. (weight parts) | | | | | | | Response time (μsec) | | |
|---|---|---|---|---|---|---|---|---|---|---|
| | | | | | | | | 10° C. | 25° C. | 40° C. |
| 48 (48-B) | 4-23 (5) | 4-68 (5) | 4-100 (4) | 4-137 (3) | 2-10 (4) | 2-54 (3) | 1-27 (6) | 37-A (70) | 764 | 288 | 118 |
| 49 (49-B) | 4-66 (4) | 4-72 (5) | 4-119 (5) | 2-82 (6) | 1-11 (6) | 1-38 (4) | | 40-A (70) | 527 | 198 | 86 |
| 50 (50-B) | 4-44 (3) | 4-125 (3) | 4-141 (3) | 2-4 (5) | 2-17 (5) | 1-64 (6) | | 40-A (75) | 449 | 170 | 70 |

As is apparent from the results shown in the above Table 3, the ferroelectric liquid crystal devices containing the liquid crystal compositions 43-B to 50-B provided improved response speed and a decrease temperature dependence of the response speed.

EXAMPLE 51

A blank cell was prepared in the same manner as in Example 1 except for omitting the SiO$_2$ layer to form an alignment control layer composed of the polyimide resin layer alone on each electrode plate. Five ferroelectric liquid crystal devices were prepared by filling such a blank cell with liquid crystal compositions 34-B, 34-A, 34-C, 34-D and 34-E, respectively, prepared in Example 34 and Comparative Example 34. These liquid crystal devices were subjected to measurement of optical response time in the same manner as in Example 34. The results are shown below.

| | Response time (μsec) | | |
|---|---|---|---|
| | 10° C. | 25° C. | 40° C. |
| 34-B | 805 | 294 | 115 |
| 34-A | 1146 | 357 | 128 |
| 34-C | 873 | 306 | 121 |
| 34-D | 940 | 334 | 133 |
| 34-E | 841 | 301 | 120 |

As is apparent from the above Example 51, also in the case of a different device structure, the device containing the ferroelectric liquid crystal composition 34-B according to the present invention provided improved operation characteristic at a lower temperature and also a decreased temperature dependence of response speed.

EXAMPLE 52

A liquid crystal composition 52-A was prepared by mixing the following compounds in respectively indicated proportions.

| Ex. Compound No. | Structural formula | Wt. parts |
|---|---|---|
| 26 | $C_8H_{17}$—[pyrimidine]—[phenyl]—O(CH$_2$)$_3$CH(CH$_3$)C$_2$H$_5$ | 4 |
| 27 | $C_{10}H_{21}$O—[phenyl]—[pyrimidine]—COO(CH$_2$)$_3$CH(CH$_3$)C$_2$H$_5$ | 2 |
| 28 | $C_{12}H_{25}$O—[phenyl]—[pyrimidine]—COO(CH$_2$)$_3$CH(CH$_3$)C$_2$H$_5$ | 3 |
| 29 | $C_{10}H_{21}$O—[pyrimidine]—[phenyl]—O(CH$_2$)$_3$CH(CH$_3$)C$_2$H$_5$ | 3 |
| 30 | $C_8H_{17}$—[pyrimidine]—[phenyl]—O(CH$_2$)$_3$CH(CH$_3$)C$_2$H$_5$ | 3 |
| 37 | $C_{12}H_{25}$O—[phenyl]—[pyrimidine]—O(CH$_2$)$_3$CH(CH$_3$)C$_2$H$_5$ | 5 |

| Ex. Compound No. | Structural formula | Wt. parts |
|---|---|---|
| 57 | $C_{10}H_{21}O$—⌬—COO—⌬—$OC_8H_{17}$ | 9 |
| 58 | $C_8H_{17}$—⌬—COO—⌬—$OC_{10}H_{21}$ | 10 |
| 59 | $C_{10}H_{21}O$—⌬—COO—⌬—$OC_6H_{13}$ | 6 |
| 60 | $C_{10}H_{21}$—⌬—COO—⌬—$OC_8H_{17}$ | 15 |
| 7 | $C_8H_{17}$—⌬—COO—⌬—⌬—$OCH_2\overset{*}{C}H(CH_3)C_2H_5$ | 5 |
| 15 | $C_3H_7O\overset{*}{C}H(CH_3)(CH_2)_3O$—⌬—COO—⌬—⌬—$OC_6H_{13}$ | 5 |
| 69 | $C_4H_9OCH_2\overset{*}{C}H(CH_3)O$—⌬—COO—⌬—⌬—$COOC_8H_{17}$ | 14 |
| 71 | $CH_3O\overset{*}{C}H(CH_3)(CH_2)_2O$—⌬—COO—⌬—⌬—$COOC_8H_{17}$ | 16 |

A liquid crystal composition 52-B was prepared by mixing the following example compounds 5-11, 5-62, 2-33, 1-6 and 1-37 with the above prepared composition 52-A.

| Ex. Comp. No. | Structural formula | Wt. parts |
|---|---|---|
| 5-11 | n-$C_7H_{15}$—(N,N-pyrimidine)—⌬—⌬—$C_6H_{13}$-n | 5 |
| 5-62 | n-$C_3H_7$—(H cyclohexyl)—CO-O—⌬—⌬—$OC_{10}H_{21}$-n | 5 |
| 2-33 | n-$C_8H_{17}$—(N,N-pyrimidine)—⌬—$OCH_2\overset{*}{C}H(F)C_8H_{17}$-n | 6 |

-continued

| Ex. Comp. No. | Structural formula | Wt. parts |
|---|---|---|
| 1-6 | n-C$_7$H$_{15}$—◯—◯—OCH$_2$—◯—OC$_8$H$_{17}$-n | 5 |
| 1-37 | n-C$_8$H$_{17}$—◯—OCH$_2$—◯—◯—CH$_2$CHC$_2$H$_5$ (CH$_3$) * | 4 |
| | Composition 52-A | 75 |

A ferroelectric liquid crystal device was prepared in the same manner as in Example 1 except that the above liquid crystal composition 52-B was used instead of the composition 1-B. The device was subjected to measurement of driving voltage margin and observation of switching states. In the device, a monodomain with a good and uniform alignment characteristic was observed. The results of the measurement are shown below.

|  | 10° C. | 25° C. | 40° C. |
|---|---|---|---|
| Response time | 527 μsec | 199 μsec | 81 μsec |

Further, a contrast of 13 was attained at 25° C. during the driving, and a clear switching function was observed.

COMPARATIVE EXAMPLE 52

A liquid crystal composition 52-C was prepared by omitting Example compounds Nos. 5-11 and 5-62 from the liquid crystal composition 52-B prepared in Example 52, i.e., by adding only Example compounds Nos. 2-33, 1-6 and 1-37 to the liquid crystal composition 52-A, and a liquid crystal composition 52-D was prepared by omitting Example compound No. 2-33 from the composition 52-B, i.e., by adding only Example compounds Nos. 5-11, 5-62, 1-6 and 1-37 to the composition 52-A and a liquid crystal composition 52-E was prepared by omitting Example compounds Nos. 1-6 and 1-37 from the composition 52-B, i.e., by adding only Example compounds Nos. 5-11, 5-62 and 2-33 to the composition 52-A.

Ferroelectric liquid crystal devices 52-C, 52-D, 52-E and 52-A were prepared by using the compositions 52-C, 52-D, 52-E and 52-A, respectively, instead of the composition 52-B, and subjected to measurement of optical response time, otherwise in the same manner as in Example 52. The results are shown below.

| | Response time | | |
|---|---|---|---|
| | 10° C. | 25° C. | 40° C. |
| 52-A | 872 μsec | 285 μsec | 115 μsec |
| 52-C | 621 μsec | 229 μsec | 89 μsec |
| 52-D | 758 μsec | 277 μsec | 110 μsec |
| 52-E | 596 μsec | 218 μsec | 85 μsec |

As apparent from the above Example 52 and Comparative Example 52, the ferroelectric liquid crystal device containing the liquid crystal composition 52-B according to the present invention provided improved response speed and operation characteristic at a lower temperature and also provided a descreased temperature dependence of response speed (ratio of response time (10° C./40° C.)).

EXAMPLE 53

A liquid crystal composition 53-B was prepared by mixing the following example compounds in the indicated proportions with the liquid crystal composition 52-A prepared in Example 52.

| Ex. Comp. No. | Structural formula | wt. parts |
|---|---|---|
| 5-29 | n-C$_{10}$H$_{21}$—◯(N,N)—◯—◯—O(CH$_2$)$_4$CHOCH$_3$ (CH$_3$) | 3 |
| 5-136 | n-C$_5$H$_{11}$—◯(H)—CH$_2$O—◯—◯(N,N)—C$_4$H$_9$-n | 5 |
| 2-1 | n-C$_4$H$_9$—◯(H)—CO—◯—COCH$_2$CHC$_5$H$_{11}$-n (F) * (O,O) | 2 |

| Ex. Comp. No. | Structural formula | wt. parts |
|---|---|---|
| 2-17 | n-$C_5H_{11}$—⟨H⟩—CO—O—⟨⟩—OCH$_2$CHC$_6$H$_{13}$-n (F substituent, * chiral) | 7 |
| 1-65 | n-$C_{10}H_{21}$O—⟨⟩—⟨⟩—CH$_2$O—⟨⟩—O(CH$_2$)$_4$CHOCH$_3$ (CH$_3$ branch) | 5 |
| Composition 52-A | | 78 |

A ferroelectric liquid crystal device was prepared in the same manner as in Example 52 except that the above liquid crystal composition 53-B was used, and the device was subjected to measurement of driving voltage margin and observation of switching states. In the device, a monodomain with a good and uniform alignment characteristic was observed. The results of the measurement are shown below.

|  | 10° C. | 25° C. | 40° C. |
|---|---|---|---|
| Response time | 584 μsec | 214 μsec | 85 μsec |

Further, a contrast of 12 was attained at 25° C. during the driving, and a clear switching function was observed. The bistability after termination of the voltage application was also good.

COMPARATIVE EXAMPLE 53

A liquid crystal composition 53-C was prepared by omitting Example compounds Nos. 2-17 and 2-1 from the liquid crystal composition 53-B prepared in Example 53, i.e., by adding only Example compounds Nos. 5-29, 5-136 and 1-65 to the liquid crystal composition 52-A.

Ferroelectric liquid crystal device 53-C and 52-A were prepared by using the compositions 53-C and 52-A, respectively, instead of the composition 52-B, and subjected to measurement of optical response time, otherwise in the same manner as in Example 52. The results are shown below.

|  | Response time | | |
|---|---|---|---|
|  | 10° C. | 25° C. | 40° C. |
| 52-A | 872 μsec | 285 μsec | 115 μsec |
| 53-C | 764 μsec | 275 μsec | 108 μsec |

As apparent from the above Example 53 and Comparative Example 53, the ferroelectric liquid crystal device containing the liquid crystal composition 53-B according to the present invention provided improved response speed and operation characteristic at a lower temperature and also provided a descreased temperature dependence of response speed.

EXAMPLE 54

A liquid crystal composition 54-B was prepared by mixing the following example compounds in the indicated proportions with the liquid crystal composition 52-A prepared in Example 52.

| Ex. Comp. No. | Structural formula | wt. parts |
|---|---|---|
| 5-67 | CH$_3$—⟨H⟩—CO—O—⟨⟩—⟨N,N-pyrazine⟩—$C_{12}H_{25}$-n | 5 |
| 5-140 | n-$C_6H_{13}$—⟨H⟩—CH$_2$O—⟨⟩—⟨⟩—O(CH$_2$)$_2$OC$_6$H$_{13}$-n | 5 |
| 2-8 | n-$C_3H_7$—⟨H⟩—CO—O—⟨⟩—COCH$_2$CHC$_7$H$_{15}$-n (F substituent, * chiral) | 2 |
| 2-46 | n-$C_{11}H_{23}$—⟨N,N⟩—⟨⟩—OCH$_2$CHC$_4$H$_9$-n (F substituent, * chiral) | 7 |

| Ex. Comp. No. | Structural formula | wt. parts |
|---|---|---|
| 1-38 | 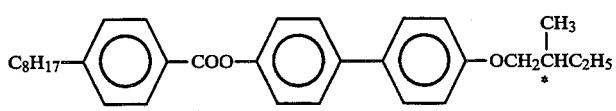 | 3 |
| Composition 52-A | | 78 |

A ferroelectric liquid crystal device was prepared in the same manner as in Example 52 except that the above liquid crystal composition 54-B was used, and the device was subjected to measurement of driving voltage margin and observation of switching states. In the device, a monodomain with a good and uniform alignment characteristic was observed. The results of the measurement are shown below.

|  | 10° C. | 25° C. | 40° C. |
|---|---|---|---|
| Response time | 513 μsec | 194 μsec | 79 μsec |

Further, a contrast of 13 was attained at 25° C. during the driving, and a clear switching function was observed. The bistability after termination of the voltage application was also good.

COMPARATIVE EXAMPLE 54

A liquid crystal composition 54-C was prepared by omitting Example compounds Nos. 2-46 and 2-8 from the liquid crystal composition 54-B prepared in Example 54, i.e., by adding only Example compounds Nos. 5-67, 5-140 and 1-38 to the liquid crystal composition 52-A.

Ferroelectric liquid crystal devices 54-C and 52-A were prepared by using the compositions 54-C and 52-A, respectively, instead of the composition 52-B, and subjected to measurement of optical response time, otherwise in the same manner as in Example 52. The results are shown below.

|  | Response time | | |
|---|---|---|---|
|  | 10° C. | 25° C. | 40° C. |
| 52-A | 872 μsec | 285 μsec | 115 μsec |
| 54-C | 731 μsec | 268 μsec | 106 μsec |

As apparent from the above Example 54 and Comparative Example 54, the ferroelectric liquid crystal device containing the liquid crystal composition 54-B according to the present invention provided improved response speed and operation characteristic at a lower temperature and also provided a descreased temperature dependence of response speed.

EXAMPLE 55

A liquid crystal composition 55-A was prepared by mixing the following compounds in respectively indicated proportions.

| Ex. Compound No. | Structural formula | Wt. parts |
|---|---|---|
| 7 | 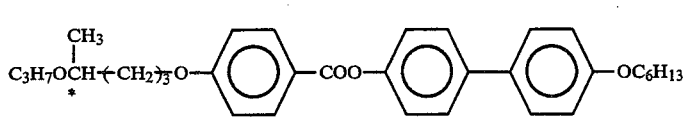 | 15 |
| 15 | 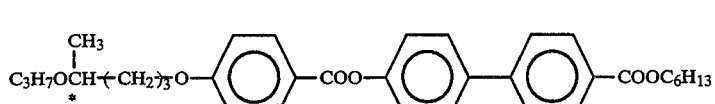 | 5 |
| 16 | 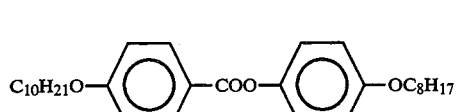 | 10 |
| 57 |  | 5 |
| 58 |  | 8 |

| Ex. Compound No. | Structural formula | Wt. parts |
|---|---|---|
| 59 | $C_{10}H_{21}O-\bigcirc-COO-\bigcirc-OC_6H_{13}$ | 5 |
| 60 | $C_{10}H_{21}-\bigcirc-COO-\bigcirc-OC_8H_{17}$ | 12 |
| 12 | $C_8H_{17}O-\bigcirc-COS-\bigcirc-OCH_2\overset{*}{\underset{CH_3}{C}H}C_2H_5$ | 9 |
| 13 | $C_{10}H_{21}O-\bigcirc-COS-\bigcirc-OCH_2\overset{*}{\underset{CH_3}{C}H}C_2H_5$ | 6 |
| 69 | $C_4H_9OCH_2\overset{*}{\underset{CH_3}{C}H}O-\bigcirc-COO-\bigcirc-\bigcirc-COOC_8H_{17}$ | 5 |
| 55 | $C_{12}H_{25}O-\bigcirc-COO-\bigcirc-COOCH_2\overset{*}{\underset{CH_3}{C}H}OC_5H_{11}$ | 15 |
| 75 | $C_{12}H_{25}O-\bigcirc-COO-\bigcirc-COO(CH_2)_3\overset{*}{\underset{CH_3}{C}H}OC_5H_{11}$ | 5 |

A liquid crystal composition 55-B was prepared by mixing the following example compounds 5-11, 5-62, 2-33, 1-6 and 1-37 with the above prepared composition 55-A.

| Ex. Comp. No. | Structural formula | wt. parts |
|---|---|---|
| 5-11 | $n\text{-}C_7H_{15}-\underset{N}{\overset{N}{\bigcirc}}-\bigcirc-\bigcirc-C_6H_{13}\text{-}n$ | 4 |
| 5-62 | $n\text{-}C_3H_7-\bigcirc_H-\overset{O}{\underset{\parallel}{C}}O-\bigcirc-\bigcirc-OC_{10}H_{21}\text{-}n$ | 8 |
| 2-33 | $n\text{-}C_8H_{17}-\underset{N}{\overset{N}{\bigcirc}}-\bigcirc-OCH_2\overset{*}{\underset{F}{C}H}C_8H_{17}\text{-}n$ | 7 |
| 1-6 | $n\text{-}C_7H_{15}-\bigcirc-\bigcirc-OCH_2-\bigcirc-OC_8H_{17}\text{-}n$ | 3 |

| Ex. Comp. No. | Structural formula | wt. parts |
|---|---|---|
| 1-37 |  | 3 |
| Composition 52-A | | 75 |

A ferroelectric liquid crystal device 55-B was prepared in the same manner as in Example 52 except that the liquid crystal composition 55-B was used instead of the composition 52-B. The device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 805 μsec | 286 μsec | 111 μsec |

Further, a contrast of 14 was attained at 25° C. during the driving, and a clear switching function was observed.

COMPARATIVE EXAMPLE 55

A liquid crystal composition 55-C was prepared by omitting Example compounds Nos. 5-11 and 5-62 from the liquid crystal composition 55-B prepared in Example 55, i.e., by adding only Example compounds Nos. 2-33, 1-6 and 1-37 to the liquid crystal composition 55-A, and a liquid crystal composition 55-D was prepared by omitting Example compound No. 2-33 from the composition 55-B, i.e., by adding only Example compounds Nos. 5-11, 5-62, 1-6 and 1-37 to the composition 55-A, and a liquid crytal composition 55-E was prepared by omitting Example compounds Nos. 1-6 and 1-37 from the composition 55-B, i.e., by adding only Example compounds Nos. 5-11, 5-62 and 2-33 to the composition 55-A.

Ferroelectric liquid crystal devices 55-C, 55-D, 55-E and 55-A were prepared by using the compositions 55-C, 55-D, 55-E and 55-A, respectively, instead of the composition 52-B, and subjected to measurement of optical response time, otherwise in the same manner as in Example 52. The results are shown below.

|  | Response time (μsec) | | |
|---|---|---|---|
|  | 10° C. | 25° C. | 40° C. |
| 55-A | 1410 | 435 | 155 |
| 55-C | 940 | 318 | 118 |
| 55-D | 1195 | 389 | 139 |
| 55-E | 899 | 303 | 113 |

As apparent from the above Example 55 and Comparative Example 55, the ferroelectric liquid crystal device containing the liquid crystal composition 55-B according to the present invention provided improved response speed and operation characteristic at a lower temperature and also provided a descreased temperature dependence of response speed.

EXAMPLE 56

A liquid crystal composition 56-B was prepared by mixing the following example compounds in the indicated proportions with the liquid crystal composition 55-A prepared in Example 55.

| Ex. Comp. No. | Structural formula | wt. parts |
|---|---|---|
| 5-6 |  | 4 |
| 5-10 | 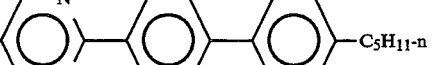 | 5 |
| 2-19 | 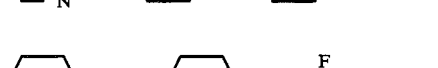 | 6 |
| 1-27 | | 3 |

| Ex. Comp. No. | Structural formula | wt. parts |
| --- | --- | --- |
| 1-41 | n-$C_6H_{13}$—〈Ph〉—$CH_2O$—〈Ph〉—〈Ph〉—$\text{COCH}_2\overset{*}{\text{CH}}C_2H_5$ (with $CH_3$ branch, C=O) | 4 |
| Composition 55-A | | 78 |

A ferroelectric liquid crystal device was prepared in the same manner as in Example 52 except that the above liquid crystal composition 56-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
| --- | --- | --- | --- |
| Response time | 878 μsec | 310 μsec | 118 μsec |

Further, a contrast of 12 was attained at 25° C. during the driving, and a clear switching function was observed. The bistability after termination of the voltage application was also good.

COMPARATIVE EXAMPLE 56

A liquid crystal composition 56-C was prepared by omitting Example compounds Nos. 5-6 and 5-10 from the liquid crystal composition 56-B prepared in Example 56, i.e., by adding only Example compounds Nos. 2-19, 1-27 and 1-41 to the liquid crystal composition 55-A.

Ferroelectric liquid crystal devices 56-C and 55-A were prepared by using the compositions 56-C and 55-A, respectively, instead of the composition 52-B, and subjected to measurement of optical response time, otherwise in the same manner as in Example 52. The results are shown below.

| | Response time (μsec) | | |
| --- | --- | --- | --- |
| | 10° C. | 25° C. | 40° C. |
| 55-A | 1410 | 435 | 155 |
| 56-C | 950 | 322 | 121 |

As apparent from the above Example 56 and Comparative Example 56, the ferroelectric liquid crystal device containing the liquid crystal composition 56-B according to the present invention provided improved response speed and operation characteristic at a lower temperature and also provided a descreased temperature dependence of response speed.

EXAMPLE 57

A liquid crystal composition 57-B was prepared by mixing the following example compounds in the indicated proportions with the liquid crystal composition 55-A prepared in Example 55.

| Ex. Comp. No. | Structural formula | wt. parts |
| --- | --- | --- |
| 5-37 | n-$C_8H_{17}O$—〈Ph〉—〈pyrimidine N,N〉—〈Ph〉—$OC_5H_{11}$-n | 5 |
| 5-155 | n-$C_{12}H_{25}$—〈H〉—$CH_2O$—〈Ph〉—〈pyrimidine N,N〉—$C_6H_{13}$-n | 6 |
| 2-23 | n-$C_5H_{11}$—〈H〉—CO-O—〈Ph〉—$\text{OCH}_2\overset{*}{\text{CH}}C_9H_{19}$-n (with F branch) | 4 |
| 2-52 | n-$C_{12}H_{25}$—〈pyridazine N,N〉—〈Ph〉—$\text{OCH}_2\overset{*}{\text{CH}}C_4H_9$-n (with F branch) | 4 |
| 1-25 | n-$C_7H_{15}O$—〈Ph〉—$CH_2O$—〈Ph〉—$\text{OCH}_2\overset{*}{\text{CH}}C_2H_5$ (with $CH_3$ branch) | 5 |
| Composition 55-A | | 76 |

A ferroelectric liquid crystal device was prepared in the same manner as in Example 52 except that the above liquid crystal composition 57-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 722 μsec | 253 μsec | 96 μsec |

Further, a contrast of 13 was attained at 25° C. during the driving, and a clear switching function was observed. The bistability after termination of the voltage application was also good.

COMPARATIVE EXAMPLE 57

A liquid crystal composition 57-C was prepared from the liquid crystal composition 57-B, i.e., by adding only Example compounds Nos. 5-37 and 5-155 to the liquid crystal composition 55-A.

Ferroelectric liquid crystal devices 57-C and 55-A were prepared by using the compositions 57-C and 55-A, respectively, instead of the composition 52-B, and subjected to measurement of optical response time, otherwise in the same manner as in Example 52. The results are shown below.

|  | Response time | | |
|---|---|---|---|
|  | 10° C. | 25° C. | 40° C. |
| 55-A | 1410 μsec | 435 μsec | 155 μsec |
| 57-C | 1183 μsec | 407 μsec | 150 μsec |

As apparent from the above Example 57 and Comparative Example 57, the ferroelectric liquid crystal device containing the liquid crystal composition 57-B according to the present invention provided improved response speed and operation characteristic at a lower temperature and also provided a descreased temperature dependence of response speed.

EXAMPLE 58

A liquid crystal composition 58-A was prepared by mixing the following compounds in respectively indicated proportions.

| Ex. Compound No. | Structural formula | Wt. parts |
|---|---|---|
| 57 | $C_{10}H_{21}O$—⟨◯⟩—COO—⟨◯⟩—$OC_8H_{17}$ | 7 |
| 58 | $C_8H_{17}$—⟨◯⟩—COO—⟨◯⟩—$OC_{10}H_{21}$ | 7 |
| 59 | $C_{10}H_{21}O$—⟨◯⟩—COO—⟨◯⟩—$OC_6H_{13}$ | 10 |
| 60 | $C_{10}H_{21}$—⟨◯⟩—COO—⟨◯⟩—$OC_8H_{17}$ | 10 |
| 8 | $C_8H_{17}O$—⟨◯⟩—COS—⟨◯⟩—$CH_2\overset{*}{C}H(CH_3)C_2H_5$ | 4 |
| 9 | $C_{12}H_{25}O$—⟨◯⟩—COS—⟨◯⟩—$CH_2\overset{*}{C}H(CH_3)C_2H_5$ | 4 |
| 12 | $C_8H_{17}O$—⟨◯⟩—COS—⟨◯⟩—$OCH_2\overset{*}{C}H(CH_3)C_2H_5$ | 4 |
| 13 | $C_{10}H_{21}O$—⟨◯⟩—COS—⟨◯⟩—$OCH_2\overset{*}{C}H(CH_3)C_2H_5$ | 4 |

-continued

| Ex. Compound No. | Structural formula | Wt. parts |
|---|---|---|
| 16 | C₃H₇OCH(CH₃)(CH₂)₃O—⌬—COO—⌬—⌬—COOC₆H₁₃ * | 10 |
| 69 | C₄H₉OCH₂CH(CH₃)O—⌬—COO—⌬—⌬—COOC₈H₁₇ * | 15 |
| 71 | CH₃OCH(CH₃)(CH₂)₂O—⌬—COO—⌬—⌬—COOC₈H₁₇ * | 10 |
| 55 | C₁₂H₂₅O—⌬—COO—⌬—COOCH₂CHOC₅H₁₁ (CH₃) * | 5 |
| 75 | C₁₂H₂₅O—⌬—COO—⌬—COO(CH₂)₃CHOC₅H₁₁ (CH₃) * | 10 |

A liquid crystal composition 58-B was prepared by mixing the following example compounds 5-11, 5-62, 2-33, 1-6 and 1-37 with the above prepared composition 58-A.

good and uniform alignment characteristic was observed. The results of the measurement are shown below.

| Ex. Comp. No. | Structural formula | Wt. parts |
|---|---|---|
| 5-11 | n-C₇H₁₅—(pyrimidine)—⌬—⌬—C₆H₁₃-n | 3 |
| 5-62 | n-C₃H₇—(cyclohexane-H)—CO-O—⌬—⌬—OC₁₀H₂₁-n | 6 |
| 2-33 | n-C₈H₁₇—(pyrimidine)—⌬—OCH₂CHC₈H₁₇-n (F) * | 7 |
| 1-6 | n-C₇H₁₅—⌬—⌬—OCH₂—⌬—OC₈H₁₇-n | 3 |
| 1-37 | n-C₈H₁₇—⌬—OCH₂—⌬—⌬—CH₂CHC₂H₅ (CH₃) * | 4 |
| Composition 58-A | | 77 |

A ferroelectric liquid crystal device 58-B was prepared in the same manner as in Example 52 except that the liquid crystal composition 58-B was used instead of the composition 52-B. The device was subjected to measurement of optical response time and observation of switching states. In the device, a monodomain with a

| | 10° C. | 25° C. | 40° C. |
|---|---|---|---|
| Response time | 811 μsec | 284 μsec | 109 μsec |

Further, a contrast of 14 was attained at 25° C. during the driving, and a clear switching function was observed.

COMPARATIVE EXAMPLE 58

A liquid crystal composition 58-C was prepared by omitting Example compound No. 2-33 from the liquid crystal composition 58-B prepared in Example 58, i.e., by adding only Example compounds Nos. 5-11, 5-62, 1-6 and 1-37 to the liquid crystal composition 58-A.

Ferroelectric liquid crystal devices 58-C and 58-A were prepared by using the compositions 58-C and 58-A, respectively, instead of the composition 52-B, and subjected to measurement of optical response time, otherwise in the same manner as in Example 52. The results are shown below.

|  | Response time ($\mu$sec) | | |
| --- | --- | --- | --- |
|  | 10° C. | 25° C. | 40° C. |
| 58-A | 1260 | 374 | 137 |
| 58-C | 1035 | 361 | 131 |

AS apparent from the above Example 58 and Comparative Example 58, the ferroelectric liquid crystal device containing the liquid crystal composition 58-B according to the present invention provided improved response speed and operation characteristic at a lower temperature and also provided a descreased temperature dependence of response speed.

EXAMPLE 59

A liquid crystal composition 59-B was prepared by mixing the following example compounds in the indicated proportions with the liquid crystal composition 58-A prepared in Example 58.

A ferroelectric liquid crystal device was prepared in the same manner as in Example 52 except that the above liquid crystal composition 59-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time | 839 $\mu$sec | 294 $\mu$sec | 114 $\mu$sec |

Further, a contrast of 12 was attained at 25° C. during the driving, and a clear switching function was observed. The bistability after termination of the voltage application was also good.

COMPARATIVE EXAMPLE 59

A liquid crystal composition 59-C was prepared by omitting Example compounds Nos. 5-6 and 5-10 from the liquid crystal composition 59-B prepared in Example 59, i.e., by adding only Example compounds Nos. 2-19, 1-27 and 1-41 to the liquid crystal composition 58-A.

Ferroelectric Liquid crystal devices 59-C and 58-A were prepared by using the compositions 59-C and 58-A, respectively, instead of the composition 52-B, and subjected to measurement of optical response time, otherwise in the same manner as in Example 52. The results are shown below.

|  | Response time ($\mu$sec) | | |
| --- | --- | --- | --- |
|  | 10° C. | 25° C. | 40° C. |
| 58-A | 1260 | 374 | 137 |
| 59-C | 961 | 327 | 123 |

| Ex. Comp. No. | Structural formula | wt. parts |
| --- | --- | --- |
| 5-6 | n-C$_4$H$_9$O—[pyrazine]—[phenyl]—[phenyl]—OC$_5$H$_{11}$-n | 3 |
| 5-10 | n-C$_8$H$_{17}$—[pyrazine]—[phenyl]—[phenyl]—C$_5$H$_{11}$-n | 6 |
| 2-19 | n-C$_5$H$_{11}$—[H cyclohexyl]—CO—O—[phenyl]—OCH$_2$CHFC$_7$H$_{15}$-n * | 7 |
| 1-27 | n-C$_6$H$_{13}$—[phenyl]—CH$_2$O—[phenyl]—[phenyl]—CH$_2$CH(CH$_3$)C$_2$H$_5$ * | 4 |
| 1-41 | n-C$_6$H$_{13}$—[phenyl]—CH$_2$O—[phenyl]—[phenyl]—COOCH$_2$CH(CH$_3$)C$_2$H$_5$ * | 3 |
| Composition 58-A | | 77 |

As apparent from the above Example 59 and Comparative Example 59, the ferroelectric liquid crystal device containing the liquid crystal composition 59-B according to the present invention provided improved response speed and operation characteristic at a lower temperature and also provided a descreased temperature dependence of response speed.

EXAMPLE 60

A liquid crystal composition 60-B was prepared by mixing the following example compounds in the indicated proportions with the liquid crystal composition 58-A prepared in Example 58.

| Ex. Comp. No. | Structural formula | wt. parts |
|---|---|---|
| 5-79 | n-$C_4H_9$—⟨H⟩—CO—⟨○⟩—⟨N=N⟩—$C_{14}H_{29}$-n | 6 |
| 5-157 | n-$C_3H_7$—⟨H⟩—$CH_2O$—⟨○⟩—⟨○⟩—$C_6H_{13}$-n | 3 |
| 2-73 | n-$C_7H_{15}$—⟨N=N⟩—⟨○⟩—$COCH_2\overset{*}{C}HC_6H_{13}$-n (F) | 3 |
| 2-81 | n-$C_{12}H_{25}$—⟨N=N⟩—⟨○⟩—$COCH_2\overset{*}{C}HC_8H_{17}$-n (F) | 4 |
| 1-28 | n-$C_5H_{11}O$—⟨○⟩—$CH_2O$—⟨○⟩—⟨○⟩—$OCH_2\overset{*}{C}HC_2H_5$ ($CH_3$) | 5 |
| Composition 58-A | | 79 |

A ferroelectric liquid crystal device was prepared in the same manner as in Example 52 except that the above liquid crystal composition 60-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 867 μsec | 309 μsec | 120 μsec |

Further, a contrast of 13 was attained at 25° C. during the driving, and a clear switching function was observed. The bistability after termination of the voltage application was also good.

COMPARATIVE EXAMPLE 60

A liquid crystal composition 60-C was prepared by omitting Example compounds Nos. 5-79, 5-157, 2-73 and 2-81 from the liquid crystal composition 60-B prepared in Example 60, i.e., by adding only Example compound No. 1-28 to the liquid crystal composition 58-A.

Ferroelectric liquid crystal devices 60-C and 58-A were prepared by using the compositions 60-C and 58-A, respectively, instead of the composition 52-B, and subjected to measurement of optical response time, otherwise in the same manner as in Example 52. The results are shown below.

| | Response time | | |
|---|---|---|---|
| | 10° C. | 25° C. | 40° C. |
| 58-A | 1260 μsec | 374 μsec | 137 μsec |
| 60-C | 1150 μsec | 365 μsec | 132 μsec |

As apparent from the above Example 60 and Comparative Example 60, the ferroelectric liquid crystal device containing the liquid crystal composition 60-B according to the present invention provided improved response speed and operation characteristic at a lower temperature and also provided a descreased temperature dependence of response speed.

EXAMPLES 61–68

Liquid crystal compositions 61-B to 68-B were prepared by replacing the example compounds and the liquid crystal compositions used in Examples 52, 55 and 58 with example compounds and liquid crystal compositions shown in the following Table 4. Ferroelectric liquid crystal devices were prepared by respectively using these compositions instead of the composition 52-B, and subjected to measurement of optical response time and observation of switching states. In the devices, a monodomain with a good and uniform alignment characteristic was observed. The results of the measurement are shown in the following Table 4.

TABLE 4

| Ex. No. (Comp. No.) | Example compound No. or liquid crystal composition No. (weight parts) | | | | | | Response time (μsec) | | |
|---|---|---|---|---|---|---|---|---|---|
| | | | | | | | 10° C. | 25° C. | 40° C. |
| 61 | 5-21 | 5-70 | 2-79 | 1-7 | 1-37 | | 52-A | 485 | 182 | 74 |
| (61-B) | (3) | (6) | (8) | (4) | (4) | | (75) | | | |
| 62 | 5-161 | 5-168 | 2-3 | 2-77 | 1-32 | | 52-A | 560 | 204 | 81 |
| (62-B) | (4) | (4) | (3) | (3) | (5) | | (81) | | | |
| 63 | 5-10 | 5-150 | 2-40 | 1-9 | 1-59 | | 52-A | 499 | 192 | 78 |
| (63-B) | (6) | (4) | (6) | (4) | (2) | | (78) | | | |
| 64 | 5-2 | 5-107 | 5-165 | 2-20 | 1-46 | | 55-A | 760 | 265 | 104 |
| (64-B) | (6) | (3) | (4) | (7) | (4) | | (76) | | | |
| 65 | 5-120 | 5-176 | 2-12 | 2-18 | 1-20 | | 55-A | 641 | 226 | 87 |
| (65-B) | (4) | (6) | (3) | (3) | (6) | | (78) | | | |
| 66 | 5-11 | 5-77 | 5-170 | 2-14 | 2-59 | 1-27 | 55-A | 703 | 253 | 101 |
| (66-B) | (4) | (5) | (3) | (4) | (4) | (6) | (74) | | | |
| 67 | 5-26 | 5-73 | 5-92 | 2-38 | 2-71 | 1-68 | 58-A | 661 | 231 | 92 |
| (67-B) | (3) | (5) | (4) | (7) | (2) | (4) | (75) | | | |
| 68 | 5-12 | 5-30 | 5-142 | 2-5 | 1-26 | 1-38 | 58-A | 720 | 254 | 97 |
| (68-B) | (5) | (4) | (3) | (6) | (4) | (3) | (75) | | | |

As is apparent from the results shown in the above Table 4, the ferroelectric liquid crystal devices containing the liquid crystal compositions 61-B to 68-B provided improved response speed and a decreased temperature dependence of the response speed.

EXAMPLE 69

A blank cell was prepared in the same manner as in Example 1 except for omitting the SiO$_2$ layer to form an alignment control layer composed of the polyimide resin layer alone on each electrode plate. Five ferroelectric liquid crystal devices were prepared by filling such a blank cell with liquid crystal compositions 52-B, 52-A, 52-C, 52-D and 52-E, respectively, prepared in Example 52 and Comparative Example 52. These liquid crystal devices were subjected to measurement of optical response time in the same manner as in Example 52. The results are shown below.

| | Response time (μsec) | | |
|---|---|---|---|
| | 10° C. | 25° C. | 40° C. |
| 52-B | 502 | 185 | 76 |
| 52-A | 848 | 269 | 110 |
| 52-C | 615 | 219 | 85 |
| 52-D | 739 | 259 | 102 |
| 52-E | 585 | 203 | 82 |

As is apparent from the above Example 69, also in the case of a different device structure, the device containing the ferroelectric liquid crystal composition 52-B according to the present invention provided improved operation characteristic at a lower temperature and also a decreased temperature dependence of response speed.

EXAMPLE 70

A liquid crystal composition 70-B was prepared by mixing the following example compound in the indicated proportion with the liquid crystal composition 1-B prepared in Example 1.

| Ex. Comp. No. | Structural formula | wt. parts |
|---|---|---|
| 6-10 | 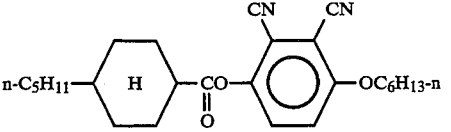 | 10 |
| Composition 1-B | | 90 |

A ferroelectric liquid crystal device was prepared in the same manner as in Example 1 except that the above liquid crystal composition was used, and the device was subjected to measurement of optical response time in the same manner as in Example 1 to obtain the following results.

| Response time | | |
|---|---|---|
| 10° C. | 25° C. | 40° C. |
| 790 μsec | 271 μsec | 102 μsec |

Then, the tilt angle of the above device was measured under right-angle cross nicols at 25° C. to provide 7.6 degrees. Further, the tilt angle of the device was again measured while being subjected to application of rectangular waveforms of ±8 V and a frequency of 60 KHz and found to be 14.2 degrees. The transmittance measured at that time was 16.0%, and a contrast of 57:1 was attained.

COMPARATIVE EXAMPLE 70

A liquid crystal composition 70-C was prepared in the same manner as in Example 70 except that the liquid crystal composition 1-A prepared in Example 1 was used instead of the composition 1-B to be mixed with the example compound No. 6-10 in the same proportions.

Ferroelectric liquid crystal devices were prepared by using the compositions 70-C, 1-A and 1-B respectively and subjected to measurement of optical response time, otherwise in the same manner as in Example 1. Further, the tilt angles of these devices were measured in the same manner as in Example 70. The results are shown below.

tively indicated proportions with the liquid crystal composition 1-B prepared in Example 1.

| Ex. Comp. No. | Structural formula | wt. parts |
| --- | --- | --- |
| 6-90 | n-C$_{10}$H$_{21}$—[thiadiazole, N—N, S]—[phenyl]—OC$_{12}$H$_{25}$ | 5 |
| 6-12 | n-C$_8$H$_{17}$—[H cyclohexyl]—CO—O—[phenyl with CN, CN]—OC$_8$H$_{17}$-n | 5 |
| 6-122 | n-C$_8$H$_{17}$—[H]—[H]—(CN)—C$_8$H$_{17}$-n | 2 |
| 6-70 | n-C$_6$H$_{13}$—[phenyl, N—N]—[phenyl]—OC$_5$H$_{11}$-n | 3 |
| 6-107 | n-C$_{10}$H$_{21}$—[thiadiazole, N—N, S]—[phenyl]—OC(O)—[H]—C$_3$H$_7$-n | 3 |
| 6-111 | n-C$_{12}$H$_{25}$—[thiadiazole, N—N, S]—[phenyl]—OCH$_2$—[H]—C$_5$H$_{11}$-n | 1 |
| 6-167 | n-C$_9$H$_{19}$O—[phenyl]—CH=C(CN)—[phenyl]—C$_7$H$_{15}$ | 1 |
| Composition 1-B | | 80 |

| | Response time | | |
| --- | --- | --- | --- |
| | 10° C. | 25° C. | 40° C. |
| 1-A | 1155 μsec | 362 μsec | 113 μsec |
| 1-B | 705 μsec | 246 μsec | 95 μsec |
| 70-C | 1326 μsec | 405 μsec | 139 μsec |

| | Tilt angle (25° C. | |
| --- | --- | --- |
| Comp. | Initial (no electric field) | Under AC appln. (60 KHz, ±8 V, rectangular) |
| 1-A | 7.5 degrees | 7.8 degrees |
| 1-B | 7.3 degrees | 7.6 degrees |
| 70-C | 7.7 degrees | 13.3 degrees |

As apparent from Example 70 and Comparative Example 70, the liquid crystal composition 70-B obtained by mixing a mesomorphic compound having a negative dielectric anisotropy (example compound No. 6-10) with the liquid crystal composition 1-B according to the present invention provided an improved response characteristic and also provided a remarkably improved display characteristic when used in a display method utilizing AC application (or AC stabilization).

EXAMPLE 71

A liquid crystal composition 71-B was prepared by mixing the following example compounds in the respec tively indicated proportions with the liquid crystal composition 1-B prepared in Example 1.

A ferroelectric liquid crystal device was prepared in the same manner as in Example 1 except that the above liquid crystal composition was used, and the device was subjected to measurement of optical response time in the same manner as in Example 1 to obtain the following results.

| | 10° C. | 25° C. | 40° C. |
| --- | --- | --- | --- |
| Response time | 827 μsec | 295 μsec | 111 μsec |

Then, the tilt angle of the above device was measured under right-angle cross nicols at 25° C. to provide 8.6 degrees. Further, the tilt angle of the device was again measured while being subjected to application of rectangular waveforms of ±8 V and a frequency of 60 KHz and found to be 13.5 degrees. The transmittance measured at that time was 14.5%, and a contrast of 59:1 was attained.

COMPARATIVE EXAMPLE 71

A liquid crystal composition 71-C was prepared in the same manner as in Example 71 except that the liquid crystal composition 1-A prepared in Example 1 was used instead of the composition 1-B to be mixed with the other example compounds in the same proportions.

Ferroelectric liquid crystal devices were prepared by using the compositions 71-C, 1-A and 1-B respectively and subjected to measurement of driving voltage margin, otherwise in the same manner as in Example 1. Further, the tilt angles of these devices were measured in the same manner as in Example 71. The results are shown below.

|       | Response time |         |         |
|-------|---------------|---------|---------|
|       | 10° C.        | 25° C.  | 40° C.  |
| 1-A   | 1155 μsec     | 362 μsec | 133 μsec |
| 1-B   | 705 μsec      | 246 μsec | 95 μsec  |
| 71-C  | 1450 μsec     | 400 μsec | 152 μsec |

|       | Tilt angle (25° C.) | |
|-------|---------------------|---|
| Comp. | Initial (no electric field) | Under AC appln. (60 KHz, ±8 V, rectangular) |
| 1-A   | 7.5 degrees         | 7.8 degrees  |
| 1-B   | 7.3 degrees         | 7.6 degrees  |
| 71-C  | 8.3 degrees         | 13.0 degrees |

As apparent from Example 71 and Comparative Example 71, the liquid crystal composition 71-B obtained by mixing mesomorphic compounds having a negative dielectric anisotropy with the liquid crystal composition 1-B according to the present invention provided an improved responsive characteristic and also provided a remarkably improved display characteristic when used in a display method utilizing AC application (or AC stabilization).

For example, the dielectric anisotropy Δε of a mesomorphic compound or a liquid crystal composition referred to herein may be measured in the following manner.

A 5 micron-thick homogeneous alignment cell having an electrode of 0.7 cm² in area and a homogeneous alignment layer (rubbed polyimide) on both substrates, and a 5 micron-thick homeotropic alignment cell having an electrode of 0.7 cm² in area and a homeotropic alignment layer (aligning agent: "ODS-E" available from Chisso K.K.) on both substrates, are provided. The respective cells are filled with a sample liquid crystal material (compound or composition) to prepare liquid crystal devices. The capacitances of the liquid crystal layers are measured by applying a sine wave with a frequency of 100 KHz and amplitudes of ±0.5 V to the respective devices at a prescribed temperature set for the liquid crystal material, and the dielectric constants ε‖ and ε⊥ are obtained from the measured capacitance values of the respective devices, whereby the dielectric anisotropy Δε is calculated by the equation of Δε = ε‖ − ε⊥.

As described hereinabove, the ferroelectric liquid crystal composition according to the present invention provides a liquid crystal device which shows a good switching characteristic, an improved operation characteristic and a decreased temperature dependence of response speed. Further, the liquid crystal composition according to the present invention further containing a mesomorphic compound having a negative dielectric anisotropy, provides a liquid crystal device which retains the above-mentioned characteristics and further shows a remarkably improved display characteristic when used in a driving method utilizing AC stabilization.

What is claimed is:

1. A ferroelectric chiral smectic liquid crystal composition, comprising:
at least one compound represented by the following formula (I):

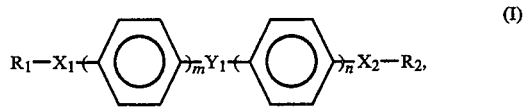

wherein $R_1$ and $R_2$ denote a linear or branched alkyl group having 1-18 carbon atoms wherein $R_1$ and $R_2$ are individually optionally substituted with halogen or alkoxy group; $X_1$ and $X_2$ denote a single bond, —O—,

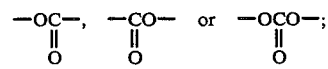

$Y_1$ denotes —CH$_2$O— or —OCH$_2$—; and m and n are 1 or 2 with the proviso that m+n=2; and
at least one compound represented by the following formula (II);

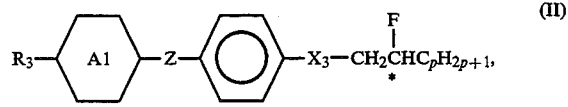

wherein $R_3$ denotes a linear or branched alkyl group having 1-18 carbon atoms wherein $R_3$ is optionally substituted with alkoxy group; $X_3$ denotes a single bond, —O— or

Z denotes a single bond or

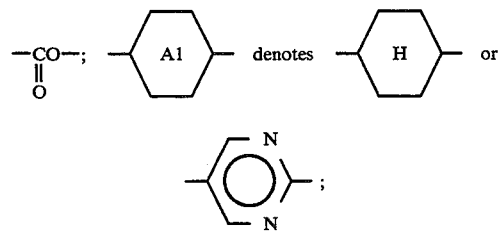

and p is an integer of 1-12.

2. A composition according to claim 1, which further comprises at least one compound represented by any of the following formulae (III) to (V);

Formula (III):

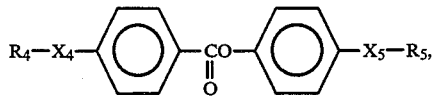

wherein $R_4$ and $R_5$ denote a linear or branched alkyl group having 1-18 carbon atoms wherein $R_4$ and $R_5$ are individually optionally substituted with alkoxy group, at least one of $R_4$ and $R_5$ being optically active; $X_4$ denotes a single bond, —O—,

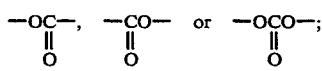

and X₅ denotes a single bond, —O—,

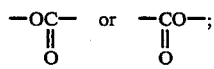

Formula (IV):

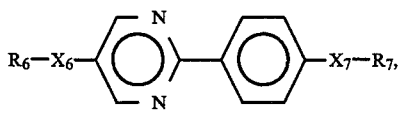

wherein R₆ and R₇ denote a linear or branched alkyl group having 1–18 carbon atoms capable of having an alkoxy group of 1–12 carbon atoms; X₆ and X₇ denote a single bond, —O—,

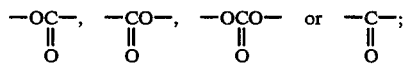

Formula (V):

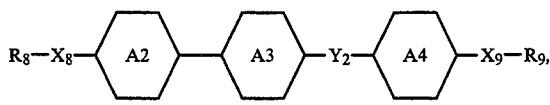

wherein R₈ and R₉ denote a linear or branched alkyl group having having 1–18 carbon atoms wherein R₈ is optionally substituted with alkoxy group, alkoxy carbonyl group or halogen and R₉ is optionally substituted with alkoxy group; X₈ and X₉ denote a single bond, —O—,

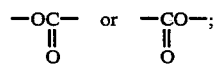

Y₂ denotes

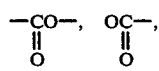

—CH₂—, —OCH₂— or a single bond;

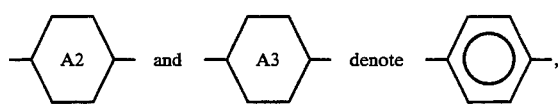

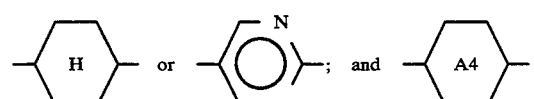

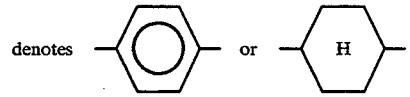

with proviso that at least one of

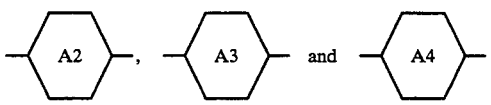

denotes 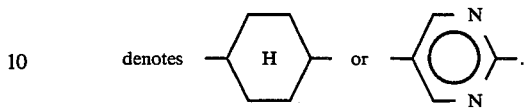.

3. A composition according to claim 1 or 2, which further comprises a mesomorphic compound having a negative dielectric anisotropy.

4. A composition according to claim 3, wherein said mesomorphic compound has a dielectric anisotropy Δε of below −2.

5. A composition according to claim 4, wherein said mesomorphic compound has a dielectric anisotropy Δε of below −5.

6. A composition according to claim 5, wherein said mesomorphic compound has a dielectric anisotropy Δε of below −10.

7. A composition according to claim 3, wherein said mesomorphic compound having a negative dielectric anisotropy is a mesomorphic compound represented by any of the following formulae (VI-1) to (VI-5);

Formula (VI-1):

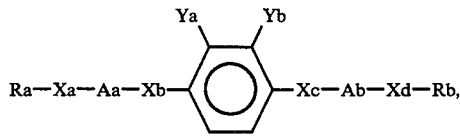

wherein Ra and Rb denote a linear or branched alkyl group wherein Rb is optionally substituted with alkoxy group; Xa and Xd denote a single bond, —O—,

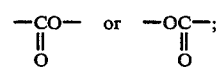

Xb and Xc respectively denote a single bond,

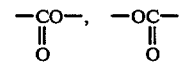

or —CH₂CH₂—; Aa and Ab denote a single bond,

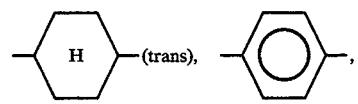

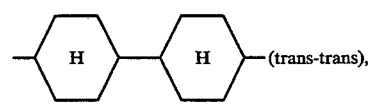

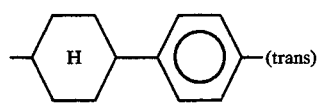

or

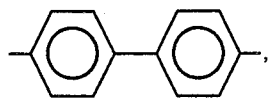

with proviso that when Aa and Ab are both single bonds, Xb and Xc are both single bonds, and Xa and Xd are both single bonds or —O—, or Xa is

and Xd is

and Ya and Yb are cyano group, halogen or hydrogen with proviso that Ya and Yb cannot be hydrogen simultaneously;

Formula (VI-2):

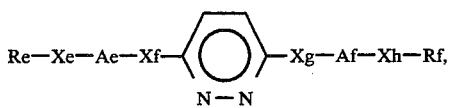

wherein Re and Rf denote a linear or branched alkyl group; Xe and Xh are a single bond, —O—,

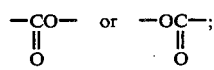

Xf and Xg are

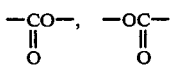

or a single bond; and Ae and Af are

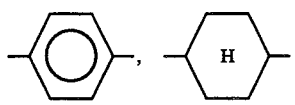

or a single bond with proviso that Ae and Af cannot be a single bond simultaneously;

Formula (VI-3):

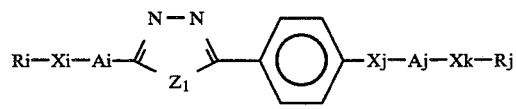

wherein Ai is a single bond or

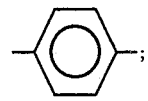

Aj is a single bond,

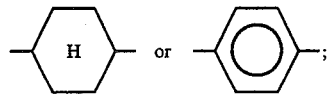

Ri and Rj are a linear or branched alkyl group substituent with proviso that Ri and Rj are linear alkyl groups when Aj is a single bond; $Z_1$ is —O— or —S—; Xi and Xk are a single bond, —O—,

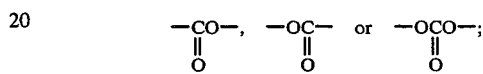

Xj is a single bond,

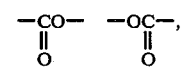

—CH$_2$O— or —OCH$_2$— with proviso that Xi is a single bond when Ai is a single bond, Xj is not a single bond when Aj is

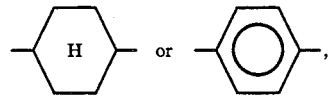

and Xk is a single bond when Aj is a single bond;

Formula (VI-4):

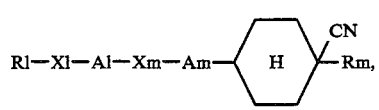

wherein Rl and Rm are a linear or branched alkyl group; Al and Am are a single bond,

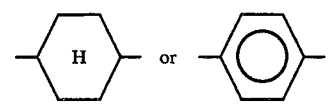

with proviso that Al and Am cannot be a single bond simultaneously; Xl is a single bond, —O—,

and Xm is a single bond,

—CH₂O—, —OCH₂—, —CH₂CH₂— or —C≡C—;

Formula (VI-5):

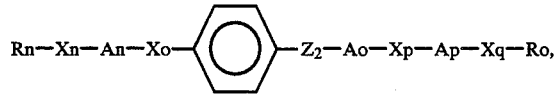

wherein Rn and Ro are a linear or branched alkyl group; Xn and Xq are a single bond, —O—,

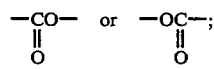

Xo and Xp are a single bond,

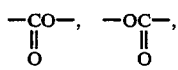

—CH₂O—, —OCH₂— or —CH₂CH₂—; An and Ap are a single bond,

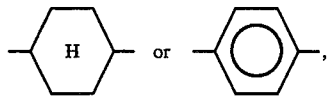

Ao is

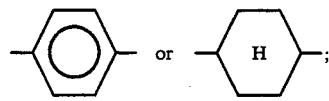

and Z₂ is

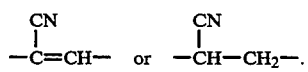

8. A liquid crystal device, comprising a pair of electrode plates and a ferroelectric liquid crystal composition according to claims 1 or 2 disposed between the electrode plates.

9. A liquid crystal device, comprising a pair of electrode plates and a ferroelectric liquid crystal composition according to claim 3, disposed between the electrode plates.

10. A liquid crystal device, comprising a pair of electrode plates and a ferroelectric liquid crystal composition according to claim 4, disposed between the electrode plates.

11. A liquid crystal device, comprising a pair of electrode plates and a ferroelectric liquid crystal composition according to claim 5, disposed between the electrode plates.

12. A liquid crystal device, comprising a pair of electrode plates and a ferroelectric liquid crystal composition according to claim 6, disposed between the electrode plates.

13. A liquid crystal device, comprising a pair of electrode plates and a ferroelectric liquid crystal composition according to claim 7, disposed between the electrode plates.

* * * * *

UNITED STATES PATENT AND TRADEMARK OFFICE
CERTIFICATE OF CORRECTION

PATENT NO. : 5,364,559
DATED : November 15, 1994
INVENTOR(S) : KENJI SHINJO, ET AL.

It is certified that error appears in the above-identified patent and that said Letters Patent is hereby corrected as shown below:

COLUMN 2

Line 8, "has" should read --have--.

COLUMN 6

Line 36, "decrease" should read --decreased--.

COLUMN 10

Line 25, "above-formulas" should read --above formulas--.

COLUMN 22

Line 3, "aboveprepared" should read --above-prepared--.

COLUMN 33

Line 65, "2-C." should read --2-C. ¶ Reaction scheme 2-A--.

COLUMN 37

Line 17, insert: --Phase transition temperature (°C)--.
Line 28, "other" should read --order--.

COLUMN 38

Line 11, "(V);" should read --(V): ¶ Formula (III):--.

COLUMN 39

Line 11, "-$CH_2$-," should read -- -$CH_2O$-,--.

UNITED STATES PATENT AND TRADEMARK OFFICE
CERTIFICATE OF CORRECTION

PATENT NO. : 5,364,559
DATED : November 15, 1994
INVENTOR(S) : KENJI SHINJO, ET AL.

It is certified that error appears in the above-identified patent and that said Letters Patent is hereby corrected as shown below:

COLUMN 40

Line 30, "and" should be deleted.

COLUMN 41

Line 53, "formula" should read --formulas--.
Line 56, "(IV--p)" should read --(IV-p)--.

COLUMN 42

Line 40, "above-formulas" should read --above formulas--.

COLUMN 65

Line 26, "amd" should read --and--.
Line 33, "toluenesulfonic" should read --toluene-sulfonic--.

COLUMN 66

Line 7, "-washed" should read --washed--.

COLUMN 96

Line 31, "hour" should read --hours--.

COLUMN 97

Line 33, "(Vi-5):" should read --(VI-5):--.

UNITED STATES PATENT AND TRADEMARK OFFICE
CERTIFICATE OF CORRECTION

PATENT NO. : 5,364,559
DATED : November 15, 1994
INVENTOR(S) : KENJI SHINJO, ET AL.

It is certified that error appears in the above-identified patent and that said Letters Patent is hereby corrected as shown below:

COLUMN 99

Line 56, "$-\overset{\underset{\|}{O}}{C}O-$" should read -- $-\overset{\underset{\|}{O}}{C}O-,$ --.

COLUMN 100

Line 35, "$-C\equiv C-,$" should read -- $-C\equiv C-;$ --.
Line 41, "Zq" should read --Xq--.

COLUMN 131

Line 23, "Ae" should read --$\Delta\epsilon$--.

COLUMN 132

Line 30, "structure" should read --structural--.

COLUMN 143

Line 57, "<-2" should read --$\Delta\epsilon$<-2--.

COLUMN 149

Line 68, "descreased" should read --decreased--.

COLUMN 152

Line 4, "descreased" should read --decreased--.

UNITED STATES PATENT AND TRADEMARK OFFICE
CERTIFICATE OF CORRECTION

PATENT NO. : 5,364,559
DATED : November 15, 1994
INVENTOR(S) : KENJI SHINJO, ET AL.

It is certified that error appears in the above-identified patent and that said Letters Patent is hereby corrected as shown below:

COLUMN 154

Line 30, "descreased" should read --decreased--.

COLUMN 156

Line 21, "descreased" should read --decreased--.

COLUMN 158

Line 47, "descreased" should read --decreased--.

COLUMN 160

Line 25, "descreased" should read --decreased--.

COLUMN 165

Line 28, "descreased" should read --decreased--.

COLUMN 167

Line 4, "descreased" should read --decreased--.

COLUMN 168

Line 52, "descreased" should read --decreased--.

COLUMN 172

Line 47, "descreased" should read --decreased--.

UNITED STATES PATENT AND TRADEMARK OFFICE
CERTIFICATE OF CORRECTION

PATENT NO. : 5,364,559
DATED : November 15, 1994
INVENTOR(S) : KENJI SHINJO, ET AL.

It is certified that error appears in the above-identified patent and that said Letters Patent is hereby corrected as shown below:

COLUMN 174

Line 34, "descreased" should read --decreased--.

COLUMN 176

Line 24, "descreased" should read --decreased--.

COLUMN 179

Line 36, "descreased" should read --decreased--.

COLUMN 181

Line 1, "descreased" should read --decreased--.

COLUMN 182

Line 53, "descreased" should read --decreased--.

COLUMN 183

Line 24, "decrease" should read --decreased--.

COLUMN 188

Line 34, "descreased" should read --decreased--.
Ex. Comp. No. 4-103, "$-(-OCH_2)_4-$" should read --$-(-CH_2)_4-$--.

COLUMN 190

Line 24, "descreased" should read --decreased--.

UNITED STATES PATENT AND TRADEMARK OFFICE
CERTIFICATE OF CORRECTION

PATENT NO. : 5,364,559
DATED : November 15, 1994
INVENTOR(S) : KENJI SHINJO, ET AL.

It is certified that error appears in the above-identified patent and that said Letters Patent is hereby corrected as shown below:

COLUMN 192

Line 17, "descreased" should read --decreased--.

COLUMN 195

Line 32, "descreased" should read --decreased--.

COLUMN 196

Line 67, "descreased" should read --decreased--.

COLUMN 198

Line 51, "descreased" should read --decreased--.

COLUMN 203

Line 4, "descreased" should read --decreased--.

COLUMN 204

Line 48, "descreased" should read --decreased--.

COLUMN 206

Line 41, "descreased" should read --decreased--.

COLUMN 207

Line 15, "decrease" should read --decreased--.

UNITED STATES PATENT AND TRADEMARK OFFICE
CERTIFICATE OF CORRECTION

PATENT NO. : 5,364,559
DATED : November 15, 1994
INVENTOR(S) : KENJI SHINJO, ET AL.

It is certified that error appears in the above-identified patent and that said Letters Patent is hereby corrected as shown below:

COLUMN 212

Line 39, "descreased" should read --decreased--.

COLUMN 214

Line 35, "descreased" should read --decreased--.

COLUMN 216

Line 30, "descreased" should read --decreased--.

COLUMN 220

Line 34, "descreased" should read --decreased--.

COLUMN 222

Line 27, "descreased" should read --decreased--.

COLUMN 223

Line 18, "prepared from" should read --prepared by omitting Example compounds Nos. 2-23, 2-52 and 1-25 from--.

COLUMN 224

Line 17, "descreased" should read --decreased--.

COLUMN 227

Line 24, "AS" should read --As--.
Line 29, "descreased" should read --decreased--.

UNITED STATES PATENT AND TRADEMARK OFFICE
CERTIFICATE OF CORRECTION

PATENT NO. : 5,364,559
DATED : November 15, 1994
INVENTOR(S) : KENJI SHINJO, ET AL.

It is certified that error appears in the above-identified patent and that said Letters Patent is hereby corrected as shown below:

COLUMN 228

Line 24, "Liquid" should read --liquid--.

COLUMN 229

Line 6, "descreased" should read --decreased--.

COLUMN 230

Line 53, "descreased" should read --decreased--.

COLUMN 236

Line 21, "m+n=2 or;" should read --m+n=2 or 3;--.
Line 23, "(II);" should read --(II):--.
Line 55, "(V);" should read --(V):--.

COLUMN 238

Line 28, "(VI-5);" should read --(VI-5):--.
Line 46, "respectively" should be deleted.

COLUMN 240

Line 14, "substitu-" should read --wherein Ri is optionally substituted with Cl radical and Rj is optionally substituted with alkoxy group--.

UNITED STATES PATENT AND TRADEMARK OFFICE
CERTIFICATE OF CORRECTION

PATENT NO. : 5,364,559
DATED : November 15, 1994
INVENTOR(S) : KENJI SHINJO, ET AL.

It is certified that error appears in the above-identified patent and that said Letters Patent is hereby corrected as shown below:

<u>COLUMN 240</u>

Line 15, "ent" should be deleted.

Signed and Sealed this

Twenty-seventh Day of June, 1995

BRUCE LEHMAN

Attest:

Attesting Officer

Commissioner of Patents and Trademarks